(12) United States Patent
Ebens, Jr. et al.

(10) Patent No.: US 8,142,784 B2
(45) Date of Patent: Mar. 27, 2012

(54) ANTIBODY-DRUG CONJUGATES AND METHODS

(75) Inventors: Allen J. Ebens, Jr., San Carlos, CA (US); Frederic S. Jacobson, Berkeley, CA (US); Paul Polakis, Burlingame, CA (US); Ralph H. Schwall, Pacifica, CA (US); Mark X. Sliwkowski, San Carlos, CA (US); Susan D. Spencer, Tiburon, CA (US)

(73) Assignee: Genentech, Inc., South San Francisco, CA (US)

( * ) Notice: Subject to any disclaimer, the term of this patent is extended or adjusted under 35 U.S.C. 154(b) by 475 days.

(21) Appl. No.: 12/326,721

(22) Filed: Dec. 2, 2008

(65) Prior Publication Data
US 2009/0202536 A1    Aug. 13, 2009

Related U.S. Application Data

(63) Continuation of application No. 11/141,344, filed on May 31, 2005, now abandoned.

(60) Provisional application No. 60/576,517, filed on Jun. 1, 2004, provisional application No. 60/616,098, filed on Oct. 5, 2004.

(51) Int. Cl.
*A61K 39/395* (2006.01)

(52) U.S. Cl. ............... 424/181.1; 424/178.1; 530/391.1; 530/391.5; 530/391.7

(58) Field of Classification Search .................. None
See application file for complete search history.

(56) References Cited

U.S. PATENT DOCUMENTS

| | | | |
|---|---|---|---|
| 4,137,230 A | 1/1979 | Hashimoto et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,450,254 A | 5/1984 | Isley et al. |
| 4,753,894 A | 6/1988 | Frankel et al. |
| 4,956,453 A | 9/1990 | Bjorn et al. |
| 4,958,009 A | 9/1990 | Bjorn et al. |
| 4,981,979 A | 1/1991 | Sivam |
| 5,206,018 A | 4/1993 | Sehgal et al. |
| 5,208,020 A | 5/1993 | Chari et al. |
| 5,416,064 A | 5/1995 | Chari et al. |
| 5,629,197 A | 5/1997 | Ring et al. |
| 5,725,856 A | 3/1998 | Hudziak et al. |
| 5,821,337 A | 10/1998 | Carter et al. |
| 6,333,410 B1 | 12/2001 | Chari et al. |
| 6,441,163 B1 | 8/2002 | Chari et al. |
| 6,632,979 B2 | 10/2003 | Erickson et al. |
| 6,716,821 B2 | 4/2004 | Zhao et al. |
| 6,913,748 B2 | 7/2005 | Widdison |
| 2002/0001587 A1 | 1/2002 | Erickson et al. |
| 2003/0103985 A1 | 6/2003 | Adolf et al. |
| 2003/0130189 A1 * | 7/2003 | Senter et al. .................. 514/12 |
| 2003/0235582 A1 | 12/2003 | Singh et al. |
| 2004/0057952 A1 | 3/2004 | Payne et al. |
| 2004/0120949 A1 | 6/2004 | Adolf et al. |
| 2004/0126379 A1 | 7/2004 | Adolf et al. |
| 2004/0016993 A1 | 8/2004 | Steeves et al. |
| 2004/0235068 A1 | 11/2004 | Levinson |
| 2004/0235840 A1 | 11/2004 | Chair et al. |
| 2004/0241174 A1 | 12/2004 | Amphlett et al. |
| 2005/0169933 A1 | 8/2005 | Steeves et al. |
| 2005/0232929 A1 * | 10/2005 | Kadkhodayan et al. ... 424/178.1 |
| 2005/0256030 A1 * | 11/2005 | Feng .............................. 514/2 |

FOREIGN PATENT DOCUMENTS

| | | |
|---|---|---|
| DE | 40 14 540 A1 | 11/1991 |
| EP | 0 425 235 A2 | 5/1991 |
| EP | 1 391 213 A1 | 2/2004 |
| WO | WO 00/74718 A1 | 12/2000 |
| WO | WO 01/00244 A2 | 1/2001 |
| WO | 01/24763 | 4/2001 |
| WO | WO 01/38490 A2 | 5/2001 |
| WO | 02/16429 | 2/2002 |
| WO | WO 03/000113 A2 | 1/2003 |
| WO | 03/022995 | 3/2003 |
| WO | 03/024392 | 3/2003 |

(Continued)

OTHER PUBLICATIONS

Poison et al Cancer Res. 2009; 69: (6) pp. 2358-2364.* Polson et al., "Anti-CD22-MCC-DM1: an antibody-drug conjugate with a stable linker for the treatment of non-hodgkin's lymphoma" *Original Article*, McMillian Publishers Limited vol. 24(2010):1566-1573 (Jul. 1, 2010).
Burris et al., "A Phase II Study of Trastuzumab-DM1 (T-DM1), A HER2 Antibody-Drug Conjugate, in Patients with HER2 Positive Metastatic Breast Cancer" (Poster 155), Washington, D.C.:ASCO Breast Cancer Symposium (Sep. 5, 2008).

(Continued)

*Primary Examiner* — Sheela J Huff
(74) *Attorney, Agent, or Firm* — Alex Andrus

(57) ABSTRACT

The present invention relates to antibody-drug conjugate compounds of Formula I:

$$Ab\text{-}(L\text{-}D)_p \qquad\qquad I$$

where one or more maytansinoid drug moieties (D) are covalently linked by L to an antibody (Ab) which binds to an ErbB receptor, or which binds to one or more tumor-associated antigens or cell-surface receptors. These compounds may be used in methods of diagnosis or treatment of cancer, and other diseases and disorders.

6 Claims, 15 Drawing Sheets

FOREIGN PATENT DOCUMENTS

| WO | 03/027135 | 4/2003 |
|---|---|---|
| WO | 03/072036 A2 | 9/2003 |
| WO | 03/075855 | 9/2003 |
| WO | 2004/005470 | 1/2004 |
| WO | 2004/016225 | 2/2004 |
| WO | 2005/037992 A2 | 4/2005 |
| WO | 2005/049075 | 6/2005 |
| WO | 2005/101017 | 10/2005 |

OTHER PUBLICATIONS

Chari et al., "Immunoconjugates Containing Novel Maytansinoids: Promising Anticancer Drugs" *Cancer Research* 52:127-131 (Jan. 1992).

Chari, Ravi V.J., "Targeted Delivery of Chemotherapeutics: Tumor-Activated Prodrug Therapy" *Advanced Drug Delivery Reviews* 31:89-104 (1998).

Chu et al., "CD79: a review" *Applied Immunohistochemistry & Molecular Morphology* 9(2):97-106 (2001).

Erickson et al., "Antibody-maytansinoid conjugates are activated in targeted cancer cell by lysosomal degradation and linker-dependent intracellular processing" *Cancer Research* 66(8):4426-4433 (Apr. 15, 2006).

*Fundamental Immunology*, William E. Paul, M.D., 3rd edition, New York:Raven Press, Ltd., Chapter 9, pp. 291-295 (1993).

Hermanson, G.T. *Bioconjugate Techniques*, San Diego, CA:Academic Press pp. 234-242 (1997).

Hu et al., "Discovery and validation of new molecular targets molecular targets for ovarian cancer" *Current Opinion in Molecular Therapeutics* 5(6):625-630 (2003).

Krop et al., "A Phase I Study of Trastuzumab-DM1, a First-in-Class HER2 Antibody-Drug Conjugate (ADC), in Patients with HER2+ Metastatic Breast Cancer" *European Cancer Conference ECCO*, Poster 2118, Sep. 23-27, 2007, Barcelona.

Liu et al., "Eradication of Large Colon Tumor Xenografts by Targeted Delivery of Maytansinoids." *Proc. Natl. Acad. Sci. USA* 93:8618-8623 (1996).

Margolin et al., "Phase Ib Trial of Intravenous Recombinant Humanized Monoclonal Antibody to Vascular Endothelial Growth Factor in Combination with Chemotherapy in Patients with Advanced Cancer" *Journal of Clinical Oncology* 3:851-856 (Feb. 1, 2001).

Niculescu-Duvaz and Springer, "Antibody-Directed Enzyme Prodrug Therapy (ADEPT): A Review" *Adv. Drg. Del. Rev.* 26:151-172 (1997).

Payne, Gillian, "Progress in Immunoconjugate Cancer Therapeutics" *Cancer Cell* 3:207-212 (2003).

Ranson & Sliwkowski, "Perspectives on anti-HER monoclonal antibodies" *Oncology* 63:17-24 (2002).

Ross et al., "Prostate Stem Cell Antigen as Therapy Target: Tissue Experssion and in Vivo Efficacy of an Immunoconjugate" *Cancer Research* 62:2546-2553 (2002).

Syrigos et al., "Antibody Directed Enzyme Prodrug Therapy (ADEPT): A Review of the Experimental and Clinical Considerations" *Anticancer Research* 19:605-613 (1999).

Tolcher et al., "Cantuzumab Mertansine, a Maytansinoid Immunoconjugate Directed to the CanAg Antigen: A Phase I, Pharmacokinetic, and Biologic Correlative Study" *Journal of Clinical Oncology* 21:211-222 (2003).

Trail et al., "Effect of linker variation on the stability, potency, and efficacy of carcinoma-reactive BR64-doxorubicin immunoconjugates" *Cancer Research* 57(1):100-105 (Jan. 1, 1997).

Trail et al., "Monoclonal Antibody Drug Immunoconjugates for Targeted Treatment of Cancer" *Cancer Immunol. Immunother* 52:328-337 (2003).

Wang et al., "Biological activity of bevacizumab, a humanized anti-VEGF antibody in vitro" *Angiogenesis* 7:335-345 (2004).

Xie et al, "Pharmacokinetics and biodistribution of the antitumor immunoconjugate, cantuzumab mertansine (huC242-DM1), and its two components in mice" *J Pharmacol Exp Ther*. 308(3):1073-1082 (Mar. 2004).

* cited by examiner

ANTIBODY-DRUG CONJUGATES AND METHODS

This application is a continuation of U.S. Ser. No. 11/141,344 filed on May 31, 2005, now abandoned, and also claims the benefit of priority under 35 USC §119(e) of U.S. Provisional Application Ser. No. 60/576,517 filed on Jun. 1, 2004 and U.S. Provisional Application Ser. No. 60/616,098 filed on Oct. 5, 2004, each of which are incorporated by reference in their entirety.

FIELD OF THE INVENTION

The invention relates generally to compounds with anticancer activity and more specifically to antibodies conjugated with chemotherapeutic maytansinoid drugs or toxins. The invention also relates to methods of using antibody-drug conjugate compounds for in vitro, in situ, and in vivo diagnosis or treatment of mammalian cells, or associated pathological conditions.

BACKGROUND OF THE INVENTION

Antibody therapy has been established for the targeted treatment of patients with cancer, immunological and angiogenic disorders. The use of antibody-drug conjugates (ADC), i.e. immunoconjugates, for the local delivery of cytotoxic or cytostatic agents, i.e. drugs to kill or inhibit tumor cells in the treatment of cancer (Payne, G. (2003) Cancer Cell 3:207-212; Trail et al (2003) Cancer Immunol. Immunother. 52:328-337; Syrigos and Epenetos (1999) Anticancer Research 19:605-614; Niculescu-Duvaz and Springer (1997) Adv. Drug Del. Rev. 26:151-172; U.S. Pat. No. 4,975,278) theoretically allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al. (eds), pp. 475-506). Maximal efficacy with minimal toxicity is sought thereby. Efforts to design and refine ADC have focused on the selectivity of monoclonal antibodies (mAbs) as well as drug-linking and drug-releasing properties. Both polyclonal antibodies and monoclonal antibodies have been reported as useful in these strategies (Rowland et al., (1986) Cancer Immunol. Immunother. 21:183-87). Drugs used in these methods include daunomycin, doxorubicin, methotrexate, mitomycin, neocarzinostatin (Takahashi et al (1988) Cancer 61:881-888) and vindesine (Rowland et al., (1986) supra). Toxins used in antibody-toxin conjugates include bacterial toxins such as diphtheria toxin, plant toxins such as ricin (U.S. Pat. No. 4,753,894; U.S. Pat. No. 5,629,197; U.S. Pat. No. 4,958,009; U.S. Pat. No. 4,956,453), small molecule toxins such as geldanamycin (Mandler et al (2000) J. of the Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

An antibody-radioisotope conjugate has been approved, ZEVALIN® (ibritumomab tiuxetan, Biogen/Idec) composed of a murine IgG1 kappa monoclonal antibody directed against CD20 antigen and $^{111}$In or $^{90}$Y radioisotope bound by a thiourea linker-chelator (Wiseman et al (2000) Eur. J. Nucl. Med. 27(7):766-77; Wiseman et al (2002) Blood 99(12):4336-42; Witzig et al (2002) J. Clin. Oncol. 20(10):2453-63; Witzig et al (2002) J. Clin. Oncol. 20(15):3262-69). MYLOTARG™ (gemtuzumab ozogamicin, Wyeth Pharmaceuticals), an antibody-drug conjugate composed of a hu CD33 antibody linked to calicheamicin, was approved in 2000 for the treatment of acute myeloid leukemia by injection (Drugs of the Future (2000) 25(7):686; U.S. Pat. No. 4,970,198; U.S. Pat. No. 5,079,233; U.S. Pat. No. 5,585,089; U.S. Pat. No. 5,606,040; U.S. Pat. No. 5,693,762; U.S. Pat. No. 5,739,116; U.S. Pat. No. 5,767,285; U.S. Pat. No. 5,773,001). Cantuzumab mertansine (Immunogen, Inc.), an antibody-drug conjugate composed of the huC242 antibody linked via the disulfide linker SPP to the maytansinoid drug moiety, DM1 (Xie et al (2004) J. of Pharm. and Exp. Ther. 308(3):1073-1082; Tolcher et al (2003) J. Clin. Oncology 21(2):211-222; U.S. Pat. No. 5,208,020), underwent Phase I trials for the treatment of cancers that express CanAg, such as colon, pancreatic, gastric, and others. MLN-2704 (Millennium Pharm., BZL Biologics, Immunogen Inc.) is an antibody-drug conjugate composed of the anti-prostate specific membrane antigen (PSMA) monoclonal antibody linked to the maytansinoid drug moiety, DM1, under development for the potential treatment of prostate tumors. The same maytansinoid drug moiety, DM1, was linked through a non-disulfide linker, SMCC, to a mouse murine monoclonal antibody, TA.1 (Chari et al. (1992) Cancer Research 52:127-131) This conjugate was reported to be 200-fold less potent than the corresponding disulfide linker conjugate. The SMCC linker was considered therein to be "noncleavable" (also, see: U.S. Pat. No. 4,981,979). HERCEPTIN® (trastuzumab) linked by SMCC to DM1 has been reported (WO 2005/037992).

In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides, i.e. tumor-associated antigens (TAA), has given rise to the ability to specifically target cancer cells for destruction via antibody-based therapies.

Monoclonal antibody therapy has been established for the targeted treatment of patients with cancer, immunological and angiogenic disorders. An example of successful antibody therapy is HERCEPTIN® (trastuzumab), a recombinant DNA-derived humanized monoclonal antibody that selectively binds with high affinity in a cell-based assay (Kd=5 nM) to the extracellular domain of the human epidermal growth factor receptor2 protein, HER2 (ErbB2) (U.S. Pat. No. 5,821,337; U.S. Pat. No. 6,054,297; U.S. Pat. No. 6,407,213; U.S. Pat. No. 6,639,055; Coussens L, et al (1985) Science 230:1132-9; Slamon D J, et al (1989) Science 244:707-12). Trastuzumab is an IgG1 kappa antibody that contains human framework regions with the complementarity-determining regions of a murine antibody (4D5) that binds to HER2. Trastuzumab binds to the HER2 antigen and thus inhibits the growth of cancerous cells. Because trastuzumab is a humanized antibody, it minimizes any HAMA response in patients. The humanized antibody against HER2 is produced by a mammalian cell (Chinese Hamster Ovary, CHO) suspension culture. The HER2 (or c-erbB2) proto-oncogene encodes a transmembrane receptor protein of 185 kDa, which is structurally related to the epidermal growth factor receptor. HER2 protein overexpression is observed in 25% 30% of primary breast cancers and can be determined using an immunohistochemistry based assessment of fixed tumor blocks (Press M F, et al (1993) Cancer Res 53:4960-70. Trastuzumab has been shown, in both in vitro assays and in animals, to inhibit the proliferation of human tumor cells that overexpress HER2 (Hudziak R M, et al (1989) Mol Cell Biol 9:1165-72; Lewis G D, et al (1993) Cancer Immunol Immunother; 37:255-63; Baselga J, et al (1998) Cancer Res. 58:2825-2831). Trastuzumab is a mediator of antibody-dependent cellular cytotoxicity, ADCC (Hotaling T E, et al (1996) [abstract]. Proc. Annual Meeting Am Assoc Cancer Res; 37:471; Pegram M D, et al (1997) [abstract]. Proc Am Assoc Cancer Res; 38:602; Sliwkowski et al (1999) Seminars in Oncology 26(4), Suppl 12:60-70; Yarden Y. and Sliwkowski, M. (2001) Nature Reviews Molecular Cell Biology, Macmillan Magazines, Ltd., Vol. 2:127-137). HERCEPTIN® (trastuzumab) is clinically active in patients with ErbB2-overexpressing metastatic breast cancers that have received extensive prior anti-cancer therapy (Baselga et al, (1996) J. Clin. Oncol. 14:737-744). Although HERCEPTIN® (trastuzumab) is a breakthrough in treating patients with ErbB2-overexpressing breast cancers that have received extensive prior anti-cancer therapy, the majority of the patients in this population fail to respond or respond only poorly to HERCEPTIN® (trastuzumab) treatment. Therefore, there is a significant clinical need for developing further HER2-directed cancer therapies for those patients with HER2-overexpressing tumors or other diseases associated with HER2 expression that do not respond, or respond poorly, to HERCEPTIN® (trastuzumab) treatment. In addition to HER2, there is an opportunity to exploit other tumor-associated antigens with targeted therapies.

SUMMARY

The present invention provides novel compounds with biological activity against cancer cells. The compounds may inhibit tumor growth in mammals and may be useful for treating human cancer patients.

The present invention relates to the delivery, transport, accumulation or retention of therapeutic antibody-drug conjugate (ADC) compounds inside cells. The invention is more particularly related to attaining high concentrations of active metabolite molecules in cancer cells. Intracellular targeting may be achieved by methods and compounds which allow accumulation or retention of biologically active agents inside cells. Such effective targeting may be applicable to a variety of therapeutic formulations and procedures.

The surprising discovery has been made that antibody-drug conjugates with stable, non-disulfide linkers groups that attach a maytansinoid drug moiety to an antibody result in increased in vitro potency and in vivo efficacy. In addition, the antibody-drug conjugates show the unexpected result of better safety in vivo relative to certain disulfide linker conjugates.

Antibody-drug conjugate (ADC) compounds comprise an antibody covalently attached by a linker to one or more maytansinoid drug moieties. ADC may be represented by Formula I:

$$Ab\text{-}(L\text{-}D)_p \qquad \qquad I$$

where one or more maytansinoid drug moieties (D) are covalently linked by L to an antibody (Ab). Ab is an antibody which binds to an ErbB receptor, or which binds to one or more tumor-associated antigens or cell-surface receptors. The linker L may be stable outside a cell, i.e. extracellular. The linker L, the maytansinoid drug moiety D, or the linker and the maytansinoid drug moiety taken together (L-D), do not comprise a disulfide group.

In one embodiment, a substantial amount of the drug moiety is not cleaved from the antibody until the antibody-drug conjugate enters a cell with a cell-surface receptor specific for the antibody of the antibody-drug conjugate, and the drug moiety is cleaved from the antibody when the antibody-drug conjugate does enter the cell.

In another embodiment, the ADC specifically binds to a receptor encoded by an ErbB gene, such as EGFR, HER2, HER3 and HER4. The ADC may specifically bind to the extracellular domain of the HER2 receptor. The ADC may inhibit growth of tumor cells which overexpress HER2 receptor.

In another embodiment, the antibody (Ab) of Formula I is a humanized antibody such as huMAb4D5-1, huMAb4D5-2, huMAb4D5-3, huMAb4D5-4, huMAb4D5-5, huMAb4D5-6, huMAb4D5-7 or huMAb4D5-8 (trastuzumab).

Another aspect of the invention is a pharmaceutical composition including a Formula I compound, or a pharmaceutically acceptable salt or solvate thereof, and a pharmaceutically acceptable diluent, carrier, or excipient.

Another aspect provides a pharmaceutical combination comprising a Formula I compound and a second compound having anti-cancer properties or other therapeutic effects.

Another aspect includes diagnostic and therapeutic uses for the compounds and compositions disclosed herein.

Another aspect is a method for killing or inhibiting the proliferation of tumor cells or cancer cells comprising treating the cells with an amount of an antibody-drug conjugate, or a pharmaceutically acceptable salt or solvate thereof, being effective to kill or inhibit the proliferation of the tumor cells or cancer cells.

Another aspect are methods of treating cancer comprising administering to a patient a formulation of a Formula I compound. One method is for the treatment of cancer in a mammal, wherein the cancer is characterized by the overexpression of an ErbB receptor. The mammal optionally does not respond, or responds poorly, to treatment with an unconjugated anti-ErbB antibody. The method comprises administering to the mammal a therapeutically effective amount of an antibody-drug conjugate compound.

Another aspect is a method of inhibiting the growth of tumor cells that overexpress a growth factor receptor selected from the group consisting of HER2 receptor and EGF receptor comprising administering to a patient an antibody-drug conjugate compound which binds specifically to said growth factor receptor and a chemotherapeutic agent wherein said antibody-drug conjugate and said chemotherapeutic agent are each administered in amounts effective to inhibit growth of tumor cells in the patient.

Another aspect is a method for the treatment of a human patient susceptible to or diagnosed with a disorder characterized by overexpression of ErbB2 receptor, comprising administering a combination of an antibody-drug conjugate compound of Formula I and a chemotherapeutic agent.

Another aspect is an assay method for detecting cancer cells comprising: exposing cells to an antibody-drug conjugate compound, and determining the extent of binding of the antibody-drug conjugate compound to the cells.

Another aspect concerns methods of screening ADC drug candidates for the treatment of a disease or disorder where the disease or disorder is characterized by the overexpression of HER2.

Another aspect includes articles of manufacture, i.e. kits, comprising an antibody-drug conjugate, a container, and a package insert or label indicating a treatment.

Another aspect includes methods of treating a disease or disorder characterized by the overexpression of HER2 in a patient with the antibody-drug conjugate compounds.

Another aspect includes methods of making, methods of preparing, methods of synthesis, methods of conjugation, and methods of purification of the antibody-drug conjugate compounds, and the intermediates for the preparation, synthesis, and conjugation of the antibody-drug conjugate compounds.

DETAILED DESCRIPTION OF EXEMPLARY EMBODIMENTS

Figures 1, 2:
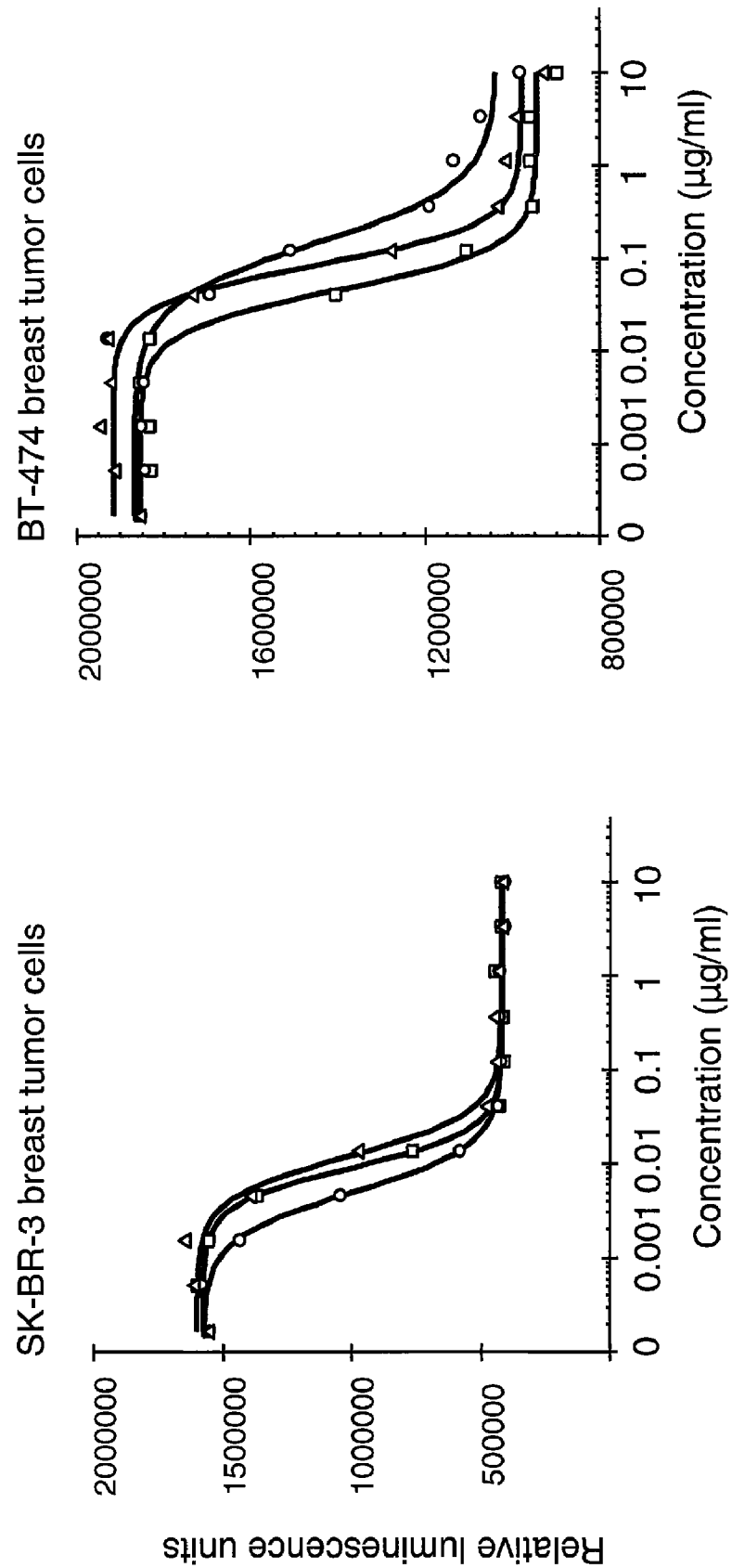
FIG. 1 shows an in vitro, cell proliferation assay with SK-BR-3 cells treated with antibody-drug conjugates: -□- trastuzumab-SPP-DM1, -Δ- trastuzumab-SPDP-DM1, and -o- trastuzumab-SMCC-DM1.
FIG. 2 shows an in vitro, cell proliferation assay with BT-474 cells treated with antibody-drug conjugates: -□- trastuzumab-SPP-DM1, -Δ- trastuzumab-SPDP-DM1, and -o- trastuzumab-SMCC-DM1.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

Unless defined otherwise, technical and scientific terms used herein have the same meaning as commonly understood by one of ordinary skill in the art to which this invention belongs, and are consistent with: Singleton et al., (1994) *Dictionary of Microbiology and Molecular Biology*, 2nd Ed., J. Wiley & Sons, New York, N.Y.; and Janeway, C., Travers, P., Walport, M., Shlomchik (2001) *Immuno Biology*, 5th Ed., Garland Publishing, New York.

DEFINITIONS

Unless stated otherwise, the following terms and phrases as used herein are intended to have the following meanings:

When trade names are used herein, applicants intend to independently include the trade name product formulation, the generic drug, and the active pharmaceutical ingredient(s) of the trade name product.

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al (2003) Jour. of Immunology 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) *Immuno Biology*, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

"Antibody fragments" comprise a portion of a full length antibody, generally the antigen binding or variable region thereof. Examples of antibody fragments include Fab, Fab', F(ab')$_2$, and Fv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) *Nature* 256:495, or may be made by recombinant DNA methods (see, U.S. Pat. No. 4,816,567). The monoclonal antibodies may also be isolated from phage antibody libraries using the techniques described in Clackson et al (1991) Nature, 352:624-628; Marks et al (1991) J. Mol. Biol., 222:581-597; for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. USA, 81:6851-6855). Chimeric antibodies of interest herein include "primatized" antibodies comprising variable domain antigen-binding sequences derived from a non-human primate (e.g., Old World Monkey or Ape) and human constant region sequences.

An "intact antibody" herein is one comprising a VL and VH domains, as well as a light chain constant domain (CL) and heavy chain constant domains, CH1, CH2 and CH3. The constant domains may be native sequence constant domains (e.g., human native sequence constant domains) or amino acid sequence variant thereof. The intact antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

Depending on the amino acid sequence of the constant domain of their heavy chains, intact antibodies can be assigned to different "classes." There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

An "ErbB receptor" is a receptor protein tyrosine kinase which belongs to the ErbB receptor family which are important mediators of cell growth, differentiation and survival. The ErbB receptor family includes four distinct members including epidermal growth factor receptor (EGFR, ErbB1, HER1), HER2 (ErbB2 or p185$^{neu}$), HER3 (ErbB3) and HER4 (ErbB4 or tyro2). A panel of anti-ErbB2 antibodies has been characterized using the human breast tumor cell line SKBR3 (Hudziak et al (1989) Mol. Cell. Biol. 9(3):1165-1172. Maximum inhibition was obtained with the antibody called 4D5 which inhibited cellular proliferation by 56%. Other antibodies in the panel reduced cellular proliferation to a lesser extent in this assay. The antibody 4D5 was further found to sensitize ErbB2-overexpressing breast tumor cell lines to the cytotoxic effects of TNF-α (U.S. Pat. No. 5,677,171). The anti-ErbB2 antibodies discussed in Hudziak et al are further characterized in Fendly et al (1990) Cancer Research 50:1550-1558; Kotts et al. (1990) In Vitro 26(3):59A; Sarup et al. (1991) Growth Regulation 1:72-82; Shepard et al. J. (1991) Clin. Immunol. 11(3):117-127; Kumar et al. (1991) Mol. Cell. Biol. 11(2):979-986; Lewis et al. (1993) Cancer Immunol. Immunother. 37:255-263; Pietras et al. (1994) Oncogene 9:1829-1838; Vitetta et al. (1994) Cancer Research 54:5301-5309; Sliwkowski et al. (1994) J. Biol. Chem. 269(20):

14661-14665; Scott et al. (1991) J. Biol. Chem. 266:14300-5; D'souza et al. Proc. Natl. Acad. Sci. (1994) 91:7202-7206; Lewis et al. (1996) Cancer Research 56:1457-1465; and Schaefer et al. (1997) Oncogene 15:1385-1394.

Other anti-ErbB2 antibodies with various properties have been described in Franklin et al (2004) Cancer Cell 5:317-328; Tagliabue et al (1991) Int. J. Cancer 47:933-937; McKenzie et al (1989) Oncogene 4:543-548; Maier et al (1991) Cancer Res. 51:5361-5369; Bacus et al (1990) Molecular Carcinogenesis 3:350-362; Stancovski et al (1991) PNAS (USA) 88:8691-8695; Bacus et al (1992) Cancer Research 52:2580-2589; Xu et al (1993) Int. J. Cancer 53:401-408; WO94/00136; Kasprzyk et al (1992) Cancer Research 52:2771-2776; Hancock et al (1991) Cancer Res. 51:4575-4580; Shawver et al (1994) Cancer Res. 54:1367-1373; Arteaga et al (1994) Cancer Res. 54:3758-3765; Harwerth et al (1992) J. Biol. Chem. 267:15160-15167; U.S. Pat. No. 5,783,186; and Klapper et al (1997) Oncogene 14:2099-2109.

Sequence identity screening has resulted in the identification of two other ErbB receptor family members; ErbB3 (U.S. Pat. No. 5,183,884; U.S. Pat. No. 5,480,968; Kraus et al (1989) PNAS (USA) 86:9193-9197) and ErbB4 (EP 599274; Plowman et al (1993) Proc. Natl. Acad. Sci. USA, 90:1746-1750; and Plowman et al (1993) Nature 366:473-475). Both of these receptors display increased expression on at least some breast cancer cell lines.

The ErbB receptor will generally comprise an extracellular domain, which may bind an ErbB ligand; a lipophilic transmembrane domain; a conserved intracellular tyrosine kinase domain; and a carboxyl-terminal signaling domain harboring several tyrosine residues which can be phosphorylated. The ErbB receptor may be a "native sequence" ErbB receptor or an "amino acid sequence variant" thereof. The ErbB receptor may be native sequence human ErbB receptor. Accordingly, a "member of the ErbB receptor family" is EGFR (ErbB1), ErbB2, ErbB3, ErbB4 or any other ErbB receptor currently known or to be identified in the future.

The terms "ErbB1", "epidermal growth factor receptor", "EGFR" and "HER1" are used interchangeably herein and refer to EGFR as disclosed, for example, in Carpenter et al (1987) Ann. Rev. Biochem. 56:881-914, including naturally occurring mutant forms thereof (e.g., a deletion mutant EGFR as in Humphrey et al., (1990) PNAS (USA), 87:4207-4211). The term erbB1 refers to the gene encoding the EGFR protein product. Antibodies against HER1 are described, for example, in Murthy et al (1987) Arch. Biochem. Biophys., 252:549-560 and in WO 95/25167.

The term "ERRP", "EGF-Receptor Related Protein", "EGFR Related Protein" and "epidermal growth factor receptor related protein" are used interchangeably herein and refer to ERRP as disclosed, for example in U.S. Pat. No. 6,399,743 and US 2003/0096373.

The expressions "ErbB2" and "HER2" are used interchangeably herein and refer to human HER2 protein described, for example, in Semba et al (1985) PNAS (USA), 82:6497-6501 and Yamamoto et al (1986) Nature, 319:230-234 (Genbank accession number X03363). The term "erbB2" refers to the gene encoding human ErbB2 and "neu" refers to the gene encoding rat p185neu.

"ErbB3" and "HER3" refer to the receptor polypeptide as disclosed, for example, in U.S. Pat. No. 5,183,884; U.S. Pat. No. 5,480,968; Kraus et al (1989) PNAS (USA) 86:9193-9197. Antibodies against ErbB3 are known in the art (U.S. Pat. No. 5,183,884; U.S. Pat. No. 5,480,968; WO 97/35885).

The terms "ErbB4" and "HER4" herein refer to the receptor polypeptide as disclosed, for example, in EP Pat Appln No 599,274; Plowman et al., Proc. Natl. Acad. Sci. USA, 90:1746-1750 (1993); and Plowman et al., Nature, 366:473-475 (1993), including isoforms thereof, e.g., as disclosed in WO 99/19488. Antibodies against HER4 are described, for example, in WO 02/18444.

Antibodies to ErbB receptors are available commercially from a number of sources, including, for example, Santa Cruz Biotechnology, Inc., California, USA.

By "ErbB ligand" is meant a polypeptide which binds to and/or activates an ErbB receptor. The ErbB ligand may be a native sequence human ErbB ligand such as epidermal growth factor (EGF) (Savage et al (1972) J. Biol. Chem., 247:7612-7621); transforming growth factor alpha (TGF-α) (Marquardt et al (1984) Science 223:1079-1082); amphiregulin also known as schwanoma or keratinocyte autocrine growth factor (Shoyab et al (1989) Science 243:1074-1076; Kimura et al (1990) Nature 348:257-260; and Cook et al (1991) Mol. Cell. Biol., 11:2547-2557); betacellulin (Shing et al (1993) Science 259:1604-1607; and Sasada et al (1993) Biochem. Biophys. Res. Commun. 190:1173); heparin-binding epidermal growth factor (HB-EGF) (Higashiyama et al (1991) Science 251:936-939); epiregulin (Toyoda et al (1995) J. Biol. Chem. 270:7495-7500; and Komurasaki et al (1997) Oncogene 15:2841-2848); a heregulin (see below); neuregulin-2 (NRG-2) (Carraway et al., Nature, 387:512-516 (1997)); neuregulin-3 (NRG-3) (Zhang et al (1997) Proc. Natl. Acad. Sci., 94:9562-9567); neuregulin-4 (NRG-4) (Harari et al (1999) Oncogene, 18:2681-89) or cripto (CR-1) (Kannan et al (1997) J. Biol. Chem., 272(6):3330-3335). ErbB ligands which bind EGFR include EGF, TGF-α, amphiregulin, betacellulin, HB-EGF and epiregulin. ErbB ligands which bind ErbB3 include heregulins. ErbB ligands capable of binding ErbB4 include betacellulin, epiregulin, HB-EGF, NRG-2, NRG-3, NRG-4 and heregulins. The ErbB ligand may also be a synthetic ErbB ligand. The synthetic ligand may be specific for a particular ErbB receptor, or may recognize particular ErbB receptor complexes. An example of a synthetic ligand is the synthetic heregulin/EGF chimera biregulin (see, for example, Jones et al (1999) FEBS Letters, 447:227-231, which is incorporated by reference).

"Heregulin" (HRG) refers to a polypeptide encoded by the heregulin gene product as disclosed in U.S. Pat. No. 5,641,869 or Marchionni et al (1993) Nature 362:312-318. Examples of heregulins include heregulin-α, heregulin-β1, heregulin-β2 and heregulin-β3 (Holmes et al (1992) Science 256:1205-1210; and U.S. Pat. No. 5,641,869); neu differentiation factor (NDF) (Peles et al (1992) Cell 69: 205-216); acetylcholine receptor-inducing activity (ARIA) (Falls et al (1993) Cell 72:801-815); glial growth factors (GGFs) (Marchionni et al (1993) Nature, 362:312-318); sensory and motor neuron derived factor (SMDF) (Ho et al (1995) J. Biol. Chem. 270:14523-14532); γ-heregulin (Schaefer et al (1997) Oncogene, 15:1385-1394). The term includes biologically active fragments and/or amino acid sequence variants of a native sequence HRG polypeptide, such as an EGF-like domain fragment thereof (e.g., HRGβ1177-244).

"ErbB hetero-oligomer" is a noncovalently associated oligomer comprising at least two different ErbB receptors. An "ErbB dimer" is a noncovalently associated oligomer that comprises two different ErbB receptors. Such complexes may form when a cell expressing two or more ErbB receptors is exposed to an ErbB ligand. ErbB oligomers, such as ErbB dimers, can be isolated by immunoprecipitation and analyzed by SDS-PAGE as described in Sliwkowski et al (1994) J. Biol. Chem., 269(20):14661-14665, for example. Examples of such ErbB hetero-oligomers include EGFR-ErbB2 (also referred to as HER1/HER2), ErbB2-ErbB3 (HER2/HER3)

and ErbB3-ErbB4 (HER3/HER4) complexes. Moreover, the ErbB hetero-oligomer may comprise two or more ErbB2 receptors combined with a different ErbB receptor, such as ErbB3, ErbB4 or EGFR (ErbB1). Other proteins, such as a cytokine receptor subunit (e.g., gp130) may be included in the hetero-oligomer.

By "ligand activation of an ErbB receptor" is meant signal transduction (e.g., that caused by an intracellular kinase domain of an ErbB receptor phosphorylating tyrosine residues in the ErbB receptor or a substrate polypeptide) mediated by ErbB ligand binding to a ErbB hetero-oligomer comprising the ErbB receptor of interest. Generally, this will involve binding of an ErbB ligand to an ErbB hetero-oligomer which activates a kinase domain of one or more of the ErbB receptors in the hetero-oligomer and thereby results in phosphorylation of tyrosine residues in one or more of the ErbB receptors and/or phosphorylation of tyrosine residues in additional substrate polypeptides(s). ErbB receptor activation can be quantified using various tyrosine phosphorylation assays.

A "native sequence" polypeptide is one which has the same amino acid sequence as a polypeptide (e.g., ErbB receptor or ErbB ligand) derived from nature. Such native sequence polypeptides can be isolated from nature or can be produced by recombinant or synthetic means. Thus, a native sequence polypeptide can have the amino acid sequence of naturally occurring human polypeptide, murine polypeptide, or polypeptide from any other mammalian species.

The term "amino acid sequence variant" refers to polypeptides having amino acid sequences that differ to some extent from a native sequence polypeptide. Ordinarily, amino acid sequence variants will possess at least about 70% sequence identity with at least one receptor binding domain of a native ErbB ligand or with at least one ligand binding domain of a native ErbB receptor, or at least about 80%, or at least about 90% homologous with such receptor or ligand binding domains. The amino acid sequence variants possess substitutions, deletions, and/or insertions at certain positions within the amino acid sequence of the native amino acid sequence.

"Sequence identity" is defined as the percentage of residues in the amino acid sequence variant that are identical after aligning the sequences and introducing gaps, if necessary, to achieve the maximum percent sequence identity. Methods and computer programs for the alignment are well known in the art. One such computer program is "Align 2," authored by Genentech, Inc., which was filed with user documentation in the United States Copyright Office, Washington, D.C. 20559, on Dec. 10, 1991.

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, (1991) Annu. Rev. Immunol, 9:457-92. To assess ADCC activity of a molecule of interest, an in vitro ADCC assay may be performed (U.S. Pat. No. 55,003,621; U.S. Pat. No. 5,821,337). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al (1998) PNAS (USA), 95:652-656.

"Maytansinoid drug moiety" means the substructure of an antibody-drug conjugate that has the structure of a maytansine compound. Maytansine was first isolated from the east African shrub *Maytenus serrata* (U.S. Pat. No. 3,896, 111). Subsequently, it was discovered that certain microbes also produce maytansinoids, such as maytansinol and C-3 maytansinol esters (U.S. Pat. No. 4,151,042). Synthetic maytansinol and maytansinol analogues have been reported. See U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, and Kawai et al (1984) Chem. Pharm. Bull. 3441-3451), each of which are expressly incorporated by reference.

The terms "Fc receptor" or "FcR" are used to describe a receptor that binds to the Fc region of an antibody, such as a native sequence human FcR. FcR may bind an IgG antibody (a gamma receptor) and includes receptors of the FcγRI, FcγRII, and Fcγ RIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (See review M. in Daëron, Annu. Rev. Immunol., 15:203-234 (1997)). FcRs are reviewed in Ravetch and Kinet, Annu. Rev. Immunol., 9:457-92 (1991); Capel et al (1994) Immunomethods, 4:25-34; and de Haas et al (1995) J. Lab. Clin. Med., 126:330-41. Other FcRs, including those to be identified in the future, are encompassed by the term "FcR" herein. The term also includes the neonatal receptor, FcRn, which is responsible for the transfer of maternal IgGs to the fetus (Guyer et al (1976) J. Immunol. 117:587, and Kim et al (1994) J. Immunol., 24:249).

"Complement dependent cytotoxicity" or "CDC" refers to the ability of a molecule to lyse a target in the presence of complement. The complement activation pathway is initiated by the binding of the first component of the complement system (Clq) to a molecule (e.g., an antibody) complexed with a cognate antigen. To assess complement activation, a CDC assay, e.g., as described in Gazzano-Santoro et al (1996) J. Immunol. Methods, 202:163, may be performed.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al (1991) Sequences of Proteins of Immunological Interest, 5th Ed. Public Health Service, National Institutes of Health, Bethesda, Md.). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g., residues 24-34 (L1), 50-56 (L2) and 89-97 (L3) in the light chain variable domain and 31-35 (H1), 50-65 (H2) and 95-102 (H3) in the heavy chain variable domain; Kabat et al supra) and/or those residues from a "hypervariable loop" (e.g., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk (1987) J. Mol. Biol., 196:901-917). "Framework Region" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (κ) and lambda (λ), based on the amino acid sequences of their constant domains.

"Single-chain Fv" or "scFv" mean single chain variable region antibody fragments which comprise the VH and VL domains of antibody, wherein these domains are present in a single polypeptide chain. The Fv polypeptide may further comprise a polypeptide linker between the VH and VL domains which enables the scFv to form the desired structure for antigen binding (Plückthun in *The Pharmacology of Monoclonal Antibodies*, vol. 113, Rosenburg and Moore eds., Springer-Verlag, New York, pp. 269-315 (1994). Anti-ErbB2 antibody scFv fragments are described in WO 93/16185; U.S. Pat. No. 5,571,894; U.S. Pat. No. 5,587,458.

The term "diabodies" refers to small antibody fragments with two antigen-binding sites, which fragments comprise a variable heavy domain (VH) connected to a variable light domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al (1993) Proc. Natl. Acad. Sci. USA 90:6444-6448.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al (1986) Nature, 321:522-525; Riechmann et al (1988) Nature 332:323-329; and Presta, (1992) Curr. Op. Struct. Biol., 2:593-596.

Humanized anti-ErbB2 antibodies include huMAb4D5-1, huMAb4D5-2, huMAb4D5-3, huMAb4D5-4, huMAb4D5-5, huMAb4D5-6, huMAb4D5-7 and huMAb4D5-8 (HERCEPTIN®, trastuzumab) as described in Table 3 of U.S. Pat. No. 5,821,337 expressly incorporated herein by reference; humanized 520C9 (WO 93/21319) and humanized 2C4 antibodies.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. The antibody may be purified (1) to greater than 95% by weight of antibody as determined by the Lowry method, or more than 99% by weight, (2) to a degree sufficient to obtain at least 15 residues of N-terminal or internal amino acid sequence by use of a spinning cup protein sequencer, or (3) to homogeneity by SDS-PAGE under reducing or nonreducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

An antibody "which binds" an antigen of interest, e.g., ErbB2 antigen, is one capable of binding that antigen with sufficient affinity such that the antibody is useful in targeting a cell expressing the antigen. Where the antibody is one which binds ErbB2, it will usually preferentially bind ErbB2 as opposed to other ErbB receptors, and may be one which does not significantly cross-react with other proteins such as EGFR, ErbB3 or ErbB4. In such embodiments, the extent of binding of the antibody to these non-ErbB2 proteins (e.g., cell surface binding to endogenous receptor) will be less than 10% as determined by fluorescence activated cell sorting (FACS) analysis or radioimmunoprecipitation (RIA). Sometimes, the anti-ErbB2 antibody will not significantly cross-react with the rat neu protein, e.g., as described in Schecter et al (1984) Nature 312:513, and Drebin et al (1984) Nature, 312:545-548.

An antibody which "blocks" ligand activation of an ErbB receptor reduces or prevents such activation, wherein the antibody is able to block ligand activation of the ErbB receptor substantially more effectively than monoclonal antibody 4D5, e.g., about as effectively as monoclonal antibodies 7F3 or 2C4 or Fab fragments thereof. For example, the antibody that blocks ligand activation of an ErbB receptor may be one which is about 50-100% more effective than 4D5 at blocking formation of an ErbB hetero-oligomer. Blocking of ligand activation of an ErbB receptor can occur by any means, e.g., by interfering with: ligand binding to an ErbB receptor, ErbB complex formation, tyrosine kinase activity of an ErbB receptor in an ErbB complex and/or phosphorylation of tyrosine kinase residue(s) in or by an ErbB receptor.

An antibody having a "biological characteristic" of a designated antibody, such as the monoclonal antibody designated 2C4 (Omnitarg, Genentech, Inc.), is one which possesses one or more of the biological characteristics of that antibody which distinguish it from other antibodies that bind to the same antigen (e.g., ErbB2). For example, an antibody with a biological characteristic of 2C4 may block HRG activation of an ErbB hetero-oligomer comprising ErbB2 and ErbB3, ErbB1 or ErbB4; block EGF, TGF-α, HB-EGF, epiregulin and/or amphiregulin activation of an ErbB receptor comprising EGFR and ErbB2; block EGF, TGF-α and/or HRG mediated activation of MAPK; and/or bind the same epitope in the extracellular domain of ErbB2 as that bound by 2C4 (e.g., which blocks binding of monoclonal antibody 2C4 to ErbB2).

Unless indicated otherwise, the expression "monoclonal antibody 2C4" refers to an antibody that has antigen binding residues of, or derived from, the murine 2C4 antibody of the Examples below. For example, the monoclonal antibody 2C4 may be murine monoclonal antibody 2C4 or a variant thereof, such as humanized antibody 2C4, possessing antigen binding amino acid residues of murine monoclonal antibody 2C4 (WO 01/00245). Unless indicated otherwise, the expression "rhuMAb 2C4" when used herein refers to an antibody comprising the variable light (VL) and variable heavy (VH) sequences of SEQ ID Nos. 3 and 4, respectively, fused to human light and heavy IgG1 (non-A allotype) constant region sequences optionally expressed by a Chinese Hamster Ovary (CHO) cell (WO 01/00245).

Unless indicated otherwise, the term "monoclonal antibody 4D5" refers to an antibody that has antigen binding residues of, or derived from, the murine 4D5 antibody (ATCC CRL 10463), deposited with American Type Culture Collection, 12301 Parklawn Drive, Rockville, Md. 20852 under the Budapest Treaty on May 24, 1990). For example, the monoclonal antibody 4D5 may be murine monoclonal antibody 4D5 or a variant thereof, such as a humanized 4D5, possessing antigen binding residues of murine monoclonal antibody 4D5. Exemplary humanized 4D5 antibodies include huMAb4D5-1, huMAb4D5-2, huMAb4D5-3, huMAb4D5-4, huMAb4D5-5, huMAb4D5-6, huMAb4D5-7 and huMAb4D5-8 (HERCEPTIN®) as in U.S. Pat. No. 5,821,337.

A "growth inhibitory agent" refers to a compound or composition which inhibits growth of a cell, e.g. an ErbB expressing cancer cell either in vitro or in vivo. Thus, the growth inhibitory agent may be one which significantly reduces the percentage of ErbB expressing cells in S phase. Examples of growth inhibitory agents include agents that block cell cycle progression (at a place other than S phase), such as agents that induce G1 arrest and M-phase arrest (The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13). Examples of "growth inhibitory" antibodies are those which bind to ErbB2 and inhibit the growth of cancer cells overexpressing ErbB2. Growth inhibitory anti-ErbB2 antibodies may inhibit growth of SK-BR-3 breast tumor cells in cell culture by greater than 20%, or greater than 50% (e.g., from about 50% to about 100%) at an antibody concentration of about 0.5 to 30 µg/ml, where the growth inhibition is determined six days after exposure of the SK-BR-3 cells to the antibody (U.S. Pat. No. 5,677,171).

An antibody which "induces cell death" is one which causes a viable cell to become nonviable. The cell is generally one which expresses the ErbB2 receptor, especially where the cell overexpresses the ErbB2 receptor. The cell may be a cancer cell, e.g., a breast, ovarian, stomach, endometrial, salivary gland, lung, kidney, colon, thyroid, pancreatic or bladder cell. In vitro, the cell may be a SK-BR-3, BT474, Calu 3, MDA-MB-453, MDA-MB-361 or SKOV3 cell. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the antibody is able to induce cell death, loss of membrane integrity as evaluated by uptake of propidium iodide (PI), trypan blue (see Moore et al (1995) Cytotechnology, 17:1-11) or 7AAD can be assessed relative to untreated cells. Cell death-inducing antibodies are those which induce PI uptake in the PI uptake assay in BT474 cells (see below).

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses the ErbB2 receptor, including a tumor cell, e.g., a breast, ovarian, stomach, endometrial, salivary gland, lung, kidney, colon, thyroid, pancreatic or bladder cell. In vitro, the cell may be a SK-BR-3, BT474, Calu 3 cell, MDA-MB-453, MDA-MB-361 or SKOV3 cell.

The terms "treat" or "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

A "disorder" is any condition that would benefit from treatment of the present invention. This includes chronic and acute disorders or diseases including those pathological conditions which predispose the mammal to the disorder in question. Non-limiting examples of disorders to be treated herein include benign and malignant tumors; leukemia and lymphoid malignancies, in particular breast, ovarian, stomach, endometrial, salivary gland, lung, kidney, colon, thyroid, pancreatic, prostate or bladder cancer; neuronal, glial, astrocytal, hypothalamic and other glandular, macrophagal, epithelial, stromal and blastocoelic disorders; and inflammatory, angiogenic and immunologic disorders. An exemplary disorder to be treated in accordance with the present invention is a solid, malignant tumor The term "therapeutically effective amount" refers to an amount of a drug effective to treat a disease or disorder in a mammal. In the case of cancer, the therapeutically effective amount of the drug may: (i) reduce the number of cancer cells; (ii) reduce the tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; and/or (vi) relieve to some extent one or more of the symptoms associated with the cancer. To the extent the drug may prevent growth and/or kill existing cancer cells, it may be cytostatic and/or cytotoxic. In animal models, efficacy may be assessed by physical measurements of the tumor during the course following administration of the ADC, and by determining partial and complete remission of tumor. For cancer therapy, efficacy can, for example, be measured by assessing the time to disease progression (TTP) and/or determining the response rate (RR).

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, gastrointestinal stromal tumor (GIST), pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

An "ErbB-expressing cancer" is one comprising cells which have ErbB protein present at their cell surface. An "ErbB2-expressing cancer" is one which produces sufficient levels of ErbB2 at the surface of cells thereof, such that an anti-ErbB2 antibody can bind thereto and have a therapeutic effect with respect to the cancer.

A cancer which "overexpresses" a receptor, e.g. an ErbB receptor, is one which has significantly higher levels of the receptor, such as ErbB2, at the cell surface thereof, compared to a noncancerous cell of the same tissue type. Such overexpression may be caused by gene amplification or by increased transcription or translation. ErbB receptor overexpression may be determined in a diagnostic or prognostic assay by evaluating increased levels of the ErbB protein present on the surface of a cell (e.g., via an immunohistochemistry assay; IHC). Alternatively, or additionally, one may measure levels of ErbB-encoding nucleic acid in the cell, e.g., via fluorescent in situ hybridization (FISH; see WO 98/45479), southern blotting, or polymerase chain reaction (PCR) techniques, such as real time quantitative PCR(RT-PCR). Overexpression of the ErbB ligand, may be determined diagnostically by evaluating levels of the ligand (or nucleic acid encoding it) in the patient, e.g., in a tumor biopsy or by various diagnostic assays such as the IHC, FISH, southern blotting, PCR or in vivo assays described above. One may also study ErbB receptor overexpression by measuring shed antigen (e.g., ErbB extracellular domain) in a biological fluid such as serum (see, e.g., U.S. Pat. No. 4,933,294; WO 91/05264; U.S. Pat. No. 5,401,638; and Sias et al (1990) J. Immunol. Methods 132: 73-80). Aside from the above assays, various other in vivo assays are available to the skilled practitioner. For example, one may expose cells within the body of the patient to an antibody which is optionally labeled with a detectable label, e.g., a radioactive isotope, and binding of the antibody to cells in the patient can be evaluated, e.g., by external scanning for radioactivity or by analyzing a biopsy taken from a patient previously exposed to the antibody.

The tumors overexpressing HER2 are rated by immunohistochemical scores corresponding to the number of copies of HER2 molecules expressed per cell, and can be determined biochemically: 0=0-10,000 copies/cell, 1+=at least about 200,000 copies/cell, 2+=at least about 500,000 copies/cell, 3+=about $1-2\times10^6$ copies/cell. Overexpression of HER2 at the 3+ level, which leads to ligand-independent activation of the tyrosine kinase (Hudziak et al., (1987) Proc. Natl. Acad. Sci. USA 84:7159-7163), occurs in approximately 30% of breast cancers, and in these patients, relapse-free survival and overall survival are diminished (Slamon et al (1989) Science 244:707-712; Slamon et al (1987) Science, 235:177-182). Conversely, a cancer which is "not characterized by overexpression of the ErbB2 receptor" is one which, in a diagnostic assay, does not express higher than normal levels of ErbB2 receptor compared to a noncancerous cell of the same tissue type. The murine monoclonal anti-HER2 antibody inhibits the growth of breast cancer cell lines that overexpress HER2 at the 2+ and 3+($1-2\times10^6$ HER2 receptors per cell) level, but has no activity on cells that express lower levels of HER2 (Lewis et al (1993) Cancer Immunol. Immunother. 37:255-263). Based on this observation, antibody 4D5 was humanized (huMAb4D5-8, rhuMAb HER2, U.S. Pat. No. 5,821, 337; Carter et al (1992) Proc. Natl. Acad. Sci. USA 89: 4285-4289) and tested in breast cancer patients whose tumors overexpress HER2 but who had progressed after conventional chemotherapy (Cobleigh et al (1999) J. Clin. Oncol. 17: 2639-2648). Most patient tumors in this trial expressed HER2 at the 3+ level, though a fraction was 2+.

A "hormone independent" cancer is one in which proliferation thereof is not dependent on the presence of a hormone which binds to a receptor expressed by cells in the cancer. Such cancers do not undergo clinical regression upon administration of pharmacological or surgical strategies that reduce the hormone concentration in or near the tumor. Examples of hormone independent cancers include androgen independent prostate cancer, estrogen independent breast cancer, endometrial cancer and ovarian cancer. Such cancers may begin as hormone dependent tumors and progress from a hormone-sensitive stage to a hormone-refractory tumor following anti-hormonal therapy.

The term "cytotoxic agent" as used herein refers to a substance that inhibits or prevents the function of cells and/or causes destruction of cells. The term is intended to include radioactive isotopes (e.g., $^{211}$At, $^{131}$I, $^{125}$I, $^{90}$Y, $^{186}$Re, $^{188}$Re, $^{153}$Sm, $^{212}$Bi, $^{32}$P, $^{60}$C, and radioactive isotopes of Lu), chemotherapeutic agents, and toxins such as small molecule toxins or enzymatically active toxins of bacterial, fungal, plant or animal origin, including synthetic analogs and derivatives thereof.

A "chemotherapeutic agent" is a chemical compound useful in the treatment of cancer. Examples of chemotherapeutic agents include erlotinib (TARCEVA®, Genentech/OSI Pharm.), bortezomib (VELCADE®, Millenium Pharm.), fulvestrant (FASLODEX®, Astrazeneca), sunitinib (SUTENT®, SU11248, Pfizer), letrozole (FEMARA®, Novartis), imatinib mesylate (GLEEVEC®, Novartis), PTK787/ZK 222584 (Novartis), oxaliplatin (ELOXATIN®, Sanofi), 5-FU (5-fluorouracil), leucovorin, rapamycin (Sirolimus, RAPAMUNE®, Wyeth), lapatinib (TYKERB®, GSK572016, GlaxoSmithKline), lonafarnib (SARASAR®, SCH 66336), sorafenib (NEXAVAR®, BAY43-9006, Bayer Labs.), and gefitinib (IRESSA®, Astrazeneca), AG1478, AG1571 (SU 5271; Sugen), alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e.g., calicheamicin, especially calicheamicin gamma1I and calicheamicin omega1I (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine (XELODA®, Roche); and pharmaceutically acceptable salts, acids or derivatives of any of the above.

Also included in this definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON. toremifene; (ii) aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; (iii) anti-androgens such as flutamide, nilutamide, bicalutamide, leuprolide, and goserelin; as well as troxacitabine (a 1,3-dioxolane nucleoside cytosine analog); (iv) aromatase inhibitors; (v) protein kinase inhibitors; (vi) lipid kinase inhibitors; (vii) antisense oligonucleotides, particularly those which inhibit expression of genes in signaling pathways implicated in abherant cell proliferation, such as, for example, PKC-alpha, Ralf and H-Ras; (viii) ribozymes such as a VEGF expression inhibitor (e.g., ANGIOZYME® ribozyme) and a HER2 expression inhibitor; (ix) vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; (x) anti-angiogenic agents such as bevacizumab (AVASTIN®, Genentech); and (xi) pharmaceutically acceptable salts, acids or derivatives of any of the above.

Protein kinase inhibitors include tyrosine kinase inhibitors which inhibit to some extent tyrosine kinase activity of a tyrosine kinase such as an ErbB receptor. Examples of tyrosine kinase inhibitors include EGFR-targeted drugs such as: (i) antibodies which bind to EGFR, including MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBITUX®, Imclone) and reshaped human 225 (H225) (WO 96/40210, Imclone Systems Inc.); antibodies that bind type II mutant EGFR (U.S. Pat. No. 5,212,290); humanized and chimeric antibodies that bind EGFR (U.S. Pat. No. 5,891,996); and human antibodies that bind EGFR, such as ABX-EGF (WO 98/50433); (ii) anti-EGFR antibody conjugated with a cyotoxic agent (EP 659439A2); and small molecules that bind to EGFR including ZD1839 or Gefitinib (IRESSA™; Astra Zeneca), Erlotinib HCl (CP-358774, TARCEVA™; Genentech/OSI) and AG1478, AG1571 (SU 5271; Sugen), quinazolines such as PD 153035,4-(3-chloroanilino) quinazoline, pyridopyrimidines, pyrimidopyrimidines, pyrrolopyrimidines, such as CGP 59326, CGP 60261 and CGP 62706, and pyrazolopyrimidines, 4-(phenylamino)-7H-pyrrolo[2,3-d]pyrimidines, curcumin (diferuloyl methane, 4,5-bis(4-fluoroanilino)phthalimide), tyrphostines containing nitrothiophene moieties; PD-0183805 (Warner-Lambert); antisense molecules (e.g., those that bind to ErbB-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-ErbB inhibitors such as CI-1033 (Pfizer); Affinitac (ISIS 3521; Isis/Lilly); Imatinib mesylate (Gleevac; Novartis); PKI 166 (Novartis); GW2016 (Glaxo SmithKline); CI-1033 (Pfizer); EKB-569 (Wyeth); Semaxanib (Sugen); ZD6474 (AstraZeneca); PTK-787 (Novartis/Schering AG); INC-1C11 (Imclone); or as described in: U.S. Pat. No. 5,804,396; WO 99/09016 (American Cyanamid); WO 98/43960 (American Cyanamid); WO 97/38983 (Warner Lambert); WO 99/06378 (Warner Lambert); WO 99/06396 (Warner Lambert); WO 96/30347 (Pfizer, Inc); WO 96/33978 (Zeneca); WO 96/3397 (Zeneca); and WO 96/33980 (Zeneca).

An "anti-angiogenic agent" refers to a compound which blocks, or interferes with to some degree, the development of blood vessels. The anti-angiogenic factor may, for instance, be a small molecule or antibody that binds to a growth factor or growth factor receptor involved in promoting angiogenesis. An exemplary anti-angiogenic agent is an antibody that binds to Vascular Endothelial Growth Factor (VEGF) such as bevacizumab (AVASTIN®, Genentech).

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified pro drugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

A "liposome" is a small vesicle composed of various types of lipids, phospholipids and/or surfactant which is useful for delivery of a drug (such as the anti-ErbB2 antibodies disclosed herein and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

A "cardioprotectant" is a compound or composition which prevents or reduces myocardial dysfunction (i.e., cardiomyopathy and/or congestive heart failure) associated with administration of a drug, such as an anthracycline antibiotic and/or an anti-ErbB2 antibody, to a patient. The cardioprotectant may, for example, block or reduce a free-radical-mediated cardiotoxic effect and/or prevent or reduce oxidative-stress injury. Examples of cardioprotectants encompassed by the present definition include the iron-chelating agent dexrazoxane (ICRF-187) (Seifert et al., *The Annals of Pharmacotherapy*, 28:1063-1072 (1994)); a lipid-lowering agent and/or anti-oxidant such as probucol (Singal et al., *J. Mol. Cell. Cardiol.*, 27:1055-1063 (1995)); amifostine (aminothiol 2-[(3-aminopropyl)amino]ethanethiol-dihydrogen phosphate ester, also called WR-2721, and the dephosphorylated cellular uptake form thereof called WR-1065) and S-3-(3-methylaminopropylamino)propylphosphorothioic acid (WR-151327), see Green et al., (1994) Cancer Research, 54:738-741; digoxin (Bristow, M. R. ed. (1980) *Drug-Induced Heart Disease*. New York: Elsevier 191-215); beta-blockers such as metoprolol (Hjalmarson et al (1994) Drugs 47:Suppl 4:31-9; and Shaddy et al (1995) Am. Heart J., 129:197-9); vitamin E; ascorbic acid (vitamin C); free radical scavengers such as oleanolic acid, ursolic acid and N-acetylcysteine (NAC); spin trapping compounds such as alpha-phenyl-tert-butyl nitrone (PBN); (Paracchini et al (1993) Anticancer Res., 13:1607-1612); selenoorganic compounds such as P251 (Elbesen); and the like.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

"Alkyl" is $C_1$-$C_{18}$ hydrocarbon containing normal, secondary, tertiary or cyclic carbon atoms. Examples of alkyl radicals include $C_1$-$C_8$ hydrocarbon moieties such as, but not limited to: methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (1-Bu, i-butyl, —$CH_2CH(CH_3)_2$), 2-butyl (s-Bu, s-butyl, —$CH(CH_3)CH_2CH_3$), 2-methyl-2-propyl (1-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$)

"Alkenyl" is $C_2$-$C_{18}$ hydrocarbon containing normal, secondary, tertiary or cyclic carbon atoms with at least one site of unsaturation, i.e. a carbon-carbon, $sp^2$ double bond. Examples of alkenyl radicals include $C_2$-$C_8$ hydrocarbon moieties such as, but not limited to: ethylene or vinyl (—CH=$CH_2$), allyl (—$CH_2$CH=$CH_2$), cyclopentenyl (—$C_5H_7$), and 5-hexenyl (—$CH_2$ $CH_2CH_2CH_2$CH=$CH_2$)

"Alkynyl" is $C_2$-$C_{18}$ hydrocarbon containing normal, secondary, tertiary or cyclic carbon atoms with at least one site of unsaturation, i.e. a carbon-carbon, sp triple bond. Examples of alkynyl radicals include $C_2$-$C_8$ hydrocarbon moieties such as, but not limited to: acetylenic (—C≡CH) and propargyl (—$CH_2$C≡CH), "Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include $C_1$-$C_8$ hydrocarbon moieties such as, but are not limited to: methylene (—$CH_2$—) 1,2-ethyl (—$CH_2CH_2$—), 1,3-propyl (—$CH_2CH_2CH_2$—), 1,4-butyl (—$CH_2CH_2CH_2CH_2$—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include $C_2$-$C_8$ hydrocarbon moieties such as, but are not limited to: 1,2-ethylene (—CH=CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include $C_2$-$C_8$ hydrocarbon moieties such as, but are not limited to: acetylene (—C≡C—), propargyl (—$CH_2$C≡C—), and 4-pentynyl (—$CH_2CH_2CH_2$C≡C—).

"Aryl", alone or in combination, means a monovalent aromatic hydrocarbon radical of 6-20 carbon atoms derived by the removal of one hydrogen atom from a single carbon atom of a parent aromatic ring system. Aryl radical may contain one, two or three rings wherein such rings may be attached together in a pendent manner, e.g. biphenyl, or may be fused, e.g. napthalene or anthracene. Some aryl groups are represented in the exemplary structures as "Ar". Typical aryl groups include $C_6$-$C_{12}$ hydrocarbon moieties such as, but are not limited to, radicals derived from benzene, substituted benzene, naphthalene, anthracene, biphenyl, and the like.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms.

"Heteroarylalkyl" refers to an acyclic alkyl radical in which one of the hydrogen atoms bonded to a carbon atom, typically a terminal or $sp^3$ carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g. the alkyl moiety, including alkanyl, alkenyl or alkynyl groups, of the heteroarylalkyl group is 1 to 6 carbon atoms and the heteroaryl moiety is 5 to 14 carbon atoms and 1 to 3 heteroatoms selected from N, O, P, and S. The heteroaryl moiety of the heteroarylalkyl group may be a monocycle having 3 to 7 ring members (2 to 6 carbon atoms or a bicycle having 7 to 10 ring members (4 to 9 carbon atoms and 1 to 3 heteroatoms selected from N, O, P, and S), for example: a bicyclo[4,5], [5,5], [5,6], or [6,6] system.

Alkyl, alkylene, aryl, arylalkyl, and heteroarylalkyl groups may be substituted where one or more hydrogen atoms are each independently replaced with a substituent. Typical substituents include, but are not limited to, —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, —NC(=O)R, —C(=O)R, —C(=O)NR$_2$, —SO$_3^-$, —SO$_3$H, —S(=O)$_2$R, —OS(=O)$_2$OR, —S(=O)$_2$NR, —S(=O)R, —OP(=O)(OR)$_2$, —P(=O)(OR)$_2$, —PO$^-_3$, —PO$_3$H$_2$, —C(=O)R, —C(=O)X, —C(=S)R, —CO$_2$R, —CO$_2^-$, —C(=S)OR, —C(=O)SR, —C(=S)SR, —C(=O)NR$_2$, —C(=S)NR$_2$, —C(=NR)NR$_2$, where each X is independently a halogen: F, Cl, Br, or I; and each R is independently H, $C_1$-$C_{18}$ is alkyl, $C_6$-$C_{20}$ aryl, $C_3$-$C_{14}$ heterocycle, protecting group or prodrug moiety. Alkylene, alkenylene, and alkynylene groups as described above may also be similarly substituted.

"Heteroaryl", also known as heterocycle or heterocyclyl, refers to a ring system radical in which one or more ring atoms is a heteroatom, e.g. nitrogen, oxygen, and sulfur. The heteroaryl radical comprises 5 to 14 carbon atoms and 1 to 3 heteroatoms selected from N, O, P, and S. A heteroaryl may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo[4,5], [5,5], [5,6], or [6,6] system. Heteroaryl compounds are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566.

"Linker" or "link" means a chemical moiety comprising a covalent bond or a chain of atoms that covalently attaches an antibody to a drug moiety. In various embodiments, a linker is specified as L. Linkers include a divalent radical such as an alkylene, an arylene, a heteroarylene, moieties such as: —$(CR_2)_nO(CR_2)_n$—, repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The phrase "pharmaceutically acceptable salt," as used herein, refers to pharmaceutically acceptable organic or inorganic salts of an ADC. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

"Pharmaceutically acceptable solvate" refers to an association of one or more solvent molecules and an ADC. Examples of solvents that form pharmaceutically acceptable solvates include, but are not limited to, water, isopropanol, ethanol, methanol, DMSO, ethyl acetate, acetic acid, and ethanolamine.

Antibody-Drug Conjugates

The compounds of the invention include those with utility for anticancer activity. In particular, the compounds include an antibody conjugated, i.e. covalently attached by a linker, to a drug moiety where the drug when not conjugated to an antibody has a cytotoxic or cytostatic effect. The biological activity of the drug moiety is thus modulated by conjugation to an antibody. The antibody-drug conjugates (ADC) of the invention may selectively deliver an effective dose of a cytotoxic agent to tumor tissue whereby greater selectivity, i.e. a lower efficacious dose may be achieved.

In one embodiment, the bioavailability of the ADC, or an intracellular metabolite of the ADC, is improved in a mammal when compared to the corresponding maytansinoid compound alone. Also, the bioavailability of the ADC, or an intracellular metabolite of the ADC is improved in a mammal when compared to the corresponding antibody alone (antibody of the ADC, without the drug moiety or linker).

In one embodiment, the maytansinoid drug moiety of the ADC is not cleaved from the antibody until the antibody-drug conjugate binds to a cell-surface receptor or enters a cell with a cell-surface receptor specific for the antibody of the antibody-drug conjugate. The drug moiety may be cleaved from the antibody after the antibody-drug conjugate enters the cell. The maytansinoid drug moiety may be intracellularly cleaved in a mammal from the antibody of the compound, or an intracellular metabolite of the compound, by enzymatic action, hydrolysis, oxidation, or other mechanism. For example, and in no way meant to limit the invention to a particular mechanism of action, the sulfur atom of the maytansinoid drug moiety of the ADC may be oxidized to a sulfone or sulfoxide group. Protons on carbons bound to the sulfone and sulfoxide may be removed under general or enzymatic catalysis inside the cell and result in a beta-elimination fragmentation that cleaves and separates the drug moiety from the antibody of the ADC. Alternatively, other electron withdrawing groups such as amides in the linker, antibody or drug moiety may effect similar fragmentation/cleavage mechanisms inside a cell.

Antibody-drug conjugates (ADC) may be represented by Formula I:

Ab-(L-D)$_p$    I or a pharmaceutically acceptable salt or solvate thereof, wherein:

Ab is an antibody which binds to an ErbB receptor, or which binds to one or more tumor-associated antigens or cell-surface receptors selected from (1)-(36):

(1) BMPR1B (bone morphogenetic protein receptor-type IB, Genbank accession no. NM_001203);

(2) E16 (LAT1, SLC7A5, Genbank accession no. NM_003486);

(3) STEAP1 (six transmembrane epithelial antigen of prostate, Genbank accession no. NM_012449);

(4) 0772P(CA125, MUC16, Genbank accession no. AF361486);

(5) MPF (MPF, MSLN, SMR, megakaryocyte potentiating factor, mesothelin, Genbank accession no. NM_005823);

(6) Napi3b (NAPI-3B, NPTIIb, SLC34A2, solute carrier family 34 (sodium phosphate), member 2, type II sodium-dependent phosphate transporter 3b, Genbank accession no. NM_006424);

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878);

(8) PSCA hlg (2700050C12Rik, C530008016Rik, RIKEN cDNA 2700050C12, RIKEN cDNA 2700050C12 gene, Genbank accession no. AY358628);

(9) ETBR (Endothelin type B receptor, Genbank accession no. AY275463);

(10) MSG783 (RNF124, hypothetical protein FLJ20315, Genbank accession no. NM_017763);

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138);

(12) TrpM4 (BR22450, FLJ20041, TRPM4, TRPM4B, transient receptor potential cation channel, subfamily M, member 4, Genbank accession no. NM_017636);

(13) CRIPTO (CR, CR1, CRGF, CRIPTO, TDGF1, teratocarcinoma-derived growth factor, Genbank accession no. NP_003203 or NM_003212);

(14) CD21 (CR2 (Complement receptor 2) or C3DR(C3d/Epstein Barr virus receptor) or Hs.73792 Genbank accession no. M26004);

(15) CD79b (CD79B, CD79β, IGb (immunoglobulin-associated beta), B29, Genbank accession no. NM_000626);

(16) FcRH2 (IFGP4, IRTA4, SPAP1A (SH2 domain containing phosphatase anchor protein 1a), SPAP1B, SPAP1C, Genbank accession no. NM_030764);

(17) HER2 (Genbank accession no. M1730);

(18) NCA (Genbank accession no. M18728);

(19) MDP (Genbank accession no. BC017023);

(20) IL20Rα (Genbank accession no. AF184971);

(21) Brevican (Genbank accession no. AF229053);

(22) EphB2R (Genbank accession no. NM_004442);

(23) ASLG659 (Genbank accession no. AX092328);

(24) PSCA (Genbank accession no. AJ297436);

(25) GEDA (Genbank accession no. AY260763;

(26) BAFF—R (B cell-activating factor receptor, BLyS receptor 3, BR3, NP_443177.1);

(27) CD22 (B-cell receptor CD22-B isoform, NP_001762.1);

(28) CD79a (CD79A, CD79α, immunoglobulin-associated alpha, a B cell-specific protein that covalently interacts with Ig beta (CD79B) and forms a complex on the surface with Ig M molecules, transduces a signal involved in B-cell differentiation, Genbank accession No. NP_001774.1);

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia, Genbank accession No. NP_001707.1);

(30) HLA-DOB (Beta subunit of MHC class II molecule (Ia antigen) that binds peptides and presents them to CD4+ T lymphocytes, Genbank accession No. NP_002111.1);

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability, Genbank accession No. NP_002552.2);

(32) CD72 (B-cell differentiation antigen CD72, Lyb-2, Genbank accession No. NP_001773.1);

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis, Genbank accession No. NP_005573.1);

(34) FcRH1 (Fc receptor-like protein 1, a putative receptor for the immunoglobulin Fc domain that contains C2 type Ig-like and ITAM domains, may have a role in B-lymphocyte differentiation, Genbank accession No. NP_443170.1);

(35) IRTA2 (Immunoglobulin superfamily receptor translocation associated 2, a putative immunoreceptor with possible roles in B cell development and lymphomagenesis; deregulation of the gene by translocation occurs in some B cell malignancies, Genbank accession No. NP_112571.1); and

(36) TENB2 (putative transmembrane proteoglycan, related to the EGF/heregulin family of growth factors and follistatin, Genbank accession No. AF 179274;

provided that the antibody is not TA. 1.

L is a non-disulfide linker. L includes but is not limited to the structures:

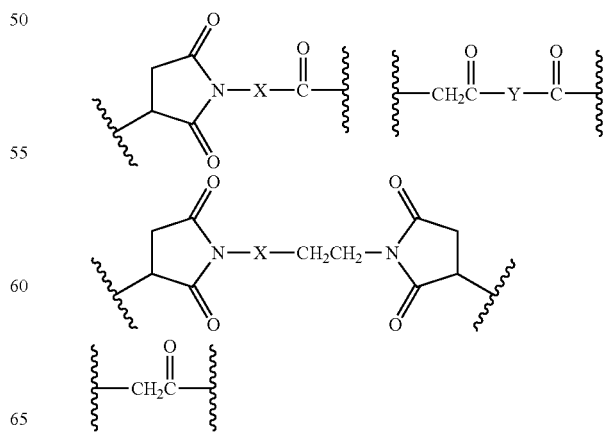

where the wavy lines indicate the covalent attachments to Ab and D;

X is:

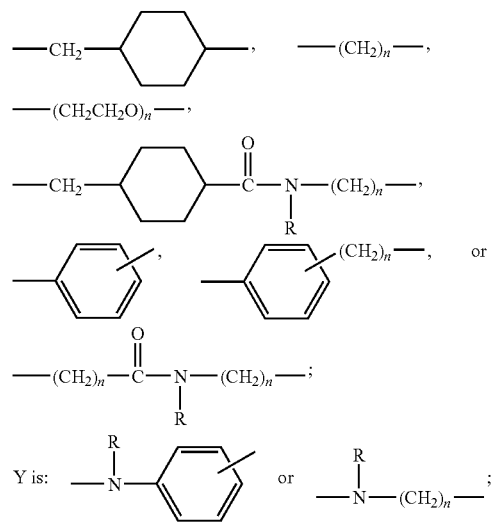

R is independently H or $C_1$-$C_6$ alkyl; and n is 1 to 12;

D is a maytansinoid drug moiety. Maytansinoids include, but are not limited to the structure:

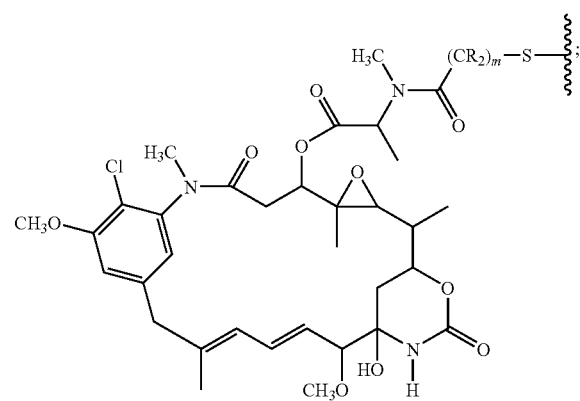

where the wavy line indicates the covalent attachment to L;

R is independently H or $C_1$-$C_6$ alkyl; and m is 1, 2, or 3.

The drug to antibody ratio or drug loading is represented by p for Formula I compounds. The drug loading value p is 1 to 8. Formula I compounds include all mixtures of variously loaded and attached antibody-drug conjugates where 1, 2, 3, 4, 5, 6, 7, and 8 drug moieties are covalently attached to the antibody.

In another embodiment, Ab is an antibody which binds to one or more tumor-associated antigens or cell-surface receptors selected from (1)-(16) and (18)-(36), i.e. not to an ErbB receptor, including HER2.

Antibodies

The antibody unit (Ab-) of Formula I includes within its scope any unit of an antibody that binds or reactively associates or complexes with a receptor, antigen or other receptive moiety associated with a given target-cell population. An antibody can be any protein or protein-like molecule that binds to, complexes with, or reacts with a moiety of a cell population sought to be therapeutically or otherwise biologically modified. In one aspect, the antibody unit acts to deliver the maytansinoid drug moiety to the particular target cell population with which the antibody unit reacts. Such antibodies include, but are not limited to, large molecular weight proteins such as, full-length antibodies and antibody fragments.

Antibodies comprising the antibody-drug conjugates of the invention preferably retain the antigen binding capability of their native, wild type counterparts. Thus, antibodies of the invention are capable of binding, preferably specifically, to antigens. Such antigens include, for example, tumor-associated antigens (TAA), cell surface receptor proteins and other cell surface molecules, cell survival regulatory factors, cell proliferation regulatory factors, molecules associated with (for e.g., known or suspected to contribute functionally to) tissue development or differentiation, lymphokines, cytokines, molecules involved in cell cycle regulation, molecules involved in vasculogenesis and molecules associated with (for e.g., known or suspected to contribute functionally to) angiogenesis. The tumor-associated antigen may be a cluster differentiation factor (i.e., a CD protein). An antigen to which an antibody of the invention is capable of binding may be a member of a subset of one of the above-mentioned categories, wherein the other subset(s) of said category comprise other molecules/antigens that have a distinct characteristic (with respect to the antigen of interest).

In one embodiment, the antibody of the antibody-drug conjugates (ADC) specifically binds to a receptor encoded by an ErbB gene. The antibody may bind specifically to an ErbB receptor selected from EGFR, HER2, HER3 and HER4. The ADC may specifically bind to the extracellular domain (ECD) of the HER2 receptor and inhibit the growth of tumor cells which overexpress HER2 receptor. The antibody of the ADC may be a monoclonal antibody, e.g. a murine monoclonal antibody, a chimeric antibody, or a humanized antibody. A humanized antibody may be huMAb4D5-1, huMAb4D5-2, huMAb4D5-3, huMAb4D5-4, huMAb4D5-5, huMAb4D5-6, huMAb4D5-7 or huMAb4D5-8 (trastuzumab). The antibody may be an antibody fragment, e.g. a Fab fragment.

Antibodies in Formula I antibody-drug conjugates (ADC) and which may be useful in the treatment of cancer include, but are not limited to, antibodies against cell surface receptors and tumor-associated antigens (TAA). Such tumor-associated antigens are known in the art, and can prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Examples of TAA include, but are not limited to, Tumor-Associated Antigens (1)-(36) listed below. For convenience, information relating to these antigens, all of which are known in the art, is listed below and includes names, alternative names, Genbank accession numbers and primary reference(s), following nucleic acid and protein sequence identification conventions of the National Center for Biotechnology Information (NCBI). Nucleic acid and protein sequences corresponding to TAA (1)-(36) are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

Figures 3, 4:
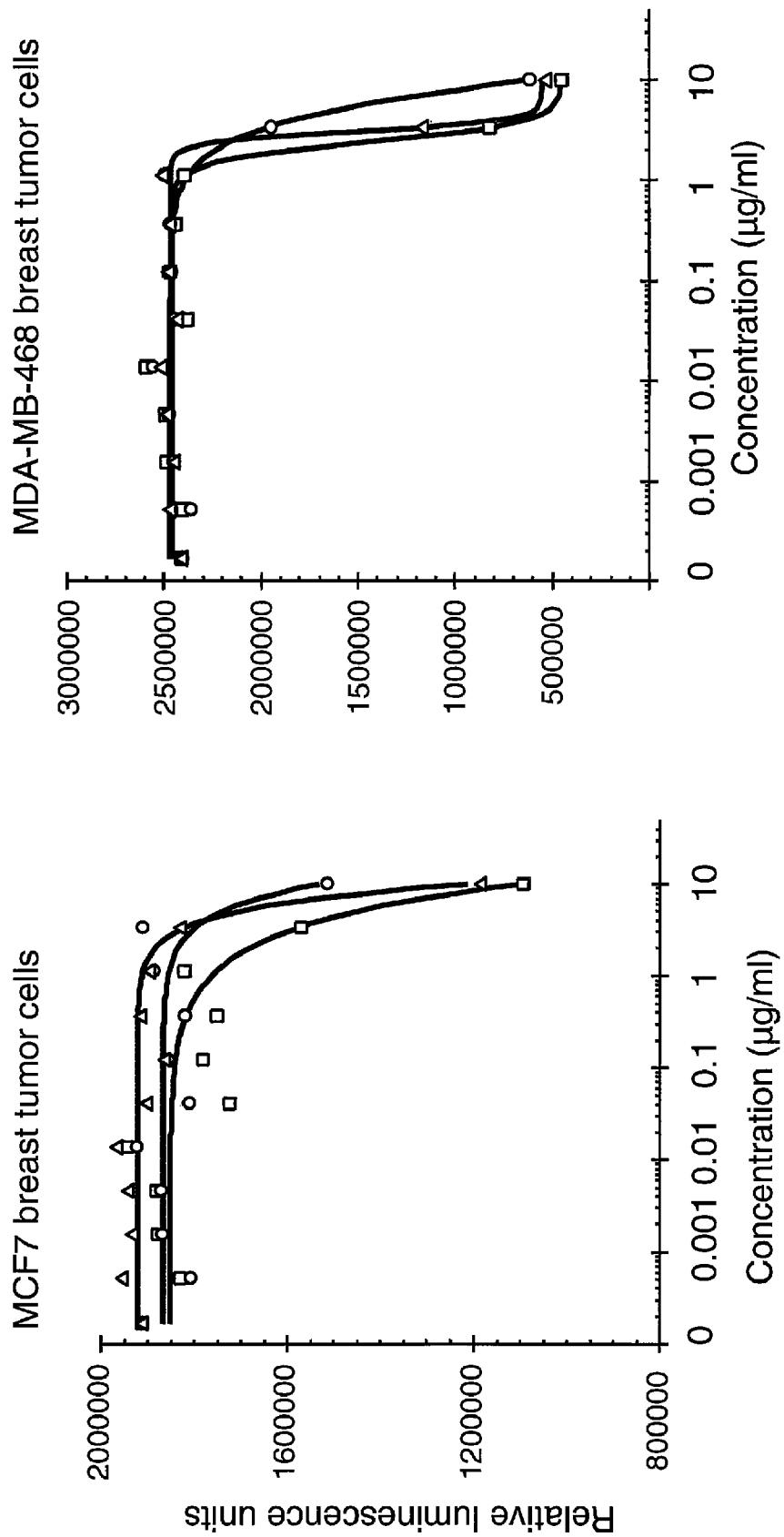
FIG. 3 shows an in vitro, cell proliferation assay with MCF7 cells treated with antibody-drug conjugates: -□- trastuzumab-SPP-DM1, -Δ- trastuzumab-SPDP-DM1, and -o- trastuzumab-SMCC-DM1.
FIG. 4 shows an in vitro, cell proliferation assay with MDA-MB-468 cells treated with antibody-drug conjugates: -□- trastuzumab-SPP-DM1, -Δ- trastuzumab-SPDP-DM1, and -o- trastuzumab-SMCC-DM1.

Tumor-Associated Antigens (1)-(36):

(1) BMPR1B (bone morphogenetic protein receptor-type IB, Genbank accession no. NM_001203)
ten Dijke, P., et al Science 264 (5155):101-104 (1994), Oncogene 14 (11):1377-1382 (1997)); WO2004063362 (claim 2); WO2003042661 (claim 12); US2003134790-A1 (Page 38-39); WO2002102235 (claim 13; Page 296); WO2003055443 (Page 91-92); WO200299122 (Example 2; Page 528-530); WO2003029421 (claim 6); WO2003024392 (claim 2; FIG. 112); WO200298358 (claim 1; Page 183); WO200254940 (Page 100-101); WO200259377(Page 349-350); WO200230268 (claim 27; Page 376); WO200148204 (Example; FIG. 4)
NP_001194 bone morphogenetic protein receptor, type IB/pid=NP_001194.1
Cross-references: MIM:603248; NP_001194.1; NM_001203_1
SEQ ID NO:1

(2) E16 (LAT1, SLC7A5, Genbank accession no. NM_003486)
Biochem. Biophys. Res. Commun. 255 (2), 283-288 (1999), Nature 395 (6699):288-291 (1998), Gaugitsch, H. W., et al (1992) J. Biol. Chem. 267 (16):11267-11273); WO2004048938 (Example 2); WO2004032842 (Example IV); WO2003042661 (claim 12); WO2003016475 (claim 1); WO200278524 (Example 2); WO200299074 (claim 19; Page 127-129); WO200286443 (claim 27; Pages 222, 393); WO2003003906 (claim 10; Page 293); WO200264798 (claim 33; Page 93-95); WO200014228 (claim 5; Page 133-136); US2003224454 (FIG. 3); WO2003025138 (claim 12; Page 150);
NP_003477 solute carrier family 7 (cationic amino acid transporter, y+system), member 5/pid=NP_003477.3—*Homo sapiens*
Cross-references: MIM:600182; NP_003477.3; NM_015923; NM_003486_1
SEQ ID NO:2

(3) STEAP1 (six transmembrane epithelial antigen of prostate, Genbank accession no. NM_012449)
Cancer Res. 61 (15), 5857-5860 (2001), Hubert, R. S., et al (1999) Proc. Natl. Acad. Sci. U.S.A. 96 (25):14523-14528); WO2004065577 (claim 6); WO2004027049 (FIG. 1L); EP1394274 (Example 11); WO2004016225 (claim 2); WO2003042661 (claim 12); US2003157089 (Example 5); US2003185830 (Example 5); US2003064397 (FIG. 2); WO200289747 (Example 5; Page 618-619); WO2003022995 (Example 9; FIG. 13A, Example 53; Page 173, Example 2; FIG. 2A);
NP_036581 six transmembrane epithelial antigen of the prostate
Cross-references: MIM:604415; NP_036581.1; NM_012449_1
SEQ ID NO:3

Figure 12:
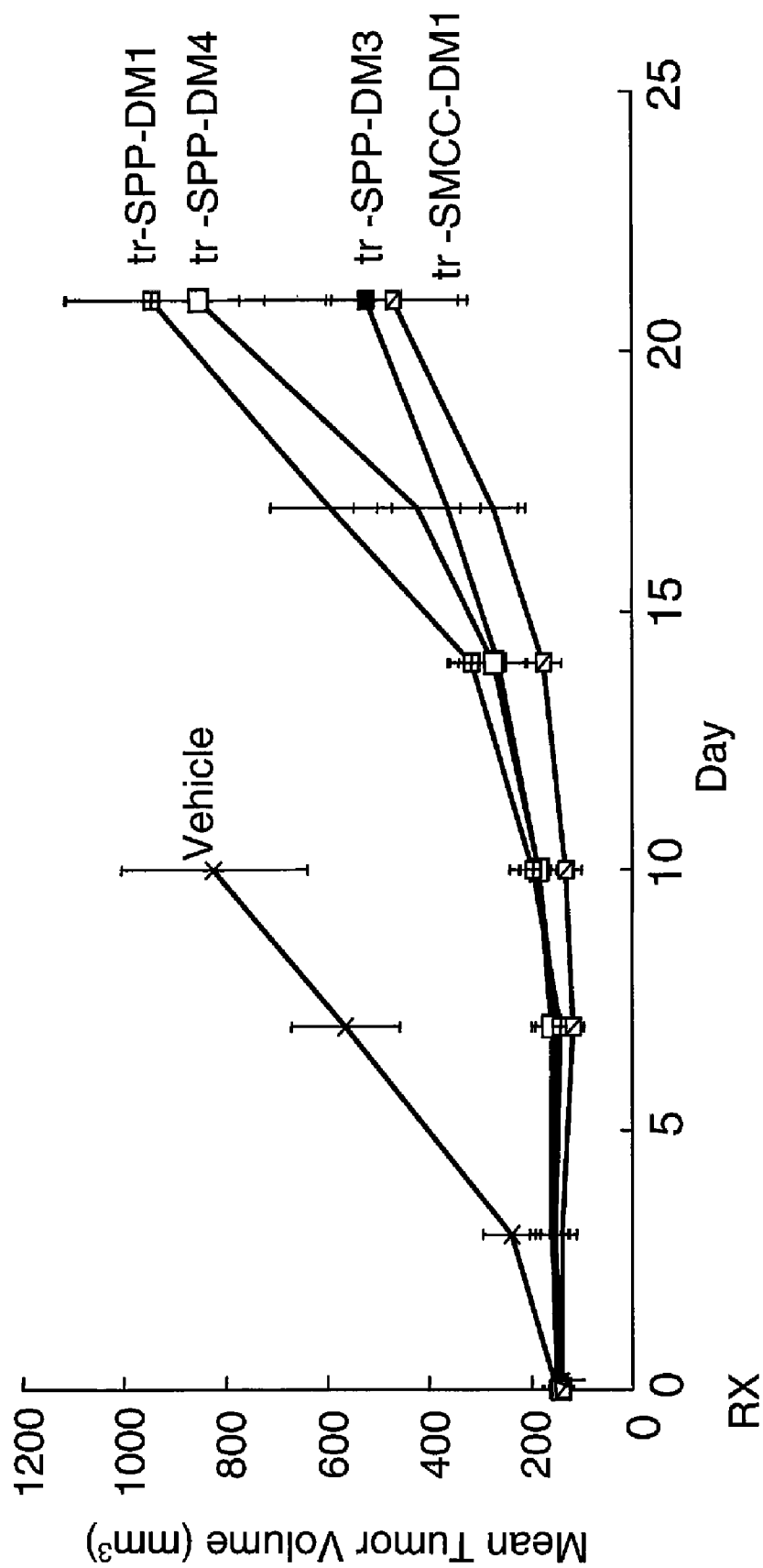
FIG. 12 shows the mean tumor volume change over time in MMTV-Her2 Fo 5 beige nude mice (seven each group, all with tumors, Ti=7) by single injection with Vehicle (PBS pH 6.5), 10 mg/kg trastuzumab-SPP-DM1, 10 mg/kg trastuzumab-SPP-DM4, 10 mg/kg trastuzumab-SPP-DM3, and 10 mg/kg trastuzumab-SMCC-DM1.

(4) 0772P (CA125, MUC16, Genbank accession no. AF361486)
J. Biol. Chem. 276 (29):27371-27375 (2001)); WO2004045553 (claim 14); WO200292836 (claim 6; FIG. 12); WO200283866 (claim 15; Page 116-121); US2003124140 (Example 16); US2003091580 (claim 6); WO200206317 (claim 6; Page 400-408);
Cross-references: GI:34501467; AAK74120.3; AF361486_1
SEQ ID NO:4

(5) MPF (MPF, MSLN, SMR, megakaryocyte potentiating factor, mesothelin, Genbank accession no. NM_005823)
Yamaguchi, N., et al Biol. Chem. 269 (2), 805-808 (1994), Proc. Natl. Acad. Sci. U.S.A. 96 (20):11531-11536 (1999), Proc. Natl. Acad. Sci. U.S.A. 93 (1):136-140 (1996), J. Biol. Chem. 270 (37):21984-21990 (1995)); WO2003101283 (claim 14); (WO2002102235 (claim 13; Page 287-288); WO2002101075 (claim 4; Page 308-309); WO200271928 (Page 320-321); WO9410312 (Page 52-57);
Cross-references: MIM:601051; NP_005814.2; NM_005823_1
SEQ ID NO:5

(6) Napi3b (NAPI-3B, NPTIIb, SLC34A2, solute carrier family 34 (sodium phosphate), member 2, type II sodium-dependent phosphate transporter 3b, Genbank accession no. NM_006424) J. Biol. Chem. 277 (22):19665-19672 (2002), Genomics 62 (2):281-284 (1999), Feild, J. A., et al (1999) Biochem. Biophys. Res. Commun. 258 (3):578-582); WO2004022778 (claim 2); EP1394274 (Example 11); WO2002102235 (claim 13; Page 326); EP875569 (claim 1; Page 17-19); WO200157188 (claim 20; Page 329); WO2004032842 (Example IV); WO200175177 (claim 24; Page 139-140);
Cross-references: MIM:604217; NP_006415.1; NM_006424_1
SEQ ID NO:6

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878) Nagase T., et al (2000) DNA Res. 7 (2):143-150); WO2004000997 (claim 1); WO2003003984 (claim 1); WO200206339 (claim 1; Page 50); WO200188133 (claim 1; Page 41-43, 48-58); WO2003054152 (claim 20); WO2003101400 (claim 11);
Accession: Q9P283; EMBL; AB040878; BAA95969.1. Genew; HGNC:10737;
SEQ ID NO:7

(8) PSCA hlg (2700050C12Rik, C530008O16Rik, RIKEN cDNA 2700050C12, RIKEN cDNA 2700050C12 gene, Genbank accession no. AY358628); US2003129192 (claim 2); US2004044180 (claim 12); US2004044179 (claim 11); US2003096961 (claim 11); US2003232056 (Example 5); WO2003105758 (claim 12); US2003206918 (Example 5); EP1347046 (claim 1); WO2003025148 (claim 20);
Cross-references: GI:37182378; AAQ88991.1; AY358628_1
SEQ ID NO:8

Figure 6:
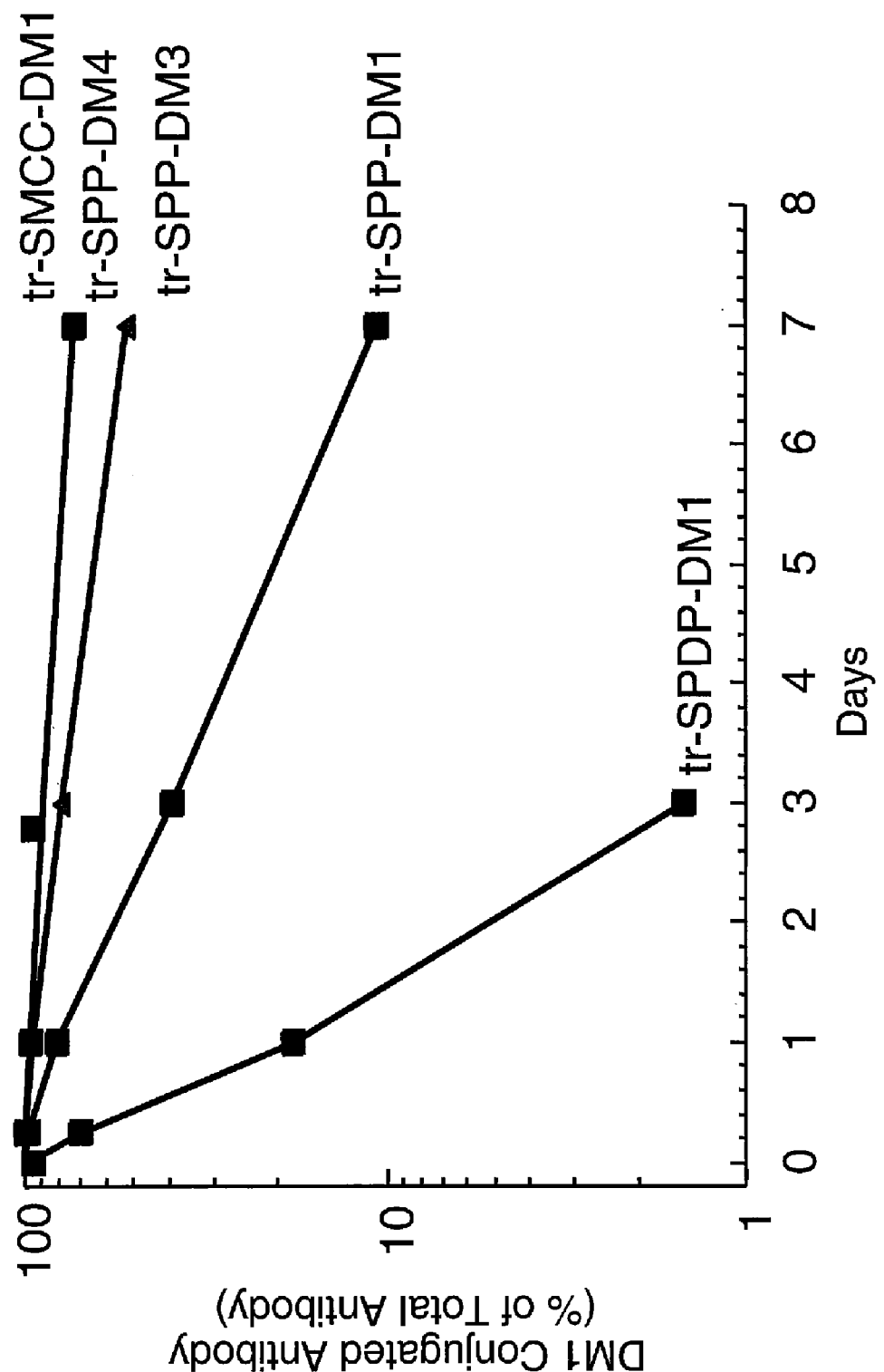
FIG. 6 shows the stability over time in nude mice without tumors of the conjugates: trastuzumab-SPDP-DM1, trastuzumab-SPP-DM1, trastuzumab-SPP-DM3, trastuzumab-SPP-DM4, and trastuzumab-SMCC-DM1, measuring serum concentration at six time points (5 minutes, 1 hour, 6 hours, 24 hours, 72, 168 hours post-dose) over 7 days.

(9) ETBR (Endothelin type B receptor, Genbank accession no. AY275463);
Nakamuta M., et al Biochem. Biophys. Res. Commun. 177, 34-39, 1991; Ogawa Y., et al Biochem. Biophys. Res. Commun. 178, 248-255, 1991; Arai H., et al Jpn. Circ. J. 56, 1303-1307, 1992; Arai H., et al J. Biol. Chem. 268, 3463-3470, 1993; Sakamoto A., Yanagisawa M., et al Biochem. Biophys. Res. Commun. 178, 656-663, 1991; Elshourbagy N. A., et al J. Biol. Chem. 268, 3873-3879, 1993; Haendler B., et al J. Cardiovasc. Pharmacol. 20, s1-S4, 1992; Tsutsumi M., et al Gene 228, 43-49, 1999; Strausberg R. L., et al Proc. Natl. Acad. Sci. U.S.A. 99, 16899-16903, 2002; Bourgeois C., et al J. Clin. Endocrinol. Metab. 82, 3116-3123, 1997; Okamoto Y., et al Biol. Chem. 272, 21589-21596, 1997; Verheij J. B., et al Am. J. Med. Genet. 108, 223-225, 2002; Hofstra R. M. W., et al Eur. J. Hum. Genet. 5, 180-185, 1997; Puffenberger E. G., et al Cell 79, 1257-1266, 1994; Attie T., et al, Hum. Mol. Genet. 4, 2407-2409, 1995; Auricchio A., et al Hum. Mol. Genet. 5:351-354, 1996; Amiel J., et al Hum. Mol. Genet. 5, 355-357, 1996; Hofstra R. M. W., et al Nat. Genet. 12, 445-447, 1996; Svensson P. J., et al Hum. Genet. 103, 145-148, 1998; Fuchs S., et al Mol. Med. 7, 115-124, 2001; Pingault V., et al (2002) Hum. Genet. 111, 198-206; WO2004045516 (claim 1); WO2004048938 (Example 2); WO2004040000 (claim 151); WO2003087768 (claim 1); WO2003016475 (claim 1); WO2003016475 (claim 1); WO200261087 (FIG. 1); WO2003016494 (FIG. 6); WO2003025138 (claim 12; Page 144); WO200198351 (claim 1; Page 124-125); EP522868 (claim 8; FIG. 2); WO200177172 (claim 1; Page 297-299); US2003109676; U.S. Pat. No. 6,518,404 (FIG. 3); U.S. Pat. No. 5,773,223 (Claim 1a; Col 31-34); WO2004001004;

SEQ ID NO:9

(10) MSG783 (RNF124, hypothetical protein FLJ20315, Genbank accession no. NM_017763); WO2003104275 (claim 1); WO2004046342 (Example 2); WO2003042661 (claim 12); WO2003083074 (claim 14; Page 61); WO2003018621 (claim 1); WO2003024392 (claim 2; FIG. 93); WO200166689 (Example 6);

Cross-references: LocusID:54894; NP_060233.2; NM_017763_1

SEQ ID NO:10

(11) STEAP2 (HGNC_8639, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138)

Figure 10:
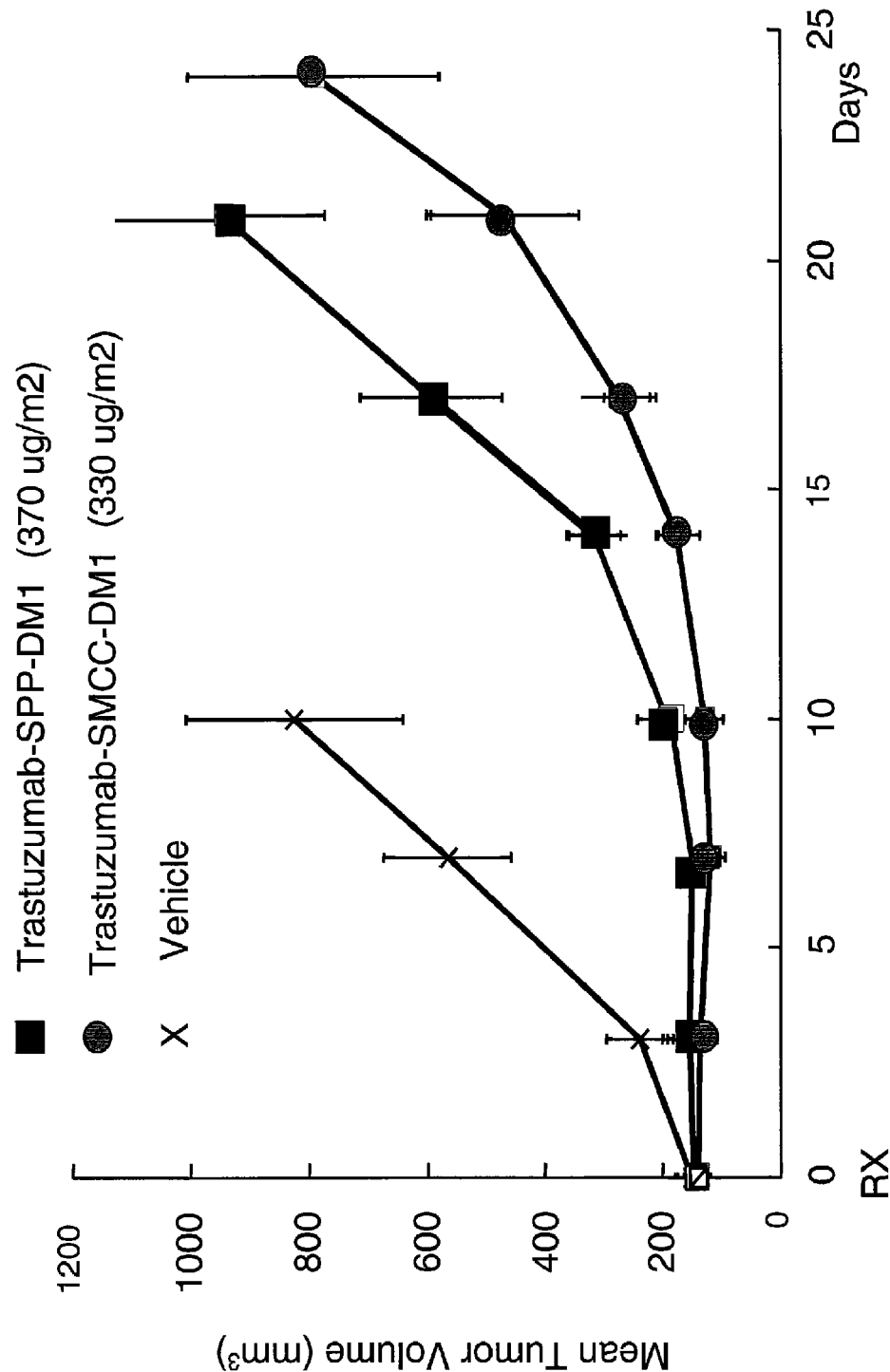
FIG. 10 shows the mean tumor volume change over time in mice dosed with: Vehicle (PBS pH 6.5), trastuzumab-SPP-DM1 (370 μg DM1/m$^2$), and trastuzumab-SMCC-DM1 (330 μg DM1/m$^2$) where dose refers to the dose of DM1 administered.

Lab. Invest. 82 (11):1573-1582 (2002)); WO2003087306; US2003064397 (claim 1; FIG. 1); WO200272596 (claim 13; Page 54-55); WO200172962 (claim 1; FIG. 4B); WO2003104270 (claim 11); WO2003104270 (claim 16); US2004005598 (claim 22); WO2003042661 (claim 12); US2003060612 (claim 12; FIG. 10); WO200226822 (claim 23; FIG. 2); WO200216429 (claim 12; FIG. 10);

Cross-references: GI:22655488; AAN04080.1; AF455138_1

SEQ ID NO:11

(12) TrpM4 (BR22450, FLJ20041, TRPM4, TRPM4B, transient receptor potential cation channel, subfamily M, member 4, Genbank accession no. NM_017636)

Xu, X. Z., et al Proc. Natl. Acad. Sci. U.S.A. 98 (19):10692-10697 (2001), Cell 109 (3):397-407 (2002), J. Biol. Chem. 278 (33):30813-30820 (2003)); US2003143557 (claim 4); WO200040614 (claim 14; Page 100-103); WO200210382 (claim 1; FIG. 9A); WO2003042661 (claim 12); WO200230268 (claim 27; Page 391); US2003219806 (claim 4); WO200162794 (claim 14; FIGS. 1A-D);

Cross-references: MIM:606936; NP_060106.2; NM_017636_1

SEQ ID NO:12

(13) CRIPTO (CR, CR1, CRGF, CRIPTO, TDGF1, teratocarcinoma-derived growth factor, Genbank accession no. NP_003203 or NM_003212)

Ciccodicola, A., et al EMBO J. 8 (7):1987-1991 (1989), Am. J. Hum. Genet. 49 (3):555-565 (1991)); US2003224411 (claim 1); WO2003083041 (Example 1); WO2003034984 (claim 12); WO200288170 (claim 2; Page 52-53); WO2003024392 (claim 2; FIG. 58); WO200216413 (claim 1; Page 94-95, 105); WO200222808 (claim 2; FIG. 1); U.S. Pat. No. 5,854,399 (Example 2; Col 17-18); U.S. Pat. No. 5,792,616 (FIG. 2);

Cross-references: MIM:187395; NP_003203.1; NM_003212_1

SEQ ID NO:13

(14) CD21 (CR2 (Complement receptor 2) or C3DR(C3d/Epstein Barr virus receptor) or Hs.73792 Genbank accession no. M26004)

Figure 9:
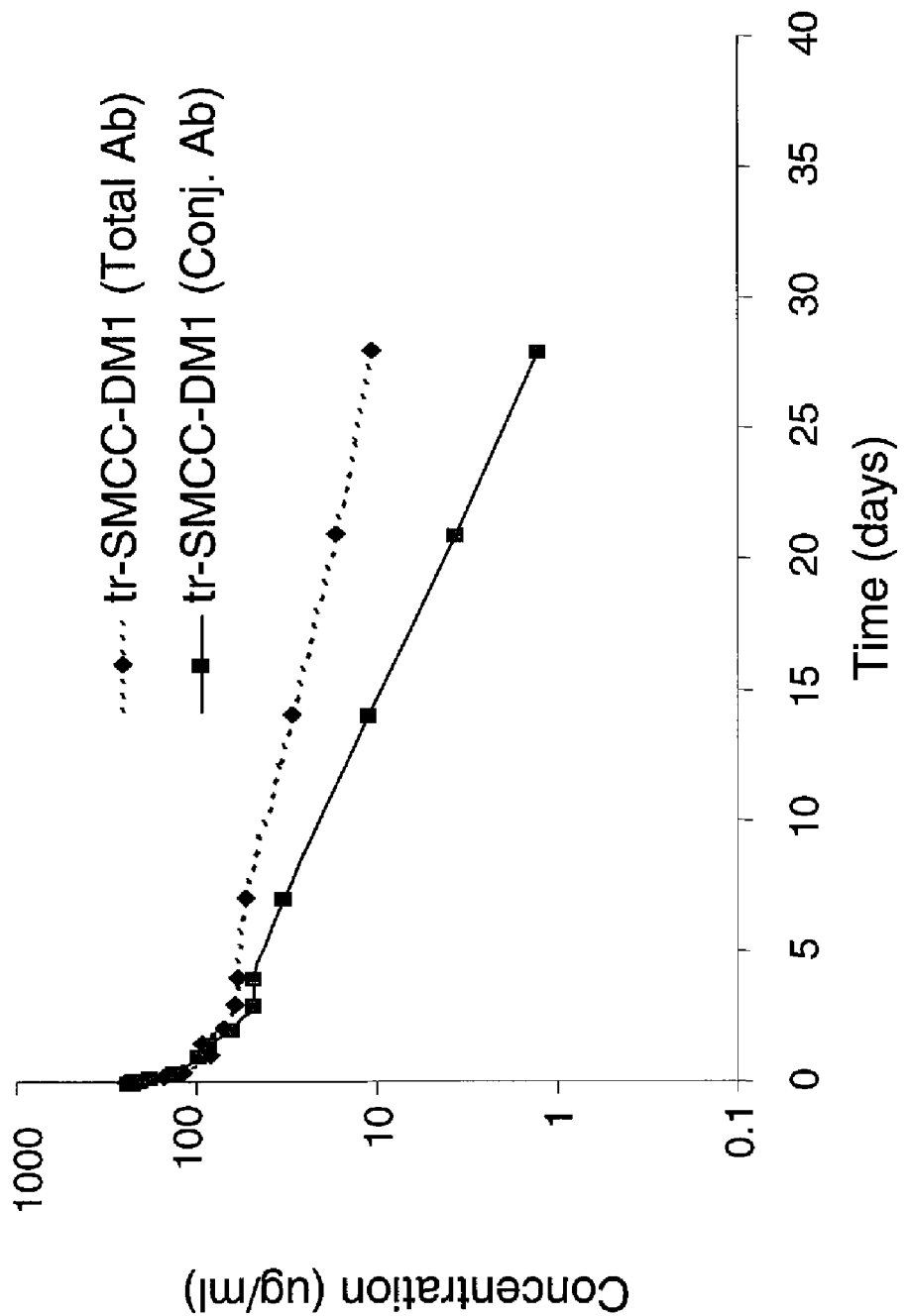
FIG. 9 shows a plasma concentration clearance study after administration of 10 mg/kg of trastuzumab-SMCC-DM1 to 4 subject rats. Concentrations of total antibody and trastuzumab-SMCC-DM1 were measured.

Fujisaku et al (1989) J. Biol. Chem. 264 (4):2118-2125); Weis J. J., et al J. Exp. Med. 167, 1047-1066, 1988; Moore M., et al Proc. Natl. Acad. Sci. U.S.A. 84, 9194-9198, 1987; Barel M., et al Mol. Immunol. 35, 1025-1031, 1998; Weis J. J., et al Proc. Natl. Acad. Sci. U.S.A. 83, 5639-5643, 1986; Sinha S. K., et al (1993) J. Immunol. 150, 5311-5320; WO2004045520 (Example 4); US2004005538 (Example 1); WO2003062401 (claim 9); WO2004045520 (Example 4); WO9102536 (FIG. 9.1-9.9); WO2004020595 (claim 1);

Accession: P20023; Q13866; Q14212; EMBL; M26004; AAA35786.1.

SEQ ID NO:14

(15) CD79b (CD79B, CD79β, 1Gb (immunoglobulin-associated beta), B29, Genbank accession no. NM_000626 or 11038674)

Proc. Natl. Acad. Sci. U.S.A. (2003) 100 (7):4126-4131, Blood (2002) 100 (9):3068-3076, Muller et al (1992) Eur. J. Immunol. 22 (6):1621-1625); WO2004016225 (claim 2, FIG. 140); WO2003087768, US2004101874 (claim 1, page 102); WO2003062401 (claim 9); WO200278524 (Example 2); US2002150573 (claim 5, page 15); U.S. Pat. No. 5,644,033; WO2003048202 (claim 1, pages 306 and 309); WO 99/558658, U.S. Pat. No. 6,534,482 (claim 13, FIG. 17A/B); WO200055351 (claim 11, pages 1145-1146);

Cross-references: MIM:147245; NP_000617.1; NM_000626_1

SEQ ID NO:15

(16) FcRH2 (IFGP4, IRTA4, SPAP1A (SH2 domain containing phosphatase anchor protein 1a), SPAP1B, SPAP1C, Genbank accession no NM_030764)

Genome Res. 13 (10):2265-2270 (2003), Immunogenetics 54 (2):87-95 (2002), Blood 99 (8):2662-2669 (2002), Proc. Natl. Acad. Sci. U.S.A. 98 (17):9772-9777 (2001), Xu, M. J., et al (2001) Biochem. Biophys. Res. Commun. 280 (3):768-775; WO2004016225 (claim 2); WO2003077836; WO200138490 (claim 5; FIGS. 18D-1-18D-2); WO2003097803 (claim 12); WO2003089624 (claim 25);

Cross-references: MIM:606509; NP_110391.2; NM_030764_1

SEQ ID NO:16

(17) HER2 (ErbB2, Genbank accession no. M11730)

Figure 7:
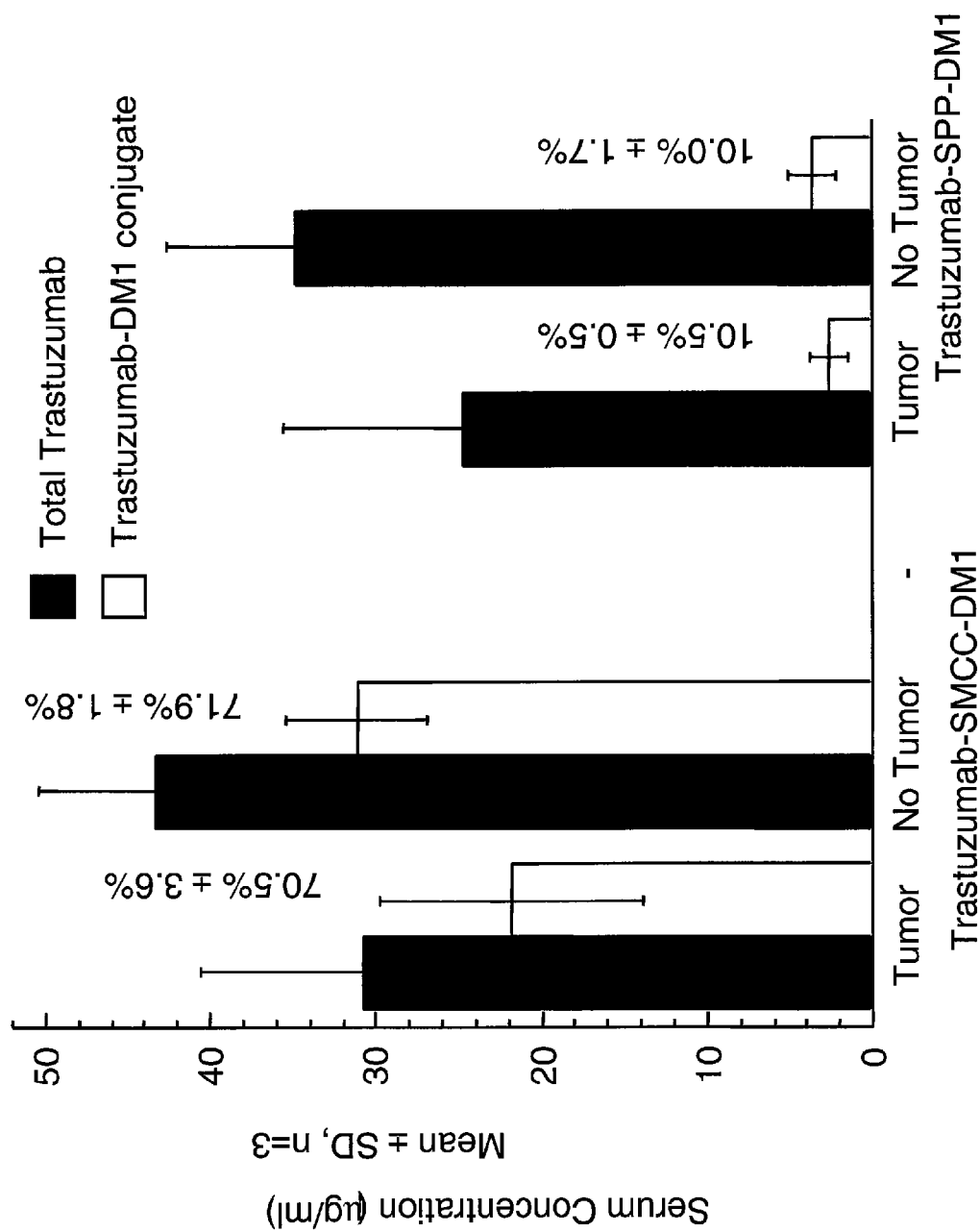
FIG. 7 shows the measurement of serum concentrations of total trastuzumab/trastuzumab-SMCC-DM1, and total trastuzumab/trastuzumab-SPP-DM1 in mice, 7 days after treatment, with and without tumor.

Coussens L., et al Science (1985) 230(4730):1132-1139); Yamamoto T., et al Nature 319, 230-234, 1986; Semba K., et al Proc. Natl. Acad. Sci. U.S.A. 82, 6497-6501, 1985; Swiercz J. M., et al J. Cell Biol. 165, 869-880, 2004; Kuhns J. J., et al J. Biol. Chem. 274, 36422-36427, 1999; Cho H.-S., et al Nature 421, 756-760, 2003; Ehsani A., et al (1993) Genomics 15, 426-429; WO2004048938 (Example 2); WO2004027049 (FIG. 1I); WO2004009622; WO2003081210; WO2003089904 (claim 9); WO2003016475 (claim 1); US2003118592; WO2003008537 (claim 1); WO2003055439 (claim 29; FIG. 1A-B); WO2003025228 (claim 37; FIG. 5C); WO200222636 (Example 13; Page 95-107); WO200212341 (claim 68; FIG. 7); WO200213847 (Page 71-74); WO200214503 (Page 114-117); WO200153463 (claim 2; Page 41-46); WO200141787

Figure 8:
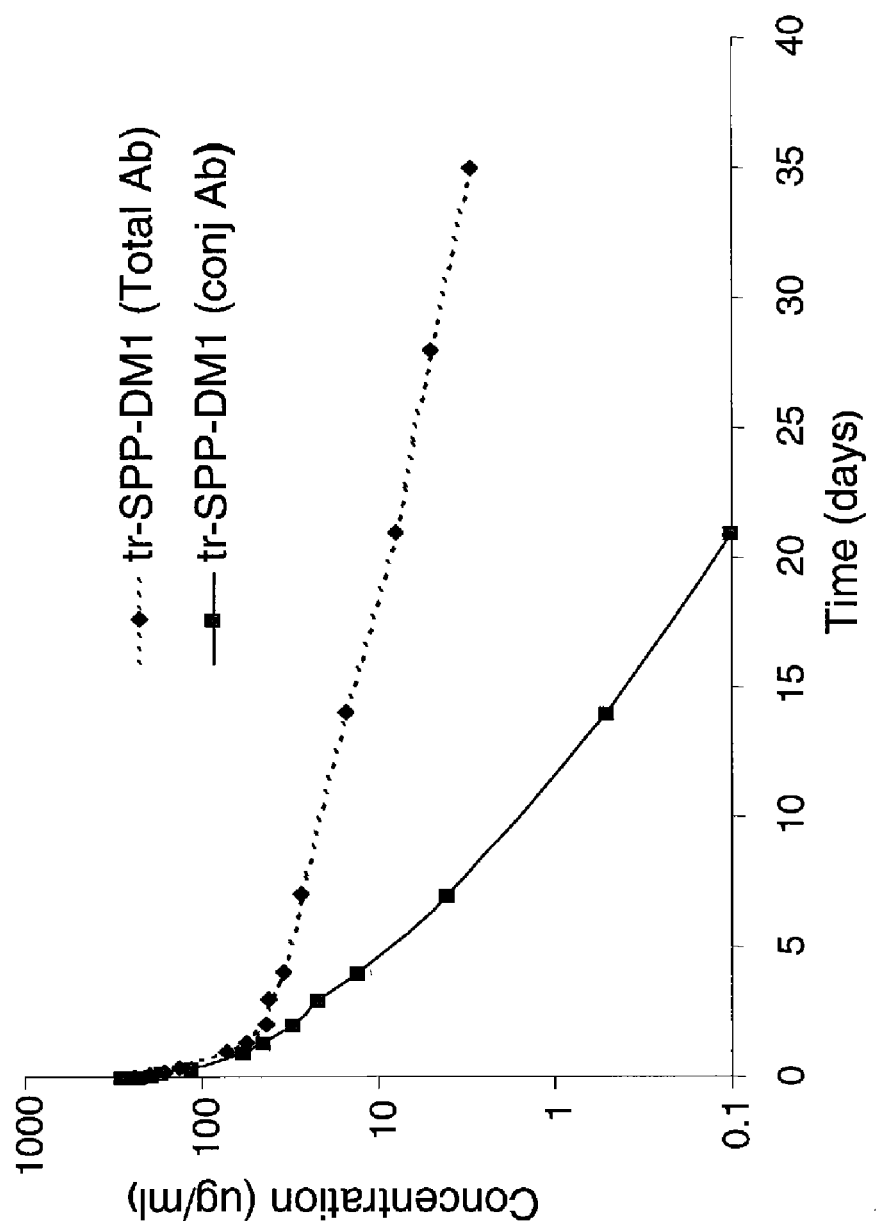
FIG. 8 shows a plasma concentration clearance study after administration of 10 mg/kg of trastuzumab-SPP-DM1 to 4 subject rats. Concentrations of total antibody and trastuzumab-SPP-DM1 were measured. (tr=trastuzumab)

(Page 15); WO200044899 (claim 52; FIG. 7); WO200020579 (claim 3; FIG. 2); U.S. Pat. No. 5,869,445 (claim 3; Col 31-38); WO9630514 (claim 2; Page 56-61); EP1439393 (claim 7); WO2004043361 (claim 7); WO2004022709; WO200100244 (Example 3; FIG. 4);
Accession: P04626; EMBL; M11767; AAA35808.1. EMBL; M11761; AAA35808.1.
SEQ ID NO:17
(18) NCA (CEACAM6, Genbank accession no. M18728); Barnett T., et al Genomics 3, 59-66, 1988; Tawaragi Y., et al Biochem. Biophys. Res. Commun. 150, 89-96, 1988; Strausberg R. L., et al Proc. Natl. Acad. Sci. U.S.A. 99:16899-16903, 2002; WO2004063709; EP1439393 (claim 7); WO2004044178 (Example 4); WO2004031238; WO2003042661 (claim 12); WO200278524 (Example 2); WO200286443 (claim 27; Page 427); WO200260317 (claim 2);
Accession: P40199; Q14920; EMBL; M29541; AAA59915.1. EMBL; M18728;
SEQ ID NO:18
(19) MDP (DPEP1, Genbank accession no. BC017023) Proc. Natl. Acad. Sci. U.S.A. 99 (26):16899-16903 (2002)); WO2003016475 (claim 1); WO200264798 (claim 33; Page 85-87); JP05003790 (FIGS. 6-8); WO9946284 (FIG. 9);
Cross-references: MIM:179780; AAH17023.1; BC017023_1
SEQ NO:19
(20) IL20Rα (IL20Ra, ZCYTOR7, Genbank accession no. AF184971);
Clark H. F., et all Genome Res. 13, 2265-2270, 2003; Mungall A. J., et al Nature 425, 805-811, 2003; Blumberg H., et al Cell 104, 9-19, 2001; Dumoutier L., et al J. Immunol. 167, 3545-3549, 2001; Parrish-Novak J., et al J. Biol. Chem. 277, 47517-47523, 2002; Pletnev S., et all (2003) Biochemistry 42:12617-12624; Sheikh F., et al (2004) J. Immunol. 172, 2006-2010; EP1394274 (Example 11); US2004005320 (Example 5); WO2003029262 (Page 74-75); WO2003002717 (claim 2; Page 63); WO200222153 (Page 45-47); US2002042366 (Page 20-21); WO200146261 (Page 57-59); WO200146232 (Page 63-65); WO9837193 (claim 1; Page 55-59);
Accession: Q9UHF4; Q6UWA9; Q96SH8; EMBL; AF184971; AAF01320.1.
SEQ ID NO:20
(21) Brevican (BCAN, BEHAB, Genbank accession no. AF229053)
Gary S. C., et al Gene 256, 139-147, 2000; Clark H. F., et al Genome Res. 13, 2265-2270, 2003; Strausberg R. L., et al Proc. Natl. Acad. Sci. U.S.A. 99, 16899-16903, 2002; US2003186372 (claim 11); US2003186373 (claim 11); US2003119131 (claim 1; FIG. 52); US2003119122 (claim 1; FIG. 52); US2003119126 (claim 1); US2003119121 (claim 1; FIG. 52); US2003119129 (claim 1); US2003119130 (claim 1); US2003119128 (claim 1; FIG. 52); US2003119125 (claim 1); WO2003016475 (claim 1); WO200202634 (claim 1);
SEQ ID NO:21
(22) EphB2R (DRT, ERK, Hek5, EPHT3, Tyro5, Genbank accession no. NM_004442)
Chan, J. and Watt, V. M., Oncogene 6 (6), 1057-1061 (1991) Oncogene 10 (5):897-905 (1995), Annu. Rev. Neurosci. 21:309-345 (1998), Int. Rev. Cytol. 196:177-244 (2000)); WO2003042661 (claim 12); WO200053216 (claim 1; Page 41); WO2004065576 (claim 1); WO2004020583 (claim 9); WO2003004529 (Page 128-132); WO200053216 (claim 1; Page 42);

Cross-references: MIM:600997; NP_004433.2; NM_004442_1
SEQ ID NO:22
(23) ASLG659 (B7h, Genbank accession no. AX092328) US20040101899 (claim 2); WO2003104399 (claim 11); WO2004000221 (FIG. 3); US2003165504 (claim 1); US2003124140 (Example 2); US2003065143 (FIG. 60); WO2002102235 (claim 13; Page 299); US2003091580 (Example 2); WO200210187 (claim 6; FIG. 10); WO200194641 (claim 12; FIG. 7b); WO200202624 (claim 13; FIGS. 1A-1B); US2002034749 (claim 54; Page 45-46); WO200206317 (Example 2; Page 320-321, claim 34; Page 321-322); WO200271928 (Page 468-469); WO200202587 (Example 1; FIG. 1); WO200140269 (Example 3; Pages 190-192); WO200036107 (Example 2; Page 205-207); WO2004053079 (claim 12); WO2003004989 (claim 1); WO200271928 (Page 233-234, 452-453); WO 0116318;
SEQ ID NO:23
(24) PSCA (Prostate stem cell antigen precursor, Genbank accession no. AJ297436)
Reiter R. E., et al Proc. Natl. Acad. Sci. U.S.A. 95, 1735-1740, 1998; Gu Z., et al Oncogene 19, 1288-1296, 2000; Biochem. Biophys. Res. Commun. (2000) 275(3):783-788; WO2004022709; EP1394274 (Example 11); US2004018553 (claim 17); WO2003008537 (claim 1); WO200281646 (claim 1; Page 164); WO2003003906 (claim 10; Page 288); WO200140309 (Example 1; FIG. 17); US2001055751 (Example 1; FIG. 1b); WO200032752 (claim 18; FIG. 1); WO9851805 (claim 17; Page 97); WO9851824 (claim 10; Page 94); WO9840403 (claim 2; FIG. 1B);
Accession: O43653; EMBL; AF043498; AAC39607.1.
SEQ ID NO:24
(25) GEDA (Genbank accession No. AY260763);
AAP14954 lipoma HMGIC fusion-partner-like protein/pid=AAP14954.1- *Homo sapiens*
Species: *Homo sapiens* (human)
WO2003054152 (claim 20); WO2003000842 (claim 1); WO2003023013 (Example 3, claim 20); US2003194704 (claim 45);
Cross-references: GI:30102449; AAP14954.1; AY260763_1
SEQ ID NO:25
(26) BAFF-R (B cell-activating factor receptor, BLyS receptor 3, BR3, Genbank accession No. NP_443177.1);
NP_443177 BAFF receptor/pid=NP_443177.1—*Homo sapiens*
Thompson, J. S., et al Science 293 (5537), 2108-2111 (2001); WO2004058309; WO2004011611; WO2003045422 (Example; Page 32-33); WO2003014294 (claim 35; FIG. 6B); WO2003035846 (claim 70; Page 615-616); WO200294852 (Col 136-137); WO200238766 (claim 3; Page 133); WO200224909 (Example 3; FIG. 3);
Cross-references: MIM:606269; NP_443177.1; NM_052945_1
SEQ ID NO:26
(27) CD22 (B-cell receptor CD22-B isoform, Genbank accession No. NP-001762.1); Stamenkovic, I. and Seed, B., Nature 345 (6270), 74-77 (1990); US2003157113; US2003118592; WO2003062401 (claim 9); WO2003072036 (claim 1; FIG. 1); WO200278524 (Example 2);
Cross-references: MIM:107266; NP_001762.1; NM_001771_1
SEQ ID NO:27
(28) CD79a (CD79A, CD79α, immunoglobulin-associated alpha, a B cell-specific protein that covalently interacts with Ig beta (CD79B) and forms a complex on the surface with Ig M molecules, transduces a signal involved in B-cell differentiation) 226 aa, pI: 4.84, MW: 25028 TM: 2 [P] Gene Chromosome: 19q13.2, Genbank accession No. NP_001774.10) WO2003088808, US20030228319; WO2003062401 (claim 9); US2002150573 (claim 4, pages 13-14); WO9958658 (claim 13, FIG. 16); WO9207574 (FIG. 1); U.S. Pat. No. 5,644,033; Ha et al (1992) J. Immunol. 148(5):1526-1531; Mueller et al (1992) Eur. J. Biochem. 22:1621-1625; Hashimoto et al (1994) Immunogenetics 40(4):287-295; Preud'homme et al (1992) Clin. Exp. Immunol. 90(1):141-146; Yu et al (1992) J. Immunol. 148(2) 633-637; Sakaguchi et al (1988) EMBO J. 7(11):3457-3464;

SEQ ID NO:28

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia) 372 aa, pI: 8.54 MW: 41959 TM: 7 [P] Gene Chromosome: 11q23.3, Genbank accession No. NP_001707.1) WO2004040000; WO2004015426; US2003105292 (Example 2); U.S. Pat. No. 6,555,339 (Example 2); WO200261087 (FIG. 1); WO200157188 (claim 20, page 269); WO200172830 (pages 12-13); WO200022129 (Example 1, pages 152-153, Example 2, pages 254-256); WO9928468 (claim 1, page 38); U.S. Pat. No. 5,440,021 (Example 2, col 49-52); WO9428931 (pages 56-58); WO9217497 (claim 7, FIG. 5); Dobner et al (1992) Eur. J. Immunol. 22:2795-2799; Barella et al (1995) Biochem. J. 309:773-779;

SEQ ID NO:29

(30) HLA-DOB (Beta subunit of MHC class II molecule (Ia antigen) that binds peptides and presents them to CD4+ T lymphocytes) 273 aa, pI: 6.56 MW: 30820 TM: 1 [P] Gene Chromosome: 6p21.3, Genbank accession No. NP_002111.1)
Tonnelle et al (1985) EMBO J. 4(11):2839-2847; Jonsson et al (1989) Immunogenetics 29(6):411-413; Beck et al (1992) J. Mol. Biol. 228:433-441; Strausberg et al (2002) Proc. Natl. Acad. Sci. USA 99:16899-16903; Servenius et al (1987) J. Biol. Chem. 262:8759-8766; Beck et al (1996) J. Mol. Biol. 255:1-13; Naruse et al (2002) Tissue Antigens 59:512-519; WO9958658 (claim 13, FIG. 15); U.S. Pat. No. 6,153,408 (Col 35-38); U.S. Pat. No. 5,976,551 (col 168-170); US6011146 (col 145-146); Kasahara et al (1989) Immunogenetics 30(1):66-68; Larhammar et al (1985) J. Biol. Chem. 260(26): 14111-14119;

SEQ ID NO:30

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability) 422 aa, pI: 7.63, MW: 47206 TM: 1 [P] Gene Chromosome: 17p13.3, Genbank accession No. NP_002552.2)
Le et al (1997) FEBS Lett. 418(1-2):195-199; WO2004047749; WO2003072035 (claim 10); Touchman et al (2000) Genome Res. 10:165-173; WO200222660 (claim 20); WO2003093444 (claim 1); WO2003087768 (claim 1); WO2003029277 (page 82);

SEQ ID NO:31

(32) CD72 (B-cell differentiation antigen CD72, Lyb-2) 359 aa, pI: 8.66, MW: 40225 TM: 1 [P] Gene Chromosome: 9p13.3, Genbank accession No. NP_001773.1)
WO2004042346 (claim 65); WO2003026493 (pages 51-52, 57-58); WO200075655 (pages 105-106); Von Hoegen et al (1990) J. Immunol. 144(12):4870-4877; Strausberg et al (2002) Proc. Natl. Acad. Sci. USA 99:16899-16903;

SEQ ID NO:32

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosus) 661 aa, pI: 6.20, MW: 74147 TM: 1 [P] Gene Chromosome: 5q12, Genbank accession No. NP_005573.1) US2002193567; WO9707198 (claim 11, pages 39-42); Miura et al (1996) Genomics 38(3):299-304; Miura et al (1998) Blood 92:2815-2822; WO2003083047; WO9744452 (claim 8, pages 57-61); WO200012130 (pages 24-26);

SEQ ID NO:33

(34) FCRH1 (Fc receptor-like protein 1, a putative receptor for the immunoglobulin Fc domain that contains C2 type Ig-like and ITAM domains, may have a role in B-lymphocyte differentiation) 429 aa, pI: 5.28, MW: 46925 TM: 1 [P] Gene Chromosome: 1q21-1q22, Genbank accession No. NP_443170.1)
WO2003077836; WO200138490 (claim 6, FIGS. 18E-1-18-E-2); Davis et al (2001) Proc. Natl. Acad. Sci. USA 98(17): 9772-9777; WO2003089624 (claim 8); EP1347046 (claim 1); WO2003089624 (claim 7);

SEQ ID NO:34

(35) IRTA2 (Immunoglobulin superfamily receptor translocation associated 2, a putative immunoreceptor with possible roles in B cell development and lymphomagenesis; deregulation of the gene by translocation occurs in some B cell malignancies) 977 aa, pI: 6.88 MW: 106468 TM: 1 [P] Gene Chromosome: 1q21, Genbank accession No. NP_112571.1) WO2003024392 (claim 2, FIG. 97); Nakayama et al (2000) Biochem. Biophys. Res. Commun. 277(1):124-127; WO2003077836; WO200138490 (claim 3, FIGS. 18B-1-18B-2);

SEQ ID NO:35

(36) TENB2 (TMEFF2, tomoregulin, TPEF, HPP1, TR, putative transmembrane proteoglycan, related to the EGF/heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; Genbank accession No. AF179274; AY358907, CAF85723, CQ782436
WO2004074320; JP2004113151; WO2003042661; WO2003009814; EP1295944 (pages 69-70); WO200230268 (page 329); WO200190304; US2004249130; US2004022727; WO2004063355; US2004197325; US2003232350; US2004005563; US2003124579; Horie et al (2000) Genomics 67:146-152; Uchida et al (1999) Biochem. Biophys. Res. Commun. 266:593-602; Liang et al (2000) Cancer Res. 60:4907-12; Glynne-Jones et al (2001) Int J. Cancer. October 15; 94(2):178-84.

SEQ ID NO:36

Production of Antibodies

Various methods have been employed to produce monoclonal antibodies (MAbs). Hybridoma technology, which refers to a cloned cell line that produces a single type of antibody, uses the cells of various species, including mice (murine), hamsters, rats, and humans. Other methods to prepare MAbs, including chimeric and humanized antibodies, uses genetic engineering, i.e. recombinant DNA techniques.

Polyclonal antibodies may be raised in animals by multiple subcutaneous (sc) or intraperitoneal (ip) injections of the relevant antigen and an adjuvant. Monoclonal antibodies are obtained from a population of substantially homogeneous antibodies, i.e., the individual antibodies comprising the population are identical except for possible naturally occurring mutations that may be present in minor amounts.

Human myeloma and mouse-human heteromyeloma cell lines also have been described for the production of human monoclonal antibodies (Kozbor, (1984) J. Immunol., 133: 3001, and Brodeur et al., *Monoclonal Antibody Production Techniques and Applications*, pp. 51-63 (Marcel Dekker, Inc., New York, 1987)). Culture medium in which hybridoma cells are growing is assayed for production of monoclonal antibodies directed against the antigen. Binding specificity of monoclonal antibodies produced by hybridoma cells may be determined by immunoprecipitation or by an in vitro binding assay, such as radioimmunoassay (RIA) or enzyme-linked immunoabsorbent assay (ELISA). The binding affinity of the monoclonal antibody can, for example, be determined by the Scatchard analysis of Munson et al (1980) Anal. Biochem. 107:220.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells (US 2005/0048572; US 2004/0229310). Review articles on recombinant expression in bacteria of DNA encoding the antibody include Skerra et al (1993) Curr. Opinion in Immunol. 5:256-262 and Plückthun (1992) Immunol. Revs. 130:151-188.

In a further embodiment, monoclonal antibodies or antibody fragments can be isolated from antibody phage libraries generated using the techniques described in McCafferty et al (1990) Nature 348:552-554; Clackson et al (1991) Nature 352:624-628; and Marks et al (1991) J. Mol. Biol., 222:581-597 describe the isolation of murine and human antibodies, respectively, using phage libraries. Subsequent publications describe the production of high affinity (nM range) human antibodies by chain shuffling (Marks et al (1992) Bio/Technology 10:779-783), as well as combinatorial infection and in vivo recombination as a strategy for constructing very large phage libraries (Waterhouse et al (1993) Nuc. Acids. Res. 21:2265-2266). Thus, these techniques are viable alternatives to traditional monoclonal antibody hybridoma techniques for isolation of monoclonal antibodies.

The DNA also may be modified, for example, by substituting the coding sequence for human heavy chain and light chain constant domains in place of the homologous murine sequences (U.S. Pat. No. 4,816,567); and Morrison et al (1984) Proc. Natl. Acad. Sci. USA 81:6851), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

A description follows as to exemplary techniques for the production of the antibodies (Ab) used in the antibody-drug conjugates (ADC) of the present invention. The production of antibodies will be illustrated with reference to anti-ErbB2 antibodies but it will be apparent for those skilled in the art that antibodies to other members of the ErbB receptor family, as well as any other receptor or tumor-associated antigen or target, can be produced and modified in a similar manner.

The ErbB2 antigen to be used for production of antibodies may be, e.g., a soluble form of the extracellular domain of ErbB2 or a portion thereof, containing the desired epitope. Alternatively, cells expressing ErbB2 at their cell surface, e.g. NIH-3T3 cells transformed to overexpress ErbB2; or a carcinoma cell line such as SK-BR-3 cells (Stancovski et al (1991) PNAS (USA) 88:8691-8695), can be used to generate antibodies. Other forms of ErbB2 useful for generating antibodies will be apparent to those skilled in the art.

Example 1 describes production of an exemplary humanized anti-ErbB2 antibody. The humanized antibody may, for example, comprise nonhuman hypervariable region residues incorporated into a human variable heavy domain and may further comprise a framework region (FR) substitution at a position selected from the group consisting of 69H, 71H and 73H utilizing the variable domain numbering system set forth in Kabat et al, *Sequences of Proteins of Immunological Interest*, 5th Ed. Public Health Service, National Institutes of Health, Bethesda, Md. (1991). In one embodiment, the humanized antibody comprises FR substitutions at two or all of positions 69H, 71H and 73H.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production (Jakobovits et al (1993) Proc. Natl. Acad. Sci. USA, 90:2551; Jakobovits et al (1993) Nature 362:255-258; Bruggermann et al (1993) Year in Immuno. 7:33; and U.S. Pat. No. 5,591,669; U.S. Pat. No. 5,589,369; U.S. Pat. No. 5,545,807).

Alternatively, phage display technology (McCafferty et al (1990) Nature 348:552-553) can be used to produce human antibodies and antibody fragments in vitro, from immunoglobulin variable (V) domain gene repertoires from unimmunized donors (Johnson, Kevin S. and Chiswell, David J. (1993) *Current Opinion in Structural Biology* 3:564-571). A repertoire of V genes from unimmunized human donors can be constructed and antibodies to a diverse array of antigens (including self-antigens) can be isolated essentially (Marks et al (1991) J. Mol. Biol. 222:581-597; Griffith et al (1993) EMBO J. 12:725-734; U.S. Pat. No. 5,565,332; U.S. Pat. No. 5,573,905). Human antibodies may also be generated by in vitro activated B cells (U.S. Pat. No. 5,567,610; U.S. Pat. No. 5,229,275). Human anti-ErbB2 antibodies are described (U.S. Pat. No. 5,772,997 and WO 97/00271.

Various techniques have been developed for the production of antibody fragments. Traditionally, these fragments were derived via proteolytic digestion of intact antibodies (see Morimoto et al (1992) Journal of Biochemical and Biophysical Methods 24:107-117; and Brennan et al (1985) Science 229:81). Antibody fragments can also be produced directly by recombinant host cells and the antibody phage libraries discussed above. Fab'-SH fragments can be directly recovered from *E. coli* and chemically coupled to form F(ab')$_2$ fragments (Carter et al (1992) Bio/Technology 10:163-167). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. The antibody fragment may also be a "linear antibody", e.g., as described in U.S. Pat. No. 5,641,870 for example. Such linear antibody fragments may be monospecific or bispecific.

Bispecific antibodies with binding specificities for at least two different epitopes (Millstein et al (1983), Nature 305: 537-539) may bind to two different epitopes of the ErbB2 protein. Other such antibodies may combine an ErbB2 binding site with binding site(s) for EGFR, ErbB3 and/or ErbB4. Alternatively, an anti-ErbB2 arm may be combined with an arm which binds to a triggering molecule on a leukocyte such as a T-cell receptor molecule (e.g. CD2 or CD3), or Fc receptors for IgG (FcγR), such as FcγRII (CD64), FcγRII (CD32) and FcγRIII (CD16) so as to focus cellular defense mechanisms to the ErbB2-expressing cell. Bispecific antibodies may also be used to localize cytotoxic agents to cells which express ErbB2 (WO 96/16673; U.S. Pat. No. 5,837,234; WO98/02463; U.S. Pat. No. 5,821,337). Purification methods for bispecific antibodies have been disclosed (WO 93/08829; Traunecker et al (1991) EMBO J. 10:3655-3659; WO 94/04690; Suresh et al (1986) *Methods in Enzymology* 121:210; U.S. Pat. No. 5,731,168). Bispecific antibodies can be produced using leucine zippers (Kostelny et al (1992) J. Immunol. 148(5):1547-1553), and single-chain Fv (sFv) dimers (Gruber et al (1994) J. Immunol. 152:5368).

Techniques for generating bispecific antibodies from antibody fragments have also been described, such as using chemical linkage wherein intact antibodies are proteolytically cleaved to generate F(ab')$_2$ fragments (Brennan et al (1985) Science 229:81). Fab'-SH fragments can be recovered from *E. coli* and chemically coupled to form bispecific antibodies (Shalaby et al (1992) J. Exp. Med. 175:217-225. The "diabody" technology provides an alternative method for making bispecific antibody fragments (Hollinger et al (1993) Proc. Natl. Acad. Sci. USA 90:6444-6448).

Antibodies with more than two valencies are contemplated. Multivalent, "Octopus" antibodies with three or more antigen binding sites and two or more variable domains can be readily produced by recombinant expression of nucleic acid encoding the polypeptide chains of the antibody (US 2002/0004586; WO 01/77342). For example, trispecific antibodies can be prepared (Tutt et al (1991) J. Immunol. 147:60.

Amino acid sequence modification(s) of antibodies are contemplated. For example, mutants and various isoforms of antibodies which bind to tumor-associated antigens are contemplated to improve the binding affinity and/or other biological properties of the antibody. Amino acid sequence variants of an antibody are prepared by introducing appropriate nucleotide changes into the nucleic acid encoding the antibody, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are preferred locations for mutagenesis is "alanine scanning mutagenesis" (Cunningham and Wells (1989) Science 244:1081-1085) where an amino acid residue, or group of target residues, are identified (e.g., charged residues such as arg, asp, his, lys, and glu) and replaced by a neutral or negatively charged amino acid, such as alanine or polyalanine, to optimize the interaction of the amino acids with antigen. Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-ErbB2 antibody with an N-terminal methionyl residue or the antibody fused to a cytotoxic polypeptide. Other insertional variants of the anti-ErbB2 antibody molecule include the fusion to the N- or C-terminus of the anti-ErbB2 antibody to an enzyme (e.g. for ADEPT: Tietze et al (2003) Current Pharm. Design 9:2155-2175) or a polypeptide which increases the serum half-life of the antibody, such as an albumin-binding peptide.

Plasma-protein binding can be an effective means of improving the pharmacokinetic properties of short lived molecules. Albumin is the most abundant protein in plasma. Serum albumin binding peptides (ABP) can alter the pharmacodynamics of fused active domain proteins, including alteration of tissue uptake, penetration, and diffusion. These pharmacodynamic parameters can be modulated by specific selection of the appropriate serum albumin binding peptide sequence (US 20040001827). A series of albumin binding peptides were identified by phage display screening (Dennis et al (2002) "Albumin Binding As A General Strategy For Improving The Pharmacokinetics Of Proteins" J Biol. Chem. 277:35035-35043; WO 01/45746). Compounds of the invention include ABP sequences taught by: (i) Dennis et al (2002) J Biol. Chem. 277:35035-35043 at Tables III and IV, page 35038; (ii) US 20040001827 at [0076] SEQ ID NOS: 9-22; and (iii) WO 01/45746 at pages 12-13, SEQ ID NOS: z1-z14, and all of which are incorporated herein by reference.

The amino acid sequence is usually altered by altering the underlying nucleic acid sequence. Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody. The sites of greatest interest for substitutional mutagenesis include the hypervariable regions, but FR alterations are also contemplated.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG$_1$, IgG$_2$, IgG$_3$, or IgG$_4$)

that is responsible for increasing the in vivo serum half-life of the IgG molecule (US 2003/0190311, U.S. Pat. No. 6,821,505; U.S. Pat. No. 6,165,745; U.S. Pat. No. 5,624,821; U.S. Pat. No. 5,648,260; U.S. Pat. No. 6,165,745;U.S. Pat. No. 5,834,597).

Glycosylation variants of antibodies are variants in which the glycosylation pattern of an antibody is altered. By altering is meant deleting one or more carbohydrate moieties found in the antibody, adding one or more carbohydrate moieties to the antibody, changing the composition of glycosylation (glycosylation pattern), or the extent of glycosylation.

Antibodies may be glycosylated at conserved positions (N-linked or O-linked) in their constant regions (Hse et al (1997) J. Biol. Chem. 272:9062-9070; Jefferis and Lund, (1997) Chem. Immunol. 65:111-128; Wright and Morrison, (1997) TibTECH 15:26-32). The oligosaccharide side chains of the immunoglobulins affect the protein's function (Boyd et al (1996) Mol. Immunol. 32:1311-1318; Wittwe and Howard, (1990) Biochem. 29:4175-4180), and the intramolecular interaction between portions of the glycoprotein which can affect the conformation and presented three-dimensional surface of the glycoprotein (Hefferis and Lund, supra; Wyss and Wagner (1996) Current Opin. Biotech. 7:409-416). Oligosaccharides may also serve to target a given glycoprotein to certain molecules based upon specific recognition structures (Malhotra et al (1995) Nature Med. 1:237-243; Umana et al (1999) Nature Biotech. 17:176-180). Removal of the oligosaccharides may optimize antigen binding and other properties of the antibody (Boyd et al (1996) Mol. Immunol. 32:1311-1318).

Factors which affect glycosylation during recombinant production of antibodies include growth mode, media formulation, culture density, oxygenation, pH, purification schemes and the like (U.S. Pat. No. 5,047,335; U.S. Pat. No. 5,510,261; U.S. Pat. No. 5,278,299). Glycosylation, or certain types of glycosylation, can be enzymatically removed from the glycoprotein, for example using endoglycosidase H (Endo H). In addition, the recombinant host cell can be genetically engineered, e.g. make defective in processing certain types of polysaccharides. These and similar techniques are well known in the art.

The glycosylation structure of antibodies can be readily analyzed by conventional techniques of carbohydrate analysis, including lectin chromatography, NMR, Mass spectrometry, HPLC, GPC, monosaccharide compositional analysis, sequential enzymatic digestion, and HPAEC-PAD, which uses high pH anion exchange chromatography to separate oligosaccharides based on charge. Methods for releasing oligosaccharides for analytical purposes are also known, and include, without limitation, enzymatic treatment (commonly performed using peptide-N-glycosidase F/endo-β-galactosidase), elimination using harsh alkaline environment to release mainly O-linked structures, and chemical methods using anhydrous hydrazine to release both N- and O-linked oligosaccharides.

Maytansinoid Drug Moieties

Maytansine compounds inhibit cell proliferation by inhibiting the formation of microtubules during mitosis through inhibition of polymerization of the microtubulin protein, tubulin (Remillard et al (1975) Science 189:1002-1005; U.S. Pat. No. 5,208,020). Maytansine and maytansinoids are highly cytotoxic but their clinical use in cancer therapy has been greatly limited by their severe systemic side-effects primarily attributed to their poor selectivity for tumors. Clinical trials with maytansine had been discontinued due to serious adverse effects on the central nervous system and gastrointestinal system (Issel et al (1978) Can. Treatment. Rev. 5:199-207.

Maytansinoid drug moieties are attractive drug moieties in antibody-drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Maytansine compounds suitable for use as maytansinoid drug moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods.

Exemplary maytansinoid drug moieties include those having a modified aromatic ring, such as: C-19-dechloro (U.S. Pat. No. 4,256,746) (prepared by lithium aluminum hydride reduction of ansamitocin P2); C-20-hydroxy (or C-20-demethyl)+/−C-19-dechloro (U.S. Pat. Nos. 4,361,650 and 4,307,016) (prepared by demethylation using $Streptomyces$ or $Actinomyces$ or dechlorination using LAH); and C-20-demethoxy, C-20-acyloxy (—OCOR), +/−dechloro (U.S. Pat. No. 4,294,757) (prepared by acylation using acyl chlorides). and those having modifications at other positions Exemplary maytansinoid drug moieties also include those having modifications such as: C-9-SH, prepared by the reaction of maytansinol with $H_2S$ or P2S5 (U.S. Pat. No. 4,424,219); C-14-alkoxymethyl(demethoxy/$CH_2$ OR)(U.S. Pat. No. 4,331,598); C-14-hydroxymethyl or acyloxymethyl ($CH_2OH$ or $CH_2OAc$) prepared from $Nocardia$ (U.S. Pat. No. 4,450,254); C-15-hydroxy/acyloxy, prepared by the conversion of maytansinol by $Streptomyces$ (U.S. Pat. No. 4,364,866); C-15-methoxy, isolated from Trewia nudlflora (U.S. Pat. No. 4,313,946 and U.S. Pat. No. 4,315,929); C-18-N-demethyl, prepared by the demethylation of maytansinol by $Streptomyces$ (U.S. Pat. No. 4,362,663 and U.S. Pat. No. 4,322,348); and 4,5-deoxy, prepared by the titanium trichloride/LAH reduction of maytansinol (U.S. Pat. No. 4,371,533).

Many positions on maytansine compounds are known to be useful as the linkage position, depending upon the type of link. For example, for forming an ester linkage, the C-3 position having a hydroxyl group, the C-14 position modified with hydroxymethyl, the C-15 position modified with a hydroxyl group and the C-20 position having a hydroxyl group are all suitable.

Maytansinoid drug moieties (D) include those having the structure:

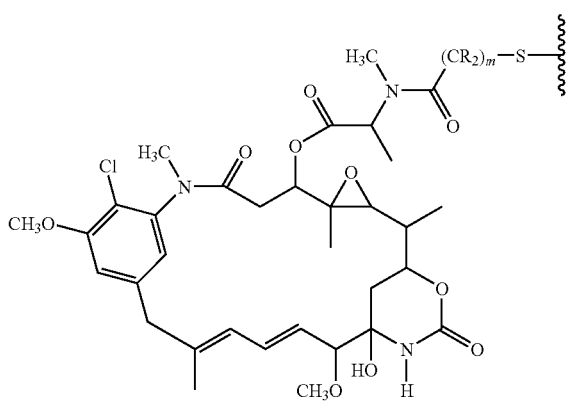

where the wavy line indicates the covalent attachment of the sulfur atom of D to a linker (L) of an antibody-drug conjugate (ADC). R may independently be H or a $C_1$-$C_6$ alkyl. The alkylene chain attaching the amide group to the sulfur atom may be methanyl, ethanyl, or propyl, i.e. m is 1, 2, or 3 (U.S. Pat. Nos. 633,410, 5,208,020, Chari et al (1992) Cancer Res. 52:127-131; Liu et al (1996) Proc. Natl. Acad. Sci. 93:8618-8623).

All stereoisomers of the maytansinoid drug moiety are contemplated for the compounds of the invention, i.e. any combination of R and S configurations at the chiral carbons of D. In one embodiment, the maytansinoid drug moiety (D) will have the following stereochemistry:

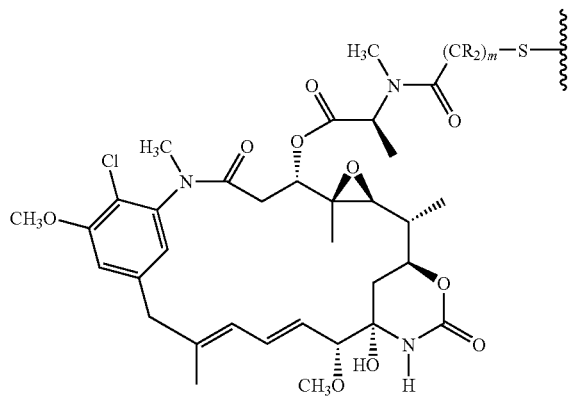

Embodiments of D include:
DM1 ($N^{2'}$-deacetyl-$N^{2'}$-(3-mercapto-1-oxopropyl)-maytansine) where $(CR_2)_m = CH_2CH_2$;

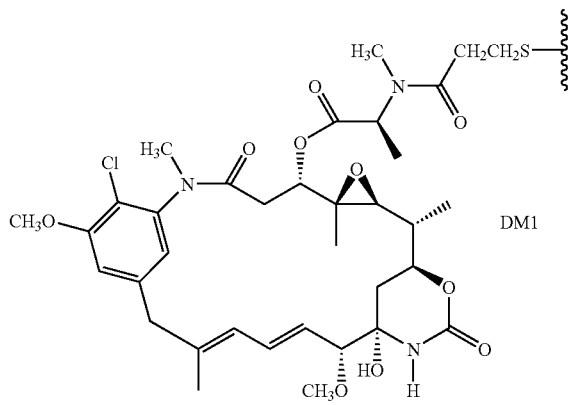

DM3 ($N^{2'}$-deacetyl-$N^{2'}$-(4-mercapto-1-oxopentyl)-maytansine) where $(CR_2)_m = CH_2CH_2CH(CH_3)$;

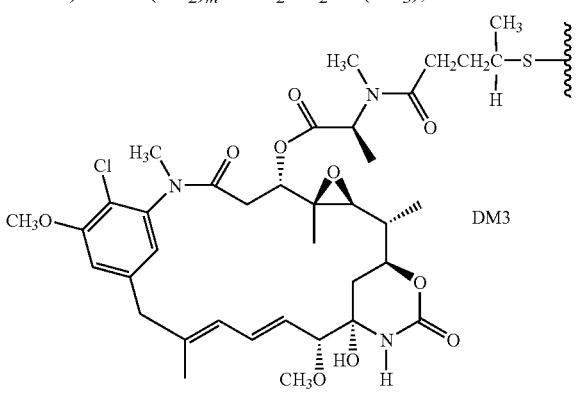

DM4 ($N^{2'}$-deacetyl-$N^{2'}$-(4-methyl-4-mercapto-1-oxopentyl)-maytansine) where $(CR_2)_m = CH_2CH_2C(CH_3)_2$:

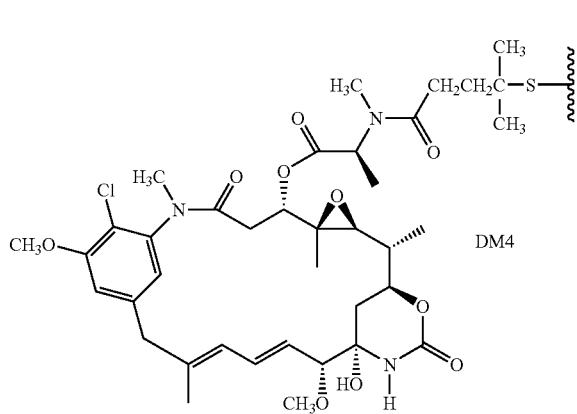

Steric hindrance conferred by alkyl groups such as the methyl groups on the carbon adjacent to the sulfur atom of DM3 and DM4 may affect the rate of intracellular cleavage of the ADC (US 2004/0235840 A1). The variable alkyl unit $(CR_2)_m$ may therefore affect potency, efficacy, and safety/toxicity in vitro and in vivo.

Linkers

The linker, L, attaches the antibody to a drug moiety through covalent bond(s), not comprising a disulfide group. The linker is a bifunctional or multifunctional moiety which can be used to link one or more Drug moieties (D) and an antibody unit (Ab) to form antibody-drug conjugates (ADC) of Formula I. Antibody-drug conjugates (ADC) can be conveniently prepared using a linker having reactive functionality for binding to the Drug and to the Antibody. A cysteine thiol, or an amine, e.g. N-terminus or amino acid side chain such as lysine, of the antibody (Ab) can form a bond with a functional group of a linker reagent, drug moiety or drug-linker reagent.

The linkers are preferably stable extracellularly. Before transport or delivery into a cell, the antibody-drug conjugate (ADC) is preferably stable and remains intact, i.e. the antibody remains linked to the drug moiety. The linkers are stable outside the target cell and may be cleaved at some efficacious rate inside the cell. An effective linker will: (i) maintain the specific binding properties of the antibody; (ii) allow intracellular delivery of the conjugate or drug moiety; (iii) remain stable and intact, i.e. not cleaved, until the conjugate has been delivered or transported to its targeted site; and (iv) maintain a cytotoxic, cell-killing effect or a cytostatic effect of the maytansinoid drug moiety. Stability of the ADC may be measured by standard analytical techniques such as mass spectroscopy, HPLC, and the separation/analysis technique LC/MS.

Covalent attachment of the antibody and the drug moiety requires the linker to have two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known, and methods have been described their resulting conjugates (Hermanson, G. T. (1996) *Bioconjugate Techniques*; Academic Press: New York, p234-242).

Linkers may have structures selected from:

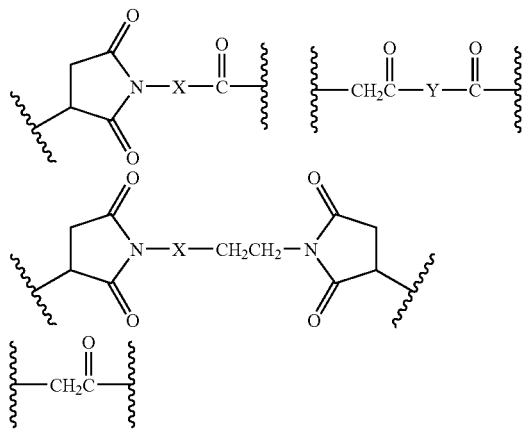

where the wavy lines indicate the covalent attachments to Ab and D in either orientation. X may have the structures, in either orientation:

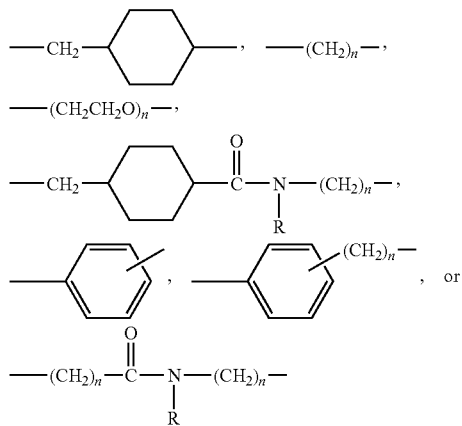

where R is independently H or $C_1$-$C_6$ alkyl; and n is 1 to 12. Y may have the structures, in either orientation:

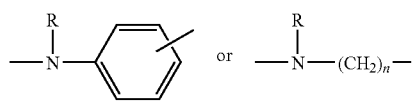

where R is independently H or $C_1$-$C_6$ alkyl; and n is 1 to 12.

For example, the linker may have the structure, designated as SMCC:

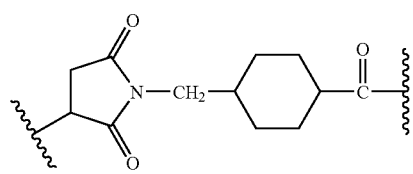

In another embodiment, linker (L) has the structure:

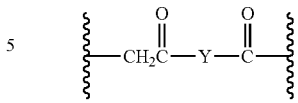

where the wavy lines indicate the covalent attachments to Ab and D in either orientation.

For example, the linker may have the structure, designated as SIAB:

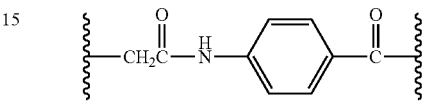

In another embodiment, linker (L) has the structure:

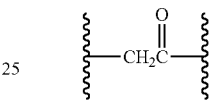

In another embodiment, the linker may be substituted with groups which modulated solubility or reactivity. For example, a sulfonate substituent may increase water solubility of the reagent and facilitate the coupling reaction of the linker reagent with the antibody or the drug moiety, or facilitate the coupling reaction of Ab-L with D, or D-L with Ab, depending on the synthetic route employed to prepare the ADC.

In another embodiment, a Linker has a reactive functional group which has a nucleophilic group that is reactive to an electrophilic group present on an antibody. Useful electrophilic groups on an antibody include, but are not limited to, aldehyde and ketone carbonyl groups. The heteroatom of a nucleophilic group of a Linker can react with an electrophilic group on an antibody and form a covalent bond to an antibody unit. Useful nucleophilic groups on a Linker include, but are not limited to, hydrazide, oxime, amino, hydrazine, thiosemicarbazone, hydrazine carboxylate, and arylhydrazide. The electrophilic group on an antibody provides a convenient site for attachment to a Linker.

Linkers can be peptidic, comprising one or more amino acid units. Peptide linker reagents may be prepared by solid phase or liquid phase synthesis methods (E. Schröder and K. Lübke, *The Peptides*, volume 1, pp 76-136 (1965) Academic Press) that are well known in the field of peptide chemistry, including t-BOC chemistry (Geiser et al "Automation of solid-phase peptide synthesis" in *Macromolecular Sequencing and Synthesis*, Alan R. Liss, Inc., 1988, pp. 199-218) and Fmoc/HBTU chemistry (Fields, G. and Noble, R. (1990) "Solid phase peptide synthesis utilizing 9-fluoroenylmethoxycarbonyl amino acids", Int. J. Peptide Protein Res. 35:161-214), on an automated synthesizer such as the Rainin Symphony Peptide Synthesizer (Protein Technologies, Inc., Tucson, Ariz.), or Model 433 (Applied Biosystems, Foster City, Calif.).

The compounds expressly contemplate, but are not limited to, ADC prepared with cross-linker reagents: BMPEO, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate), and including bis-maleimide reagents:

DTME, BMB, BMDB, BMH, BMOE, BM(PEO)$_2$, and BM(PEO)$_3$, which are commercially available from Pierce Biotechnology, Inc., Customer Service Department, P.O. Box 117, Rockford, Ill. 61105 U.S.A., U.S.A. 1-800-874-3723, International +815-968-0747. See pages 467-498, 2003-2004 Applications Handbook and Catalog. Bis-maleimide reagents allow the attachment of a free thiol group of a cysteine residue of an antibody to a thiol-containing drug moiety, label, or linker intermediate, in a sequential or concurrent fashion. Other functional groups besides maleimide, which are reactive with a thiol group of an antibody, maytansinoid drug moiety, or linker intermediate include iodoacetamide, bromoacetamide, vinyl pyridine, disulfide, pyridyl disulfide, isocyanate, and isothiocyanate.

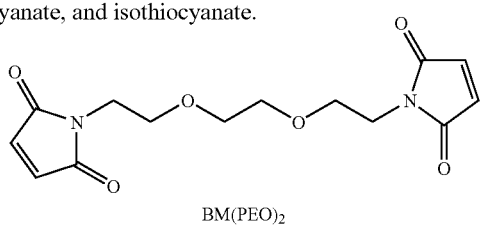

BM(PEO)$_2$

-continued

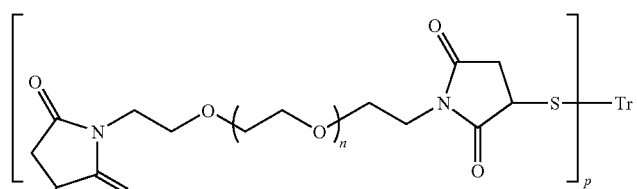

BM(PEO)$_3$

Exemplary antibody-drug conjugates where DM1 is linked through a BMPEO linker to a thiol group of trastuzumab have the structure:

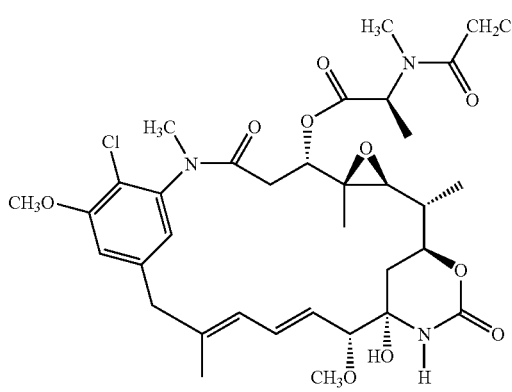

where Tr is trastuzumab; n is 0, 1, or 2; and p is 1, 2, 3, or 4.

Useful linker reagents can also be obtained via other commercial sources, such as Molecular Biosciences Inc. (Boulder, Colo.), or synthesized in accordance with procedures described in Toki et al (2002) J. Org. Chem. 67:1866-1872; U.S. Pat. No. 6,214,345 to Firestone et al; WO 02/088172; US 2003130189; US2003096743; WO 03/026577; WO 03/043583; and WO 04/032828.

The Linker may be a dendritic type linker for covalent attachment of more than one drug moiety through a branching, multifunctional linker moiety to an antibody (Sun et al (2002) Bioorganic & Medicinal Chemistry Letters 12:2213-2215; Sun et al (2003) Bioorganic & Medicinal Chemistry 11:1761-1768; King et al (2002) Tetrahedron Letters 43:1987-1990). Dendritic linkers can increase the molar ratio of drug to antibody, i.e. loading, which is related to the potency of the ADC. Thus, where an antibody bears only one reactive cysteine thiol group, a multitude of drug moieties may be attached through a dendritic linker.

The following exemplary embodiments of dendritic linker reagents allow up to nine nucleophilic drug moiety reagents to be conjugated by reaction with the chloroethyl nitrogen mustard functional groups:

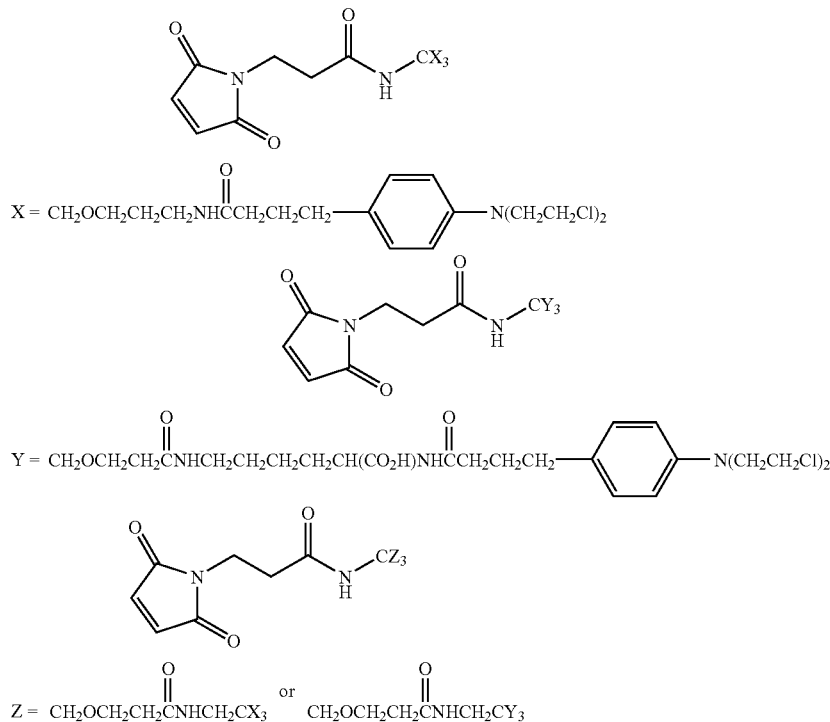

Drug Loading

The drug loading is represented by p in a molecule of Formula I, the average number of maytansinoid drugs per antibody. Drug loading may range from 1 to 8 drugs (D) per antibody (Ab), i.e. where 1, 2, 3, 4, 5, 6, 7, and 8 drug moieties are covalently attached to the antibody. Compositions of ADC of Formula I include collections of antibodies conjugated with a range of drugs, from 1 to 8. The average number of drugs per antibody in preparations of ADC from conjugation reactions may be characterized by conventional means such as mass spectroscopy, ELISA assay, electrophoresis, and HPLC. The quantitative distribution of ADC in terms of p may also be determined. By ELISA, the averaged value of p in a particular preparation of ADC may be determined (Hamblett et al (2004) Clinical Cancer Res. 10:7063-7070; Sanderson et al (2005) Clinical Cancer Res. 11:843-852). However, the distribution of p (drug) values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues. In some instances, separation, purification, and characterization of homogeneous ADC where p is a certain value from ADC with other drug loadings may be achieved by means such as reverse phase HPLC or electrophoresis.

For some antibody-drug conjugates, p may be limited by the number of attachment sites on the antibody. For example, where the attachment is a cysteine thiol, as in the exemplary embodiments above, an antibody may have only one or several cysteine thiol groups, or may have only one or several sufficiently reactive thiol groups through which a linker may be attached. Higher drug loading, e.g. p>5, may cause aggregation, insolubility, toxicity, or loss of cellular permeability of certain antibody-drug conjugates.

Typically, fewer than the theoretical maximum of drug moieties are conjugated to an antibody during a conjugation reaction. An antibody may contain, for example, many lysine residues that do not react with the drug-linker intermediate (D-L) or linker reagent. Only the most reactive lysine groups may react with an amine-reactive linker reagent. Also, only the most reactive cysteine thiol groups may react with a thiol-reactive linker reagent. Generally, antibodies do not contain many, if any, free and reactive cysteine thiol groups which may be linked to a drug moiety. Most cysteine thiol residues in the antibodies of the compounds exist as disulfide bridges and must be reduced with a reducing agent such as dithiothreitol (DTT) or TCEP, under partial or total reducing conditions. Additionally, the antibody must be subjected to denaturing conditions to reveal reactive nucleophilic groups such as lysine or cysteine. The loading (drug/antibody ratio) of an ADC may be controlled in several different manners, including: (i) limiting the molar excess of drug-linker intermediate (D-L) or linker reagent relative to antibody, (ii) limiting the conjugation reaction time or temperature, and (iii) partial or limiting reductive conditions for cysteine thiol modification.

Where more than one nucleophilic or electrophilic group of the antibody reacts with a drug-linker intermediate, or linker reagent followed by drug moiety reagent, then the resulting product is a mixture of ADC compounds with a distribution of drug moieties attached to an antibody, e.g. 1, 2, 3, etc. Liquid chromatography methods such as polymeric reverse phase (PLRP) and hydrophobic interaction (HIC) may separate compounds in the mixture by drug loading value. Preparations of ADC with a single drug loading value (p) may be isolated ("Effect of drug loading on the pharmacology, pharmacokinetics, and toxicity of an anti-CD30 antibody-drug conjugate", Hamblett, K. J., et al, Abstract No. 624, American Association for Cancer Research; 2004 Annual Meeting, Mar. 27-31, 2004, Proceedings of the AACR, Volume 45, March 2004; "Controlling the Location of Drug Attachment in Antibody-Drug Conjugates", Alley, S. C., et al, Abstract No. 627, American Association for Cancer Research; 2004 Annual Meeting, Mar. 27-31, 2004, Proceedings of the AACR, Volume 45, March 2004). However, these single loading value ADCs may still be heterogeneous mixtures because the drug moieties may be attached, via the linker, at different sites on the antibody.

Preparation of Antibody-Drug Conjugates

The ADC of Formula I may be prepared by several routes, employing organic chemistry reactions, conditions, and reagents known to those skilled in the art, including: (1) reaction of a nucleophilic group or an electrophilic group of an antibody with a bivalent linker reagent, to form antibody-linker intermediate Ab-L, via a covalent bond, followed by reaction with an activated drug moiety D; and (2) reaction of a nucleophilic group or an electrophilic group of a drug moiety with a linker reagent, to form drug-linker intermediate D-L, via a covalent bond, followed by reaction with the nucleophilic group or an electrophilic group of an antibody. Conjugation methods (1) and (2) may be employed with a variety of antibodies, drug moieties, and linkers to prepare the antibody-drug conjugates of Formula I.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (Cleland's reagent, dithiothreitol) or TCEP (tris(2-carboxyethyl)phosphine hydrochloride; Getz et al (1999) Anal. Biochem. Vol 273:73-80; Soltec Ventures, Beverly, Mass.). Each cysteine disulfide bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol.

Antibody-drug conjugates may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the protein that can react with appropriate groups on the drug (Hermanson, G. T. (1996) Bioconjugate Techniques; Academic Press: New York, p234-242). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Maytansine may, for example, be converted to May-SSCH$_3$, which can be reduced to the free thiol, May-SH, and reacted with a modified antibody (Chari et al (1992) Cancer Research 52:127-131) to generate a maytansinoid-antibody immunoconjugate with a disulfide linker. Antibody-maytansinoid conjugates with disulfide linkers have been reported (WO 04/016801; U.S. Pat. No. 6,884,874; US 2004/039176 A1; WO 03/068144; US 2004/001838 A1; U.S. Pat. No. 6,441,163; U.S. Pat. No. 5,208,020; U.S. Pat. No. 5,416,064; WO 01/024763). The disulfide linker SPP is constructed with linker reagent N-succinimidyl 4-(2-pyridylthio) pentanoate. Antibody-SPP-DM1 conjugates are represented by the structure:

Disulfide (S-S) linker antibody-drug conjugates were tested for purposes of comparison to the non-disulfide linker ADC of the invention. Trastuzumab-SPP-DM1 was prepared according to Example 3 (Ranson, M. and Sliwkowski M. (2002) Oncology 63(suppl 1): 17-24). Disulfide antibody-drug conjugates: trastuzumab-SPDP-DM1, trastuzumab-SPP-DM3, and trastuzumab-SPP-DM4 were also tested, and have the structures below:

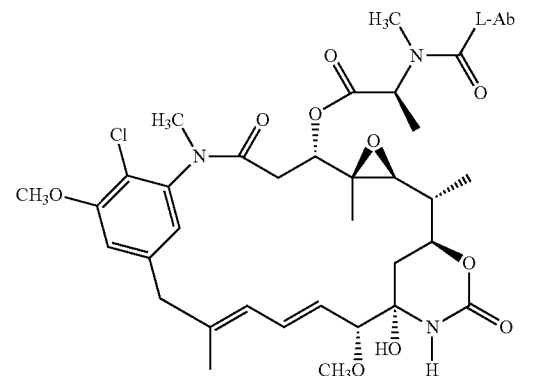

Trastuzumab-SPDP-DM1

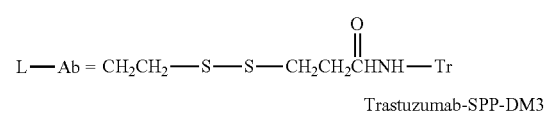

Trastuzumab-SPP-DM3

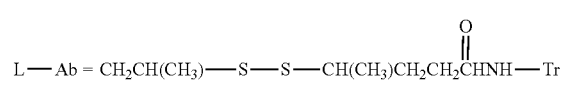

Trastuzumab-SPP-DM4

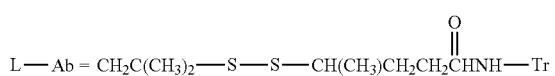

ADC of the invention include SMCC linkers and the DM1 maytansinoid drug moiety, represented as Ab-SMCC-DM1:

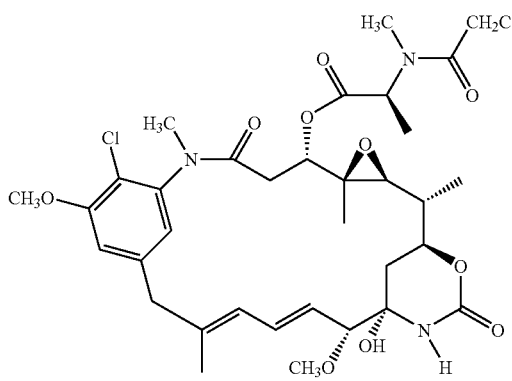

One embodiment of Ab-SMCC-DM1 is trastuzumab-SMCC-DM1 where p is 1, 2, 3, or 4 (Ab=trastuzumab, Tr, WO 2005/037992). Another embodiment of an ADC is trastuzumab-SIAB-DM1 (trastuzumab=Tr) having the structure:

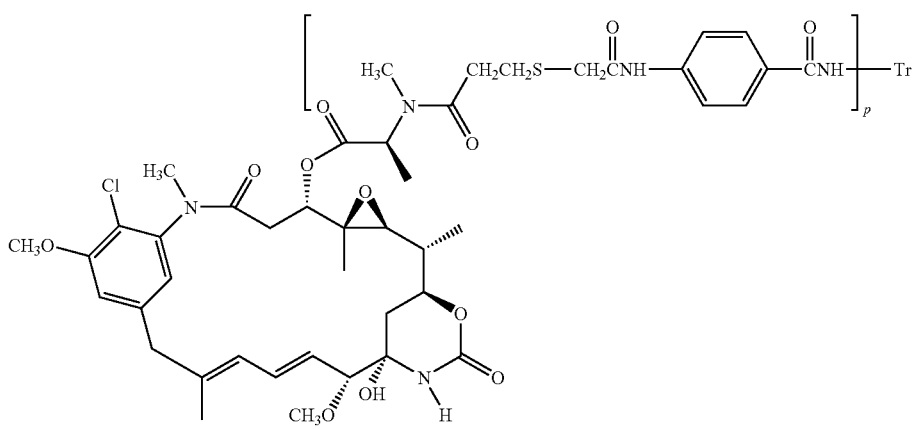

istering candidate ADC over a range of doses to the transgenic animal, and assaying at various time points for the effect(s) of the ADC on the disease or disorder being evaluated. Alternatively, or additionally, the drug can be administered prior to or simultaneously with exposure to an inducer of the disease, if applicable. Candidate ADC may be screened serially and individually, or in parallel under medium or high-throughput screening format. The rate at which ADC may be screened for utility for prophylactic or therapeutic treatments of diseases or disorders is limited only by the rate of synthesis or screening methodology, including detecting/measuring/analysis of data.

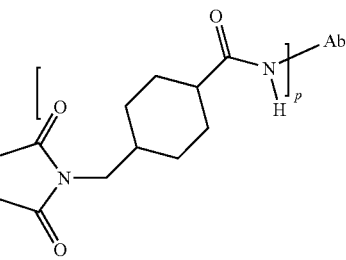

Screening for Antibody-Drug Conjugates (ADC) Directed Against Tumor-Associated Antigens and Cell Surface Receptors Transgenic animals and cell lines are particularly useful in screening antibody-drug conjugates (ADC) that have potential as prophylactic or therapeutic treatments of diseases or disorders involving overexpression of tumor-associated antigens and cell surface receptors, e.g. HER2 (U.S. Pat. No. 6,632,979). Screening for a useful ADC may involve admin- One embodiment is a screening method comprising (a) transplanting cells from a stable breast cancer cell line into a non-human animal, (b) administering an ADC drug candidate to the non-human animal and (c) determining the ability of the candidate to inhibit the formation of tumors from the transplanted cell line. The invention also concerns a method of screening ADC candidates for the treatment of a disease or disorder characterized by the overexpression of a receptor protein comprising (a) contacting cells from a stable breast cancer cell line with a drug candidate and (b) evaluating the ability of the ADC candidate to inhibit the growth of the stable cell line.

One embodiment is a screening method comprising (a) contacting cells from a stable breast cancer cell line with an ADC drug candidate and (b) evaluating the ability of the ADC candidate to block ligand activation of HER2. Another embodiment the ability of the ADC candidate to block heregulin binding is evaluated. In another embodiment the ability of the ADC candidate to block ligand-stimulated tyrosine phosphorylation is evaluated.

Another embodiment is a screening method comprising (a) contacting cells from a stable breast cancer cell line with an ADC drug candidate and (b) evaluating the ability of the ADC candidate to induce cell death. In one embodiment the ability of the ADC candidate to induce apoptosis is evaluated.

Another embodiment is a screening method comprising (a) administering an ADC drug candidate to a transgenic non-human mammal that overexpresses, e.g. in its mammary gland cells, a native human protein, e.g. HER2 or a fragment thereof, wherein such transgenic mammal has stably integrated into its genome a nucleic acid sequence encoding the native human protein or a fragment thereof having the biological activity of the native human protein, operably linked to transcriptional regulatory sequences directing its expression, and develops a tumor, e.g. a mammary tumor, not responding or poorly responding to antibody treatment, e.g. anti-HER2, or to a non-human mammal bearing a tumor transplanted from said transgenic non-human mammal; and (b) evaluating the effect of the ADC candidate on the target disease or disorder. Without limitations, the disease or disorder may be a HER2-overexpressing cancer, such as breast, ovarian, stomach, endometrial, salivary gland, lung, kidney, colon, thyroid, pancreatic and bladder cancer. The cancer may be breast cancer which expressed HER2 in at least about 500,000 copies per cell, or at least about 2,000,000 copies per cell. ADC drug candidates may, for example, be evaluated for their ability to induce cell death and/or apoptosis, using assay methods well known in the art and described hereinafter.

In one embodiment, candidate ADC are screened by being administered to the transgenic animal over a range of doses, and evaluating the animal's physiological response to the compounds over time. Administration may be oral, or by suitable injection, depending on the chemical nature of the compound being evaluated. In some cases, it may be appropriate to administer the compound in conjunction with co-factors that would enhance the efficacy of the compound. If cell lines derived from the subject transgenic animals are used to screen for compounds useful in treating various disorders associated with overexpression of certain tumor-associated antigen proteins or cell surface receptors, e.g. HER2-overexpression, the test compounds are added to the cell culture medium at an appropriate time, and the cellular response to the compound is evaluated over time using the appropriate biochemical and/or histological assays. In some cases, it may be appropriate to apply the compound of interest to the culture medium in conjunction with co-factors that would enhance the efficacy of the compound.

Thus, the present invention provides assays for identifying ADC which specifically target and bind the overexpressed HER2 protein, the presence of which is correlated with abnormal cellular function, and in the pathogenesis of cellular proliferation and/or differentiation of mammary gland that is causally related to the development of breast tumors.

To identify an ADC which blocks ligand activation of an ErbB (e.g. ErbB2) receptor, the ability of the compound to block ErbB ligand binding to cells expressing the ErbB (ErbB2) receptor (e.g. in conjugation with another ErbB receptor with which the ErbB receptor of interest forms an ErbB hetero-oligomer) may be determined. For example, cells isolated from the transgenic animal overexpressing HER2 and transfected to express another ErbB receptor (with which HER2 forms hetero-oligomer) may be incubated, i.e. culturing, with the ADC and then exposed to labeled ErbB ligand. The ability of the compound to block ligand binding to the ErbB receptor in the ErbB hetero-oligomer may then be evaluated.

For example, inhibition of heregulin (HRG) binding to breast tumor cell lines, overexpressing HER2 and established from the transgenic non-human mammals (e.g. mice) herein, by the candidate ADC may be performed using monolayer cultures on ice in a 24-well-plate format. Anti-ErbB2 monoclonal antibodies may be added to each well and incubated for 30 minutes. $^{125}$I-labeled rHRGβ$1_{177-224}$ (25,000 cpm) may then be added, and the incubation may be continued for 4 to 16 hours. Dose response curves may be prepared and an IC$_{50}$ value may be calculated for the compound of interest.

Alternatively, or additionally, the ability of an ADC to block ErbB ligand-stimulated tyrosine phosphorylation of an ErbB receptor present in an ErbB hetero-oligomer may be assessed. For example, cell lines established from the transgenic animals herein may be incubated with a test ADC and then assayed for ErbB ligand-dependent tyrosine phosphorylation activity using an anti-phosphotyrosine monoclonal antibody (which is optionally conjugated with a detectable label). The kinase receptor activation assay described in U.S. Pat. No. 5,766,863 is also available for determining ErbB receptor activation and blocking of that activity by the compound.

In one embodiment, one may screen for ADC which inhibit HRG stimulation of p180 tyrosine phosphorylation in MCF7 cells essentially as described below. For example, a cell line established from a HER2-transgenic animal may be plated in 24-well plates and the compound may be added to each well and incubated for 30 minutes at room temperature; then rHRGβ$_{1177-244}$ may be added to each well to a final concentration of 0.2 nM, and the incubation may be continued for about 8 minutes. Media may be aspirated from each well, and reactions may be stopped by the addition of 100 μl of SDS sample buffer (5% SDS, 25 mM DTT, and 25 mM Tris-HCl, pH 6.8). Each sample (25 μl) may be electrophoresed on a 4-12% gradient gel (Novex) and then electrophoretically transferred to polyvinylidene difluoride membrane. Antiphosphotyrosine (at 1 μg/ml) immunoblots may be developed, and the intensity of the predominant reactive band at M$_r$-180,000 may be quantified by reflectance densitometry. An alternate method to evaluate inhibition of receptor phosphorylation is the KIRA (kinase receptor activation) assay (Sadick et al (1998) Jour. of Pharm. and Biomed. Anal. 1-9). Some of the well-established monoclonal antibodies against HER2 that are known to inhibit HRG stimulation of p180 tyrosine phosphorylation can be used as positive control in this assay. A dose-response curve for inhibition of HRG stimulation of p180 tyrosine phosphorylation as determined by reflectance densitometry may be prepared and an IC$_{50}$ for the compound of interest may be calculated.

One may also assess the growth inhibitory effects of a test ADC on cell lines derived from a HER2-transgenic animal (Schaefer et al (1997) Oncogene 15:1385-1394). According to this assay, the cells may be treated with a test compound at various concentrations for 4 days and stained with crystal violet or the redox dye Alamar Blue. Incubation with the compound may show a growth inhibitory effect on this cell line similar to that displayed by monoclonal antibody 2C4 on MDA-MB-175 cells (Schaefer et al., supra). In a further embodiment, exogenous HRG will not significantly reverse this inhibition.

To identify growth inhibitory ADC compounds that specifically target HER2, one may screen for ADC which inhibit the growth of HER2-overexpressing cancer cells derived from transgenic animals (U.S. Pat. No. 5,677,171). According to this assay, HER2 overexpressing cells are grown in a 1:1 mixture of F12 and DMEM medium supplemented with 10% fetal bovine serum, glutamine and penicillin streptomycin. The cells are plated at 20,000 cells in a 35 mm cell culture dish (2 mls/35 mm dish) and the test compound is added at various concentrations. After six days, the number of cells, compared to untreated cells is counted using an electronic COULTER™ cell counter. Those ADC which inhibit cell growth by about 20-100% or about 50-100% may be selected as growth inhibitory compounds.

To select for ADC which induce cell death, loss of membrane integrity as indicated by, e.g., PI, trypan blue or 7AAD uptake may be assessed relative to control. The PI uptake assay uses cells isolated from the breast tumor tissue of a transgenic animal. According to this assay, the cells are cultured in Dulbecco's Modified Eagle Medium (D-MEM): Ham's F-12 (50:50) supplemented with 10% heat-inactivated FBS (Hyclone) and 2 mM L-glutamine. Thus, the assay is performed in the absence of complement and immune effector cells. The cells are seeded at a density of 3×106 per dish in 100×20 mm dishes and allowed to attach overnight. The medium is then removed and replaced with fresh medium alone or medium containing various concentrations of the compound. The cells are incubated for a 3-day time period. Following each treatment, monolayers are washed with PBS and detached by trypsinization. Cells are then centrifuged at 1200 rpm for 5 minutes at 4° C., the pellet resuspended in 3 ml cold $Ca^{2+}$ binding buffer (10 mM Hepes, pH 7.4, 140 mM NaCl, 2.5 mM $CaCl_2$) and aliquoted into 35 mm strainer-capped 12×75 mm tubes (1 ml per tube, 3 tubes per treatment group) for removal of cell clumps. Tubes then receive PI (10 μg/ml). Samples may be analyzed using a FACSCAN™ flow cytometer and FACSCONVERT™ CellQuest software (Becton Dickinson). Those compounds which induce statistically significant levels of cell death as determined by PI uptake may be selected as cell death-inducing compounds.

In order to select for compounds which induce apoptosis, an annexin binding assay using cells established from the breast tumor tissue of the transgenic animal is performed. The cells are cultured and seeded in dishes as discussed in the preceding paragraph. The medium is then removed and replaced with fresh medium alone or medium containing 10 μg/ml of the antibody-drug conjugate (ADC). Following a three-day incubation period, monolayers are washed with PBS and detached by trypsinization. Cells are then centrifuged, resuspended in $Ca^{2+}$ binding buffer and aliquoted into tubes as discussed above for the cell death assay. Tubes then receive labeled annexin (e.g. annexin V-FITC) (1 μg/ml). Samples may be analyzed using a FACSCAN™ flow cytometer and FACSCONVERT™ CellQuest software (Becton Dickinson). Those compounds which induce statistically significant levels of annexin binding relative to control are selected as apoptosis-inducing compounds.

In Vitro Cell Proliferation Assays

Generally, the cytotoxic or cytostatic activity of an antibody-drug conjugate (ADC) is measured by: exposing mammalian cells having tumor-associated antigens or receptor proteins to the antibody of the ADC in a cell culture medium; culturing the cells for a period from about 6 hours to about 5 days; and measuring cell viability. Cell-based in vitro assays were used to measure viability, i.e. proliferation ($IC_{50}$), cytotoxicity ($EC_{50}$), and induction of apoptosis (caspase activation) of the ADC.

The in vitro potency of antibody-drug conjugates was measured by a cell proliferation assay (FIGS. 1-4). The CellTiter-Glo® Luminescent Cell Viability Assay is a commercially available (Promega Corp., Madison, Wis.), homogeneous assay method based on the recombinant expression of *Coleoptera luciferase* (U.S. Pat. No. 5,583,024; U.S. Pat. No. 5,674,713; U.S. Pat. No. 5,700,670). This cell proliferation assay determines the number of viable cells in culture based on quantitation of the ATP present, an indicator of metabolically active cells (Crouch et al (1993) J. Immunol. Meth. 160:81-88; U.S. Pat. No. 6,602,677). The CellTiter-Glo® Assay was conducted in 96 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay an be used with various multiwell formats, e.g. 96 or 384 well format. Data can be recorded by luminometer or CCD camera imaging device. The luminescence output is presented as relative light units (RLU), measured over time.

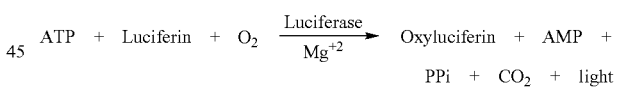

$$ATP + Luciferin + O_2 \xrightarrow[Mg^{+2}]{Luciferase} Oxyluciferin + AMP + PPi + CO_2 + light$$

The anti-proliferative effects of three antibody-drug conjugates were measured by the cell proliferation, in vitro cell killing assay above against four different breast tumor cell lines (FIGS. 1-4). FIG. 1 shows the potency measurements at increasing concentrations of trastuzumab-SPP-DM1, trastuzumab-SPDP-DM1 and trastuzumab-SMCC-DM1 after a 3 day treatment on SK-BR-3 (HER2 3+) breast tumor cells. FIG. 2 shows the potency measurements of at increasing concentrations of trastuzumab-SPP-DM1, trastuzumab-SPDP-DM1 and trastuzumab-SMCC-DM1 after a 3 day treatment on BT-474 (HER2 3+) breast tumor cells. FIG. 3 shows the potency measurements of at increasing concentrations of trastuzumab-SPP-DM1, trastuzumab-SPDP-DM1 and trastuzumab-SMCC-DM1 after a 3 day treatment on MCF7 (HER2 low) breast tumor cells. FIG. 4 shows the potency measurements at increasing concentrations of trastuzumab-SPP-DM1, trastuzumab-SPDP-DM1 and trastuzumab-SMCC-DM1 after a 3 day treatment on MDA-MB-468 (HER2 negative) breast tumor cells.

IC$_{50}$ values were established for SK-BR-3 and BT-474 which are known to overexpress HER2 receptor protein. A lot of conjugate trastuzumab-SPP-DM1 with 2.8 DM1 per trastuzumab (drug/Ab) gave a mean IC$_{50}$ of 14.4 μg/ml with a range 9.1 to 22.3 μg/ml for 6 experiments against SK-BR-3 cells and a mean IC$_{50}$ of 51.7 μg/ml with a range 28.7 to 63.1 μg/ml for 4 experiments against BT-474 cells. A lot of conjugate trastuzumab-SMCC-DM1 with 2.7 DM1 per trastuzumab (drug/Ab) gave a mean IC$_{50}$ of 15.2 μg/ml with a range 12.6 to 18.8 μg/ml for 4 experiments against SK-BR-3 cells and a mean IC$_{50}$ of 94.9 μg/ml with a range 75.2 to 114.6 μg/ml for 2 experiments against BT-474 cells. The conjugates were inactive against cells MCF7 and MDA-MB-468 which do not overexpress HER2.

AntiCD19-SMCC-DM1 showed potent cell killing in vitro with Raji cells (IC$_{50}$=<0.25 μg/ml) where the naked antibody and control ADC, trastuzumab-SMCC-DM1 showed no effect. AntiCD79a-SMCC-DM1 and antiCD79b-SMCC-DM1 showed potent cell killing in vitro with Ramos cells (IC$_{50}$=<0.25 μg/ml) where the naked antibody and control ADC, trastuzumab-SMCC-DM1 showed no effect.

FIG. 17 shows an in vitro, cell proliferation assay (Example 5) with HT1080EphB2 (C8) cells treated with antiEphB2R 2H9 antibody-drug conjugates: 2H9-SPP-DM1 (IC$_{50}$ 80 ng/ml), and 2H9-SMCC-DM1 (IC$_{50}$ 50 ng/ml).

In Vivo Serum Clearance and Stability in Mice

Figure 5:
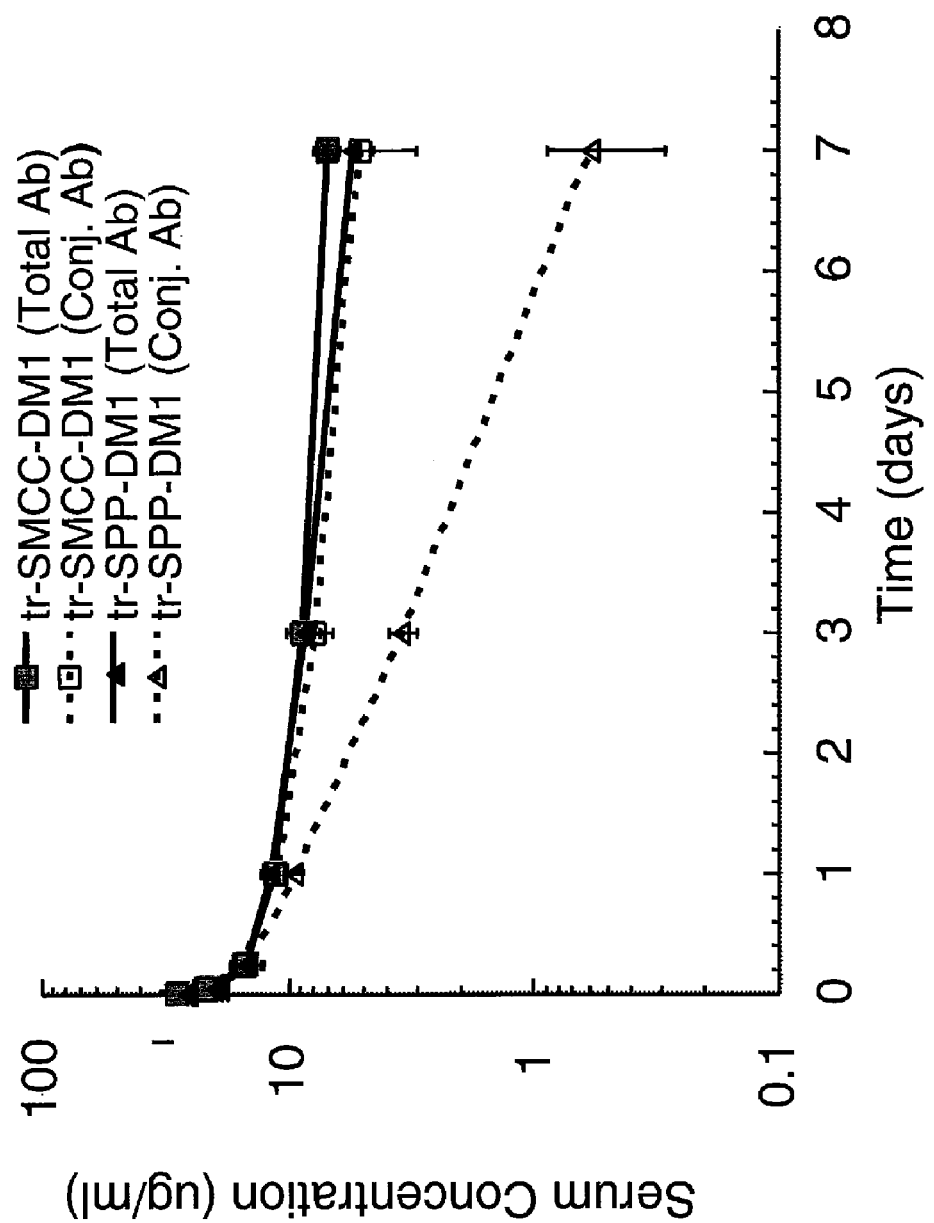
FIG. 5 shows the serum clearance in beige nude mice without tumors of trastuzumab-SMCC-DM1 vs. trastuzumab-SPP-DM1, measuring conjugate and total antibody serum concentration at six time points (5 minutes, 1 hour, 6 hours, 24 hours, 72, 168 hours post-dose) over 7 days.

Serum clearance and stability of ADC were investigated in nude, naive (without tumors received by exogenous grafts) mice. FIG. 5 shows the serum clearance in beige nude mice without tumors of trastuzumab-SMCC-DM1 vs. trastuzumab-SPP-DM1, measuring conjugate and total antibody serum concentration at six time points over 7 days. A difference in the amount of total antibody and ADC indicates cleavage of the linker and separation of the antibody from its DM1 moiety. As illustrated by the higher conjugated antibody serum concentration at seven days, SMCC-linked ADC remained intact in vivo longer than did SPP-linked conjugates.

FIG. 6 shows the stability over time in nude mice without tumors of the conjugates: trastuzumab-SPDP-DM1, trastuzumab-SPP-DM1, trastuzumab-SPP-DM3, trastuzumab-SPP-DM4, and trastuzumab-SMCC-DM1, measuring serum concentration at six time points over 7 days. ADC with the SMCC linker were more stable in vivo than were conjugates linked by SPP or SPDP, although trastuzumab-SMCC-DM1 had approximately the same stability as the most hindered disulfide conjugate, trastuzumab-SPP-DM4.

The experiments shown in FIGS. 5 and 6 were performed in nude mice without tumors. However, SMCC-linked conjugates showed the same increased stability compared to SPP-linked conjugates in nude mice with tumors. As shown in FIG. 7, approximately 72% of the initial trastuzumab-SMCC-DM1 remained as a conjugate 7 days after treatment, while only approximately 10% of the initial trastuzumab-SPP-DM1 remained as a conjugate 7 days after treatment, illustrating the improved stability of non-enzymatically cleavable trastuzumab-SMCC-DM1 conjugates in nude mice with tumors.

In Vivo Serum Clearance and Stability in Rats

FIGS. 8 and 9 show the comparative stability and clearance profiles of a disulfide linker ADC (trastuzumab-SPP-DM1 and a non-disulfide linker ADC (trastuzumab-SMCC-DM1) in rats. The parameters of the study include:

| Parameter | trastuzumab-SPP-DM1 | trastuzumab-SMCC-DM1 |
|---|---|---|
| Vd (ml/kg) | 41 | 41 |
| Clearance (ml/day/kg) | 52 | 15 |
| T ½ alpha | 0.09 | 0.15 |
| T ½ beta | 0.7 | 0.85 |
| T ½ gamma (days) | 2.6 | 5.5 |

The non-disulfide linker ADC, trastuzumab-SMCC-DM1 (FIG. 9), showed better stability in rat serum than the disulfide linker ADC, trastuzumab-SPP-DM1 (FIG. 8).

In Vivo Efficacy

The efficacy of the antibody-drug conjugates of the invention may be measured in vivo by implanting allografts or xenografts of cancer cells in rodents and treating the tumors with ADC. Variable results are to be expected depending on the cell line, the specificity of antibody binding of the ADC to receptors present on the cancer cells, dosing regimen, and other factors. The in vivo efficacy of anti-HER2 ADC was measured by a high expressing HER2 transgenic explant mouse model. An allograft was propagated from the Fo5 mmtv transgenic mouse which does not respond to, or responds poorly to, HERCEPTIN® (trastuzumab) therapy. Subjects were treated once with ADC and monitored over 3-6 weeks to measure the time to tumor doubling, log cell kill, and tumor shrinkage. Follow up dose-response and multi-dose experiments were conducted.

Tumors arise readily in transgenic mice that express a mutationally activated form of neu, the rat homolog of HER2, but the HER2 that is overexpressed in breast cancers is not mutated and tumor formation is much less robust in transgenic mice that overexpress nonmutated HER2 (Webster et al (1994) Semin. Cancer Biol. 5:69-76).

To improve tumor formation with nonmutated HER2, transgenic mice were produced using a HER2 cDNA plasmid in which an upstream ATG was deleted in order to prevent initiation of translation at such upstream ATG codons, which would otherwise reduce the frequency of translation initiation from the downstream authentic initiation codon of HER2 (for example, see Child et al (1999) J. Biol. Chem. 274: 24335-24341). Additionally, a chimeric intron was added to the 5' end, which should also enhance the level of expression as reported earlier (Neuberger and Williams (1988) Nucleic Acids Res. 16: 6713; Buchman and Berg (1988) Mol. Cell. Biol. 8: 4395; Brinster et al (1988) Proc. Natl. Acad. Sci. USA 85:836). The chimeric intron was derived from a Promega vector, pCI-neo mammalian expression vector (bp 890-1022). The cDNA 3'-end is flanked by human growth hormone exons 4 and 5, and polyadenylation sequences. Moreover, FVB mice were used because this strain is more susceptible to tumor development. The promoter from MMTV-LTR was used to ensure tissue-specific HER2 expression in the mammary gland. Animals were fed the AIN 76A diet in order to increase susceptibility to tumor formation (Rao et al (1997) Breast Cancer Res. and Treatment 45:149-158).

Figure 11:
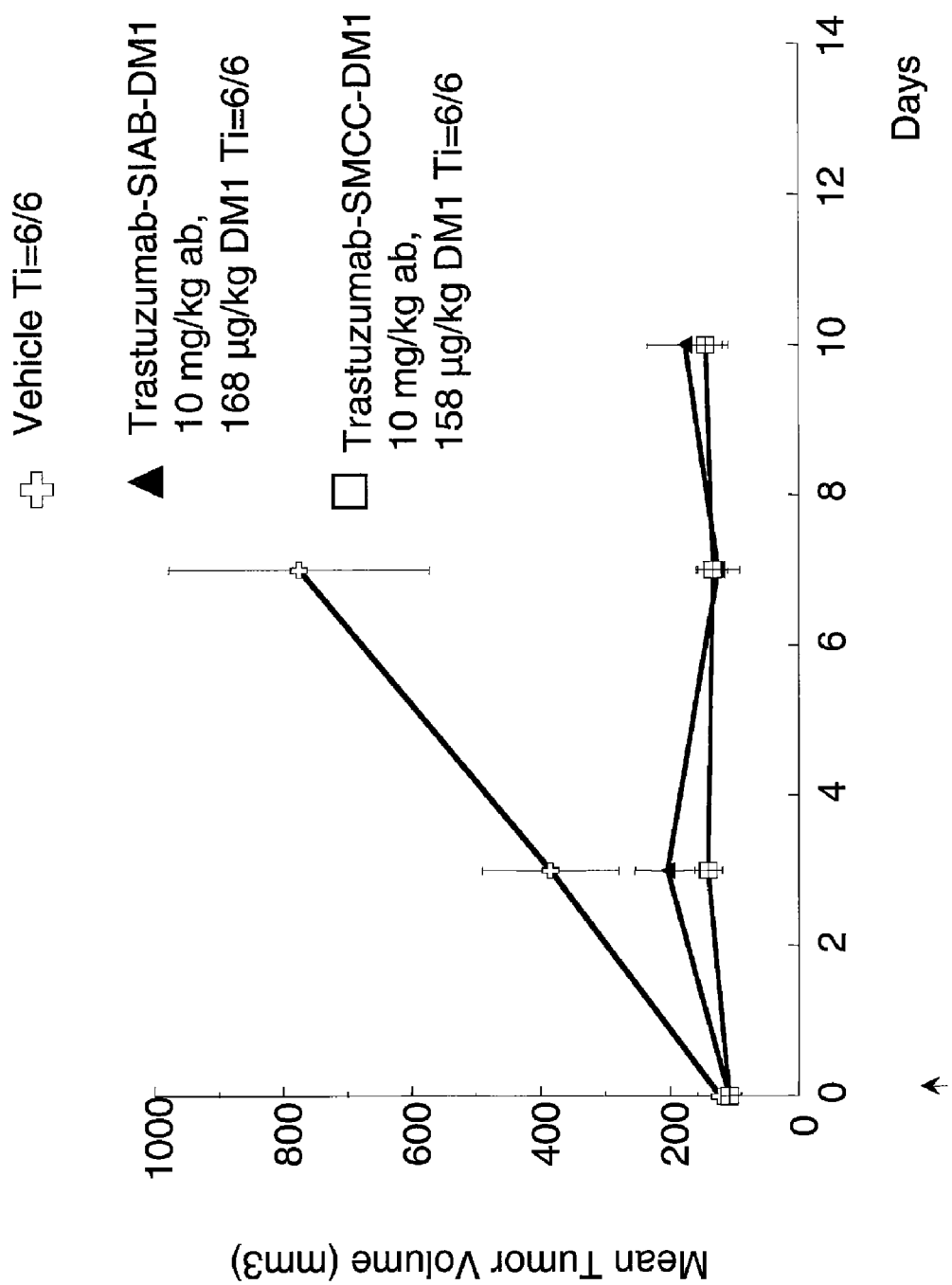
FIG. 11 shows the mean tumor volume change over time in athymic nude mice with Fo5 tumor allografts dosed on Day 0 with: Vehicle (PBS pH 6.5), 10 mg/kg trastuzumab-SIAB-DM1 (3.4 DM1/Ab; 168 μg DM1/kg), and 10 mg/kg trastuzumab-SMCC-DM1 (3.2 DM1/Ab; 158 μg DM1/kg) where dose refers to the dose amount of the antibody-drug conjugate administered.
Figure 13:
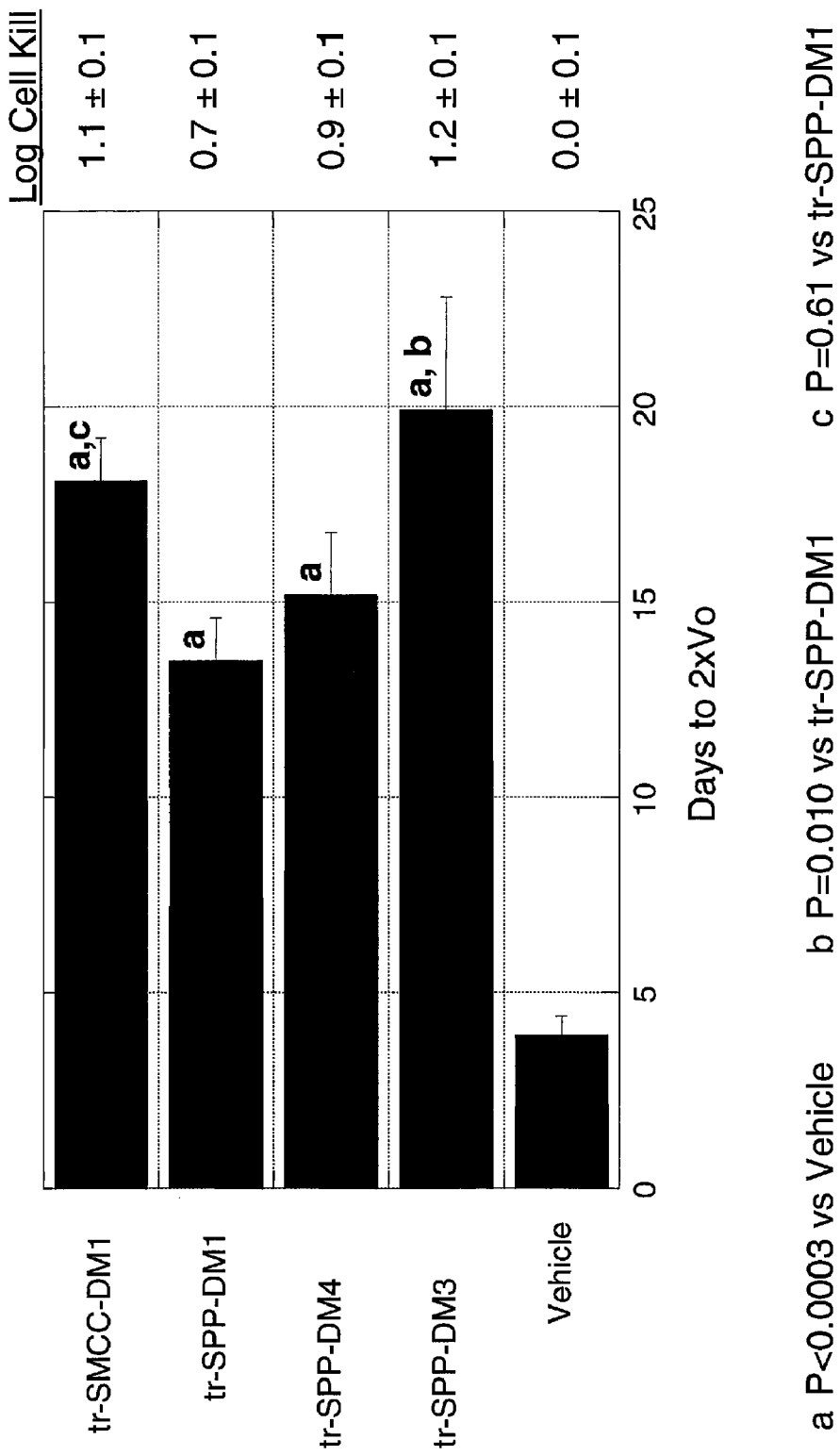
FIG. 13 shows the time to double tumor volume and log cell kill analysis for Vehicle (PBS pH 6.5), trastuzumab-SPP-DM1, trastuzumab-SPP-DM4, trastuzumab-SPP-DM3, and trastuzumab-SMCC-DM1 in HER2—Fo5 tumors.

FIGS. 10-13 show that the ADC have strong anti-tumor activity in the allograft of a HER2 positive tumor (Fo5) that originally arose in an MMTV-HER2 transgenic mouse. The antibody alone (e.g. trastuzumab) does not have significant anti-tumor activity in this model (Erickson et al U.S. Pat. No. 6,632,979). As illustrated in FIGS. 10 and 11, the growth of the tumors was retarded by treatment with ADC as compared to control (Vehicle) level of growth. Tumor growth was slowed most by treatment with trastuzumab-SMCC-DM1 and trastuzumab-SIAB-DM1 conjugates. As shown in FIGS. 10, 12 and 13, the trastuzumab-SMCC-DM1 conjugate slowed tumor growth more than conjugates with SPP linkers, i.e. more potency, whether measured as doubling time of tumors in nude mice or as Log Cell Kill corresponding to the doubling time measurements shown (FIG. 13).

The in vivo efficacy of anti-CD22 ADC was measured with a mouse tumor xenograft model. Groups of eight SCID mice with 20 million Bjab-luc (luciferase expressing Bjab cells) xenograft tumor cells per mouse were dosed once at day 1 (except where noted) with an anti-CD22 antibody-drug conjugate, or a naked antibody (Example 8).

| ADC or Ab | µg DM1/m2 | Ab mg/kg mouse | average drug loading (p) | MTD (days) |
|---|---|---|---|---|
| Tr-SMCC-DM1 | 200 | 4.2 | 3.2 | 3 |
| 7A2-SMCC-DM1 | 200 | 3.8 | 3.6 | 6 |
| 5E8-SMCC-DM1 | 200 | 3.8 | 3.6 | 10 |
| RFB4-SMCC-DM1 | 200 | 3.2 | 4.25 | 18 |
| RFB4-SMCC-DM1 (dosed 3× at 1, 7, 14 days) | 405 | 10 | 2.75 | 55 |
| 7A2 | — | 4 | — | 3 |
| 5E8 | — | 4 | — | 3 |
| RFB4 | — | 4 | — | 3 |

The time for tumor size to double was measured (MTD, mean tumor doubling time). The three naked anti-CD22 antibodies showed essentially no efficacy relative to a non-specific binding ADC (trastuzumab-SMCC-DM1). The corresponding conjugates all showed the effect of significantly retarding tumor growth. The effect of multiple dosing was established with RFB4-SMCC-DM1 where the MTD for singly dosed mice was 18 days whereas the MTD for mice dosed three times, at days 1, 7, and 14, was 55 days. Complete remission of tumor occurred in all 8 mice in the triple-dosed group. Other antiCD22-SMCC-DM1 conjugates, with antibodies 12F7, 9A8, 8C9, 8G10, 3F11, 10D2, 6C9, 14D1, and 11H10, showed shrinkage of initial tumor volume or retardation of tumor growth relative to control (trastuzumab-SMCC-DM1), after 7 days following a single dose (400 µg DM1/m2) in SCID mice with 20 million Bjab-luc xenograft tumor cells per mouse. AntiCD22 conjugates, RFB4-SMCC-DM1, 5E8-SMCC-DM1, and 7A2-SMCC-DM1 were also effective in retardation of tumor growth relative to control (trastuzumab-SMCC-DM1), after 11 days following a single dose (200 µg DM1/m2) in SCID mice with 5 million Ramos RA1 xenograft tumor cells per mouse.

The conjugate RFB4-SMCC-DM1 was studied at three different drug loadings on groups of ten SCID mice with Bjab-luc xenografts (Example 8). The low (1.95) and medium (3.7) drug loaded conjugates each showed the effect of significantly retarding tumor growth, with an MTD of about 15 days. The high loaded (6.75) conjugate did not show an effect significantly different than control conjugate GP120-SMCC-DM1, or naked antibody RFB4.

| anti-CD22 ADC or Ab | µg DM1/m2 | Ab mg/kg mouse | average drug loading (p) | MTD (days) |
|---|---|---|---|---|
| RFB4 | — | 10 | — | 3 |
| RFB4-SMCC-DM1 (low loaded) | 144 | 5 | 1.95 | 15 |
| RFB4-SMCC-DM1 (medium loaded) | 273 | 5 | 3.7 | 15 |
| RFB4-SMCC-DM1 (high loaded) | 497 | 5 | 6.75 | 3 |
| GP120-SMCC-DM1 (high loaded) | 449 | 5 | 6.1 | 3 |

AntiCD19-SMCC-DM1 and antiCD22-SMCC-DM1 conjugates did not show in vivo activity in a Raji cell mouse tumor xenograft model. Other antiCD19 and antiCD22 conjugates may have in vivo activity against other cancer cell tumor models.

The in vivo efficacy of anti-CD79a (alpha) and anti-CD79b (beta) ADC was measured with a mouse tumor xenograft model. Groups of eight SCID mice with 20 million Bjab-luc xenograft tumor cells per mouse were dosed at day 1 with samples in the table below and following Example 8.

| ADC, Ab, or control | µg DM1/m2 | Ab mg/kg mouse | average drug loading (p) | MTD (days) |
|---|---|---|---|---|
| PBS (buffer control) | — | — | — | 3.5 |
| antiGP120 | — | 3.2 | — | 3.5 |
| SN8 antiCD79b | — | 3.1 | — | 4 |
| 17A7 antiCD79b | — | 3.1 | — | 4 |
| 8H9 antiCD79a | — | 4.0 | — | 3 |
| antiGP120-SMCC-DM1 | 200 | 3.2 | 4.2 | 3.5 |
| SN8 antiCD79b-SMCC-DM1 | 200 | 3.1 | 4.4 | >7 |
| 17A7 antiCD79b-SMCC-DM1 | 200 | 3.1 | 4.4 | >7 |
| 8H9 antiCD79a-SMCC-DM1 | 200 | 4.0 | 3.4 | >7 |

Conjugates SN8 antiCD79b-SMCC-DM1, 17A7 antiCD79b-SMCC-DM1, and 8H9 antiCD79a-SMCC-DM1, all showed shrinkage of initial tumor volume (mean 160 mm3) after 7 days. In the groups of 8 mice, conjugate SN8 antiCD79b-SMCC-DM1 gave partial remission (PR) in 4 animals and complete remission (CR) in 2 animals. Conjugate 17A7 antiCD79b-SMCC-DM1 gave CR in 1 animal. Conjugate 8H9 antiCD79a-SMCC-DM1 gave PR in 2 animals and CR in 1 animal. Other antiCD79b-SMCC-DM1 conjugates, with antibodies 2F2, 5C3, 7H7, 8D11, 15E4, and 16C11, showed retardation of tumor growth or shrinkage of initial tumor volume, relative to control (trastuzumab-SMCC-DM1), after 8 days following a single dose (192 µg DM1/m2) in CB17 ICR SCID mice with 20 million Bjab-luc xenograft tumor cells per mouse.

The dose response effect on mice administered with antiCD79b-SMCC-DM1 was measured. Groups of eight SCID mice with 20 million Bjab-luc xenograft tumor cells per mouse were dosed at day 1 with samples in the table below (Example 8). The antiCD79b-SMCC-DM1 was dosed at levels of 0.5, 2.0, and 3.64 mg Ab/kg mouse.

| ADC, Ab, or control | µg DM1/m2 | Ab mg/kg mouse | MTD (days) |
|---|---|---|---|
| Vehicle control (PBS) | — | — | 4 |
| antiCD79b-SMCC-DM1 | 32 | 0.5 | 10 |
| antiCD79b-SMCC-DM1 | 130 | 2.0 | 35 |
| antiCD79b-SMCC-DM1 | 236 | 3.64 | >70 |

The in vivo efficacy of antiTENB2 ADC was measured with a mouse tumor xenograft model. TENB2 is a tumor antigen that is shown to be almost exclusively expressed in the human prostate and overexpressed in human prostate tumors (Glynne-Jones et al (2001) Int J Cancer. October 15; 94(2):178-84). PC3-TVA-919cv1:5 is a human prostate cancer cell line expressing high level of TENB2.

Athymic nude mice were subcutaneously injected with 5 million PC3-TVA-919 high expressor or medium expressor cells in a volume of 0.2 ml per mouse. Cells were suspended in HBSS. When mean tumor size reached 100-200 mm$^3$, the mice were randomly grouped into 8 groups of 8-10 mice each and give a single IV treatment of the samples below (Example 8).

| ADC or control | μg DM1/m2 | Ab mg/kg mouse | medium expressor MTD (days) | high expressor MTD (days) |
|---|---|---|---|---|
| PBS (vehicle control) | — | — | 30 | 22 |
| murine anti-ragweed-SPP-DM1 (negative control) | 373 | 6.68 | 18 | 22 |
| murine anti-ragweed-SMCC-DM1 (negative control) | 373 | 9.34 | 14 | 18 |
| murine antiTENB2: 3146-SPP-DM1 | 373 | 7.34 | 58 | 35 |
| murine antiTENB2: 3146-SMCC-DM1 | 373 | 10.6 | 44 | 19 |
| chimeric antiTENB2-SPP-DM1 | 373 | 8.7 | 57 | 43 |
| chimeric antiTENB2-SMCC-DM1 | 373 | 7.63 | 43 | 22 |

Murine anti-TENB2-DM1 conjugates showed anti-tumor efficacy against PC3-TENB2 tumors, relative to negative control and vehicle control. Murine 10H1 antiNaPi3b-SMCC-DM1 conjugate showed no anti-tumor efficacy against PC3-NaPi3b tumors, relative to negative control and vehicle control. Other antibody variants of antiNaPi3b conjugates may have in vivo activity against PC3-NaPi3b tumors, or other cancer cell lines.

Rodent Toxicity

Antibody-drug conjugates and an ADC-minus control, "Vehicle", were evaluated in an acute toxicity rat model. Toxicity of ADC was investigated by treatment of female Sprague-Dawley rats with the ADC and subsequent inspection and analysis of the effects on various organs. Based on gross observations (body weights), clinical pathology parameters (serum chemistry and hematology) and histopathology, the toxicity of ADC may be observed, characterized, and measured. It was found that at equivalent dose levels, trastuzumab-SMCC-DM1 was associated with less acute toxicity than trastuzumab-SPP-DM1.

A 5-day acute toxicity study in adolescent female rats (100-125 gms) was conducted by a single injection of trastuzumab-SMCC-DM1 (two doses: 1860 and 3260 μg DM1/m$^2$), a comparison disulfide ADC, trastuzumab-SPP-DM1 (two doses: 1860 and 3260 μg DM1/m$^2$), free DM1 maytansine (thiol) and a control Vehicle (day 0). Body weight was measured daily. Clinical chemistry, serum enzymes and hematology analysis was conducted on days 3 and 5; concluding with complete necropsy with histopathological assessment. Toxicity signals included the clinical observation of weight loss.

Figure 14:
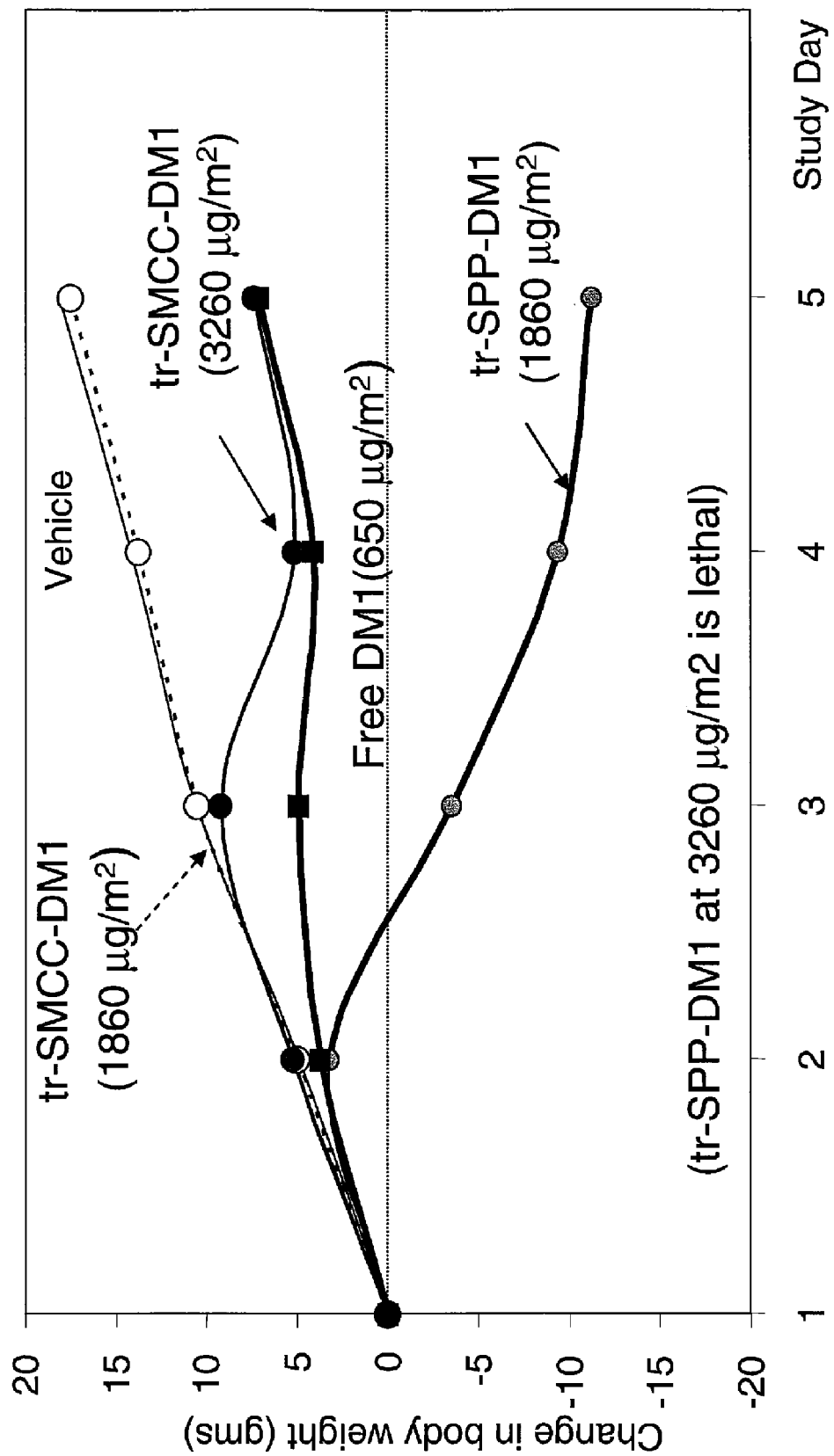
FIG. 14 shows the change in body weight over time of rats dosed with: Vehicle (10 mM sodium succinate, 100 mg/mL sucrose, 0.1% Tween 20, pH 5.0), trastuzumab-SPP-DM1 (1860 μg DM1/m$^2$), trastuzumab-SMCC-DM1 (1860 μg DM1/m$^2$), trastuzumab-SMCC-DM1 (3260 μg DM1/m$^2$), and free DM1 (650 μg/m$^2$).

It is considered that weight loss, or weight change relative to animals dosed only with Vehicle in animals after dosing with ADC, is a gross and general indicator of systemic or localized toxicity. FIG. 14 shows the changes in body weight (grams) over 5 days. Rats receiving the disulfide ADC, trastuzumab-SPP-DM1 showed a marked, dose-dependent toxicity, indicated by lethality at the higher dose and a decline in body weight at the lower dose. In contrast, rats receiving trastuzumab-SMCC-DM1 gained weight, with the lower dosed rats showing no decline in the rate of weight gain, relative to the placebo Vehicle-dosed rats. Rats dosed at the higher level of trastuzumab-SMCC-DM1 also gained weight, comparable to the free DM1 cytotoxin.

Hepatotoxicity was measured by elevated liver enzymes, increased numbers of mitotic and apoptotic figures and hepatocyte necrosis. Hematolymphoid toxicity was observed by depletion of leukocytes, primarily granuloctyes (neutrophils), and/or platelets, and lymphoid organ involvement, i.e. atrophy or apoptotic activity. Toxicity was also noted by gastrointestinal tract lesions such as increased numbers of mitotic and apoptotic figures and degenerative enterocolitis.

Figure 15:
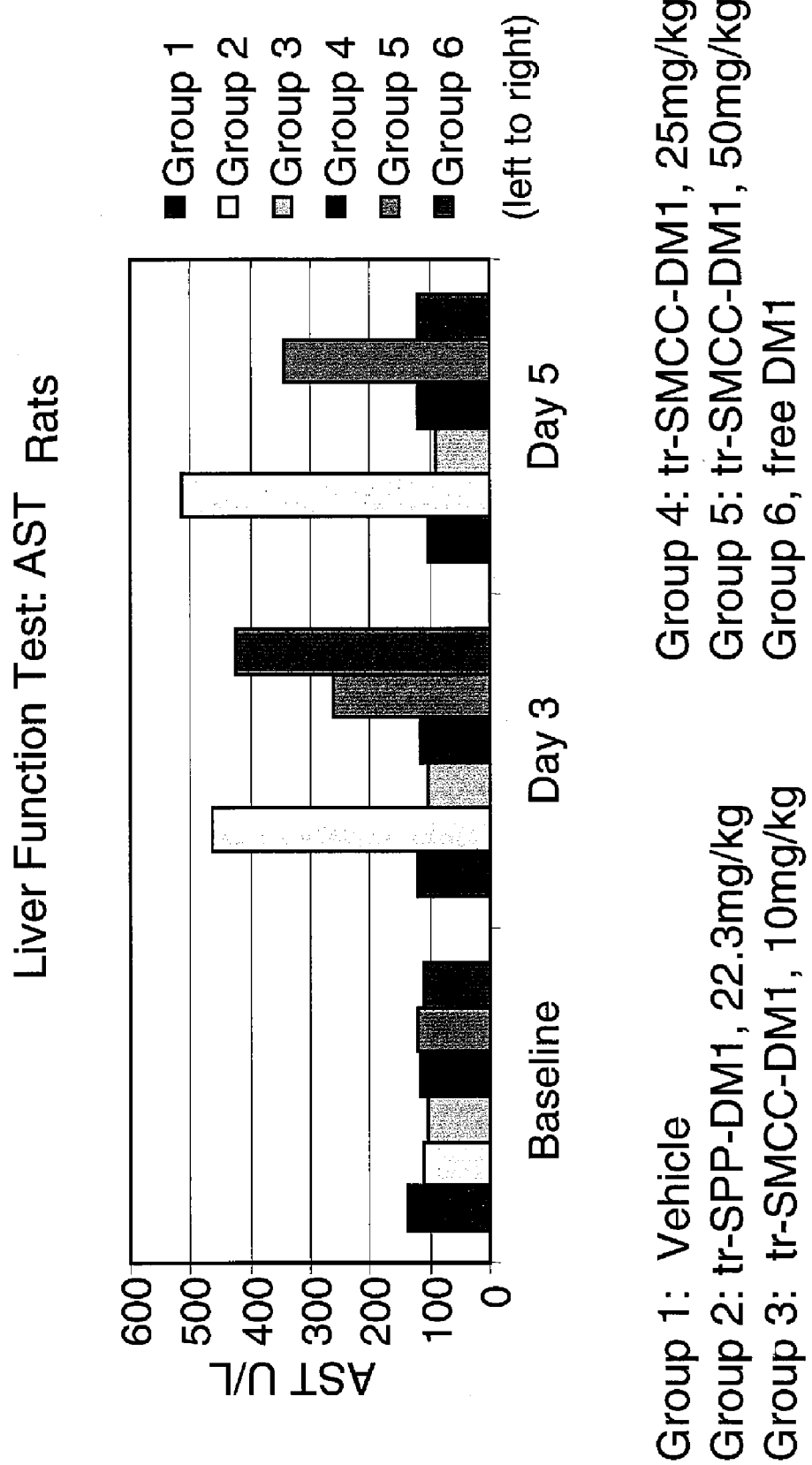
FIG. 15 shows a liver function test measured in AST units per liter over time in the rat model dosed with: Vehicle (10 mM sodium succinate, 100 mg/mL sucrose, 0.1% Tween 20, pH 5.0), trastuzumab-SPP-DM1 (22.3 mg/kg), trastuzumab-SMCC-DM1 (10 mg/kg), trastuzumab-SMCC-DM1 (25 mg/kg), trastuzumab-SMCC-DM1 (50 mg/kg), and free DM1.

Enzymes indicative of liver injury that were studied include:

AST (aspartate aminotransferase)
  Localization: cytoplasmic; liver, heart, skeletal muscle, kidney
  Liver:Plasma ratio of 7000:1
  T1/2: 17 hrs
ALT (alanine aminotransferase)
  Localization: cytoplasmic; liver, kidney, heart, skeletal muscle
  Liver:Plasma ratio of 3000:1
  T1/2: 42 hrs; diurnal variation
GGT (g-glutamyl transferase)
  Localization: plasma membrane of cells with high secretory or absorptive capacity; liver, kidney, intestine
  Poor predictor of liver injury; commonly elevated in bile duct disorders None of the three enzymes measured above are liver-specific. It was found that the ADC of the present invention caused a transient, mild elevation of liver enzymes ALT and AST, with transient reticulocytopenia (FIG. 15). No significant effect on peripheral blood granulocytes or platelets was observed (FIG. 16).

Figure 16:
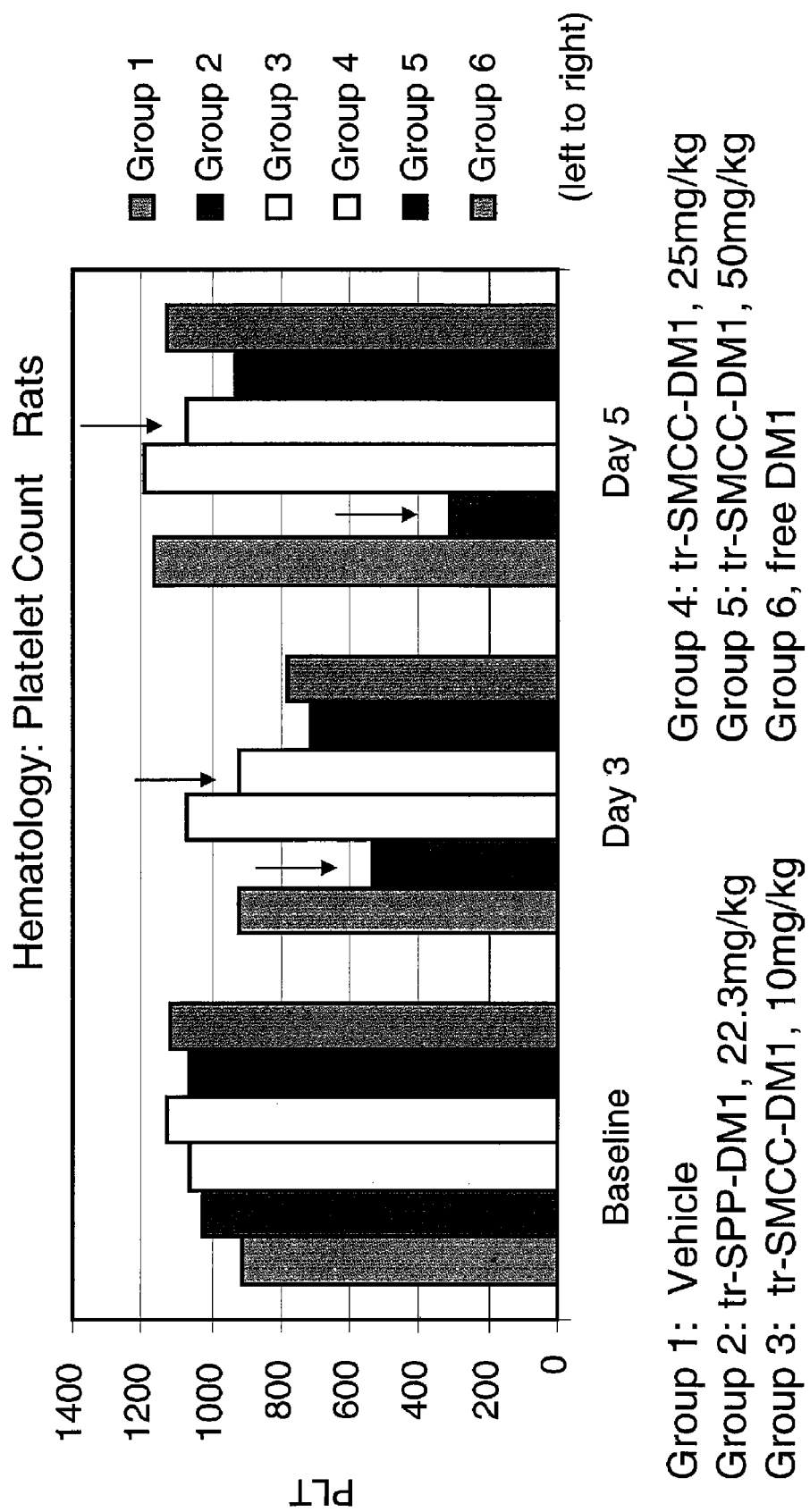
FIG. 16 shows a safety profile measured in PLT units in cells per liter over time in the rat model dosed with: Vehicle (10 mM sodium succinate, 100 mg/mL sucrose, 0.1% Tween 20, pH 5.0), trastuzumab-SPP-DM1 (22.3 mg/kg), trastuzumab-SMCC-DM1 (10 mg/kg), trastuzumab-SMCC-DM1 (25 mg/kg), trastuzumab-SMCC-DM1 (50 mg/kg), and free DM1.
Figure 17:
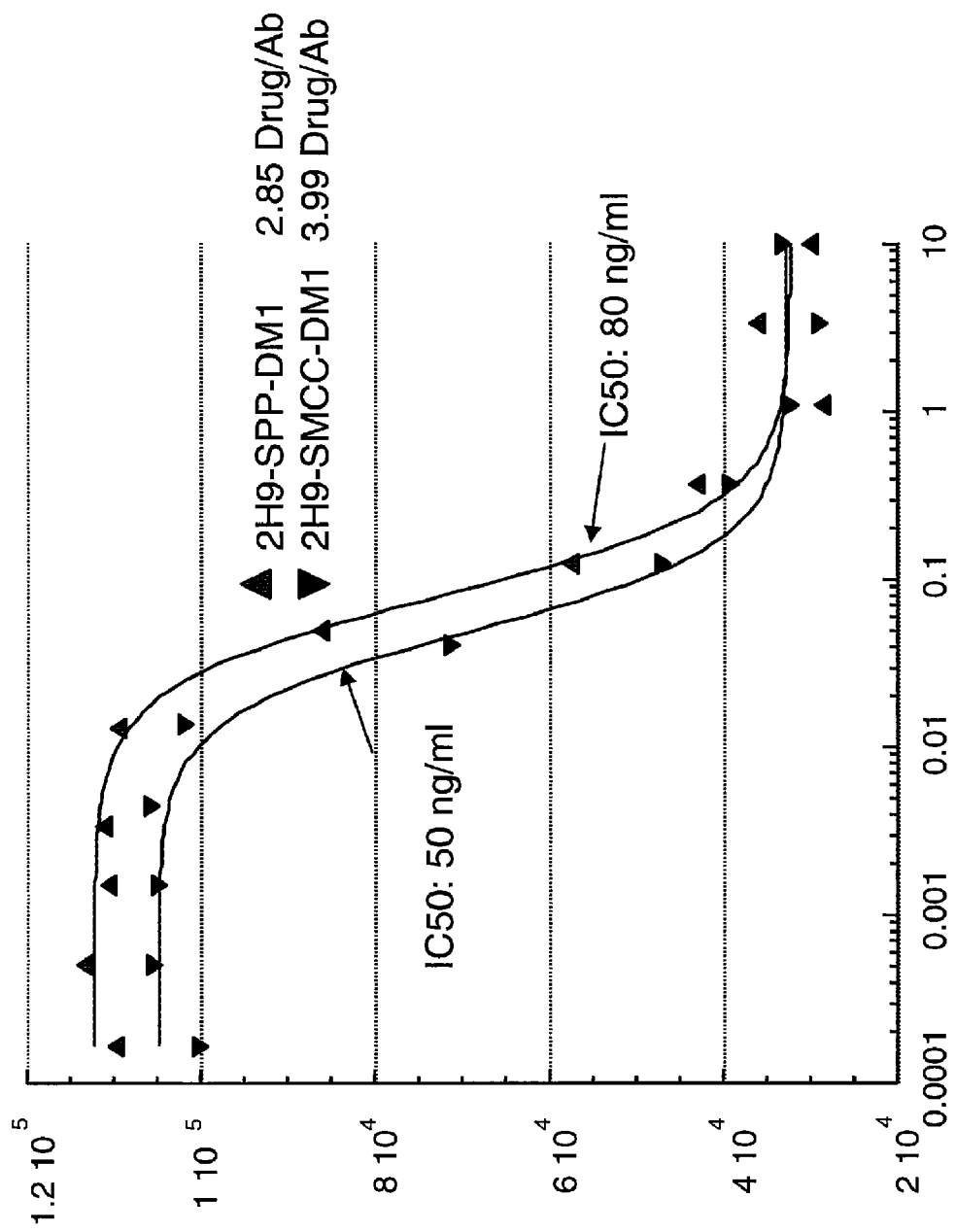
FIG. 17 shows an in vitro, cell proliferation assay with HT1080EphB2 (C8) cells treated with antibody-drug conjugates: -▲- antiEphB2R 2H9-SPP-DM1, and -▼- antiEphB2R 2H9-SMCC-DM1.

FIGS. 15 and 16 show that rats exposed to 22.3 mg/kg trastuzumab-SPP-DM1, (Group 2) demonstrated the most severe clinical toxicity in this five day acute toxicity study. These animals showed the most profound loss of body weight, elevations of liver function tests, leuko- and thrombocytopenia and morphologic evidence of toxicity against hematolymphoid tissues. The extent of toxicity was similar compared to that encountered in previous studies using a dose of 25 mg/kg. In contrast, animals in Groups 3 and 4 given trastuzumab-SMCC-DM1 at 10 and 20 mg/kg, respectively, were indistinguishable from vehicle-treated animals based on clinical pathology and body weight data. Morphologically, these animals showed a mildly increased number of mitotic figures in the liver, however, peripheral lymphoid and hematopoietic tissues were within normal limits.

Group 5 animals, 50 mg/kg trastuzumab-SMCC-DM1, showed evidence of toxicity. However, with the exception of one liver function test (ALT), the severity of toxicity was less than in animals receiving 50% of the same drug dose as trastuzumab-SPP-DM1 (Group 2). At about the same dose, trastuzumab-SMCC-DM1 (Group 4, 22.3 mg/kg) showed about 25% of the AST level as trastuzumab-SPP-DM1 (Group 2, 25 mg/kg). By day 5 of this study, Group 5 animals showed increases in body weights (following a transitory loss during days 3 and 4), a decreasing serum bilirubin and a rising platelet count (FIG. 15).

Animals exposed to free maytansinoid DM1 (Group 6) show the same pattern of toxicity as animals treated with trastuzumab conjugates. This dose of free DM1 corresponds to the amount of drug given as a 10 mg/kg trastuzumab-SPP-DM1 dose in previous studies. The severity of toxicity in animals of group 6 was less than that seen in animals of Group 2, but more than previously seen in animals treated with 10 mg/kg trastuzumab-SPP-DM1. Recovery appeared to be rather fast: The sections of spleen showed increased numbers of immature hematopoietic elements in animals treated with free maytansine; also, LFTs and clinical hematology parameters showed a distinct trend towards normalization in animals of Group 6 by day 5.

Cynomolgus Monkey Toxicity/Safety

Toxicity and safety of ADC administered to Cynomolgus monkeys may be assessed. A toxicity/safety study of the antibody-drug conjugate, trastuzumab-SMCC-DM1, was conducted in Cynomolgus monkeys. Three groups of monkeys were studied to assess the toxicity of trastuzumab-SMCC-DM1 administered via intravenous injection at escalating doses, relative to control (Vehicle). Group 1 (4 subjects) received only Vehicle (PBS, pH 6.5, i.e. formulation minus ADC) at day 1 and day 22, followed by necropsy at day 36. Group 2 (4 subjects) received trastuzumab-SMCC-DM1 4900 µg/m2 at day 1 and at day 22. Group 3 (4 subjects) received trastuzumab-SMCC-DM1 7200 µg/m2 at day 22.

Hepatotoxicity was inferred by measurement of the elevated liver enzymes from the Rodent Toxicity study. Cynomolgus monkeys were dosed with Vehicle (Group 1) and trastuzumab-SMCC-DM1 (Group 2: 4900 µg/m$^2$; Group 3: 7200 µg/m$^2$. Liver enzyme AST, platelet counts, white blood cells, absolute neutrophil, red blood cells, reticulocytes, and a comparison of 2 IV dose regimens were measured for trastuzumab-SMCC-DM1 in Cynomolgus Monkeys (Example 10).

Administration of Antibody-Drug Conjugate Pharmaceutical Formulations

Therapeutic antibody-drug conjugates (ADC) may be administered by any route appropriate to the condition to be treated. The ADC will typically be administered parenterally, i.e. infusion, subcutaneous, intramuscular, intravenous, intradermal, intrathecal, bolus, intratumor injection or epidural (Shire et al (2004) J. Pharm. Sciences 93(6):1390-1402). Pharmaceutical formulations of therapeutic antibody-drug conjugates (ADC) are typically prepared for parenteral administration with a pharmaceutically acceptable parenteral vehicle and in a unit dosage injectable form. An antibody-drug conjugate (ADC) having the desired degree of purity is optionally mixed with pharmaceutically acceptable diluents, carriers, excipients or stabilizers, in the form of a lyophilized formulation or an aqueous solution (Remington's Pharmaceutical Sciences (1980) 16th edition, Osol, A. Ed.).

Acceptable parenteral vehicles, diluents, carriers, excipients, and stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). For example, lyophilized anti-ErbB2 antibody formulations are described in WO 97/04801, expressly incorporated herein by reference. An exemplary formulation of an ADC such as trastuzumab-SMCC-DM1 contains about 100 mg/ml of trehalose (2-(hydroxymethyl)-6-[3,4,5-trihydroxy-6-(hydroxymethyl)tetrahydropyran-2-yl]oxy-tetrahydropyran-3,4,5-triol; $C_{12}H_{22}O_{11}$; CAS Number 99-20-7) and about 0.1% TWEEN™ 20 (polysorbate 20; dodecanoic acid 2-[2-[3,4-bis(2-hydroxyethoxy)tetrahydrofuran-2-yl]-2-(2-hydroxyethoxy)ethoxy]ethyl ester; $C_{26}H_{50}O_{10}$; CAS Number 9005-64-5) at approximately pH 6.

Pharmaceutical formulations of a therapeutic antibody-drug conjugate (ADC) may contain certain amounts of unreacted drug moiety (D), antibody-linker intermediate (Ab-L), and/or drug-linker intermediate (D-L), as a consequence of incomplete purification and separation of excess reagents, impurities, and by-products, in the process of making the ADC; or time/temperature hydrolysis or degradation upon storage of the bulk ADC or formulated ADC composition. For example, a formulation of the ADC, trastuzumab-SMCC-DM1 may contain a detectable amount of free drug DM1. Alternatively, or in addition to, it may contain a detectable amount of drug-linker intermediate DM1-SMCC. Alternatively, or in addition to, it may contain a detectable amount of the antibody, trastuzumab. An exemplary formulation of trastuzumab-SMCC-DM1 may contain up to 10% molar equivalent of DM1-SMCC. Unexpectedly, it was determined by the in vitro cellular proliferation assay (Example 5), that DM1-SMCC ($IC_{50}$ 0.05 µM) is about 20 times less potent in cell killing than free drug DM1 ($IC_{50}$ 0.0045 µM) against SK-BR-3 and BT-474 breast cancer cells.

The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semi permeable matrices of solid hydrophobic polymers containing the ADC, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid.

The formulations to be used for in vivo administration must be sterile, which is readily accomplished by filtration through sterile filtration membranes.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Aqueous suspensions contain the active materials (ADC) in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of ADC may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, an aqueous solution intended for intravenous infusion may contain from about 3 to 500 µg of the active ingredient per milliliter of solution in order that infusion of a suitable volume at a rate of about 30 mL/hr can occur. Subcutaneous (bolus) administration may be effected with about 1.5 ml or less of total volume and a concentration of about 100 mg ADC per ml. For ADC that require frequent and chronic administration, the subcutaneous route may be employed, such as by pre-filled syringe or autoinjector device technology.

As a general proposition, the initial pharmaceutically effective amount of ADC administered per dose will be in the range of about 0.01-100 mg/kg, namely about 0.1 to 20 mg/kg of patient body weight per day, with the typical initial range of compound used being 0.3 to 15 mg/kg/day. For example, human patients may be initially dosed at about 1.5 mg ADC per kg patient body weight. The dose may be escalated to the maximally tolerated dose (MTD). The dosing schedule may be about every 3 weeks, but according to diagnosed condition or response, the schedule may be more or less frequent. The dose may be further adjusted during the course of treatment to be at or below MTD which can be safely administered for multiple cycles, such as about 4 or more.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Although oral administration of protein therapeutics are generally disfavored due to poor bioavailability due to limited absorption, hydrolysis or denaturation in the gut, formulations of ADC suitable for oral administration may be prepared as discrete units such as capsules, cachets or tablets each containing a predetermined amount of the ADC.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Exemplary unit dosage formulations contain a daily dose or unit daily sub-dose, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Antibody-Drug Conjugate Treatments

It is contemplated that the antibody-drug conjugates (ADC) of the present invention may be used to treat various diseases or disorders, such as cancer and autoimmune conditions. Exemplary conditions or disorders include benign or malignant tumors; leukemia and lymphoid malignancies; other disorders such as neuronal, glial, astrocytal, hypothalamic, glandular, macrophagal, epithelial, stromal, blastocoelic, inflammatory, angiogenic and immunologic disorders. Cancer susceptible to ADC treatment include those which are characterized by the overexpression of certain tumor associated antigens or cell surface receptors, e.g. HER2.

The ADC compounds which are identified in the animal models and cell-based assays can be further tested in tumor-bearing higher primates and human clinical trials. Human clinical trials can be designed similar to the clinical trials testing the efficacy of the anti-HER2 monoclonal antibody HERCEPTIN® (trastuzumab) in patients with HER2 overexpressing metastatic breast cancers that had received extensive prior anti-cancer therapy as reported by Baselga et al. (1996) J. Clin. Oncol. 14:737-744. The clinical trial may be designed to evaluate the efficacy of an ADC in combination with known therapeutic regimens, such as radiation and/or chemotherapy involving known chemotherapeutic and/or cytotoxic agents (Pegram et al (1999) Oncogene 18:2241-2251).

Generally, the disease or disorder to be treated is cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, gastrointestinal stromal tumor (GIST), pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

The cancer to be treated herein may be one characterized by excessive activation of an ErbB receptor, e.g. HER2. Such excessive activation may be attributable to overexpression or increased production of the ErbB receptor or an ErbB ligand. In one embodiment, a diagnostic or prognostic assay will be performed to determine whether the patient's cancer is characterized by excessive activation of an ErbB receptor. For example, ErbB gene amplification and/or overexpression of an ErbB receptor in the cancer may be determined. Various assays for determining such amplification/overexpression are available in the art and include the IHC, FISH and shed antigen assays described above. Alternatively, or additionally, levels of an ErbB ligand, such as TGF-alpha., in or associated with the tumor may be determined according to known procedures. Such assays may detect protein and/or nucleic acid encoding it in the sample to be tested. In one embodiment, ErbB ligand levels in the tumor may be determined using immunohistochemistry (IHC); see, for example, Scher et al. (1995) Clin. Cancer Research 1:545-550. Alternatively, or additionally, one may evaluate levels of ErbB ligand-encoding nucleic acid in the sample to be tested; e.g. via FISH, southern blotting, or PCR techniques. In one embodiment, ErbB2 overexpression may be analyzed by IHC, e.g. using the HERCEPTEST (Dako). Parrafin embedded tissue sections from a tumor biopsy may be subjected to the IHC assay and accorded a ErbB2 protein staining intensity criteria as follows: Score 0, no staining is observed or membrane staining is observed in less than 10% of tumor cells; Score 1+, a faint/barely perceptible membrane staining is detected in more than 10% of the tumor cells, the cells are only stained in part of their membrane; Score 2+, a weak to moderate complete membrane staining is observed in more than 10% of the tumor cells; Score 3+, a moderate to strong complete membrane staining is observed in more than 10% of the tumor cells. Those tumors with 0 or 1+ scores for ErbB2 overexpression assessment may be characterized as not overexpressing ErbB2, whereas those tumors with 2+ or 3+ scores may be characterized as overexpressing ErbB2.

Alternatively, or additionally, FISH assays such as the INFORM™ (Ventana Co., Ariz.) or PATHVISION™ (Vysis, Ill.) may be carried out on formalin-fixed, paraffin-embedded tumor tissue to determine the extent (if any) of ErbB2 overexpression in the tumor.

Moreover, ErbB receptor or ErbB ligand overexpression or amplification may be evaluated using an in vivo diagnostic assay, e.g. by administering a molecule (such as an antibody) which binds the molecule to be detected and is tagged with a detectable label (e.g. a radioactive isotope) and externally scanning the patient for localization of the label.

For the prevention or treatment of disease, the appropriate dosage of an ADC will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 µg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 µg/kg to 100 mg/kg or more, depending on the factors mentioned above. An exemplary dosage of ADC to be administered to a patient is in the range of about 0.1 to about 10 mg/kg of patient weight.

For repeated administrations over several days or longer, depending on the condition, the treatment is sustained until a desired suppression of disease symptoms occurs. An exemplary dosing regimen comprises administering an initial loading dose of about 4 mg/kg, followed by a weekly maintenance dose of about 2 mg/kg of the anti-ErbB2 antibody. Other dosage regimens may be useful. The progress of this therapy is easily monitored by conventional techniques and assays.

Combination Therapy

An antibody-drug conjugate (ADC) may be combined in a pharmaceutical combination formulation, or dosing regimen as combination therapy, with a second compound having anti-cancer properties. The second compound of the pharmaceutical combination formulation or dosing regimen preferably has complementary activities to the ADC of the combination such that they do not adversely affect each other.

The second compound may be a chemotherapeutic agent, cytotoxic agent, cytokine, growth inhibitory agent, anti-hormonal agent, aromatase inhibitor, protein kinase inhibitor, lipid kinase inhibitor, anti-androgen, antisense oligonucleotide, ribozyme, gene therapy vaccine, anti-angiogenic agent and/or cardioprotectant. Such molecules are suitably present in combination in amounts that are effective for the purpose intended. A pharmaceutical composition containing an ADC may also have a therapeutically effective amount of a chemotherapeutic agent such as a tubulin-forming inhibitor, a topoisomerase inhibitor, or a DNA binder.

Alternatively, or additionally, the second compound may be an antibody which binds ErbB2 and blocks ligand activation of an ErbB receptor. The second antibody may be monoclonal antibody 2C4 or humanized 2C4 "Omnitarg" (WO 01/00245). The second antibody may be conjugated with a cytotoxic or chemotherapeutic agent, e.g., a maytansinoid, an auristatin, a calicheamicin, or a 1,8 bis-naphthalimide moiety. For example, it may be desirable to further provide antibodies which bind to EGFR, ErbB2, ErbB3, ErbB4, or vascular endothelial factor (VEGF) in the one formulation or dosing regimen.

Other therapeutic regimens may be combined with the administration of an anticancer agent identified in accordance with this invention. The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein there is a time period while both (or all) active agents simultaneously exert their biological activities.

In one embodiment, treatment with an ADC of the present invention involves the combined administration of an anticancer agent identified herein, and one or more chemotherapeutic agents or growth inhibitory agents, including coadministration of cocktails of different chemotherapeutic agents, optionally along with treatment with an anti-ErbB2 antibody, such as trastuzumab. Chemotherapeutic agents include Erlotinib HCl (CP-358774, TARCEVA™; Genentech/OSI), taxanes (such as paclitaxel and doxetaxel) and/or anthracycline antibiotics. Preparation and dosing schedules for such chemotherapeutic agents may be used according to manufacturers's instructions or as determined empirically by the skilled practitioner. Preparation and dosing schedules for such chemotherapy are also described in Chemotherapy Service Ed., M. C. Perry, Williams & Wilkins, Baltimore, Md. (1992).

The anticancer agent may be combined with an anti-hormonal compound; e.g., an anti-estrogen compound such as tamoxifen; an anti-progesterone such as onapristone (EP 616812); or an anti-androgen such as flutamide, in dosages known for such molecules. Where the cancer to be treated is hormone independent cancer, the patient may previously have been subjected to anti-hormonal therapy and, after the cancer becomes hormone independent, the anti-ErbB2 antibody (and optionally other agents as described herein) may be administered to the patient. It may be beneficial to also coadminister a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

Metabolites of the Antibody-Drug Conjugates

Also falling within the scope of this invention are the in vivo metabolic products of the ADC compounds described herein, to the extent such products are novel and unobvious over the prior art. Such products may result for example from the oxidation, reduction, hydrolysis, amidation, esterification, enzymatic cleavage, and the like, of the administered compound. Accordingly, the invention includes novel and unobvious compounds produced by a process comprising contacting a compound of this invention with a mammal for a period of time sufficient to yield a metabolic product thereof.

Metabolite products may be identified by preparing a radiolabelled (e.g. $^{14}C$ or $^{3}H$) ADC, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS, LC/MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the ADC compounds.

Metabolites include the products of in vivo cleavage of the ADC where cleavage of any bond occurs that links the drug moiety to the antibody. Metabolic cleavage may thus result in the naked antibody, or an antibody fragment. The antibody metabolite may be linked to a part, or all, of the linker. Metabolic cleavage may also result in the production a drug moiety or part thereof. The drug moiety metabolite may be linked to a part, or all, of the linker.

Articles of Manufacture

In another embodiment, an article of manufacture, or "kit", containing ADC and materials useful for the treatment of the disorders described above is provided. The article of manufacture comprises a container and a label or package insert on or associated with the container. Suitable containers include, for example, bottles, vials, syringes, or blister pack. The containers may be formed from a variety of materials such as glass or plastic. The container holds an antibody-drug conjugate (ADC) composition which is effective for treating the condition and may have a sterile access port (for example the container may be an intravenous solution bag or a vial having a stopper pierceable by a hypodermic injection needle). At least one active agent in the composition is an ADC. The label or package insert indicates that the composition is used for treating the condition of choice, such as cancer. In one embodiment, the label or package inserts indicates that the composition comprising the antibody which binds ErbB2 can be used to treat cancer which expresses an ErbB receptor selected from the group consisting of epidermal growth factor receptor (EGFR), ErbB2, ErbB3 and ErbB4. In addition, the label or package insert may indicate that the patient to be treated is one having cancer characterized by excessive activation of an ErbB receptor selected from EGFR, ErbB2, ErbB3 or ErbB4. For example, the cancer may be one which overexpresses one of these receptors and/or which overexpresses an ErbB ligand (such as TGF-α). The label or package insert may also indicate that the composition can be used to treat cancer, wherein the cancer is not characterized by overexpression of the ErbB2 receptor. In other embodiments, the package insert may indicate that the ADC composition can be used also to treat hormone independent cancer, prostate cancer, colon cancer or colorectal cancer.

The article of manufacture may comprise (a) a first container with a compound contained therein, wherein the compound comprises an ADC of the present invention in which the antibody of the ADC is a first antibody which binds ErbB2 and inhibits growth of cancer cells which overexpress ErbB2; and (b) a second container with a compound contained therein, wherein the compound comprises a second antibody which binds ErbB2 and blocks ligand activation of an ErbB receptor, or a conjugate of this second antibody with a maytansinoid. The article of manufacture in this embodiment may further comprise a package insert indicating that the first and second compounds can be used to treat cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

Example 1

Production, Characterization and Humanization of Anti-ErbB2 Monoclonal Antibody 4D5

The murine monoclonal antibody 4D5 which specifically binds the extracellular domain of ErbB2 was produced as described in Fendly et al (1990) Cancer Research 50:1550-1558. Briefly, NIH 3T3/HER2-$3_{400}$ cells (expressing approximately $1\times10^5$ ErbB2 molecules/cell) produced as described in Hudziak et al (1987) Proc. Natl. Acad. Sci. (USA) 84:7158-7163 were harvested with phosphate buffered saline (PBS) containing 25 mM EDTA and used to immunize BALB/c mice. The mice were given injections i.p. of $10^7$ cells in 0.5 ml PBS on weeks 0, 2, 5 and 7. The mice with antisera that immunoprecipitated $^{32}$P-labeled ErbB2 were given i.p. injections of a wheat germ agglutinin-Sepharose (WGA) purified ErbB2 membrane extract on weeks 9 and 13. This was followed by an i.v. injection of 0.1 ml of the ErbB2 preparation and the splenocytes were fused with mouse myeloma line X63-Ag8.653. Hybridoma supernatants were screened for ErbB2-binding by ELISA and radioimmunoprecipitation.

The murine monoclonal antibody 4D5 was humanized, using a "gene conversion mutagenesis" strategy, as described in U.S. Pat. No. 5,821,337, the entire disclosure of which is hereby expressly incorporated by reference. The humanized monoclonal antibody 4D5 used in the following experiments is designated huMAb4D5-8. This antibody is of IgG1 isotype.

Example 2

Purification of Trastuzumab

One vial containing 440 mg HERCEPTIN® (huMAb4D5-8, rhuMAb HER2, U.S. Pat. No. 5,821,337) antibody) was dissolved in 50 mL MES buffer (25 mM MES, 50 mM NaCl, pH 5.6) and loaded on a cation exchange column (Sepharose S, 15 cm×1.7 cm) that had been equilibrated in the same buffer. The column was then washed with the same buffer (5 column volumes). Trastuzumab was eluted by raising the NaCl concentration of the buffer to 200 mM. Fractions containing the antibody were pooled, diluted to 10 mg/mL, and dialyzed into a buffer containing 50 mm potassium phosphate, 50 mM NaCl, 2 mM EDTA, pH 6.5.

Example 3

Preparation of Antibody-Drug Conjugates: Trastuzumab-SPP-DM1

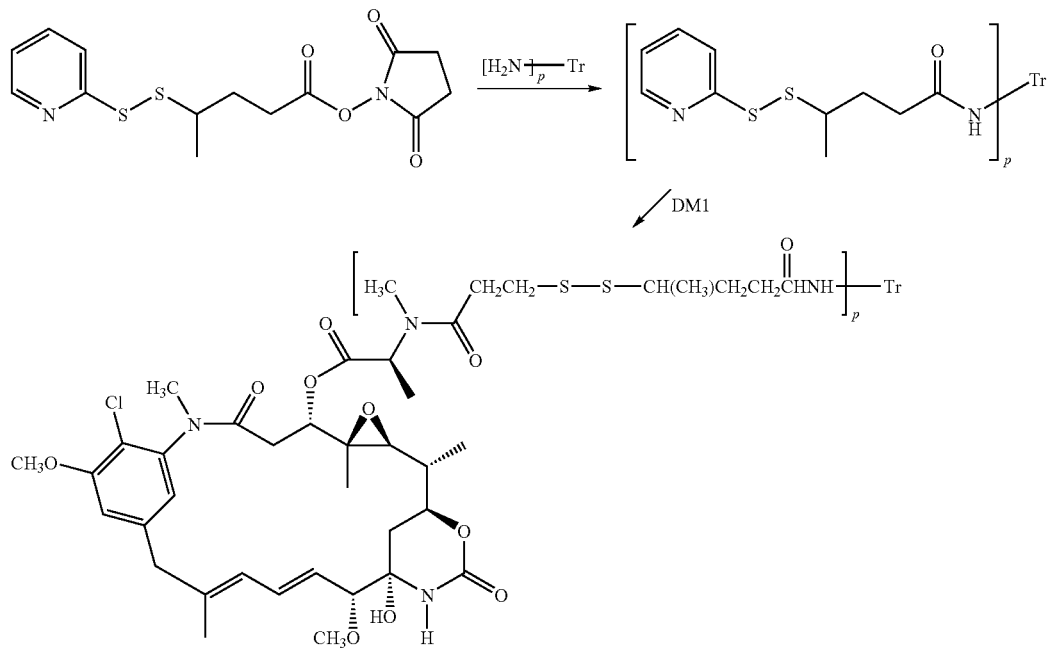

Purified trastuzumab was derivatized with N-succinimidyl-4-(2-pyridylthio)pentanoate to introduce dithiopyridyl groups. Trastuzumab (376.0 mg, 8 mg/mL) in 44.7 mL of 50 mM potassium phosphate buffer (pH 6.5) containing NaCl (50 mM) and EDTA (1 mM) was treated with SPP (5.3 molar equivalents in 2.3 mL ethanol). After incubation for 90 minutes under argon at ambient temperature, the reaction mixture was gel filtered through a Sephadex G25 column equilibrated with 35 mM sodium citrate, 154 mM NaCl, 2 mM EDTA. Antibody containing fractions were pooled and assayed. The degree of modification of the antibody was determined as described above. Recovery of the modified antibody (trastuzumab-SPP-Py) was 337 mg (89.7%) with 4.5 releasable 2-thiopyridine groups linked per antibody (p').

Trastuzumab-SPP-Py (337.0 mg, 9.5 μmols of releasable 2-thiopyridine groups) was diluted with the above 35 mM sodium citrate buffer, pH 6.5, to a final concentration of 2.5 mg/mL. DM1 ($N^{2'}$-deacetyl-$N^{2'}$-(3-mercapto-1-oxopropyl)-maytansine), the structure of which is shown in FIG. 1, (1.7 equivalents, 16.1 μmols) in 3.0 mM dimethylacetamide (DMA, 3% v/v in the final reaction mixture) was then added to the antibody solution. The reaction proceeded at ambient temperature under argon for 20 hours.

The reaction was loaded on a Sephacryl S300 gel filtration column (5.0 cm×90.0 cm, 1.77 L) equilibrated with 35 mM sodium citrate, 154 mM NaCl, pH 6.5. The flow rate was 5.0 mL/min and 65 fractions (20.0 mL each) were collected. A major peak centered around fraction No. 47 (FIG. 3). The major peak comprises monomeric trastuzumab-SPP-DM1. Fractions 44-51 were pooled and assayed. The number of DM1 drug molecules linked per antibody molecule (p') was determined by measuring the absorbance at 252 nm and 280 nm, and found to be 3.7 drug molecules per antibody molecule.

Example 4

Preparation of Antibody-Drug Conjugates: Trastuzumab-SMCC-DM1

Purified trastuzumab was derivatized with (Succinimidyl 4-(N-maleimidomethyl)cyclohexane-1-carboxylate, SMCC, Pierce Biotechnology, Inc) to introduce the SMCC linker. Trastuzumab was purified from HERCEPTIN® as in Example 2 and buffer-exchange treated at 20 mg/mL in 50 mM potassium phosphate/50 mM sodium chloride/2 mM EDTA, pH 6.5 with 7.5 to 10 molar equivalents of SMCC (20 mM in DMSO or DMA (dimethylacetamide), 6.7 mg/mL). After stirring for 2 to 4 hours under argon at ambient temperature, the reaction mixture was filtered through a Sephadex G25 column equilibrated with 50 mM potassium phosphate/50 mM sodium chloride/2 mM EDTA, pH 6.5. Alternatively, the reaction mixture was gel filtered with 30 mM citrate and 150 mM sodium chloride at pH 6. Antibody containing fractions were pooled and assayed. Recovery of trastuzumab-SMCC was 88%.

The drug-linker intermediate, trastuzumab-SMCC from above, was diluted with 50 mM potassium phosphate/50 mM sodium chloride/2 mM EDTA, pH 6.5, to a final concentration of 10 mg/ml, and reacted with a 10 mM solution of DM1 (1.7 equivalents assuming 5 SMCC/trastuzumab, 7.37 mg/ml) in dimethylacetamide. The reaction was stirred at ambient temperature under argon for 4 to about 16 hours. The conjugation reaction mixture was filtered through a Sephadex G25 gel filtration column (1.5×4.9 cm) with 1×PBS at pH 6.5. Alternatively, the reaction mixture was gel filtered with 10 mM succinate and 150 mM sodium chloride at pH 5. The DM1/trastuzumab ratio (p) was 3.1, as measured by the absorbance at 252 nm and at 280 nm. The drug to antibody ratio (p) may also be measured by mass spectrometry. Conjugation may also be monitored by SDS polyacrylamide gel electrophoresis. Aggregation may be assessed by laser light scattering analysis.

Antibody-SMCC-DM1 Conjugates:

Following this protocol, other antibody-drug conjugates with the SMCC linker and DM1 drug moiety were prepared, including:

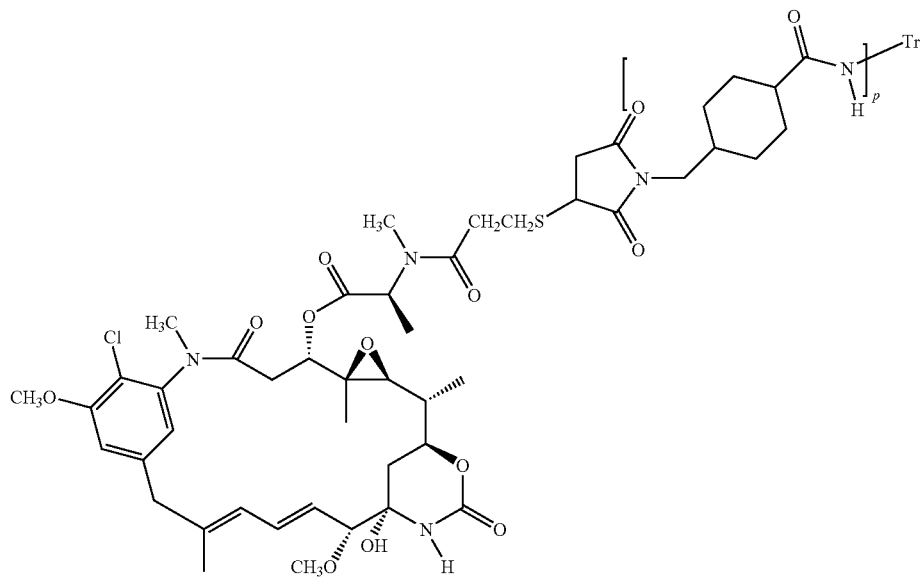

| Antibody-drug conjugate (ADC) | antibody (Ab) | antigen | average drug loading (DM1/Ab) |
|---|---|---|---|
| 10H-SMCC-DM1 | 10H1 (murine) anti-NaPi3b | NaPi3b | 5.0 |
| 2H9-SMCC-DM1 | 2H9 Mab | anti-EphB2R | 4.0 |
| ragweed-SMCC-DM1 | ragweed | | 2.7 |
| antiTENB2-SMCC-DM1 | anti-TENB2-3416#2 Mouse MAb | TENB2 | 2.5 |
| anti-TENB2 20D1 Fc Chimera-SMCC-DM1 | Chimeric Human Mouse anti-TENB2 | TENB2 | 3.32 |
| antiCD19-SMCC-DM1 | antiCD19 (mIgG1 isotype) | CD19 | 5.05 |
| 2H7-SMCC-DM1 | antiCD20 (mIgG2a isotype) | CD20 | 2.44, 3.84 (two lots) |
| CD20 LC-SMCC-DM1 | antiCD20 (Rituxan ®) | CD20 | |
| HB5-SMCC-DM1 | antiCD21 (mIgG2a isotype) | CD21 | 4.05 |
| RFB4-SMCC-DM1 | antiCD22 | CD22 | 1.95-6.75 (multiple lots) |
| Cy34.1.2-SMCC-DM1 | antiCD22 | CD22 | 2.70 |
| 12F7.1.5-SMCC-DM1 | antiCD22 | CD22 | 5.90 |
| 9A8.1.1-SMCC-DM1 | antiCD22 | CD22 | 5.00 |
| 8C9.1.2-SMCC-DM1 | antiCD22 | CD22 | 2.90 |
| 14B3.3.1-SMCC-DM1 | antiCD22 | CD22 | 5.20 |
| 8G10.4.2-SMCC-DM1 | antiCD22 | CD22 | 3.60 |
| 2B4.1.4-SMCC-DM1 | antiCD22 | CD22 | 5.20 |
| 7A2.4.1-SMCC-DM1 | antiCD22 | CD22 | 3.60 |
| 4H3.2.2-SMCC-DM1 | antiCD22 | CD22 | 3.60 |
| 5E8.1.8-SMCC-DM1 | antiCD22 | CD22 | 3.60 |
| 3F11.2.1-SMCC-DM1 | antiCD22 | CD22 | 4.50 |
| 6C9.1.3-SMCC-DM1 | antiCD22 | CD22 | 3.70 |
| 10D2.4.3-SMCC-DM1 | antiCD22 | CD22 | 3.65 |
| 10D6.8.1-SMCC-DM1 | antiCD72 | CD72 | 2.90 |
| ZL7-SMCC-DM1 | antiCD79a (alpha) | CD79a | 3.60 |
| 5C3-SMCC-DM1 | antiCD79a (alpha) | CD79a | 1.85 |
| 6G1-SMCC-DM1 | antiCD79a (alpha) | CD79a | 3.50 |
| 7H7-SMCC-DM1 | antiCD79a (alpha) | CD79a | 3.25 |
| 8D11-SMCC-DM1 | antiCD79a (alpha) | CD79a | 3.60 |
| 8H9-SMCC-DM1 | antiCD79a (alpha) | CD79a | 3.40 |
| 11E5-SMCC-DM1 | antiCD79a (alpha) | CD79a | 3.60 |
| 15E4-SMCC-DM1 | antiCD79a (alpha) | CD79a | 3.25 |
| 16C11-SMCC-DM1 | antiCD79a (alpha) | CD79a | 2.50 |
| 2F2-SMCC-DM1 | antiCD79b (beta) | CD79b | 3.20 |
| 17A7-SMCC-DM1 | antiCD79b (beta) | CD79b | 4.40 |
| SN8-SMCC-DM1 | antiCD79b (beta) | CD79b | 4.40, 0.80 (two lots) |
| 1F9-SMCC-DM1 | antiFcRH1 | FcRH1 | 4.20 |
| 7A2-SMCC-DM1 | antiFcRH2 | FcRH2 | 4.20, 3.95 (two lots) |
| 7G7-SMCC-DM1 | antiFcRH2 | FcRH2 | 3.80 |
| cl1D6-SMCC-DM1 | antiFcRH2 | FcRH2 | 2.20 |
| 51505.111-SMCC-DM1 | antiCXCR5 | CXCR5 | 6.10 |
| 12C7 Fc Chimera-SMCC-DM1 | antiBrevican | brevican | 4.60 |
| H2: PSCA hlog-SMCC-DM1 | antiPSCA hlog | PSCA | 3 |
| H6: xPSCAhlog-SMCC-DM1 | antiPSCA hlog | PSCA | 2.6 |
| xFcRH5: 3909 7D11.1.1-SMCC-DM1 | antiIRTA2 | IRTA2 | 2.6 |
| xFCRH5.7D11-SMCC-DM1 | antiIRTA2 | IRTA2 | 4.4 |
| 11D10 LC-SMCC-DM1 | Mouse anti-CA 0772P MAb | CA 0772P MUC16 | |
| xNCA LC-SMCC-DM1 | Mouse anti-CEACAM6 MAb | CEACAM6 NCA | |

Antibody-BMPEO-DM1 Conjugates:

For cysteine conjugation, the antibody may be reduced with a reducing agent such as dithiothreitol (DTT) or TCEP, in the presence of EDTA. After incubating for about one hour at 37° C., the pH is adjusted to about 7 with 100 mM potassium phosphate. The reduced antibody is modified by the bis-maleimido reagent BM(PEO)3 (Pierce Chemical), leaving an unreacted maleimido group on the surface of the antibody. This may be accomplished by dissolving BM(PEO)$_3$ in a 50% ethanol/water mixture to a concentration of 10 mM and adding a tenfold molar excess to a solution containing antibody in phosphate buffered saline at a concentration of approximately 1.6 mg/ml (10 μM) and allowing it to react for 1 hour to form Ab-BMPEO. Excess BM(PEO)$_3$ is removed by gel filtration (HiTrap column, Pharmacia) in 30 mM citrate, pH 6 with 150 mM NaCl buffer. An approximate 10 fold molar excess DM1 is dissolved in dimethyl acetamide (DMA) and added to the Ab-BMPEO intermediate. Dimethyl formamide (DMF) may also be employed to dissolve the drug moiety reagent. The reaction mixture is allowed to react overnight before gel filtration or dialysis into PBS to remove unreacted DM1. Gel filtration on S200 columns in PBS was used to remove high molecular weight aggregates and furnish purified Ab-BMPEO-DM1.

Following this protocol, other antibody-drug conjugates with the BMPEO linker and DM1 drug moiety were prepared, including:

| Antibody-drug conjugate (ADC) | antibody (Ab) | antigen | average drug loading (DM1/Ab) |
|---|---|---|---|
| trastuzumab-BM(PEO)-DM1 | trastuzumab (Herceptin ®) | HER2 | 2.94 |
| CD120-BMPEO3-DM1 | Mouse anti-GP120 MAb | GP120 | 2 |
| RFB4-BMPEO3-DM1 | antiCD22 | CD22 | 3.7 and 4.25 (two lots) |

Example 5

In Vitro Cell Proliferation Assay

Efficacy of ADC were measured by a cell proliferation assay employing the following protocol (Promega Corp. Technical Bulletin TB288; Mendoza et al (2002) Cancer Res. 62:5485-5488):
1. An aliquot of 100 μl of cell culture containing about $10^4$ cells (SKBR-3, BT474, MCF7 or MDA-MB-468) in medium was deposited in each well of a 96-well, opaque-walled plate.
2. Control wells were prepared containing medium and without cells.
3. ADC was added to the experimental wells and incubated for 3-5 days.
4. The plates were equilibrated to room temperature for approximately 30 minutes.
5. A volume of CellTiter-Glo Reagent equal to the volume of cell culture medium present in each well was added.
6. The contents were mixed for 2 minutes on an orbital shaker to induce cell lysis.
7. The plate was incubated at room temperature for 10 minutes to stabilize the luminescence signal.
8. Luminescence was recorded and reported in graphs as RLU=relative luminescence units.

Example 6

Serum Clearance and Stability in Mice

A beige mutation, nude, naive (without tumors) mice in six Groups of four animals were studied. At Day 0, each mouse received a single 2 mg/kg dose of ADC in 200 μl aqueous carrier, except the Vehicle Group which received only carrier. Blood was collected by cardiac puncture under anesthesia at each time point (5 minutes, 1 hour, 6 hours, 24 hours, 72 hours, and 168 hours) post-dose. The serum was isolated and antibody and ADC were measured.
Group 1: Vehicle (PBS, pH 6.5, no ADC)
Group 2: Trastuzumab-SMCC-DM1
Group 3: Trastuzumab-SPP-DM1
Group 4: Trastuzumab-SPDP-DM1
Group 5: Trastuzumab-SPP-DM3
Group 5: Trastuzumab-SPP-DM4

Example 7

Serum Stability in Rats

Six dose groups with 6 Sprague-Dawley rats (100-125 gms each) per dose group were studied. At Day 0, Animals were administered a single IV dose of Vehicle, 10 mg/kg trastuzumab-SPP-DM1, or 10 mg/kg trastuzumab-SMCC-DM1, at a dose volume of 10 ml/kg via the lateral tail vein. Approximately 300 μl whole blood was collected at each timepoint: 0 (predose), 10, and 30 minutes; 1, 2, 4, 8, 24 and 36 hours; and 2, 3, 4, 7, 14, 21, 28 days post dose.

Example 8

Tumor Volume In Vivo Efficacy

High Expressing HER2 Transgenic Explant Mice:
Animals suitable for transgenic experiments can be obtained from standard commercial sources such as Taconic (Germantown, N.Y.). Many strains are suitable, but FVB female mice are preferred because of their higher susceptibility to tumor formation. FVB males were used for mating and vasectomized CD.1 studs were used to stimulate pseudopregnancy. Vasectomized mice can be obtained from any commercial supplier. Founders were bred with either FVB mice or with 129/BL6×FVB p53 heterozygous mice. The mice with heterozygosity at p53 allele were used to potentially increase tumor formation. However, this has proven unnecessary. Therefore, some F1 tumors are of mixed strain. Founder tumors are FVB only. Six founders were obtained with some developing tumors without having litters.
Animals having tumors (allograft propagated from Fo5 mmtv transgenic mice) were treated with a single injection of a trastuzumab-DM1 maytansinoid conjugate (10 mg/kg dose) and tumor volume was assessed for over 20 days after injection.
Bjab-luc Xenograft SCID Mice:
Groups of eight to ten SCID mice with 20 million Bjab-luc xenograft tumor cells per mouse were dosed at day 1 with an antibody-drug conjugate, or a naked antibody. A group of eight mice were tested each with anti-CD22 ADC, naked anti-CD22 antibodies, and control. Control ADC (trastuzumab-SMCC-DM1; loading: DM1/trastuzumab=3.2) is not a specific binder and was administered at 200 μg DM1/m2, 4.2 trastuzumab/kg mouse, and resulted in a mean tumor doubling time of about 3 days. Anti-CD22 conjugates 7A2-SMCC-DM1 (loading: DM1/Ab=3.6), 5E8-SMCC-DM1 (loading: DM1/Ab=3.6), and RFB4-SMCC-DM1 (loading: DM1/Ab=4.3). Naked antibodies, 7A2, 5E8, and RFB4 were dosed at 4 mg/kg mouse.

Example 9

Rat Toxicity

The acute toxicity profile of trastuzumab-SPP-DM1 (disulfide linker) compared with that of free DM1 and trastuzumab-SMCC-DM1 (non-disulfide linker) was evaluated). Animals were injected on day 1, complete chemistry and hematology profiles were obtained at baseline, day 3 and day 5 and a complete necropsy was performed on day 5. Routine histology was performed on three random animals for each group for the following tissues: sternum, liver, kidney, thymus, spleen, large and small intestine. The experimental groups were as follows:
Group 1: Vehicle (10 mM sodium succinate, 100 mg/mL sucrose, 0.1% Tween 20, pH 5.0)
Group 2: Trastuzumab-SPP-DM1, 22.3 mg/kg
Group 3: Trastuzumab-SMCC-DM1, 10 mg/kg
Group 4: Trastuzumab-SMCC-DM1, 25 mg/kg
Group 5: Trastuzumab-SMCC-DM1, 50 mg/kg
Group 6: Free DM1, 160 μg/kg

Example 10

Cynomolgus Monkey Toxicity/Safety

Three groups of four (2 male, 2 female) naive *Macaca fascicularis* (cynomolgus monkey) were studied.

Group 1: (4 animals) received only Vehicle (PBS, pH 6.5, i.e. formulation minus ADC) at day 1 and day 22, followed by necropsy at day 36.

Group 2: (4 animals) received trastuzumab-SMCC-DM1 4900 µg/m2 at day 1 and at day 22.

Group 3: (4 animals) received trastuzumab-SMCC-DM1 7200 µg/m2 at day 22.

Dosing is expressed in surface area of an animal so as to be relevant to other species, i.e. dosage at µg/m2 is independent of species and thus comparable between species. Formulations of trastuzumab-SMCC-DM1 for Group 2 and Group 3 studies contained PBS, 5.4 mM sodium phosphate, 4.2 mM potassium phosphate, 140 mM sodium chloride, pH 6.5.

Blood was collected for hematology analysis prior to first dosing (acclimation period) and at days 3, 7, 11, and 14 after the first dose (Groups 1 and 2) and at days 3, 7, 11, 14, and 21 after the second dose (Groups 1, 2 and 3). Erythrocyte (RBC) and platelet (PLT) counts were measured by the light scattering method. Leukocyte (WBC) count was measured by the peroxidase/basophil method. Reticulocyte count was measured by the light scattering method with cationic dye. Cell counts were measured on an Advia 120 apparatus. ALT (alanine aminotransferase) and AST (aspartate aminotransferase) were measured in U/L by UV/NADH; IFCC methodology on an Olympus AU400 apparatus, and using Total Ab ELISA—ECD/GxhuFc-HRP. Conj. Ab ELISA—xDM1/ECD-Bio/SA-HRP tests.

All patents, patent applications, and references cited throughout the specification are expressly incorporated by reference.

---

We claim:

1. A composition comprising a mixture of antibody-drug conjugate compounds having the structure:

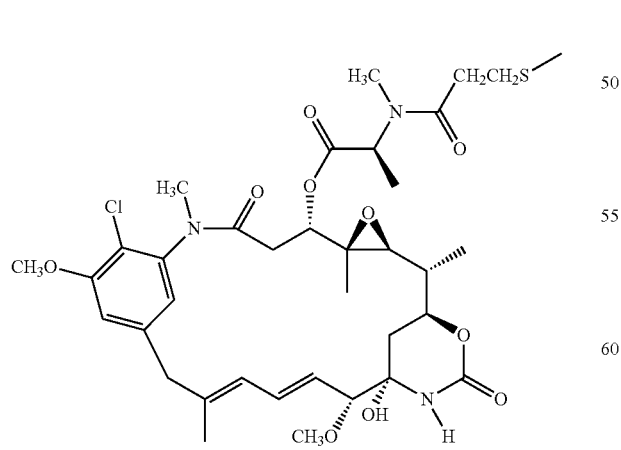

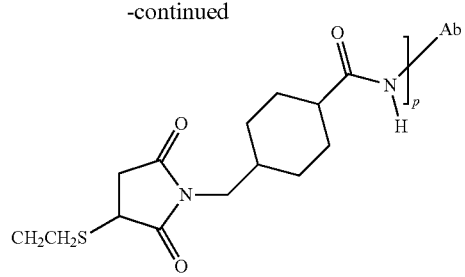

wherein Ab is an antibody which binds to CD22;

p is an integer from 1 to 8; and the average drug loading per antibody in the mixture of antibody-drug conjugate compounds is about 2 to about 5.

2. The antibody-drug conjugate compound of claim 1 wherein the antibody is selected from a monoclonal antibody, an antibody fragment, a chimeric antibody, and a humanized antibody.

3. The antibody-drug conjugate of claim 2 wherein the antibody is a Fab fragment.

4. A pharmaceutical composition comprising the antibody-drug conjugate compound of claim 1, or a pharmaceutically acceptable salt thereof, and a pharmaceutically acceptable diluent, carrier or excipient.

5. An article of manufacture comprising
an antibody-drug conjugate compound of claim 1;
a container; and
a package insert or label indicating that the compound can be used to treat cancer.

6. A method of making the composition of claim 1; wherein the method comprises:
reacting Ab with linker reagent succinimidyl 4-(N-maleimidomethyl)cyclohexane-1-carboxylate (SMCC) to form antibody-linker intermediate Ab-L, and then reacting Ab-L with drug moiety DM1 having the structure:

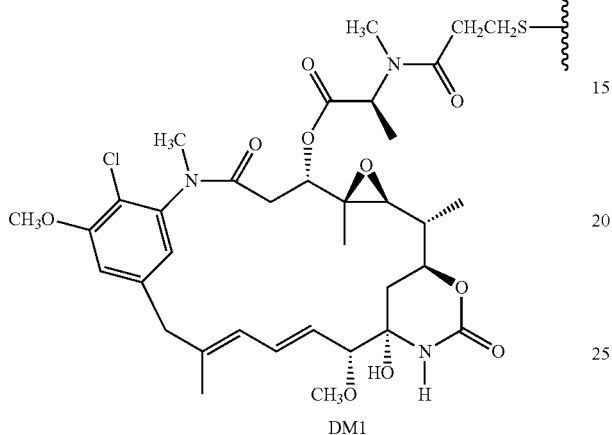

DM1 to form the mixture of antibody-drug conjugate compounds; or reacting drug moiety DM1 with linker reagent SMCC to form a drug-linker intermediate D-L, and then reacting D-L with Ab to form the mixture of antibody-drug conjugate compounds.

* * * * *

SEQUENCE LISTING

```
<160> NUMBER OF SEQ ID NOS: 36

<210> SEQ ID NO 1
<211> LENGTH: 502
<212> TYPE: PRT
<213> ORGANISM: Homo sapiens

<400> SEQUENCE: 1

Met Leu Leu Arg Ser Ala Gly Lys Leu Asn Val Gly Thr Lys Lys
 1               5                  10                  15

Glu Asp Gly Glu Ser Thr Ala Pro Thr Pro Arg Pro Lys Val Leu
                20                  25                  30

Arg Cys Lys Cys His His His Cys Pro Glu Asp Ser Val Asn Asn
                35                  40                  45

Ile Cys Ser Thr Asp Gly Tyr Cys Phe Thr Met Ile Glu Glu Asp
                50                  55                  60

Asp Ser Gly Leu Pro Val Val Thr Ser Gly Cys Leu Gly Leu Glu
                65                  70                  75

Gly Ser Asp Phe Gln Cys Arg Asp Thr Pro Ile Pro His Gln Arg
                80                  85                  90

Arg Ser Ile Glu Cys Cys Thr Glu Arg Asn Glu Cys Asn Lys Asp
                95                  100                 105

Leu His Pro Thr Leu Pro Pro Leu Lys Asn Arg Asp Phe Val Asp
                110                 115                 120

Gly Pro Ile His His Arg Ala Leu Leu Ile Ser Val Thr Val Cys
                125                 130                 135

Ser Leu Leu Leu Val Leu Ile Ile Leu Phe Cys Tyr Phe Arg Tyr
                140                 145                 150

Lys Arg Gln Glu Thr Arg Pro Arg Tyr Ser Ile Gly Leu Glu Gln
                155                 160                 165

Asp Glu Thr Tyr Ile Pro Pro Gly Glu Ser Leu Arg Asp Leu Ile
                170                 175                 180

Glu Gln Ser Gln Ser Ser Gly Ser Gly Leu Pro Leu Leu
                185                 190                 195

Val Gln Arg Thr Ile Ala Lys Gln Ile Gln Met Val Lys Gln Ile
                200                 205                 210

Gly Lys Gly Arg Tyr Gly Glu Val Trp Met Gly Lys Trp Arg Gly
                215                 220                 225
```

```
Glu Lys Val Ala Val Lys Val Phe Phe Thr Thr Glu Ala Ser
            230                 235                 240

Trp Phe Arg Glu Thr Glu Ile Tyr Gln Thr Val Leu Met Arg His
            245                 250                 255

Glu Asn Ile Leu Gly Phe Ile Ala Ala Asp Ile Lys Gly Thr Gly
            260                 265                 270

Ser Trp Thr Gln Leu Tyr Leu Ile Thr Asp Tyr His Glu Asn Gly
            275                 280                 285

Ser Leu Tyr Asp Tyr Leu Lys Ser Thr Thr Leu Asp Ala Lys Ser
            290                 295                 300

Met Leu Lys Leu Ala Tyr Ser Ser Val Ser Gly Leu Cys His Leu
            305                 310                 315

His Thr Glu Ile Phe Ser Thr Gln Gly Lys Pro Ala Ile Ala His
            320                 325                 330

Arg Asp Leu Lys Ser Lys Asn Ile Leu Val Lys Lys Asn Gly Thr
            335                 340                 345

Cys Cys Ile Ala Asp Leu Gly Leu Ala Val Lys Phe Ile Ser Asp
            350                 355                 360

Thr Asn Glu Val Asp Ile Pro Pro Asn Thr Arg Val Gly Thr Lys
            365                 370                 375

Arg Tyr Met Pro Pro Glu Val Leu Asp Glu Ser Leu Asn Arg Asn
            380                 385                 390

His Phe Gln Ser Tyr Ile Met Ala Asp Met Tyr Ser Phe Gly Leu
            395                 400                 405

Ile Leu Trp Glu Val Ala Arg Arg Cys Val Ser Gly Gly Ile Val
            410                 415                 420

Glu Glu Tyr Gln Leu Pro Tyr His Asp Leu Val Pro Ser Asp Pro
            425                 430                 435

Ser Tyr Glu Asp Met Arg Glu Ile Val Cys Ile Lys Lys Leu Arg
            440                 445                 450

Pro Ser Phe Pro Asn Arg Trp Ser Ser Asp Glu Cys Leu Arg Gln
            455                 460                 465

Met Gly Lys Leu Met Thr Glu Cys Trp Ala His Asn Pro Ala Ser
            470                 475                 480

Arg Leu Thr Ala Leu Arg Val Lys Lys Thr Leu Ala Lys Met Ser
            485                 490                 495

Glu Ser Gln Asp Ile Lys Leu
            500

<210> SEQ ID NO 2
<211> LENGTH: 507
<212> TYPE: PRT
<213> ORGANISM: Homo sapiens

<400> SEQUENCE: 2

Met Ala Gly Ala Gly Pro Lys Arg Arg Ala Leu Ala Ala Pro Ala
  1               5                  10                  15

Ala Glu Glu Lys Glu Glu Ala Arg Glu Lys Met Leu Ala Ala Lys
             20                  25                  30

Ser Ala Asp Gly Ser Ala Pro Ala Gly Glu Gly Glu Gly Val Thr
             35                  40                  45

Leu Gln Arg Asn Ile Thr Leu Leu Asn Gly Val Ala Ile Ile Val
             50                  55                  60

Gly Thr Ile Ile Gly Ser Gly Ile Phe Val Thr Pro Thr Gly Val
             65                  70                  75
```

-continued

```
Leu Lys Glu Ala Gly Ser Pro Gly Leu Ala Leu Val Val Trp Ala
             80                  85                  90
Ala Cys Gly Val Phe Ser Ile Val Gly Ala Leu Cys Tyr Ala Glu
             95                 100                 105
Leu Gly Thr Thr Ile Ser Lys Ser Gly Gly Asp Tyr Ala Tyr Met
            110                 115                 120
Leu Glu Val Tyr Gly Ser Leu Pro Ala Phe Leu Lys Leu Trp Ile
            125                 130                 135
Glu Leu Leu Ile Ile Arg Pro Ser Ser Gln Tyr Ile Val Ala Leu
            140                 145                 150
Val Phe Ala Thr Tyr Leu Leu Lys Pro Leu Phe Pro Thr Cys Pro
            155                 160                 165
Val Pro Glu Glu Ala Ala Lys Leu Val Ala Cys Leu Cys Val Leu
            170                 175                 180
Leu Leu Thr Ala Val Asn Cys Tyr Ser Val Lys Ala Ala Thr Arg
            185                 190                 195
Val Gln Asp Ala Phe Ala Ala Ala Lys Leu Leu Ala Leu Ala Leu
            200                 205                 210
Ile Ile Leu Leu Gly Phe Val Gln Ile Gly Lys Gly Val Val Ser
            215                 220                 225
Asn Leu Asp Pro Asn Phe Ser Phe Glu Gly Thr Lys Leu Asp Val
            230                 235                 240
Gly Asn Ile Val Leu Ala Leu Tyr Ser Gly Leu Phe Ala Tyr Gly
            245                 250                 255
Gly Trp Asn Tyr Leu Asn Phe Val Thr Glu Glu Met Ile Asn Pro
            260                 265                 270
Tyr Arg Asn Leu Pro Leu Ala Ile Ile Ile Ser Leu Pro Ile Val
            275                 280                 285
Thr Leu Val Tyr Val Leu Thr Asn Leu Ala Tyr Phe Thr Thr Leu
            290                 295                 300
Ser Thr Glu Gln Met Leu Ser Ser Glu Ala Val Ala Val Asp Phe
            305                 310                 315
Gly Asn Tyr His Leu Gly Val Met Ser Trp Ile Ile Pro Val Phe
            320                 325                 330
Val Gly Leu Ser Cys Phe Gly Ser Val Asn Gly Ser Leu Phe Thr
            335                 340                 345
Ser Ser Arg Leu Phe Phe Val Gly Ser Arg Glu Gly His Leu Pro
            350                 355                 360
Ser Ile Leu Ser Met Ile His Pro Gln Leu Leu Thr Pro Val Pro
            365                 370                 375
Ser Leu Val Phe Thr Cys Val Met Thr Leu Leu Tyr Ala Phe Ser
            380                 385                 390
Lys Asp Ile Phe Ser Val Ile Asn Phe Phe Ser Phe Phe Asn Trp
            395                 400                 405
Leu Cys Val Ala Leu Ala Ile Ile Gly Met Ile Trp Leu Arg His
            410                 415                 420
Arg Lys Pro Glu Leu Glu Arg Pro Ile Lys Val Asn Leu Ala Leu
            425                 430                 435
Pro Val Phe Phe Ile Leu Ala Cys Leu Phe Leu Ile Ala Val Ser
            440                 445                 450
Phe Trp Lys Thr Pro Val Glu Cys Gly Ile Gly Phe Thr Ile Ile
            455                 460                 465
Leu Ser Gly Leu Pro Val Tyr Phe Phe Gly Val Trp Trp Lys Asn
```

```
                    470                 475                 480
Lys Pro Lys Trp Leu Leu Gln Gly Ile Phe Ser Thr Thr Val Leu
                485                 490                 495
Cys Gln Lys Leu Met Gln Val Val Pro Gln Glu Thr
                500                 505

<210> SEQ ID NO 3
<211> LENGTH: 339
<212> TYPE: PRT
<213> ORGANISM: Homo sapiens

<400> SEQUENCE: 3

Met Glu Ser Arg Lys Asp Ile Thr Asn Gln Glu Leu Trp Lys
  1               5                  10                  15

Met Lys Pro Arg Arg Asn Leu Glu Glu Asp Asp Tyr Leu His Lys
                 20                  25                  30

Asp Thr Gly Glu Thr Ser Met Leu Lys Arg Pro Val Leu Leu His
                 35                  40                  45

Leu His Gln Thr Ala His Ala Asp Glu Phe Asp Cys Pro Ser Glu
                 50                  55                  60

Leu Gln His Thr Gln Glu Leu Phe Pro Gln Trp His Leu Pro Ile
                 65                  70                  75

Lys Ile Ala Ala Ile Ala Ser Leu Thr Phe Leu Tyr Thr Leu
                 80                  85                  90

Leu Arg Glu Val Ile His Pro Leu Ala Thr Ser His Gln Gln Tyr
                 95                 100                 105

Phe Tyr Lys Ile Pro Ile Leu Val Ile Asn Lys Val Leu Pro Met
                110                 115                 120

Val Ser Ile Thr Leu Leu Ala Leu Val Tyr Leu Pro Gly Val Ile
                125                 130                 135

Ala Ala Ile Val Gln Leu His Asn Gly Thr Lys Tyr Lys Lys Phe
                140                 145                 150

Pro His Trp Leu Asp Lys Trp Met Leu Thr Arg Lys Gln Phe Gly
                155                 160                 165

Leu Leu Ser Phe Phe Phe Ala Val Leu His Ala Ile Tyr Ser Leu
                170                 175                 180

Ser Tyr Pro Met Arg Arg Ser Tyr Arg Tyr Lys Leu Leu Asn Trp
                185                 190                 195

Ala Tyr Gln Gln Val Gln Gln Asn Lys Glu Asp Ala Trp Ile Glu
                200                 205                 210

His Asp Val Trp Arg Met Glu Ile Tyr Val Ser Leu Gly Ile Val
                215                 220                 225

Gly Leu Ala Ile Leu Ala Leu Leu Ala Val Thr Ser Ile Pro Ser
                230                 235                 240

Val Ser Asp Ser Leu Thr Trp Arg Glu Phe His Tyr Ile Gln Ser
                245                 250                 255

Lys Leu Gly Ile Val Ser Leu Leu Gly Thr Ile His Ala Leu
                260                 265                 270

Ile Phe Ala Trp Asn Lys Trp Ile Asp Ile Lys Gln Phe Val Trp
                275                 280                 285

Tyr Thr Pro Pro Thr Phe Met Ile Ala Val Phe Leu Pro Ile Val
                290                 295                 300

Val Leu Ile Phe Lys Ser Ile Leu Phe Leu Pro Cys Leu Arg Lys
                305                 310                 315

Lys Ile Leu Lys Ile Arg His Gly Trp Glu Asp Val Thr Lys Ile
```

Asn Lys Thr Glu Ile Cys Ser Gln Leu
            335

<210> SEQ ID NO 4
<211> LENGTH: 6995
<212> TYPE: PRT
<213> ORGANISM: Homo sapiens

<400> SEQUENCE: 4

Pro Val Thr Ser Leu Leu Thr Pro Gly Leu Val Ile Thr Thr Asp
  1               5                  10                  15

Arg Met Gly Ile Ser Arg Glu Pro Gly Thr Ser Ser Thr Ser Asn
                 20                  25                  30

Leu Ser Ser Thr Ser His Glu Arg Leu Thr Thr Leu Glu Asp Thr
                 35                  40                  45

Val Asp Thr Glu Ala Met Gln Pro Ser Thr His Thr Ala Val Thr
                 50                  55                  60

Asn Val Arg Thr Ser Ile Ser Gly His Glu Ser Gln Ser Ser Val
                 65                  70                  75

Leu Ser Asp Ser Glu Thr Pro Lys Ala Thr Ser Pro Met Gly Thr
                 80                  85                  90

Thr Tyr Thr Met Gly Glu Thr Ser Val Ser Ile Ser Thr Ser Asp
                 95                 100                 105

Phe Phe Glu Thr Ser Arg Ile Gln Ile Glu Pro Thr Ser Ser Leu
                110                 115                 120

Thr Ser Gly Leu Arg Glu Thr Ser Ser Ser Glu Arg Ile Ser Ser
                125                 130                 135

Ala Thr Glu Gly Ser Thr Val Leu Ser Glu Val Pro Ser Gly Ala
                140                 145                 150

Thr Thr Glu Val Ser Arg Thr Glu Val Ile Ser Ser Arg Gly Thr
                155                 160                 165

Ser Met Ser Gly Pro Asp Gln Phe Thr Ile Ser Pro Asp Ile Ser
                170                 175                 180

Thr Glu Ala Ile Thr Arg Leu Ser Thr Ser Pro Ile Met Thr Glu
                185                 190                 195

Ser Ala Glu Ser Ala Ile Thr Ile Glu Thr Gly Ser Pro Gly Ala
                200                 205                 210

Thr Ser Glu Gly Thr Leu Thr Leu Asp Thr Ser Thr Thr Thr Phe
                215                 220                 225

Trp Ser Gly Thr His Ser Thr Ala Ser Pro Gly Phe Ser His Ser
                230                 235                 240

Glu Met Thr Thr Leu Met Ser Arg Thr Pro Gly Asp Val Pro Trp
                245                 250                 255

Pro Ser Leu Pro Ser Val Glu Glu Ala Ser Ser Val Ser Ser Ser
                260                 265                 270

Leu Ser Ser Pro Ala Met Thr Ser Thr Ser Phe Phe Ser Thr Leu
                275                 280                 285

Pro Glu Ser Ile Ser Ser Ser Pro His Pro Val Thr Ala Leu Leu
                290                 295                 300

Thr Leu Gly Pro Val Lys Thr Thr Asp Met Leu Arg Thr Ser Ser
                305                 310                 315

Glu Pro Glu Thr Ser Ser Pro Pro Asn Leu Ser Ser Thr Ser Ala
                320                 325                 330

Glu Ile Leu Ala Thr Ser Glu Val Thr Lys Asp Arg Glu Lys Ile

```
                335                 340                 345
His Pro Ser Ser Asn Thr Pro Val Val Asn Val Gly Thr Val Ile
                350                 355                 360
Tyr Lys His Leu Ser Pro Ser Val Leu Ala Asp Leu Val Thr
                365                 370                 375
Thr Lys Pro Thr Ser Pro Met Ala Thr Thr Ser Thr Leu Gly Asn
                380                 385                 390
Thr Ser Val Ser Thr Ser Pro Ala Phe Pro Glu Thr Met Met
                395                 400                 405
Thr Gln Pro Thr Ser Ser Leu Thr Ser Gly Leu Arg Glu Ile Ser
                410                 415                 420
Thr Ser Gln Glu Thr Ser Ser Ala Thr Glu Arg Ser Ala Ser Leu
                425                 430                 435
Ser Gly Met Pro Thr Gly Ala Thr Thr Lys Val Ser Arg Thr Glu
                440                 445                 450
Ala Leu Ser Leu Gly Arg Thr Ser Thr Pro Gly Pro Ala Gln Ser
                455                 460                 465
Thr Ile Ser Pro Glu Ile Ser Thr Glu Thr Ile Thr Arg Ile Ser
                470                 475                 480
Thr Pro Leu Thr Thr Thr Gly Ser Ala Glu Met Thr Ile Thr Pro
                485                 490                 495
Lys Thr Gly His Ser Gly Ala Ser Ser Gln Gly Thr Phe Thr Leu
                500                 505                 510
Asp Thr Ser Ser Arg Ala Ser Trp Pro Gly Thr His Ser Ala Ala
                515                 520                 525
Thr His Arg Ser Pro His Ser Gly Met Thr Thr Pro Met Ser Arg
                530                 535                 540
Gly Pro Glu Asp Val Ser Trp Pro Ser Arg Pro Ser Val Glu Lys
                545                 550                 555
Thr Ser Pro Pro Ser Ser Leu Val Ser Leu Ser Ala Val Thr Ser
                560                 565                 570
Pro Ser Pro Leu Tyr Ser Thr Pro Ser Glu Ser Ser His Ser Ser
                575                 580                 585
Pro Leu Arg Val Thr Ser Leu Phe Thr Pro Val Met Met Lys Thr
                590                 595                 600
Thr Asp Met Leu Asp Thr Ser Leu Glu Pro Val Thr Thr Ser Pro
                605                 610                 615
Pro Ser Met Asn Ile Thr Ser Asp Glu Ser Leu Ala Thr Ser Lys
                620                 625                 630
Ala Thr Met Glu Thr Glu Ala Ile Gln Leu Ser Glu Asn Thr Ala
                635                 640                 645
Val Thr Gln Met Gly Thr Ile Ser Ala Arg Gln Glu Phe Tyr Ser
                650                 655                 660
Ser Tyr Pro Gly Leu Pro Glu Pro Ser Lys Val Thr Ser Pro Val
                665                 670                 675
Val Thr Ser Ser Thr Ile Lys Asp Ile Val Ser Thr Thr Ile Pro
                680                 685                 690
Ala Ser Ser Glu Ile Thr Arg Ile Glu Met Glu Ser Thr Ser Thr
                695                 700                 705
Leu Thr Pro Thr Pro Arg Glu Thr Ser Thr Ser Gln Glu Ile His
                710                 715                 720
Ser Ala Thr Lys Pro Ser Thr Val Pro Tyr Lys Ala Leu Thr Ser
                725                 730                 735
```

-continued

```
Ala Thr Ile Glu Asp Ser Met Thr Gln Val Met Ser Ser Arg
                740                 745                 750

Gly Pro Ser Pro Asp Gln Ser Thr Met Ser Gln Asp Ile Ser Thr
            755                 760                 765

Glu Val Ile Thr Arg Leu Ser Thr Ser Pro Ile Lys Thr Glu Ser
            770                 775                 780

Thr Glu Met Thr Ile Thr Thr Gln Thr Gly Ser Pro Gly Ala Thr
            785                 790                 795

Ser Arg Gly Thr Leu Thr Leu Asp Thr Ser Thr Thr Phe Met Ser
            800                 805                 810

Gly Thr His Ser Thr Ala Ser Gln Gly Phe Ser His Ser Gln Met
            815                 820                 825

Thr Ala Leu Met Ser Arg Thr Pro Gly Glu Val Pro Trp Leu Ser
            830                 835                 840

His Pro Ser Val Glu Glu Ala Ser Ser Ala Ser Phe Ser Leu Ser
            845                 850                 855

Ser Pro Val Met Thr Ser Ser Pro Val Ser Ser Thr Leu Pro
            860                 865                 870

Asp Ser Ile His Ser Ser Leu Pro Val Thr Ser Leu Leu Thr
            875                 880                 885

Ser Gly Leu Val Lys Thr Thr Glu Leu Leu Gly Thr Ser Ser Glu
            890                 895                 900

Pro Glu Thr Ser Ser Pro Pro Asn Leu Ser Ser Thr Ser Ala Glu
            905                 910                 915

Ile Leu Ala Thr Thr Glu Val Thr Thr Asp Thr Glu Lys Leu Glu
            920                 925                 930

Met Thr Asn Val Val Thr Ser Gly Tyr Thr His Glu Ser Pro Ser
            935                 940                 945

Ser Val Leu Ala Asp Ser Val Thr Thr Lys Ala Thr Ser Ser Met
            950                 955                 960

Gly Ile Thr Tyr Pro Thr Gly Asp Thr Asn Val Leu Thr Ser Thr
            965                 970                 975

Pro Ala Phe Ser Asp Thr Ser Arg Ile Gln Thr Lys Ser Lys Leu
            980                 985                 990

Ser Leu Thr Pro Gly Leu Met Glu Thr Ser Ile Ser Glu Glu Thr
            995                 1000                1005

Ser Ser Ala Thr Glu Lys Ser Thr Val Leu Ser Ser Val Pro Thr
            1010                1015                1020

Gly Ala Thr Thr Glu Val Ser Arg Thr Glu Ala Ile Ser Ser Ser
            1025                1030                1035

Arg Thr Ser Ile Pro Gly Pro Ala Gln Ser Thr Met Ser Ser Asp
            1040                1045                1050

Thr Ser Met Glu Thr Ile Thr Arg Ile Ser Thr Pro Leu Thr Arg
            1055                1060                1065

Lys Glu Ser Thr Asp Met Ala Ile Thr Pro Lys Thr Gly Pro Ser
            1070                1075                1080

Gly Ala Thr Ser Gln Gly Thr Phe Thr Leu Asp Ser Ser Ser Thr
            1085                1090                1095

Ala Ser Trp Pro Gly Thr His Ser Ala Thr Thr Gln Arg Phe Pro
            1100                1105                1110

Arg Ser Val Val Thr Thr Pro Met Ser Arg Gly Pro Glu Asp Val
            1115                1120                1125

Ser Trp Pro Ser Pro Leu Ser Val Glu Lys Asn Ser Pro Pro Ser
            1130                1135                1140
```

```
Ser Leu Val Ser Ser Ser Val Thr Ser Pro Ser Pro Leu Tyr
                1145                1150                1155

Ser Thr Pro Ser Gly Ser Ser His Ser Ser Pro Val Pro Val Thr
            1160                1165                1170

Ser Leu Phe Thr Ser Ile Met Met Lys Ala Thr Asp Met Leu Asp
        1175                1180                1185

Ala Ser Leu Glu Pro Glu Thr Thr Ser Ala Pro Asn Met Asn Ile
    1190                1195                1200

Thr Ser Asp Glu Ser Leu Ala Ala Ser Lys Ala Thr Thr Glu Thr
1205                1210                1215

Glu Ala Ile His Val Phe Glu Asn Thr Ala Ala Ser His Val Glu
            1220                1225                1230

Thr Thr Ser Ala Thr Glu Glu Leu Tyr Ser Ser Ser Pro Gly Phe
        1235                1240                1245

Ser Glu Pro Thr Lys Val Ile Ser Pro Val Thr Ser Ser Ser
    1250                1255                1260

Ile Arg Asp Asn Met Val Ser Thr Thr Met Pro Gly Ser Ser Gly
1265                1270                1275

Ile Thr Arg Ile Glu Ile Glu Ser Met Ser Ser Leu Thr Pro Gly
            1280                1285                1290

Leu Arg Glu Thr Arg Thr Ser Gln Asp Ile Thr Ser Ser Thr Glu
        1295                1300                1305

Thr Ser Thr Val Leu Tyr Lys Met Pro Ser Gly Ala Thr Pro Glu
    1310                1315                1320

Val Ser Arg Thr Glu Val Met Pro Ser Ser Arg Thr Ser Ile Pro
1325                1330                1335

Gly Pro Ala Gln Ser Thr Met Ser Leu Asp Ile Ser Asp Glu Val
            1340                1345                1350

Val Thr Arg Leu Ser Thr Ser Pro Ile Met Thr Glu Ser Ala Glu
        1355                1360                1365

Ile Thr Ile Thr Thr Gln Thr Gly Tyr Ser Leu Ala Thr Ser Gln
    1370                1375                1380

Val Thr Leu Pro Leu Gly Thr Ser Met Thr Phe Leu Ser Gly Thr
1385                1390                1395

His Ser Thr Met Ser Gln Gly Leu Ser His Ser Glu Met Thr Asn
            1400                1405                1410

Leu Met Ser Arg Gly Pro Glu Ser Leu Ser Trp Thr Ser Pro Arg
        1415                1420                1425

Phe Val Glu Thr Thr Arg Ser Ser Ser Leu Thr Ser Leu Pro
    1430                1435                1440

Leu Thr Thr Ser Leu Ser Pro Val Ser Ser Thr Leu Leu Asp Ser
1445                1450                1455

Ser Pro Ser Ser Pro Leu Pro Val Thr Ser Leu Ile Leu Pro Gly
            1460                1465                1470

Leu Val Lys Thr Thr Glu Val Leu Asp Thr Ser Ser Glu Pro Lys
        1475                1480                1485

Thr Ser Ser Ser Pro Asn Leu Ser Ser Thr Ser Val Glu Ile Pro
    1490                1495                1500

Ala Thr Ser Glu Ile Met Thr Asp Thr Glu Lys Ile His Pro Ser
1505                1510                1515

Ser Asn Thr Ala Val Ala Lys Val Arg Thr Ser Ser Ser Val His
            1520                1525                1530

Glu Ser His Ser Ser Val Leu Ala Asp Ser Glu Thr Thr Ile Thr
```

```
                    1535                1540                1545

Ile Pro Ser Met Gly Ile Thr Ser Ala Val Glu Asp Thr Thr Val
                    1550                1555                1560

Phe Thr Ser Asn Pro Ala Phe Ser Glu Thr Arg Arg Ile Pro Thr
                    1565                1570                1575

Glu Pro Thr Phe Ser Leu Thr Pro Gly Phe Arg Glu Thr Ser Thr
                    1580                1585                1590

Ser Glu Glu Thr Thr Ser Ile Thr Glu Thr Ser Ala Val Leu Phe
                    1595                1600                1605

Gly Val Pro Thr Ser Ala Thr Thr Glu Val Ser Met Thr Glu Ile
                    1610                1615                1620

Met Ser Ser Asn Arg Thr His Ile Pro Asp Ser Asp Gln Ser Thr
                    1625                1630                1635

Met Ser Pro Asp Ile Ile Thr Glu Val Ile Thr Arg Leu Ser Ser
                    1640                1645                1650

Ser Ser Met Met Ser Glu Ser Thr Gln Met Thr Ile Thr Thr Gln
                    1655                1660                1665

Lys Ser Ser Pro Gly Ala Thr Ala Gln Ser Thr Leu Thr Leu Ala
                    1670                1675                1680

Thr Thr Thr Ala Pro Leu Ala Arg Thr His Ser Thr Val Pro Pro
                    1685                1690                1695

Arg Phe Leu His Ser Glu Met Thr Thr Leu Met Ser Arg Ser Pro
                    1700                1705                1710

Glu Asn Pro Ser Trp Lys Ser Ser Pro Phe Val Glu Lys Thr Ser
                    1715                1720                1725

Ser Ser Ser Ser Leu Leu Ser Leu Pro Val Thr Thr Ser Pro Ser
                    1730                1735                1740

Val Ser Ser Thr Leu Pro Gln Ser Ile Pro Ser Ser Ser Phe Ser
                    1745                1750                1755

Val Thr Ser Leu Leu Thr Pro Gly Met Val Lys Thr Thr Asp Thr
                    1760                1765                1770

Ser Thr Glu Pro Gly Thr Ser Leu Ser Pro Asn Leu Ser Gly Thr
                    1775                1780                1785

Ser Val Glu Ile Leu Ala Ala Ser Glu Val Thr Thr Asp Thr Glu
                    1790                1795                1800

Lys Ile His Pro Ser Ser Ser Met Ala Val Thr Asn Val Gly Thr
                    1805                1810                1815

Thr Ser Ser Gly His Glu Leu Tyr Ser Ser Val Ser Ile His Ser
                    1820                1825                1830

Glu Pro Ser Lys Ala Thr Tyr Pro Val Gly Thr Pro Ser Ser Met
                    1835                1840                1845

Ala Glu Thr Ser Ile Ser Thr Ser Met Pro Ala Asn Phe Glu Thr
                    1850                1855                1860

Thr Gly Phe Glu Ala Glu Pro Phe Ser His Leu Thr Ser Gly Leu
                    1865                1870                1875

Arg Lys Thr Asn Met Ser Leu Asp Thr Ser Ser Val Thr Pro Thr
                    1880                1885                1890

Asn Thr Pro Ser Ser Pro Gly Ser Thr His Leu Leu Gln Ser Ser
                    1895                1900                1905

Lys Thr Asp Phe Thr Ser Ser Ala Lys Thr Ser Ser Pro Asp Trp
                    1910                1915                1920

Pro Pro Ala Ser Gln Tyr Thr Glu Ile Pro Val Asp Ile Ile Thr
                    1925                1930                1935
```

-continued

```
Pro Phe Asn Ala Ser Pro Ser Ile Thr Glu Ser Thr Gly Ile Thr
            1940                1945                1950

Ser Phe Pro Glu Ser Arg Phe Thr Met Ser Val Thr Glu Ser Thr
            1955                1960                1965

His His Leu Ser Thr Asp Leu Leu Pro Ser Ala Glu Thr Ile Ser
            1970                1975                1980

Thr Gly Thr Val Met Pro Ser Leu Ser Glu Ala Met Thr Ser Phe
            1985                1990                1995

Ala Thr Thr Gly Val Pro Arg Ala Ile Ser Gly Ser Gly Ser Pro
            2000                2005                2010

Phe Ser Arg Thr Glu Ser Gly Pro Gly Asp Ala Thr Leu Ser Thr
            2015                2020                2025

Ile Ala Glu Ser Leu Pro Ser Ser Thr Pro Val Pro Phe Ser Ser
            2030                2035                2040

Ser Thr Phe Thr Thr Thr Asp Ser Ser Thr Ile Pro Ala Leu His
            2045                2050                2055

Glu Ile Thr Ser Ser Ser Ala Thr Pro Tyr Arg Val Asp Thr Ser
            2060                2065                2070

Leu Gly Thr Glu Ser Ser Thr Thr Glu Gly Arg Leu Val Met Val
            2075                2080                2085

Ser Thr Leu Asp Thr Ser Ser Gln Pro Gly Arg Thr Ser Ser Ser
            2090                2095                2100

Pro Ile Leu Asp Thr Arg Met Thr Glu Ser Val Glu Leu Gly Thr
            2105                2110                2115

Val Thr Ser Ala Tyr Gln Val Pro Ser Leu Ser Thr Arg Leu Thr
            2120                2125                2130

Arg Thr Asp Gly Ile Met Glu His Ile Thr Lys Ile Pro Asn Glu
            2135                2140                2145

Ala Ala His Arg Gly Thr Ile Arg Pro Val Lys Gly Pro Gln Thr
            2150                2155                2160

Ser Thr Ser Pro Ala Ser Pro Lys Gly Leu His Thr Gly Gly Thr
            2165                2170                2175

Lys Arg Met Glu Thr Thr Thr Thr Ala Leu Lys Thr Thr Thr Thr
            2180                2185                2190

Ala Leu Lys Thr Thr Ser Arg Ala Thr Leu Thr Thr Ser Val Tyr
            2195                2200                2205

Thr Pro Thr Leu Gly Thr Leu Thr Pro Leu Asn Ala Ser Met Gln
            2210                2215                2220

Met Ala Ser Thr Ile Pro Thr Glu Met Met Ile Thr Thr Pro Tyr
            2225                2230                2235

Val Phe Pro Asp Val Pro Glu Thr Thr Ser Ser Leu Ala Thr Ser
            2240                2245                2250

Leu Gly Ala Glu Thr Ser Thr Ala Leu Pro Arg Thr Thr Pro Ser
            2255                2260                2265

Val Phe Asn Arg Glu Ser Glu Thr Thr Ala Ser Leu Val Ser Arg
            2270                2275                2280

Ser Gly Ala Glu Arg Ser Pro Val Ile Gln Thr Leu Asp Val Ser
            2285                2290                2295

Ser Ser Glu Pro Asp Thr Thr Ala Ser Trp Val Ile His Pro Ala
            2300                2305                2310

Glu Thr Ile Pro Thr Val Ser Lys Thr Thr Pro Asn Phe Phe His
            2315                2320                2325

Ser Glu Leu Asp Thr Val Ser Ser Thr Ala Thr Ser His Gly Ala
            2330                2335                2340
```

Asp Val Ser Ser Ala Ile Pro Thr Asn Ile Ser Pro Ser Glu Leu
                2345                2350                2355

Asp Ala Leu Thr Pro Leu Val Thr Ile Ser Gly Thr Asp Thr Ser
                2360                2365                2370

Thr Thr Phe Pro Thr Leu Thr Lys Ser Pro His Glu Thr Glu Thr
                2375                2380                2385

Arg Thr Thr Trp Leu Thr His Pro Ala Glu Thr Ser Ser Thr Ile
                2390                2395                2400

Pro Arg Thr Ile Pro Asn Phe Ser His His Glu Ser Asp Ala Thr
                2405                2410                2415

Pro Ser Ile Ala Thr Ser Pro Gly Ala Glu Thr Ser Ser Ala Ile
                2420                2425                2430

Pro Ile Met Thr Val Ser Pro Gly Ala Glu Asp Leu Val Thr Ser
                2435                2440                2445

Gln Val Thr Ser Ser Gly Thr Asp Arg Asn Met Thr Ile Pro Thr
                2450                2455                2460

Leu Thr Leu Ser Pro Gly Glu Pro Lys Thr Ile Ala Ser Leu Val
                2465                2470                2475

Thr His Pro Glu Ala Gln Thr Ser Ser Ala Ile Pro Thr Ser Thr
                2480                2485                2490

Ile Ser Pro Ala Val Ser Arg Leu Val Thr Ser Met Val Thr Ser
                2495                2500                2505

Leu Ala Ala Lys Thr Ser Thr Thr Asn Arg Ala Leu Thr Asn Ser
                2510                2515                2520

Pro Gly Glu Pro Ala Thr Thr Val Ser Leu Val Thr His Ser Ala
                2525                2530                2535

Gln Thr Ser Pro Thr Val Pro Trp Thr Thr Ser Ile Phe Phe His
                2540                2545                2550

Ser Lys Ser Asp Thr Thr Pro Ser Met Thr Thr Ser His Gly Ala
                2555                2560                2565

Glu Ser Ser Ser Ala Val Pro Thr Pro Thr Val Ser Thr Glu Val
                2570                2575                2580

Pro Gly Val Val Thr Pro Leu Val Thr Ser Ser Arg Ala Val Ile
                2585                2590                2595

Ser Thr Thr Ile Pro Ile Leu Thr Leu Ser Pro Gly Glu Pro Glu
                2600                2605                2610

Thr Thr Pro Ser Met Ala Thr Ser His Gly Glu Glu Ala Ser Ser
                2615                2620                2625

Ala Ile Pro Thr Pro Thr Val Ser Pro Gly Val Pro Gly Val Val
                2630                2635                2640

Thr Ser Leu Val Thr Ser Ser Arg Ala Val Thr Ser Thr Thr Ile
                2645                2650                2655

Pro Ile Leu Thr Phe Ser Leu Gly Glu Pro Glu Thr Thr Pro Ser
                2660                2665                2670

Met Ala Thr Ser His Gly Thr Glu Ala Gly Ser Ala Val Pro Thr
                2675                2680                2685

Val Leu Pro Glu Val Pro Gly Met Val Thr Ser Leu Val Ala Ser
                2690                2695                2700

Ser Arg Ala Val Thr Ser Thr Thr Leu Pro Thr Leu Thr Leu Ser
                2705                2710                2715

Pro Gly Glu Pro Glu Thr Thr Pro Ser Met Ala Thr Ser His Gly
                2720                2725                2730

Ala Glu Ala Ser Ser Thr Val Pro Thr Val Ser Pro Glu Val Pro

```
                    2735                2740                2745
Gly Val Val Thr Ser Leu Val Thr Ser Ser Ser Gly Val Asn Ser
            2750                2755                2760
Thr Ser Ile Pro Thr Leu Ile Leu Ser Pro Gly Glu Leu Glu Thr
            2765                2770                2775
Thr Pro Ser Met Ala Thr Ser His Gly Ala Glu Ala Ser Ser Ala
            2780                2785                2790
Val Pro Thr Pro Thr Val Ser Pro Gly Val Ser Gly Val Val Thr
            2795                2800                2805
Pro Leu Val Thr Ser Ser Arg Ala Val Thr Ser Thr Thr Ile Pro
            2810                2815                2820
Ile Leu Thr Leu Ser Ser Ser Glu Pro Glu Thr Thr Pro Ser Met
            2825                2830                2835
Ala Thr Ser His Gly Val Glu Ala Ser Ser Ala Val Leu Thr Val
            2840                2845                2850
Ser Pro Glu Val Pro Gly Met Val Thr Phe Leu Val Thr Ser Ser
            2855                2860                2865
Arg Ala Val Thr Ser Thr Thr Ile Pro Thr Leu Thr Ile Ser Ser
            2870                2875                2880
Asp Glu Pro Glu Thr Thr Thr Ser Leu Val Thr His Ser Glu Ala
            2885                2890                2895
Lys Met Ile Ser Ala Ile Pro Thr Leu Gly Val Ser Pro Thr Val
            2900                2905                2910
Gln Gly Leu Val Thr Ser Leu Val Thr Ser Ser Gly Ser Glu Thr
            2915                2920                2925
Ser Ala Phe Ser Asn Leu Thr Val Ala Ser Ser Gln Pro Glu Thr
            2930                2935                2940
Ile Asp Ser Trp Val Ala His Pro Gly Thr Glu Ala Ser Ser Val
            2945                2950                2955
Val Pro Thr Leu Thr Val Ser Thr Gly Glu Pro Phe Thr Asn Ile
            2960                2965                2970
Ser Leu Val Thr His Pro Ala Glu Ser Ser Ser Thr Leu Pro Arg
            2975                2980                2985
Thr Thr Ser Arg Phe Ser His Ser Glu Leu Asp Thr Met Pro Ser
            2990                2995                3000
Thr Val Thr Ser Pro Glu Ala Glu Ser Ser Ser Ala Ile Ser Thr
            3005                3010                3015
Thr Ile Ser Pro Gly Ile Pro Gly Val Leu Thr Ser Leu Val Thr
            3020                3025                3030
Ser Ser Gly Arg Asp Ile Ser Ala Thr Phe Pro Thr Val Pro Glu
            3035                3040                3045
Ser Pro His Glu Ser Glu Ala Thr Ala Ser Trp Val Thr His Pro
            3050                3055                3060
Ala Val Thr Ser Thr Thr Val Pro Arg Thr Thr Pro Asn Tyr Ser
            3065                3070                3075
His Ser Glu Pro Asp Thr Thr Pro Ser Ile Ala Thr Ser Pro Gly
            3080                3085                3090
Ala Glu Ala Thr Ser Asp Phe Pro Thr Ile Thr Val Ser Pro Asp
            3095                3100                3105
Val Pro Asp Met Val Thr Ser Gln Val Thr Ser Ser Gly Thr Asp
            3110                3115                3120
Thr Ser Ile Thr Ile Pro Thr Leu Thr Leu Ser Ser Gly Glu Pro
            3125                3130                3135
```

-continued

```
Glu Thr Thr Thr Ser Phe Ile Thr Tyr Ser Glu Thr His Thr Ser
            3140                3145                3150

Ser Ala Ile Pro Thr Leu Pro Val Ser Pro Asp Ala Ser Lys Met
            3155                3160                3165

Leu Thr Ser Leu Val Ile Ser Ser Gly Thr Asp Ser Thr Thr Thr
            3170                3175                3180

Phe Pro Thr Leu Thr Glu Thr Pro Tyr Glu Pro Glu Thr Thr Ala
            3185                3190                3195

Ile Gln Leu Ile His Pro Ala Glu Thr Asn Thr Met Val Pro Arg
            3200                3205                3210

Thr Thr Pro Lys Phe Ser His Ser Lys Ser Asp Thr Thr Leu Pro
            3215                3220                3225

Val Ala Ile Thr Ser Pro Gly Pro Glu Ala Ser Ser Ala Val Ser
            3230                3235                3240

Thr Thr Thr Ile Ser Pro Asp Met Ser Asp Leu Val Thr Ser Leu
            3245                3250                3255

Val Pro Ser Ser Gly Thr Asp Thr Ser Thr Thr Phe Pro Thr Leu
            3260                3265                3270

Ser Glu Thr Pro Tyr Glu Pro Glu Thr Thr Ala Thr Trp Leu Thr
            3275                3280                3285

His Pro Ala Glu Thr Ser Thr Thr Val Ser Gly Thr Ile Pro Asn
            3290                3295                3300

Phe Ser His Arg Gly Ser Asp Thr Ala Pro Ser Met Val Thr Ser
            3305                3310                3315

Pro Gly Val Asp Thr Arg Ser Gly Val Pro Thr Thr Thr Ile Pro
            3320                3325                3330

Pro Ser Ile Pro Gly Val Val Thr Ser Gln Val Thr Ser Ser Ala
            3335                3340                3345

Thr Asp Thr Ser Thr Ala Ile Pro Thr Leu Thr Pro Ser Pro Gly
            3350                3355                3360

Glu Pro Glu Thr Thr Ala Ser Ser Ala Thr His Pro Gly Thr Gln
            3365                3370                3375

Thr Gly Phe Thr Val Pro Ile Arg Thr Val Pro Ser Ser Glu Pro
            3380                3385                3390

Asp Thr Met Ala Ser Trp Val Thr His Pro Pro Gln Thr Ser Thr
            3395                3400                3405

Pro Val Ser Arg Thr Thr Ser Ser Phe Ser His Ser Ser Pro Asp
            3410                3415                3420

Ala Thr Pro Val Met Ala Thr Ser Pro Arg Thr Glu Ala Ser Ser
            3425                3430                3435

Ala Val Leu Thr Thr Ile Ser Pro Gly Ala Pro Glu Met Val Thr
            3440                3445                3450

Ser Gln Ile Thr Ser Ser Gly Ala Ala Thr Ser Thr Thr Val Pro
            3455                3460                3465

Thr Leu Thr His Ser Pro Gly Met Pro Glu Thr Thr Ala Leu Leu
            3470                3475                3480

Ser Thr His Pro Arg Thr Glu Thr Ser Lys Thr Phe Pro Ala Ser
            3485                3490                3495

Thr Val Phe Pro Gln Val Ser Glu Thr Thr Ala Ser Leu Thr Ile
            3500                3505                3510

Arg Pro Gly Ala Glu Thr Ser Thr Ala Leu Pro Thr Gln Thr Thr
            3515                3520                3525

Ser Ser Leu Phe Thr Leu Leu Val Thr Gly Thr Ser Arg Val Asp
            3530                3535                3540
```

```
Leu Ser Pro Thr Ala Ser Pro Gly Val Ser Ala Lys Thr Ala Pro
            3545                3550                3555

Leu Ser Thr His Pro Gly Thr Glu Thr Ser Thr Met Ile Pro Thr
            3560                3565                3570

Ser Thr Leu Ser Leu Gly Leu Leu Glu Thr Thr Gly Leu Leu Ala
            3575                3580                3585

Thr Ser Ser Ser Ala Glu Thr Ser Thr Ser Thr Leu Thr Leu Thr
            3590                3595                3600

Val Ser Pro Ala Val Ser Gly Leu Ser Ser Ala Ser Ile Thr Thr
            3605                3610                3615

Asp Lys Pro Gln Thr Val Thr Ser Trp Asn Thr Glu Thr Ser Pro
            3620                3625                3630

Ser Val Thr Ser Val Gly Pro Pro Glu Phe Ser Arg Thr Val Thr
            3635                3640                3645

Gly Thr Thr Met Thr Leu Ile Pro Ser Glu Met Pro Thr Pro Pro
            3650                3655                3660

Lys Thr Ser His Gly Glu Gly Val Ser Pro Thr Thr Ile Leu Arg
            3665                3670                3675

Thr Thr Met Val Glu Ala Thr Asn Leu Ala Thr Thr Gly Ser Ser
            3680                3685                3690

Pro Thr Val Ala Lys Thr Thr Thr Thr Phe Asn Thr Leu Ala Gly
            3695                3700                3705

Ser Leu Phe Thr Pro Leu Thr Thr Pro Gly Met Ser Thr Leu Ala
            3710                3715                3720

Ser Glu Ser Val Thr Ser Arg Thr Ser Tyr Asn His Arg Ser Trp
            3725                3730                3735

Ile Ser Thr Thr Ser Ser Tyr Asn Arg Arg Tyr Trp Thr Pro Ala
            3740                3745                3750

Thr Ser Thr Pro Val Thr Ser Thr Phe Ser Pro Gly Ile Ser Thr
            3755                3760                3765

Ser Ser Ile Pro Ser Ser Thr Ala Ala Thr Val Pro Phe Met Val
            3770                3775                3780

Pro Phe Thr Leu Asn Phe Thr Ile Thr Asn Leu Gln Tyr Glu Glu
            3785                3790                3795

Asp Met Arg His Pro Gly Ser Arg Lys Phe Asn Ala Thr Glu Arg
            3800                3805                3810

Glu Leu Gln Gly Leu Leu Lys Pro Leu Phe Arg Asn Ser Ser Leu
            3815                3820                3825

Glu Tyr Leu Tyr Ser Gly Cys Arg Leu Ala Ser Leu Arg Pro Glu
            3830                3835                3840

Lys Asp Ser Ser Ala Thr Ala Val Asp Ala Ile Cys Thr His Arg
            3845                3850                3855

Pro Asp Pro Glu Asp Leu Gly Leu Asp Arg Glu Arg Leu Tyr Trp
            3860                3865                3870

Glu Leu Ser Asn Leu Thr Asn Gly Ile Gln Glu Leu Gly Pro Tyr
            3875                3880                3885

Thr Leu Asp Arg Asn Ser Leu Tyr Val Asn Gly Phe Thr His Arg
            3890                3895                3900

Ser Ser Met Pro Thr Thr Ser Thr Pro Gly Thr Ser Thr Val Asp
            3905                3910                3915

Val Gly Thr Ser Gly Thr Pro Ser Ser Ser Pro Ser Pro Thr Thr
            3920                3925                3930

Ala Gly Pro Leu Leu Met Pro Phe Thr Leu Asn Phe Thr Ile Thr
```

```
                    3935                3940                3945
Asn Leu Gln Tyr Glu Glu Asp Met Arg Arg Thr Gly Ser Arg Lys
                    3950                3955                3960
Phe Asn Thr Met Glu Ser Val Leu Gln Gly Leu Leu Lys Pro Leu
                    3965                3970                3975
Phe Lys Asn Thr Ser Val Gly Pro Leu Tyr Ser Gly Cys Arg Leu
                    3980                3985                3990
Thr Leu Leu Arg Pro Glu Lys Asp Gly Ala Thr Gly Val Asp
                    3995                4000                4005
Ala Ile Cys Thr His Arg Leu Asp Pro Lys Ser Pro Gly Leu Asn
                    4010                4015                4020
Arg Glu Gln Leu Tyr Trp Glu Leu Ser Lys Leu Thr Asn Asp Ile
                    4025                4030                4035
Glu Glu Leu Gly Pro Tyr Thr Leu Asp Arg Asn Ser Leu Tyr Val
                    4040                4045                4050
Asn Gly Phe Thr His Gln Ser Ser Val Ser Thr Thr Ser Thr Pro
                    4055                4060                4065
Gly Thr Ser Thr Val Asp Leu Arg Thr Ser Gly Thr Pro Ser Ser
                    4070                4075                4080
Leu Ser Ser Pro Thr Ile Met Ala Ala Gly Pro Leu Leu Val Pro
                    4085                4090                4095
Phe Thr Leu Asn Phe Thr Ile Thr Asn Leu Gln Tyr Gly Glu Asp
                    4100                4105                4110
Met Gly His Pro Gly Ser Arg Lys Phe Asn Thr Thr Glu Arg Val
                    4115                4120                4125
Leu Gln Gly Leu Leu Gly Pro Ile Phe Lys Asn Thr Ser Val Gly
                    4130                4135                4140
Pro Leu Tyr Ser Gly Cys Arg Leu Thr Ser Leu Arg Ser Glu Lys
                    4145                4150                4155
Asp Gly Ala Ala Thr Gly Val Asp Ala Ile Cys Ile His His Leu
                    4160                4165                4170
Asp Pro Lys Ser Pro Gly Leu Asn Arg Glu Arg Leu Tyr Trp Glu
                    4175                4180                4185
Leu Ser Gln Leu Thr Asn Gly Ile Lys Glu Leu Gly Pro Tyr Thr
                    4190                4195                4200
Leu Asp Arg Asn Ser Leu Tyr Val Asn Gly Phe Thr His Arg Thr
                    4205                4210                4215
Ser Val Pro Thr Thr Ser Thr Pro Gly Thr Ser Thr Val Asp Leu
                    4220                4225                4230
Gly Thr Ser Gly Thr Pro Phe Ser Leu Pro Ser Pro Ala Thr Ala
                    4235                4240                4245
Gly Pro Leu Leu Val Leu Phe Thr Leu Asn Phe Thr Ile Thr Asn
                    4250                4255                4260
Leu Lys Tyr Glu Glu Asp Met His Arg Pro Gly Ser Arg Lys Phe
                    4265                4270                4275
Asn Thr Thr Glu Arg Val Leu Gln Thr Leu Val Gly Pro Met Phe
                    4280                4285                4290
Lys Asn Thr Ser Val Gly Leu Leu Tyr Ser Gly Cys Arg Leu Thr
                    4295                4300                4305
Leu Leu Arg Ser Glu Lys Asp Gly Ala Ala Thr Gly Val Asp Ala
                    4310                4315                4320
Ile Cys Thr His Arg Leu Asp Pro Lys Ser Pro Gly Val Asp Arg
                    4325                4330                4335
```

-continued

```
Glu Gln Leu Tyr Trp Glu Leu Ser Gln Leu Thr Asn Gly Ile Lys
            4340                4345                4350

Glu Leu Gly Pro Tyr Thr Leu Asp Arg Asn Ser Leu Tyr Val Asn
            4355                4360                4365

Gly Phe Thr His Trp Ile Pro Val Pro Thr Ser Ser Thr Pro Gly
            4370                4375                4380

Thr Ser Thr Val Asp Leu Gly Ser Gly Thr Pro Ser Ser Leu Pro
            4385                4390                4395

Ser Pro Thr Ser Ala Thr Ala Gly Pro Leu Leu Val Pro Phe Thr
            4400                4405                4410

Leu Asn Phe Thr Ile Thr Asn Leu Lys Tyr Glu Glu Asp Met His
            4415                4420                4425

Cys Pro Gly Ser Arg Lys Phe Asn Thr Thr Glu Arg Val Leu Gln
            4430                4435                4440

Ser Leu Leu Gly Pro Met Phe Lys Asn Thr Ser Val Gly Pro Leu
            4445                4450                4455

Tyr Ser Gly Cys Arg Leu Thr Leu Leu Arg Ser Glu Lys Asp Gly
            4460                4465                4470

Ala Ala Thr Gly Val Asp Ala Ile Cys Thr His Arg Leu Asp Pro
            4475                4480                4485

Lys Ser Pro Gly Val Asp Arg Glu Gln Leu Tyr Trp Glu Leu Ser
            4490                4495                4500

Gln Leu Thr Asn Gly Ile Lys Glu Leu Gly Pro Tyr Thr Leu Asp
            4505                4510                4515

Arg Asn Ser Leu Tyr Val Asn Gly Phe Thr His Gln Thr Ser Ala
            4520                4525                4530

Pro Asn Thr Ser Thr Pro Gly Thr Ser Thr Val Asp Leu Gly Thr
            4535                4540                4545

Ser Gly Thr Pro Ser Ser Leu Pro Ser Pro Thr Ser Ala Gly Pro
            4550                4555                4560

Leu Leu Val Pro Phe Thr Leu Asn Phe Thr Ile Thr Asn Leu Gln
            4565                4570                4575

Tyr Glu Glu Asp Met His His Pro Gly Ser Arg Lys Phe Asn Thr
            4580                4585                4590

Thr Glu Arg Val Leu Gln Gly Leu Leu Gly Pro Met Phe Lys Asn
            4595                4600                4605

Thr Ser Val Gly Leu Leu Tyr Ser Gly Cys Arg Leu Thr Leu Leu
            4610                4615                4620

Arg Pro Glu Lys Asn Gly Ala Ala Thr Gly Met Asp Ala Ile Cys
            4625                4630                4635

Ser His Arg Leu Asp Pro Lys Ser Pro Gly Leu Asn Arg Glu Gln
            4640                4645                4650

Leu Tyr Trp Glu Leu Ser Gln Leu Thr His Gly Ile Lys Glu Leu
            4655                4660                4665

Gly Pro Tyr Thr Leu Asp Arg Asn Ser Leu Tyr Val Asn Gly Phe
            4670                4675                4680

Thr His Arg Ser Ser Val Ala Pro Thr Ser Thr Pro Gly Thr Ser
            4685                4690                4695

Thr Val Asp Leu Gly Thr Ser Gly Thr Pro Ser Ser Leu Pro Ser
            4700                4705                4710

Pro Thr Thr Ala Val Pro Leu Leu Val Pro Phe Thr Leu Asn Phe
            4715                4720                4725

Thr Ile Thr Asn Leu Gln Tyr Gly Glu Asp Met Arg His Pro Gly
            4730                4735                4740
```

```
Ser Arg Lys Phe Asn Thr Thr Glu Arg Val Leu Gln Gly Leu Leu
            4745                4750                4755

Gly Pro Leu Phe Lys Asn Ser Ser Val Gly Pro Leu Tyr Ser Gly
            4760                4765                4770

Cys Arg Leu Ile Ser Leu Arg Ser Glu Lys Asp Gly Ala Ala Thr
            4775                4780                4785

Gly Val Asp Ala Ile Cys Thr His His Leu Asn Pro Gln Ser Pro
            4790                4795                4800

Gly Leu Asp Arg Glu Gln Leu Tyr Trp Gln Leu Ser Gln Met Thr
            4805                4810                4815

Asn Gly Ile Lys Glu Leu Gly Pro Tyr Thr Leu Asp Arg Asn Ser
            4820                4825                4830

Leu Tyr Val Asn Gly Phe Thr His Arg Ser Ser Gly Leu Thr Thr
            4835                4840                4845

Ser Thr Pro Trp Thr Ser Thr Val Asp Leu Gly Thr Ser Gly Thr
            4850                4855                4860

Pro Ser Pro Val Pro Ser Pro Thr Thr Ala Gly Pro Leu Leu Val
            4865                4870                4875

Pro Phe Thr Leu Asn Phe Thr Ile Thr Asn Leu Gln Tyr Glu Glu
            4880                4885                4890

Asp Met His Arg Pro Gly Ser Arg Lys Phe Asn Ala Thr Glu Arg
            4895                4900                4905

Val Leu Gln Gly Leu Leu Ser Pro Ile Phe Lys Asn Ser Ser Val
            4910                4915                4920

Gly Pro Leu Tyr Ser Gly Cys Arg Leu Thr Ser Leu Arg Pro Glu
            4925                4930                4935

Lys Asp Gly Ala Ala Thr Gly Met Asp Ala Val Cys Leu Tyr His
            4940                4945                4950

Pro Asn Pro Lys Arg Pro Gly Leu Asp Arg Glu Gln Leu Tyr Trp
            4955                4960                4965

Glu Leu Ser Gln Leu Thr His Asn Ile Thr Glu Leu Gly Pro Tyr
            4970                4975                4980

Ser Leu Asp Arg Asp Ser Leu Tyr Val Asn Gly Phe Thr His Gln
            4985                4990                4995

Asn Ser Val Pro Thr Thr Ser Thr Pro Gly Thr Ser Thr Val Tyr
            5000                5005                5010

Trp Ala Thr Thr Gly Thr Pro Ser Ser Phe Pro Gly His Thr Glu
            5015                5020                5025

Pro Gly Pro Leu Leu Ile Pro Phe Thr Phe Asn Phe Thr Ile Thr
            5030                5035                5040

Asn Leu His Tyr Glu Glu Asn Met Gln His Pro Gly Ser Arg Lys
            5045                5050                5055

Phe Asn Thr Thr Glu Arg Val Leu Gln Gly Leu Leu Lys Pro Leu
            5060                5065                5070

Phe Lys Asn Thr Ser Val Gly Pro Leu Tyr Ser Gly Cys Arg Leu
            5075                5080                5085

Thr Leu Leu Arg Pro Glu Lys Gln Glu Ala Ala Thr Gly Val Asp
            5090                5095                5100

Thr Ile Cys Thr His Arg Val Asp Pro Ile Gly Pro Gly Leu Asp
            5105                5110                5115

Arg Glu Arg Leu Tyr Trp Glu Leu Ser Gln Leu Thr Asn Ser Ile
            5120                5125                5130

Thr Glu Leu Gly Pro Tyr Thr Leu Asp Arg Asp Ser Leu Tyr Val
```

-continued

```
                5135                5140                5145
Asn Gly Phe Asn Pro Trp Ser Ser Val Pro Thr Thr Ser Thr Pro
                5150                5155                5160
Gly Thr Ser Thr Val His Leu Ala Thr Ser Gly Thr Pro Ser Ser
                5165                5170                5175
Leu Pro Gly His Thr Ala Pro Val Pro Leu Leu Ile Pro Phe Thr
                5180                5185                5190
Leu Asn Phe Thr Ile Thr Asn Leu His Tyr Glu Glu Asn Met Gln
                5195                5200                5205
His Pro Gly Ser Arg Lys Phe Asn Thr Thr Glu Arg Val Leu Gln
                5210                5215                5220
Gly Leu Leu Lys Pro Leu Phe Lys Ser Thr Ser Val Gly Pro Leu
                5225                5230                5235
Tyr Ser Gly Cys Arg Leu Thr Leu Leu Arg Pro Glu Lys His Gly
                5240                5245                5250
Ala Ala Thr Gly Val Asp Ala Ile Cys Thr Leu Arg Leu Asp Pro
                5255                5260                5265
Thr Gly Pro Gly Leu Asp Arg Glu Arg Leu Tyr Trp Glu Leu Ser
                5270                5275                5280
Gln Leu Thr Asn Ser Val Thr Glu Leu Gly Pro Tyr Thr Leu Asp
                5285                5290                5295
Arg Asp Ser Leu Tyr Val Asn Gly Phe Thr His Arg Ser Ser Val
                5300                5305                5310
Pro Thr Thr Ser Ile Pro Gly Thr Ser Ala Val His Leu Glu Thr
                5315                5320                5325
Ser Gly Thr Pro Ala Ser Leu Pro Gly His Thr Ala Pro Gly Pro
                5330                5335                5340
Leu Leu Val Pro Phe Thr Leu Asn Phe Thr Ile Thr Asn Leu Gln
                5345                5350                5355
Tyr Glu Glu Asp Met Arg His Pro Gly Ser Arg Lys Phe Asn Thr
                5360                5365                5370
Thr Glu Arg Val Leu Gln Gly Leu Leu Lys Pro Leu Phe Lys Ser
                5375                5380                5385
Thr Ser Val Gly Pro Leu Tyr Ser Gly Cys Arg Leu Thr Leu Leu
                5390                5395                5400
Arg Pro Glu Lys Arg Gly Ala Ala Thr Gly Val Asp Thr Ile Cys
                5405                5410                5415
Thr His Arg Leu Asp Pro Leu Asn Pro Gly Leu Asp Arg Glu Gln
                5420                5425                5430
Leu Tyr Trp Glu Leu Ser Lys Leu Thr Arg Gly Ile Ile Glu Leu
                5435                5440                5445
Gly Pro Tyr Leu Leu Asp Arg Gly Ser Leu Tyr Val Asn Gly Phe
                5450                5455                5460
Thr His Arg Asn Phe Val Pro Ile Thr Ser Thr Pro Gly Thr Ser
                5465                5470                5475
Thr Val His Leu Gly Thr Ser Glu Thr Pro Ser Ser Leu Pro Arg
                5480                5485                5490
Pro Ile Val Pro Gly Pro Leu Leu Val Pro Phe Thr Leu Asn Phe
                5495                5500                5505
Thr Ile Thr Asn Leu Gln Tyr Glu Glu Ala Met Arg His Pro Gly
                5510                5515                5520
Ser Arg Lys Phe Asn Thr Thr Glu Arg Val Leu Gln Gly Leu Leu
                5525                5530                5535
```

-continued

```
Arg Pro Leu Phe Lys Asn Thr Ser Ile Gly Pro Leu Tyr Ser Ser
            5540                5545                5550

Cys Arg Leu Thr Leu Leu Arg Pro Glu Lys Asp Lys Ala Ala Thr
            5555                5560                5565

Arg Val Asp Ala Ile Cys Thr His His Pro Asp Pro Gln Ser Pro
            5570                5575                5580

Gly Leu Asn Arg Glu Gln Leu Tyr Trp Glu Leu Ser Gln Leu Thr
            5585                5590                5595

His Gly Ile Thr Glu Leu Gly Pro Tyr Thr Leu Asp Arg Asp Ser
            5600                5605                5610

Leu Tyr Val Asp Gly Phe Thr His Trp Ser Pro Ile Pro Thr Thr
            5615                5620                5625

Ser Thr Pro Gly Thr Ser Ile Val Asn Leu Gly Thr Ser Gly Ile
            5630                5635                5640

Pro Pro Ser Leu Pro Glu Thr Thr Ala Thr Gly Pro Leu Leu Val
            5645                5650                5655

Pro Phe Thr Leu Asn Phe Thr Ile Thr Asn Leu Gln Tyr Glu Glu
            5660                5665                5670

Asn Met Gly His Pro Gly Ser Arg Lys Phe Asn Ile Thr Glu Ser
            5675                5680                5685

Val Leu Gln Gly Leu Leu Lys Pro Leu Phe Lys Ser Thr Ser Val
            5690                5695                5700

Gly Pro Leu Tyr Ser Gly Cys Arg Leu Thr Leu Leu Arg Pro Glu
            5705                5710                5715

Lys Asp Gly Val Ala Thr Arg Val Asp Ala Ile Cys Thr His Arg
            5720                5725                5730

Pro Asp Pro Lys Ile Pro Gly Leu Asp Arg Gln Gln Leu Tyr Trp
            5735                5740                5745

Glu Leu Ser Gln Leu Thr His Ser Ile Thr Glu Leu Gly Pro Tyr
            5750                5755                5760

Thr Leu Asp Arg Asp Ser Leu Tyr Val Asn Gly Phe Thr Gln Arg
            5765                5770                5775

Ser Ser Val Pro Thr Thr Ser Thr Pro Gly Thr Phe Thr Val Gln
            5780                5785                5790

Pro Glu Thr Ser Glu Thr Pro Ser Ser Leu Pro Gly Pro Thr Ala
            5795                5800                5805

Thr Gly Pro Val Leu Leu Pro Phe Thr Leu Asn Phe Thr Ile Ile
            5810                5815                5820

Asn Leu Gln Tyr Glu Glu Asp Met His Arg Pro Gly Ser Arg Lys
            5825                5830                5835

Phe Asn Thr Thr Glu Arg Val Leu Gln Gly Leu Leu Met Pro Leu
            5840                5845                5850

Phe Lys Asn Thr Ser Val Ser Ser Leu Tyr Ser Gly Cys Arg Leu
            5855                5860                5865

Thr Leu Leu Arg Pro Glu Lys Asp Gly Ala Ala Thr Arg Val Asp
            5870                5875                5880

Ala Val Cys Thr His Arg Pro Asp Pro Lys Ser Pro Gly Leu Asp
            5885                5890                5895

Arg Glu Arg Leu Tyr Trp Lys Leu Ser Gln Leu Thr His Gly Ile
            5900                5905                5910

Thr Glu Leu Gly Pro Tyr Thr Leu Asp Arg His Ser Leu Tyr Val
            5915                5920                5925

Asn Gly Phe Thr His Gln Ser Ser Met Thr Thr Thr Arg Thr Pro
            5930                5935                5940
```

```
Asp Thr Ser Thr Met His Leu Ala Thr Ser Arg Thr Pro Ala Ser
              5945                5950                5955

Leu Ser Gly Pro Thr Thr Ala Ser Pro Leu Leu Val Leu Phe Thr
              5960                5965                5970

Ile Asn Phe Thr Ile Thr Asn Leu Arg Tyr Glu Glu Asn Met His
              5975                5980                5985

His Pro Gly Ser Arg Lys Phe Asn Thr Thr Glu Arg Val Leu Gln
              5990                5995                6000

Gly Leu Leu Arg Pro Val Phe Lys Asn Thr Ser Val Gly Pro Leu
              6005                6010                6015

Tyr Ser Gly Cys Arg Leu Thr Leu Leu Arg Pro Lys Lys Asp Gly
              6020                6025                6030

Ala Ala Thr Lys Val Asp Ala Ile Cys Thr Tyr Arg Pro Asp Pro
              6035                6040                6045

Lys Ser Pro Gly Leu Asp Arg Glu Gln Leu Tyr Trp Glu Leu Ser
              6050                6055                6060

Gln Leu Thr His Ser Ile Thr Glu Leu Gly Pro Tyr Thr Leu Asp
              6065                6070                6075

Arg Asp Ser Leu Tyr Val Asn Gly Phe Thr Gln Arg Ser Ser Val
              6080                6085                6090

Pro Thr Thr Ser Ile Pro Gly Thr Pro Thr Val Asp Leu Gly Thr
              6095                6100                6105

Ser Gly Thr Pro Val Ser Lys Pro Gly Pro Ser Ala Ala Ser Pro
              6110                6115                6120

Leu Leu Val Leu Phe Thr Leu Asn Phe Thr Ile Thr Asn Leu Arg
              6125                6130                6135

Tyr Glu Glu Asn Met Gln His Pro Gly Ser Arg Lys Phe Asn Thr
              6140                6145                6150

Thr Glu Arg Val Leu Gln Gly Leu Leu Arg Ser Leu Phe Lys Ser
              6155                6160                6165

Thr Ser Val Gly Pro Leu Tyr Ser Gly Cys Arg Leu Thr Leu Leu
              6170                6175                6180

Arg Pro Glu Lys Asp Gly Thr Ala Thr Gly Val Asp Ala Ile Cys
              6185                6190                6195

Thr His His Pro Asp Pro Lys Ser Pro Arg Leu Asp Arg Glu Gln
              6200                6205                6210

Leu Tyr Trp Glu Leu Ser Gln Leu Thr His Asn Ile Thr Glu Leu
              6215                6220                6225

Gly Pro Tyr Ala Leu Asp Asn Asp Ser Leu Phe Val Asn Gly Phe
              6230                6235                6240

Thr His Arg Ser Ser Val Ser Thr Thr Ser Thr Pro Gly Thr Pro
              6245                6250                6255

Thr Val Tyr Leu Gly Ala Ser Lys Thr Pro Ala Ser Ile Phe Gly
              6260                6265                6270

Pro Ser Ala Ala Ser His Leu Leu Ile Leu Phe Thr Leu Asn Phe
              6275                6280                6285

Thr Ile Thr Asn Leu Arg Tyr Glu Glu Asn Met Trp Pro Gly Ser
              6290                6295                6300

Arg Lys Phe Asn Thr Thr Glu Arg Val Leu Gln Gly Leu Leu Arg
              6305                6310                6315

Pro Leu Phe Lys Asn Thr Ser Val Gly Pro Leu Tyr Ser Gly Cys
              6320                6325                6330

Arg Leu Thr Leu Leu Arg Pro Glu Lys Asp Gly Glu Ala Thr Gly
```

```
                      6335                6340                6345
Val Asp Ala Ile Cys Thr His Arg Pro Asp Pro Thr Gly Pro Gly
                 6350                6355                6360

Leu Asp Arg Glu Gln Leu Tyr Leu Glu Leu Ser Gln Leu Thr His
                 6365                6370                6375

Ser Ile Thr Glu Leu Gly Pro Tyr Thr Leu Asp Arg Asp Ser Leu
                 6380                6385                6390

Tyr Val Asn Gly Phe Thr His Arg Ser Ser Val Pro Thr Thr Ser
                 6395                6400                6405

Thr Gly Val Val Ser Glu Glu Pro Phe Thr Leu Asn Phe Thr Ile
                 6410                6415                6420

Asn Asn Leu Arg Tyr Met Ala Asp Met Gly Gln Pro Gly Ser Leu
                 6425                6430                6435

Lys Phe Asn Ile Thr Asp Asn Val Met Gln His Leu Leu Ser Pro
                 6440                6445                6450

Leu Phe Gln Arg Ser Ser Leu Gly Ala Arg Tyr Thr Gly Cys Arg
                 6455                6460                6465

Val Ile Ala Leu Arg Ser Val Lys Asn Gly Ala Glu Thr Arg Val
                 6470                6475                6480

Asp Leu Leu Cys Thr Tyr Leu Gln Pro Leu Ser Gly Pro Gly Leu
                 6485                6490                6495

Pro Ile Lys Gln Val Phe His Glu Leu Ser Gln Gln Thr His Gly
                 6500                6505                6510

Ile Thr Arg Leu Gly Pro Tyr Ser Leu Asp Lys Asp Ser Leu Tyr
                 6515                6520                6525

Leu Asn Gly Tyr Asn Glu Pro Gly Pro Asp Glu Pro Pro Thr Thr
                 6530                6535                6540

Pro Lys Pro Ala Thr Thr Phe Leu Pro Pro Leu Ser Glu Ala Thr
                 6545                6550                6555

Thr Ala Met Gly Tyr His Leu Lys Thr Leu Thr Leu Asn Phe Thr
                 6560                6565                6570

Ile Ser Asn Leu Gln Tyr Ser Pro Asp Met Gly Lys Gly Ser Ala
                 6575                6580                6585

Thr Phe Asn Ser Thr Glu Gly Val Leu Gln His Leu Leu Arg Pro
                 6590                6595                6600

Leu Phe Gln Lys Ser Ser Met Gly Pro Phe Tyr Leu Gly Cys Gln
                 6605                6610                6615

Leu Ile Ser Leu Arg Pro Glu Lys Asp Gly Ala Ala Thr Gly Val
                 6620                6625                6630

Asp Thr Thr Cys Thr Tyr His Pro Asp Pro Val Gly Pro Gly Leu
                 6635                6640                6645

Asp Ile Gln Gln Leu Tyr Trp Glu Leu Ser Gln Leu Thr His Gly
                 6650                6655                6660

Val Thr Gln Leu Gly Phe Tyr Val Leu Asp Arg Asp Ser Leu Phe
                 6665                6670                6675

Ile Asn Gly Tyr Ala Pro Gln Asn Leu Ser Ile Arg Gly Glu Tyr
                 6680                6685                6690

Gln Ile Asn Phe His Ile Val Asn Trp Asn Leu Ser Asn Pro Asp
                 6695                6700                6705

Pro Thr Ser Ser Glu Tyr Ile Thr Leu Leu Arg Asp Ile Gln Asp
                 6710                6715                6720

Lys Val Thr Thr Leu Tyr Lys Gly Ser Gln Leu His Asp Thr Phe
                 6725                6730                6735
```

-continued

```
Arg Phe Cys Leu Val Thr Asn Leu Thr Met Asp Ser Val Leu Val
            6740                6745                6750

Thr Val Lys Ala Leu Phe Ser Ser Asn Leu Asp Pro Ser Leu Val
            6755                6760                6765

Glu Gln Val Phe Leu Asp Lys Thr Leu Asn Ala Ser Phe His Trp
            6770                6775                6780

Leu Gly Ser Thr Tyr Gln Leu Val Asp Ile His Val Thr Glu Met
            6785                6790                6795

Glu Ser Ser Val Tyr Gln Pro Thr Ser Ser Ser Thr Gln His
            6800                6805                6810

Phe Tyr Leu Asn Phe Thr Ile Thr Asn Leu Pro Tyr Ser Gln Asp
            6815                6820                6825

Lys Ala Gln Pro Gly Thr Thr Asn Tyr Gln Arg Asn Lys Arg Asn
            6830                6835                6840

Ile Glu Asp Ala Leu Asn Gln Leu Phe Arg Asn Ser Ser Ile Lys
            6845                6850                6855

Ser Tyr Phe Ser Asp Cys Gln Val Ser Thr Phe Arg Ser Val Pro
            6860                6865                6870

Asn Arg His His Thr Gly Val Asp Ser Leu Cys Asn Phe Ser Pro
            6875                6880                6885

Leu Ala Arg Arg Val Asp Arg Val Ala Ile Tyr Glu Glu Phe Leu
            6890                6895                6900

Arg Met Thr Arg Asn Gly Thr Gln Leu Gln Asn Phe Thr Leu Asp
            6905                6910                6915

Arg Ser Ser Val Leu Val Asp Gly Tyr Ser Pro Asn Arg Asn Glu
            6920                6925                6930

Pro Leu Thr Gly Asn Ser Asp Leu Pro Phe Trp Ala Val Ile Leu
            6935                6940                6945

Ile Gly Leu Ala Gly Leu Leu Gly Leu Ile Thr Cys Leu Ile Cys
            6950                6955                6960

Gly Val Leu Val Thr Thr Arg Arg Arg Lys Lys Glu Gly Glu Tyr
            6965                6970                6975

Asn Val Gln Gln Gln Cys Pro Gly Tyr Tyr Gln Ser His Leu Asp
            6980                6985                6990

Leu Glu Asp Leu Gln
            6995

<210> SEQ ID NO 5
<211> LENGTH: 622
<212> TYPE: PRT
<213> ORGANISM: Homo sapiens

<400> SEQUENCE: 5

Met Ala Leu Pro Thr Ala Arg Pro Leu Leu Gly Ser Cys Gly Thr
  1               5                  10                  15

Pro Ala Leu Gly Ser Leu Leu Phe Leu Leu Phe Ser Leu Gly Trp
                 20                  25                  30

Val Gln Pro Ser Arg Thr Leu Ala Gly Glu Thr Gly Gln Glu Ala
                 35                  40                  45

Ala Pro Leu Asp Gly Val Leu Ala Asn Pro Pro Asn Ile Ser Ser
                 50                  55                  60

Leu Ser Pro Arg Gln Leu Leu Gly Phe Pro Cys Ala Glu Val Ser
                 65                  70                  75

Gly Leu Ser Thr Glu Arg Val Arg Glu Leu Ala Val Ala Leu Ala
                 80                  85                  90
```

```
Gln Lys Asn Val Lys Leu Ser Thr Glu Gln Leu Arg Cys Leu Ala
             95                 100                 105

His Arg Leu Ser Glu Pro Pro Glu Asp Leu Asp Ala Leu Pro Leu
            110                 115                 120

Asp Leu Leu Leu Phe Leu Asn Pro Asp Ala Phe Ser Gly Pro Gln
            125                 130                 135

Ala Cys Thr Arg Phe Phe Ser Arg Ile Thr Lys Ala Asn Val Asp
            140                 145                 150

Leu Leu Pro Arg Gly Ala Pro Glu Arg Gln Arg Leu Leu Pro Ala
            155                 160                 165

Ala Leu Ala Cys Trp Gly Val Arg Gly Ser Leu Leu Ser Glu Ala
            170                 175                 180

Asp Val Arg Ala Leu Gly Gly Leu Ala Cys Asp Leu Pro Gly Arg
            185                 190                 195

Phe Val Ala Glu Ser Ala Glu Val Leu Leu Pro Arg Leu Val Ser
            200                 205                 210

Cys Pro Gly Pro Leu Asp Gln Asp Gln Gln Glu Ala Ala Arg Ala
            215                 220                 225

Ala Leu Gln Gly Gly Gly Pro Pro Tyr Gly Pro Pro Ser Thr Trp
            230                 235                 240

Ser Val Ser Thr Met Asp Ala Leu Arg Gly Leu Leu Pro Val Leu
            245                 250                 255

Gly Gln Pro Ile Ile Arg Ser Ile Pro Gln Gly Ile Val Ala Ala
            260                 265                 270

Trp Arg Gln Arg Ser Ser Arg Asp Pro Ser Trp Arg Gln Pro Glu
            275                 280                 285

Arg Thr Ile Leu Arg Pro Arg Phe Arg Arg Glu Val Glu Lys Thr
            290                 295                 300

Ala Cys Pro Ser Gly Lys Lys Ala Arg Glu Ile Asp Glu Ser Leu
            305                 310                 315

Ile Phe Tyr Lys Lys Trp Glu Leu Glu Ala Cys Val Asp Ala Ala
            320                 325                 330

Leu Leu Ala Thr Gln Met Asp Arg Val Asn Ala Ile Pro Phe Thr
            335                 340                 345

Tyr Glu Gln Leu Asp Val Leu Lys His Lys Leu Asp Glu Leu Tyr
            350                 355                 360

Pro Gln Gly Tyr Pro Glu Ser Val Ile Gln His Leu Gly Tyr Leu
            365                 370                 375

Phe Leu Lys Met Ser Pro Glu Asp Ile Arg Lys Trp Asn Val Thr
            380                 385                 390

Ser Leu Glu Thr Leu Lys Ala Leu Leu Glu Val Asn Lys Gly His
            395                 400                 405

Glu Met Ser Pro Gln Val Ala Thr Leu Ile Asp Arg Phe Val Lys
            410                 415                 420

Gly Arg Gly Gln Leu Asp Lys Asp Thr Leu Asp Thr Leu Thr Ala
            425                 430                 435

Phe Tyr Pro Gly Tyr Leu Cys Ser Leu Ser Pro Glu Glu Leu Ser
            440                 445                 450

Ser Val Pro Pro Ser Ser Ile Trp Ala Val Arg Pro Gln Asp Leu
            455                 460                 465

Asp Thr Cys Asp Pro Arg Gln Leu Asp Val Leu Tyr Pro Lys Ala
            470                 475                 480

Arg Leu Ala Phe Gln Asn Met Asn Gly Ser Glu Tyr Phe Val Lys
            485                 490                 495
```

```
Ile Gln Ser Phe Leu Gly Gly Ala Pro Thr Glu Asp Leu Lys Ala
                500                 505                 510

Leu Ser Gln Gln Asn Val Ser Met Asp Leu Ala Thr Phe Met Lys
                515                 520                 525

Leu Arg Thr Asp Ala Val Leu Pro Leu Thr Val Ala Glu Val Gln
                530                 535                 540

Lys Leu Leu Gly Pro His Val Glu Gly Leu Lys Ala Glu Glu Arg
                545                 550                 555

His Arg Pro Val Arg Asp Trp Ile Leu Arg Gln Arg Gln Asp Asp
                560                 565                 570

Leu Asp Thr Leu Gly Leu Gly Leu Gln Gly Gly Ile Pro Asn Gly
                575                 580                 585

Tyr Leu Val Leu Asp Leu Ser Met Gln Glu Ala Leu Ser Gly Thr
                590                 595                 600

Pro Cys Leu Leu Gly Pro Gly Pro Val Leu Thr Val Leu Ala Leu
                605                 610                 615

Leu Leu Ala Ser Thr Leu Ala
                620

<210> SEQ ID NO 6
<211> LENGTH: 690
<212> TYPE: PRT
<213> ORGANISM: Homo sapiens

<400> SEQUENCE: 6

Met Ala Pro Trp Pro Glu Leu Gly Asp Ala Gln Pro Asn Pro Asp
  1               5                  10                  15

Lys Tyr Leu Glu Gly Ala Ala Gly Gln Gln Pro Thr Ala Pro Asp
                 20                  25                  30

Lys Ser Lys Glu Thr Asn Lys Thr Asp Asn Thr Glu Ala Pro Val
                 35                  40                  45

Thr Lys Ile Glu Leu Leu Pro Ser Tyr Ser Thr Ala Thr Leu Ile
                 50                  55                  60

Asp Glu Pro Thr Glu Val Asp Asp Pro Trp Asn Leu Pro Thr Leu
                 65                  70                  75

Gln Asp Ser Gly Ile Lys Trp Ser Glu Arg Asp Thr Lys Gly Lys
                 80                  85                  90

Ile Leu Cys Phe Phe Gln Gly Ile Gly Arg Leu Ile Leu Leu Leu
                 95                 100                 105

Gly Phe Leu Tyr Phe Phe Val Cys Ser Leu Asp Ile Leu Ser Ser
                110                 115                 120

Ala Phe Gln Leu Val Gly Gly Lys Met Ala Gly Gln Phe Phe Ser
                125                 130                 135

Asn Ser Ser Ile Met Ser Asn Pro Leu Leu Gly Leu Val Ile Gly
                140                 145                 150

Val Leu Val Thr Val Leu Val Gln Ser Ser Ser Thr Ser Thr Ser
                155                 160                 165

Ile Val Val Ser Met Val Ser Ser Ser Leu Leu Thr Val Arg Ala
                170                 175                 180

Ala Ile Pro Ile Ile Met Gly Ala Asn Ile Gly Thr Ser Ile Thr
                185                 190                 195

Asn Thr Ile Val Ala Leu Met Gln Val Gly Asp Arg Ser Glu Phe
                200                 205                 210

Arg Arg Ala Phe Ala Gly Ala Thr Val His Asp Phe Phe Asn Trp
                215                 220                 225
```

```
Leu Ser Val Leu Val Leu Pro Val Glu Val Ala Thr His Tyr
            230                 235                 240

Leu Glu Ile Ile Thr Gln Leu Ile Val Glu Ser Phe His Phe Lys
            245                 250                 255

Asn Gly Glu Asp Ala Pro Asp Leu Leu Lys Val Ile Thr Lys Pro
            260                 265                 270

Phe Thr Lys Leu Ile Val Gln Leu Asp Lys Lys Val Ile Ser Gln
            275                 280                 285

Ile Ala Met Asn Asp Glu Lys Ala Lys Asn Lys Ser Leu Val Lys
            290                 295                 300

Ile Trp Cys Lys Thr Phe Thr Asn Lys Thr Gln Ile Asn Val Thr
            305                 310                 315

Val Pro Ser Thr Ala Asn Cys Thr Ser Pro Ser Leu Cys Trp Thr
            320                 325                 330

Asp Gly Ile Gln Asn Trp Thr Met Lys Asn Val Thr Tyr Lys Glu
            335                 340                 345

Asn Ile Ala Lys Cys Gln His Ile Phe Val Asn Phe His Leu Pro
            350                 355                 360

Asp Leu Ala Val Gly Thr Ile Leu Leu Ile Leu Ser Leu Leu Val
            365                 370                 375

Leu Cys Gly Cys Leu Ile Met Ile Val Lys Ile Leu Gly Ser Val
            380                 385                 390

Leu Lys Gly Gln Val Ala Thr Val Ile Lys Lys Thr Ile Asn Thr
            395                 400                 405

Asp Phe Pro Phe Pro Phe Ala Trp Leu Thr Gly Tyr Leu Ala Ile
            410                 415                 420

Leu Val Gly Ala Gly Met Thr Phe Ile Val Gln Ser Ser Ser Val
            425                 430                 435

Phe Thr Ser Ala Leu Thr Pro Leu Ile Gly Ile Gly Val Ile Thr
            440                 445                 450

Ile Glu Arg Ala Tyr Pro Leu Thr Leu Gly Ser Asn Ile Gly Thr
            455                 460                 465

Thr Thr Thr Ala Ile Leu Ala Ala Leu Ala Ser Pro Gly Asn Ala
            470                 475                 480

Leu Arg Ser Ser Leu Gln Ile Ala Leu Cys His Phe Phe Asn
            485                 490                 495

Ile Ser Gly Ile Leu Leu Trp Tyr Pro Ile Pro Phe Thr Arg Leu
            500                 505                 510

Pro Ile Arg Met Ala Lys Gly Leu Gly Asn Ile Ser Ala Lys Tyr
            515                 520                 525

Arg Trp Phe Ala Val Phe Tyr Leu Ile Ile Phe Phe Leu Ile
            530                 535                 540

Pro Leu Thr Val Phe Gly Leu Ser Leu Ala Gly Trp Arg Val Leu
            545                 550                 555

Val Gly Val Gly Val Pro Val Val Phe Ile Ile Ile Leu Val Leu
            560                 565                 570

Cys Leu Arg Leu Leu Gln Ser Arg Cys Pro Arg Val Leu Pro Lys
            575                 580                 585

Lys Leu Gln Asn Trp Asn Phe Leu Pro Leu Trp Met Arg Ser Leu
            590                 595                 600

Lys Pro Trp Asp Ala Val Val Ser Lys Phe Thr Gly Cys Phe Gln
            605                 610                 615

Met Arg Cys Cys Tyr Cys Cys Arg Val Cys Cys Arg Ala Cys Cys
```

```
                    620                 625                 630
Leu Leu Cys Gly Cys Pro Lys Cys Cys Arg Cys Ser Lys Cys Cys
                635                 640                 645
Glu Asp Leu Glu Glu Ala Gln Glu Gly Gln Asp Val Pro Val Lys
            650                 655                 660
Ala Pro Glu Thr Phe Asp Asn Ile Thr Ile Ser Arg Glu Ala Gln
        665                 670                 675
Gly Glu Val Pro Ala Ser Asp Ser Lys Thr Glu Cys Thr Ala Leu
    680                 685                 690

<210> SEQ ID NO 7
<211> LENGTH: 1093
<212> TYPE: PRT
<213> ORGANISM: Homo sapiens

<400> SEQUENCE: 7

Met Val Leu Ala Gly Pro Leu Ala Val Ser Leu Leu Pro Ser
1               5                   10                  15
Leu Thr Leu Leu Val Ser His Leu Ser Ser Gln Asp Val Ser
            20                  25                  30
Ser Glu Pro Ser Ser Glu Gln Gln Leu Cys Ala Leu Ser Lys His
        35                  40                  45
Pro Thr Val Ala Phe Glu Asp Leu Gln Pro Trp Val Ser Asn Phe
    50                  55                  60
Thr Tyr Pro Gly Ala Arg Asp Phe Ser Gln Leu Ala Leu Asp Pro
65                  70                  75
Ser Gly Asn Gln Leu Ile Val Gly Ala Arg Asn Tyr Leu Phe Arg
            80                  85                  90
Leu Ser Leu Ala Asn Val Ser Leu Leu Gln Ala Thr Glu Trp Ala
        95                  100                 105
Ser Ser Glu Asp Thr Arg Arg Ser Cys Gln Ser Lys Gly Lys Thr
    110                 115                 120
Glu Glu Glu Cys Gln Asn Tyr Val Arg Val Leu Ile Val Ala Gly
                125                 130                 135
Arg Lys Val Phe Met Cys Gly Thr Asn Ala Phe Ser Pro Met Cys
                140                 145                 150
Thr Ser Arg Gln Val Gly Asn Leu Ser Arg Thr Thr Glu Lys Ile
                155                 160                 165
Asn Gly Val Ala Arg Cys Pro Tyr Asp Pro Arg His Asn Ser Thr
                170                 175                 180
Ala Val Ile Ser Ser Gln Gly Glu Leu Tyr Ala Ala Thr Val Ile
                185                 190                 195
Asp Phe Ser Gly Arg Asp Pro Ala Ile Tyr Arg Ser Leu Gly Ser
                200                 205                 210
Gly Pro Pro Leu Arg Thr Ala Gln Tyr Asn Ser Lys Trp Leu Asn
                215                 220                 225
Glu Pro Asn Phe Val Ala Ala Tyr Asp Ile Gly Leu Phe Ala Tyr
                230                 235                 240
Phe Phe Leu Arg Glu Asn Ala Val Glu His Asp Cys Gly Arg Thr
                245                 250                 255
Val Tyr Ser Arg Val Ala Arg Val Cys Lys Asn Asp Val Gly Gly
                260                 265                 270
Arg Phe Leu Leu Glu Asp Thr Trp Thr Thr Phe Met Lys Ala Arg
                275                 280                 285
Leu Asn Cys Ser Arg Pro Gly Glu Val Pro Phe Tyr Tyr Asn Glu
```

```
                290                 295                 300
Leu Gln Ser Ala Phe His Leu Pro Glu Gln Asp Leu Ile Tyr Gly
            305                 310                 315
Val Phe Thr Thr Asn Val Asn Ser Ile Ala Ser Ala Val Cys
        320                 325                 330
Ala Phe Asn Leu Ser Ala Ile Ser Gln Ala Phe Asn Gly Pro Phe
            335                 340                 345
Arg Tyr Gln Glu Asn Pro Arg Ala Ala Trp Leu Pro Ile Ala Asn
            350                 355                 360
Pro Ile Pro Asn Phe Gln Cys Gly Thr Leu Pro Glu Thr Gly Pro
            365                 370                 375
Asn Glu Asn Leu Thr Glu Arg Ser Leu Gln Asp Ala Gln Arg Leu
            380                 385                 390
Phe Leu Met Ser Glu Ala Val Gln Pro Val Thr Pro Glu Pro Cys
            395                 400                 405
Val Thr Gln Asp Ser Val Arg Phe Ser His Leu Val Val Asp Leu
            410                 415                 420
Val Gln Ala Lys Asp Thr Leu Tyr His Val Leu Tyr Ile Gly Thr
            425                 430                 435
Glu Ser Gly Thr Ile Leu Lys Ala Leu Ser Thr Ala Ser Arg Ser
            440                 445                 450
Leu His Gly Cys Tyr Leu Glu Glu Leu His Val Leu Pro Pro Gly
            455                 460                 465
Arg Arg Glu Pro Leu Arg Ser Leu Arg Ile Leu His Ser Ala Arg
            470                 475                 480
Ala Leu Phe Val Gly Leu Arg Asp Gly Val Leu Arg Val Pro Leu
            485                 490                 495
Glu Arg Cys Ala Ala Tyr Arg Ser Gln Gly Ala Cys Leu Gly Ala
            500                 505                 510
Arg Asp Pro Tyr Cys Gly Trp Asp Gly Lys Gln Gln Arg Cys Ser
            515                 520                 525
Thr Leu Glu Asp Ser Ser Asn Met Ser Leu Trp Thr Gln Asn Ile
            530                 535                 540
Thr Ala Cys Pro Val Arg Asn Val Thr Arg Asp Gly Gly Phe Gly
            545                 550                 555
Pro Trp Ser Pro Trp Gln Pro Cys Glu His Leu Asp Gly Asp Asn
            560                 565                 570
Ser Gly Ser Cys Leu Cys Arg Ala Arg Ser Cys Asp Ser Pro Arg
            575                 580                 585
Pro Arg Cys Gly Gly Leu Asp Cys Leu Gly Pro Ala Ile His Ile
            590                 595                 600
Ala Asn Cys Ser Arg Asn Gly Ala Trp Thr Pro Trp Ser Ser Trp
            605                 610                 615
Ala Leu Cys Ser Thr Ser Cys Gly Ile Gly Phe Gln Val Arg Gln
            620                 625                 630
Arg Ser Cys Ser Asn Pro Ala Pro Arg His Gly Gly Arg Ile Cys
            635                 640                 645
Val Gly Lys Ser Arg Glu Glu Arg Phe Cys Asn Glu Asn Thr Pro
            650                 655                 660
Cys Pro Val Pro Ile Phe Trp Ala Ser Trp Gly Ser Trp Ser Lys
            665                 670                 675
Cys Ser Ser Asn Cys Gly Gly Gly Met Gln Ser Arg Arg Arg Ala
            680                 685                 690
```

-continued

```
Cys Glu Asn Gly Asn Ser Cys Leu Gly Cys Gly Val Glu Phe Lys
                 695                 700                 705

Thr Cys Asn Pro Glu Gly Cys Pro Glu Val Arg Arg Asn Thr Pro
                 710                 715                 720

Trp Thr Pro Trp Leu Pro Val Asn Val Thr Gln Gly Gly Ala Arg
                 725                 730                 735

Gln Glu Gln Arg Phe Arg Phe Thr Cys Arg Ala Pro Leu Ala Asp
                 740                 745                 750

Pro His Gly Leu Gln Phe Gly Arg Arg Arg Thr Glu Thr Arg Thr
                 755                 760                 765

Cys Pro Ala Asp Gly Ser Gly Ser Cys Asp Thr Asp Ala Leu Val
                 770                 775                 780

Glu Asp Leu Leu Arg Ser Gly Ser Thr Ser Pro His Thr Val Ser
                 785                 790                 795

Gly Gly Trp Ala Ala Trp Gly Pro Trp Ser Ser Cys Ser Arg Asp
                 800                 805                 810

Cys Glu Leu Gly Phe Arg Val Arg Lys Arg Thr Cys Thr Asn Pro
                 815                 820                 825

Glu Pro Arg Asn Gly Gly Leu Pro Cys Val Gly Asp Ala Ala Glu
                 830                 835                 840

Tyr Gln Asp Cys Asn Pro Gln Ala Cys Pro Val Arg Gly Ala Trp
                 845                 850                 855

Ser Cys Trp Thr Ser Trp Ser Pro Cys Ser Ala Ser Cys Gly Gly
                 860                 865                 870

Gly His Tyr Gln Arg Thr Arg Ser Cys Thr Ser Pro Ala Pro Ser
                 875                 880                 885

Pro Gly Glu Asp Ile Cys Leu Gly Leu His Thr Glu Glu Ala Leu
                 890                 895                 900

Cys Ala Thr Gln Ala Cys Pro Glu Gly Trp Ser Pro Trp Ser Glu
                 905                 910                 915

Trp Ser Lys Cys Thr Asp Asp Gly Ala Gln Ser Arg Ser Arg His
                 920                 925                 930

Cys Glu Glu Leu Leu Pro Gly Ser Ser Ala Cys Ala Gly Asn Ser
                 935                 940                 945

Ser Gln Ser Arg Pro Cys Pro Tyr Ser Glu Ile Pro Val Ile Leu
                 950                 955                 960

Pro Ala Ser Ser Met Glu Glu Ala Thr Gly Cys Ala Gly Phe Asn
                 965                 970                 975

Leu Ile His Leu Val Ala Thr Gly Ile Ser Cys Phe Leu Gly Ser
                 980                 985                 990

Gly Leu Leu Thr Leu Ala Val Tyr Leu Ser Cys Gln His Cys Gln
                 995                1000                1005

Arg Gln Ser Gln Glu Ser Thr Leu Val His Pro Ala Thr Pro Asn
                1010                1015                1020

His Leu His Tyr Lys Gly Gly Gly Thr Pro Lys Asn Glu Lys Tyr
                1025                1030                1035

Thr Pro Met Glu Phe Lys Thr Leu Asn Lys Asn Asn Leu Ile Pro
                1040                1045                1050

Asp Asp Arg Ala Asn Phe Tyr Pro Leu Gln Gln Thr Asn Val Tyr
                1055                1060                1065

Thr Thr Thr Tyr Tyr Pro Ser Pro Leu Asn Lys His Ser Phe Arg
                1070                1075                1080

Pro Glu Ala Ser Pro Gly Gln Arg Cys Phe Pro Asn Ser
                1085                1090
```

<210> SEQ ID NO 8
<211> LENGTH: 141
<212> TYPE: PRT
<213> ORGANISM: Homo sapiens

<400> SEQUENCE: 8

Met Trp Val Leu Gly Ile Ala Ala Thr Phe Cys Gly Leu Phe Leu
1               5                   10                  15

Leu Pro Gly Phe Ala Leu Gln Ile Gln Cys Tyr Gln Cys Glu Glu
                20                  25                  30

Phe Gln Leu Asn Asn Asp Cys Ser Ser Pro Glu Phe Ile Val Asn
                35                  40                  45

Cys Thr Val Asn Val Gln Asp Met Cys Gln Lys Glu Val Met Glu
                50                  55                  60

Gln Ser Ala Gly Ile Met Tyr Arg Lys Ser Cys Ala Ser Ser Ala
                65                  70                  75

Ala Cys Leu Ile Ala Ser Ala Gly Tyr Gln Ser Phe Cys Ser Pro
                80                  85                  90

Gly Lys Leu Asn Ser Val Cys Ile Ser Cys Cys Asn Thr Pro Leu
                95                  100                 105

Cys Asn Gly Pro Arg Pro Lys Lys Arg Gly Ser Ser Ala Ser Ala
                110                 115                 120

Leu Arg Pro Gly Leu Arg Thr Thr Ile Leu Phe Leu Lys Leu Ala
                125                 130                 135

Leu Phe Ser Ala His Cys
                140

<210> SEQ ID NO 9
<211> LENGTH: 442
<212> TYPE: PRT
<213> ORGANISM: Homo sapiens

<400> SEQUENCE: 9

Met Gln Pro Pro Pro Ser Leu Cys Gly Arg Ala Leu Val Ala Leu
1               5                   10                  15

Val Leu Ala Cys Gly Leu Ser Arg Ile Trp Gly Glu Glu Arg Gly
                20                  25                  30

Phe Pro Pro Asp Arg Ala Thr Pro Leu Leu Gln Thr Ala Glu Ile
                35                  40                  45

Met Thr Pro Pro Thr Lys Thr Leu Trp Pro Lys Gly Ser Asn Ala
                50                  55                  60

Ser Leu Ala Arg Ser Leu Ala Pro Ala Glu Val Pro Lys Gly Asp
                65                  70                  75

Arg Thr Ala Gly Ser Pro Pro Arg Thr Ile Ser Pro Pro Pro Cys
                80                  85                  90

Gln Gly Pro Ile Glu Ile Lys Glu Thr Phe Lys Tyr Ile Asn Thr
                95                  100                 105

Val Val Ser Cys Leu Val Phe Val Leu Gly Ile Ile Gly Asn Ser
                110                 115                 120

Thr Leu Leu Arg Ile Ile Tyr Lys Asn Lys Cys Met Arg Asn Gly
                125                 130                 135

Pro Asn Ile Leu Ile Ala Ser Leu Ala Leu Gly Asp Leu Leu His
                140                 145                 150

Ile Val Ile Asp Ile Pro Ile Asn Val Tyr Lys Leu Leu Ala Glu
                155                 160                 165

```
Asp Trp Pro Phe Gly Ala Glu Met Cys Lys Leu Val Pro Phe Ile
            170                 175                 180

Gln Lys Ala Ser Val Gly Ile Thr Val Leu Ser Leu Cys Ala Leu
            185                 190                 195

Ser Ile Asp Arg Tyr Arg Ala Val Ala Ser Trp Ser Arg Ile Lys
            200                 205                 210

Gly Ile Gly Val Pro Lys Trp Thr Ala Val Glu Ile Val Leu Ile
            215                 220                 225

Trp Val Val Ser Val Val Leu Ala Val Pro Glu Ala Ile Gly Phe
            230                 235                 240

Asp Ile Ile Thr Met Asp Tyr Lys Gly Ser Tyr Leu Arg Ile Cys
            245                 250                 255

Leu Leu His Pro Val Gln Lys Thr Ala Phe Met Gln Phe Tyr Lys
            260                 265                 270

Thr Ala Lys Asp Trp Trp Leu Phe Ser Phe Tyr Phe Cys Leu Pro
            275                 280                 285

Leu Ala Ile Thr Ala Phe Phe Tyr Thr Leu Met Thr Cys Glu Met
            290                 295                 300

Leu Arg Lys Lys Ser Gly Met Gln Ile Ala Leu Asn Asp His Leu
            305                 310                 315

Lys Gln Arg Arg Glu Val Ala Lys Thr Val Phe Cys Leu Val Leu
            320                 325                 330

Val Phe Ala Leu Cys Trp Leu Pro Leu His Leu Ser Arg Ile Leu
            335                 340                 345

Lys Leu Thr Leu Tyr Asn Gln Asn Asp Pro Asn Arg Cys Glu Leu
            350                 355                 360

Leu Ser Phe Leu Leu Val Leu Asp Tyr Ile Gly Ile Asn Met Ala
            365                 370                 375

Ser Leu Asn Ser Cys Ile Asn Pro Ile Ala Leu Tyr Leu Val Ser
            380                 385                 390

Lys Arg Phe Lys Asn Cys Phe Lys Ser Cys Leu Cys Cys Trp Cys
            395                 400                 405

Gln Ser Phe Glu Glu Lys Gln Ser Leu Glu Glu Lys Gln Ser Cys
            410                 415                 420

Leu Lys Phe Lys Ala Asn Asp His Gly Tyr Asp Asn Phe Arg Ser
            425                 430                 435

Ser Asn Lys Tyr Ser Ser Ser
            440

<210> SEQ ID NO 10
<211> LENGTH: 783
<212> TYPE: PRT
<213> ORGANISM: Homo sapiens

<400> SEQUENCE: 10

Met Ser Gly Gly His Gln Leu Gln Leu Ala Ala Leu Trp Pro Trp
  1               5                  10                  15

Leu Leu Met Ala Thr Leu Gln Ala Gly Phe Gly Arg Thr Gly Leu
             20                  25                  30

Val Leu Ala Ala Ala Val Glu Ser Glu Arg Ser Ala Glu Gln Lys
             35                  40                  45

Ala Ile Ile Arg Val Ile Pro Leu Lys Met Asp Pro Thr Gly Lys
             50                  55                  60

Leu Asn Leu Thr Leu Glu Gly Val Phe Ala Gly Val Ala Glu Ile
             65                  70                  75
```

-continued

```
Thr Pro Ala Glu Gly Lys Leu Met Gln Ser His Pro Leu Tyr Leu
             80                  85                  90

Cys Asn Ala Ser Asp Asp Asn Leu Glu Pro Gly Phe Ile Ser
         95                 100                 105

Ile Val Lys Leu Glu Ser Pro Arg Arg Ala Pro Arg Pro Cys Leu
            110                 115                 120

Ser Leu Ala Ser Lys Ala Arg Met Ala Gly Glu Arg Gly Ala Ser
            125                 130                 135

Ala Val Leu Phe Asp Ile Thr Glu Asp Arg Ala Ala Ala Glu Gln
            140                 145                 150

Leu Gln Gln Pro Leu Gly Leu Thr Trp Pro Val Val Leu Ile Trp
            155                 160                 165

Gly Asn Asp Ala Glu Lys Leu Met Glu Phe Val Tyr Lys Asn Gln
            170                 175                 180

Lys Ala His Val Arg Ile Glu Leu Lys Glu Pro Pro Ala Trp Pro
            185                 190                 195

Asp Tyr Asp Val Trp Ile Leu Met Thr Val Val Gly Thr Ile Phe
            200                 205                 210

Val Ile Ile Leu Ala Ser Val Leu Arg Ile Arg Cys Arg Pro Arg
            215                 220                 225

His Ser Arg Pro Asp Pro Leu Gln Gln Arg Thr Ala Trp Ala Ile
            230                 235                 240

Ser Gln Leu Ala Thr Arg Arg Tyr Gln Ala Ser Cys Arg Gln Ala
            245                 250                 255

Arg Gly Glu Trp Pro Asp Ser Gly Ser Ser Cys Ser Ser Ala Pro
            260                 265                 270

Val Cys Ala Ile Cys Leu Glu Glu Phe Ser Glu Gly Gln Glu Leu
            275                 280                 285

Arg Val Ile Ser Cys Leu His Glu Phe His Arg Asn Cys Val Asp
            290                 295                 300

Pro Trp Leu His Gln His Arg Thr Cys Pro Leu Cys Val Phe Asn
            305                 310                 315

Ile Thr Glu Gly Asp Ser Phe Ser Gln Ser Leu Gly Pro Ser Arg
            320                 325                 330

Ser Tyr Gln Glu Pro Gly Arg Arg Leu His Leu Ile Arg Gln His
            335                 340                 345

Pro Gly His Ala His Tyr His Leu Pro Ala Ala Tyr Leu Leu Gly
            350                 355                 360

Pro Ser Arg Ser Ala Val Ala Arg Pro Pro Arg Pro Gly Pro Phe
            365                 370                 375

Leu Pro Ser Gln Glu Pro Gly Met Gly Pro Arg His His Arg Phe
            380                 385                 390

Pro Arg Ala Ala His Pro Arg Ala Pro Gly Glu Gln Gln Arg Leu
            395                 400                 405

Ala Gly Ala Gln His Pro Tyr Ala Gln Gly Trp Gly Met Ser His
            410                 415                 420

Leu Gln Ser Thr Ser Gln His Pro Ala Ala Cys Pro Val Pro Leu
            425                 430                 435

Arg Arg Ala Arg Pro Pro Asp Ser Ser Gly Ser Gly Glu Ser Tyr
            440                 445                 450

Cys Thr Glu Arg Ser Gly Tyr Leu Ala Asp Gly Pro Ala Ser Asp
            455                 460                 465

Ser Ser Ser Gly Pro Cys His Gly Ser Ser Ser Asp Ser Val Val
            470                 475                 480
```

```
Asn Cys Thr Asp Ile Ser Leu Gln Gly Val His Gly Ser Ser
            485                 490                 495

Thr Phe Cys Ser Ser Leu Ser Ser Asp Phe Asp Pro Leu Val Tyr
        500                 505                 510

Cys Ser Pro Lys Gly Asp Pro Gln Arg Val Asp Met Gln Pro Ser
        515                 520                 525

Val Thr Ser Arg Pro Arg Ser Leu Asp Ser Val Val Pro Thr Gly
        530                 535                 540

Glu Thr Gln Val Ser Ser His Val His Tyr His Arg His Arg His
        545                 550                 555

His His Tyr Lys Lys Arg Phe Gln Trp His Gly Arg Lys Pro Gly
        560                 565                 570

Pro Glu Thr Gly Val Pro Gln Ser Arg Pro Pro Ile Pro Arg Thr
        575                 580                 585

Gln Pro Gln Pro Glu Pro Pro Ser Pro Asp Gln Gln Val Thr Gly
        590                 595                 600

Ser Asn Ser Ala Ala Pro Ser Gly Arg Leu Ser Asn Pro Gln Cys
        605                 610                 615

Pro Arg Ala Leu Pro Glu Pro Ala Pro Gly Pro Val Asp Ala Ser
        620                 625                 630

Ser Ile Cys Pro Ser Thr Ser Ser Leu Phe Asn Leu Gln Lys Ser
        635                 640                 645

Ser Leu Ser Ala Arg His Pro Gln Arg Lys Arg Arg Gly Gly Pro
        650                 655                 660

Ser Glu Pro Thr Pro Gly Ser Arg Pro Gln Asp Ala Thr Val His
        665                 670                 675

Pro Ala Cys Gln Ile Phe Pro His Tyr Thr Pro Ser Val Ala Tyr
        680                 685                 690

Pro Trp Ser Pro Glu Ala His Pro Leu Ile Cys Gly Pro Pro Gly
        695                 700                 705

Leu Asp Lys Arg Leu Leu Pro Glu Thr Pro Gly Pro Cys Tyr Ser
        710                 715                 720

Asn Ser Gln Pro Val Trp Leu Cys Leu Thr Pro Arg Gln Pro Leu
        725                 730                 735

Glu Pro His Pro Pro Gly Glu Gly Pro Ser Glu Trp Ser Ser Asp
        740                 745                 750

Thr Ala Glu Gly Arg Pro Cys Pro Tyr Pro His Cys Gln Val Leu
        755                 760                 765

Ser Ala Gln Pro Gly Ser Glu Glu Leu Glu Glu Leu Cys Glu
        770                 775                 780

Gln Ala Val

<210> SEQ ID NO 11
<211> LENGTH: 490
<212> TYPE: PRT
<213> ORGANISM: Homo sapiens

<400> SEQUENCE: 11

Met Glu Ser Ile Ser Met Met Gly Ser Pro Lys Ser Leu Ser Glu
  1               5                  10                  15

Thr Val Leu Pro Asn Gly Ile Asn Gly Ile Lys Asp Ala Arg Lys
                 20                  25                  30

Val Thr Val Gly Val Ile Gly Ser Gly Asp Phe Ala Lys Ser Leu
                 35                  40                  45
```

-continued

```
Thr Ile Arg Leu Ile Arg Cys Gly Tyr His Val Val Ile Gly Ser
                 50                  55                  60

Arg Asn Pro Lys Phe Ala Ser Glu Phe Phe Pro His Val Val Asp
             65                  70                  75

Val Thr His His Glu Asp Ala Leu Thr Lys Thr Asn Ile Ile Phe
             80                  85                  90

Val Ala Ile His Arg Glu His Tyr Thr Ser Leu Trp Asp Leu Arg
             95                 100                 105

His Leu Leu Val Gly Lys Ile Leu Ile Asp Val Ser Asn Asn Met
            110                 115                 120

Arg Ile Asn Gln Tyr Pro Glu Ser Asn Ala Glu Tyr Leu Ala Ser
            125                 130                 135

Leu Phe Pro Asp Ser Leu Ile Val Lys Gly Phe Asn Val Val Ser
            140                 145                 150

Ala Trp Ala Leu Gln Leu Gly Pro Lys Asp Ala Ser Arg Gln Val
            155                 160                 165

Tyr Ile Cys Ser Asn Asn Ile Gln Ala Arg Gln Gln Val Ile Glu
            170                 175                 180

Leu Ala Arg Gln Leu Asn Phe Ile Pro Ile Asp Leu Gly Ser Leu
            185                 190                 195

Ser Ser Ala Arg Glu Ile Glu Asn Leu Pro Leu Arg Leu Phe Thr
            200                 205                 210

Leu Trp Arg Gly Pro Val Val Ala Ile Ser Leu Ala Thr Phe
            215                 220                 225

Phe Phe Leu Tyr Ser Phe Val Arg Asp Val Ile His Pro Tyr Ala
            230                 235                 240

Arg Asn Gln Gln Ser Asp Phe Tyr Lys Ile Pro Ile Glu Ile Val
            245                 250                 255

Asn Lys Thr Leu Pro Ile Val Ala Ile Thr Leu Leu Ser Leu Val
            260                 265                 270

Tyr Leu Ala Gly Leu Leu Ala Ala Ala Tyr Gln Leu Tyr Tyr Gly
            275                 280                 285

Thr Lys Tyr Arg Arg Phe Pro Pro Trp Leu Glu Thr Trp Leu Gln
            290                 295                 300

Cys Arg Lys Gln Leu Gly Leu Leu Ser Phe Phe Ala Met Val
            305                 310                 315

His Val Ala Tyr Ser Leu Cys Leu Pro Met Arg Arg Ser Glu Arg
            320                 325                 330

Tyr Leu Phe Leu Asn Met Ala Tyr Gln Gln Val His Ala Asn Ile
            335                 340                 345

Glu Asn Ser Trp Asn Glu Glu Glu Val Trp Arg Ile Glu Met Tyr
            350                 355                 360

Ile Ser Phe Gly Ile Met Ser Leu Gly Leu Leu Ser Leu Leu Ala
            365                 370                 375

Val Thr Ser Ile Pro Ser Val Ser Asn Ala Leu Asn Trp Arg Glu
            380                 385                 390

Phe Ser Phe Ile Gln Ser Thr Leu Gly Tyr Val Ala Leu Leu Ile
            395                 400                 405

Ser Thr Phe His Val Leu Ile Tyr Gly Trp Lys Arg Ala Phe Glu
            410                 415                 420

Glu Glu Tyr Tyr Arg Phe Tyr Thr Pro Pro Asn Phe Val Leu Ala
            425                 430                 435

Leu Val Leu Pro Ser Ile Val Ile Leu Gly Lys Ile Ile Leu Phe
            440                 445                 450
```

```
Leu Pro Cys Ile Ser Gln Lys Leu Lys Arg Ile Lys Lys Gly Trp
            455                 460                 465

Glu Lys Ser Gln Phe Leu Glu Glu Gly Ile Gly Gly Thr Ile Pro
            470                 475                 480

His Val Ser Pro Glu Arg Val Thr Val Met
            485                 490

<210> SEQ ID NO 12
<211> LENGTH: 1214
<212> TYPE: PRT
<213> ORGANISM: Homo sapiens

<400> SEQUENCE: 12

Met Val Val Pro Glu Lys Glu Gln Ser Trp Ile Pro Lys Ile Phe
  1               5                  10                  15

Lys Lys Lys Thr Cys Thr Thr Phe Ile Val Asp Ser Thr Asp Pro
             20                  25                  30

Gly Gly Thr Leu Cys Gln Cys Gly Arg Pro Arg Thr Ala His Pro
             35                  40                  45

Ala Val Ala Met Glu Asp Ala Phe Gly Ala Ala Val Val Thr Val
             50                  55                  60

Trp Asp Ser Asp Ala His Thr Thr Glu Lys Pro Thr Asp Ala Tyr
             65                  70                  75

Gly Glu Leu Asp Phe Thr Gly Ala Gly Arg Lys His Ser Asn Phe
             80                  85                  90

Leu Arg Leu Ser Asp Arg Thr Asp Pro Ala Ala Val Tyr Ser Leu
             95                 100                 105

Val Thr Arg Thr Trp Gly Phe Arg Ala Pro Asn Leu Val Val Ser
            110                 115                 120

Val Leu Gly Gly Ser Gly Gly Pro Val Leu Gln Thr Trp Leu Gln
            125                 130                 135

Asp Leu Leu Arg Arg Gly Leu Val Arg Ala Ala Gln Ser Thr Gly
            140                 145                 150

Ala Trp Ile Val Thr Gly Gly Leu His Thr Gly Ile Gly Arg His
            155                 160                 165

Val Gly Val Ala Val Arg Asp His Gln Met Ala Ser Thr Gly Gly
            170                 175                 180

Thr Lys Val Val Ala Met Gly Val Ala Pro Trp Gly Val Val Arg
            185                 190                 195

Asn Arg Asp Thr Leu Ile Asn Pro Lys Gly Ser Phe Pro Ala Arg
            200                 205                 210

Tyr Arg Trp Arg Gly Asp Pro Glu Asp Gly Val Gln Phe Pro Leu
            215                 220                 225

Asp Tyr Asn Tyr Ser Ala Phe Phe Leu Val Asp Asp Gly Thr His
            230                 235                 240

Gly Cys Leu Gly Gly Glu Asn Arg Phe Arg Leu Arg Leu Glu Ser
            245                 250                 255

Tyr Ile Ser Gln Gln Lys Thr Gly Val Gly Gly Thr Gly Ile Asp
            260                 265                 270

Ile Pro Val Leu Leu Leu Leu Ile Asp Gly Asp Glu Lys Met Leu
            275                 280                 285

Thr Arg Ile Glu Asn Ala Thr Gln Ala Gln Leu Pro Cys Leu Leu
            290                 295                 300

Val Ala Gly Ser Gly Gly Ala Ala Asp Cys Leu Ala Glu Thr Leu
            305                 310                 315
```

```
Glu Asp Thr Leu Ala Pro Gly Ser Gly Ala Arg Gln Gly Glu
            320                 325                 330

Ala Arg Asp Arg Ile Arg Arg Phe Phe Pro Lys Gly Asp Leu Glu
            335                 340                 345

Val Leu Gln Ala Gln Val Glu Arg Ile Met Thr Arg Lys Glu Leu
            350                 355                 360

Leu Thr Val Tyr Ser Ser Glu Asp Gly Ser Glu Glu Phe Glu Thr
            365                 370                 375

Ile Val Leu Lys Ala Leu Val Lys Ala Cys Gly Ser Ser Glu Ala
            380                 385                 390

Ser Ala Tyr Leu Asp Glu Leu Arg Leu Ala Val Ala Trp Asn Arg
            395                 400                 405

Val Asp Ile Ala Gln Ser Glu Leu Phe Arg Gly Asp Ile Gln Trp
            410                 415                 420

Arg Ser Phe His Leu Glu Ala Ser Leu Met Asp Ala Leu Leu Asn
            425                 430                 435

Asp Arg Pro Glu Phe Val Arg Leu Leu Ile Ser His Gly Leu Ser
            440                 445                 450

Leu Gly His Phe Leu Thr Pro Met Arg Leu Ala Gln Leu Tyr Ser
            455                 460                 465

Ala Ala Pro Ser Asn Ser Leu Ile Arg Asn Leu Leu Asp Gln Ala
            470                 475                 480

Ser His Ser Ala Gly Thr Lys Ala Pro Ala Leu Lys Gly Gly Ala
            485                 490                 495

Ala Glu Leu Arg Pro Pro Asp Val Gly His Val Leu Arg Met Leu
            500                 505                 510

Leu Gly Lys Met Cys Ala Pro Arg Tyr Pro Ser Gly Gly Ala Trp
            515                 520                 525

Asp Pro His Pro Gly Gln Gly Phe Gly Glu Ser Met Tyr Leu Leu
            530                 535                 540

Ser Asp Lys Ala Thr Ser Pro Leu Ser Leu Asp Ala Gly Leu Gly
            545                 550                 555

Gln Ala Pro Trp Ser Asp Leu Leu Leu Trp Ala Leu Leu Leu Asn
            560                 565                 570

Arg Ala Gln Met Ala Met Tyr Phe Trp Glu Met Gly Ser Asn Ala
            575                 580                 585

Val Ser Ser Ala Leu Gly Ala Cys Leu Leu Arg Val Met Ala
            590                 595                 600

Arg Leu Glu Pro Asp Ala Glu Ala Ala Arg Arg Lys Asp Leu
            605                 610                 615

Ala Phe Lys Phe Glu Gly Met Gly Val Asp Leu Phe Gly Glu Cys
            620                 625                 630

Tyr Arg Ser Ser Glu Val Arg Ala Ala Arg Leu Leu Leu Arg Arg
            635                 640                 645

Cys Pro Leu Trp Gly Asp Ala Thr Cys Leu Gln Leu Ala Met Gln
            650                 655                 660

Ala Asp Ala Arg Ala Phe Phe Ala Gln Asp Gly Val Gln Ser Leu
            665                 670                 675

Leu Thr Gln Lys Trp Trp Gly Asp Met Ala Ser Thr Thr Pro Ile
            680                 685                 690

Trp Ala Leu Val Leu Ala Phe Phe Cys Pro Pro Leu Ile Tyr Thr
            695                 700                 705

Arg Leu Ile Thr Phe Arg Lys Ser Glu Glu Glu Pro Thr Arg Glu
```

```
                710             715             720
Glu Leu Glu Phe Asp Met Asp Ser Val Ile Asn Gly Glu Gly Pro
            725             730             735
Val Gly Thr Ala Asp Pro Ala Glu Lys Thr Pro Leu Gly Val Pro
            740             745             750
Arg Gln Ser Gly Arg Pro Gly Cys Cys Gly Arg Cys Gly Gly
            755             760             765
Arg Arg Cys Leu Arg Arg Trp Phe His Phe Trp Gly Ala Pro Val
            770             775             780
Thr Ile Phe Met Gly Asn Val Val Ser Tyr Leu Leu Phe Leu Leu
            785             790             795
Leu Phe Ser Arg Val Leu Leu Val Asp Phe Gln Pro Ala Pro Pro
            800             805             810
Gly Ser Leu Glu Leu Leu Leu Tyr Phe Trp Ala Phe Thr Leu Leu
            815             820             825
Cys Glu Glu Leu Arg Gln Gly Leu Ser Gly Gly Gly Ser Leu
            830             835             840
Ala Ser Gly Gly Pro Gly Pro Gly His Ala Ser Leu Ser Gln Arg
            845             850             855
Leu Arg Leu Tyr Leu Ala Asp Ser Trp Asn Gln Cys Asp Leu Val
            860             865             870
Ala Leu Thr Cys Phe Leu Leu Gly Val Gly Cys Arg Leu Thr Pro
            875             880             885
Gly Leu Tyr His Leu Gly Arg Thr Val Leu Cys Ile Asp Phe Met
            890             895             900
Val Phe Thr Val Arg Leu Leu His Ile Phe Thr Val Asn Lys Gln
            905             910             915
Leu Gly Pro Lys Ile Val Ile Val Ser Lys Met Met Lys Asp Val
            920             925             930
Phe Phe Phe Leu Phe Phe Leu Gly Val Trp Leu Val Ala Tyr Gly
            935             940             945
Val Ala Thr Glu Gly Leu Leu Arg Pro Arg Asp Ser Asp Phe Pro
            950             955             960
Ser Ile Leu Arg Arg Val Phe Tyr Arg Pro Tyr Leu Gln Ile Phe
            965             970             975
Gly Gln Ile Pro Gln Glu Asp Met Asp Val Ala Leu Met Glu His
            980             985             990
Ser Asn Cys Ser Ser Glu Pro Gly Phe Trp Ala His Pro Pro Gly
            995             1000            1005
Ala Gln Ala Gly Thr Cys Val Ser Gln Tyr Ala Asn Trp Leu Val
            1010            1015            1020
Val Leu Leu Leu Val Ile Phe Leu Leu Val Ala Asn Ile Leu Leu
            1025            1030            1035
Val Asn Leu Leu Ile Ala Met Phe Ser Tyr Thr Phe Gly Lys Val
            1040            1045            1050
Gln Gly Asn Ser Asp Leu Tyr Trp Lys Ala Gln Arg Tyr Arg Leu
            1055            1060            1065
Ile Arg Glu Phe His Ser Arg Pro Ala Leu Ala Pro Pro Phe Ile
            1070            1075            1080
Val Ile Ser His Leu Arg Leu Leu Leu Arg Gln Leu Cys Arg Arg
            1085            1090            1095
Pro Arg Ser Pro Gln Pro Ser Ser Pro Ala Leu Glu His Phe Arg
            1100            1105            1110
```

Val Tyr Leu Ser Lys Glu Ala Glu Arg Lys Leu Leu Thr Trp Glu
            1115                1120                1125

Ser Val His Lys Glu Asn Phe Leu Leu Ala Arg Ala Arg Asp Lys
            1130                1135                1140

Arg Glu Ser Asp Ser Glu Arg Leu Lys Arg Thr Ser Gln Lys Val
            1145                1150                1155

Asp Leu Ala Leu Lys Gln Leu Gly His Ile Arg Glu Tyr Glu Gln
            1160                1165                1170

Arg Leu Lys Val Leu Glu Arg Glu Val Gln Gln Cys Ser Arg Val
            1175                1180                1185

Leu Gly Trp Val Ala Glu Ala Leu Ser Arg Ser Ala Leu Leu Pro
            1190                1195                1200

Pro Gly Gly Pro Pro Pro Pro Asp Leu Pro Gly Ser Lys Asp
            1205                1210

<210> SEQ ID NO 13
<211> LENGTH: 188
<212> TYPE: PRT
<213> ORGANISM: Homo sapiens

<400> SEQUENCE: 13

Met Asp Cys Arg Lys Met Ala Arg Phe Ser Tyr Ser Val Ile Trp
 1               5                  10                  15

Ile Met Ala Ile Ser Lys Val Phe Glu Leu Gly Leu Val Ala Gly
                20                  25                  30

Leu Gly His Gln Glu Phe Ala Arg Pro Ser Arg Gly Tyr Leu Ala
                35                  40                  45

Phe Arg Asp Asp Ser Ile Trp Pro Gln Glu Glu Pro Ala Ile Arg
                50                  55                  60

Pro Arg Ser Ser Gln Arg Val Pro Pro Met Gly Ile Gln His Ser
                65                  70                  75

Lys Glu Leu Asn Arg Thr Cys Cys Leu Asn Gly Gly Thr Cys Met
                80                  85                  90

Leu Gly Ser Phe Cys Ala Cys Pro Pro Ser Phe Tyr Gly Arg Asn
                95                  100                 105

Cys Glu His Asp Val Arg Lys Glu Asn Cys Gly Ser Val Pro His
                110                 115                 120

Asp Thr Trp Leu Pro Lys Lys Cys Ser Leu Cys Lys Cys Trp His
                125                 130                 135

Gly Gln Leu Arg Cys Phe Pro Gln Ala Phe Leu Pro Gly Cys Asp
                140                 145                 150

Gly Leu Val Met Asp Glu His Leu Val Ala Ser Arg Thr Pro Glu
                155                 160                 165

Leu Pro Pro Ser Ala Arg Thr Thr Thr Phe Met Leu Val Gly Ile
                170                 175                 180

Cys Leu Ser Ile Gln Ser Tyr Tyr
                185

<210> SEQ ID NO 14
<211> LENGTH: 1033
<212> TYPE: PRT
<213> ORGANISM: Homo sapiens

<400> SEQUENCE: 14

Met Gly Ala Ala Gly Leu Leu Gly Val Phe Leu Ala Leu Val Ala
 1               5                  10                  15

Pro Gly Val Leu Gly Ile Ser Cys Gly Ser Pro Pro Pro Ile Leu

```
                    20                  25                  30
Asn Gly Arg Ile Ser Tyr Tyr Ser Thr Pro Ile Ala Val Gly Thr
                35                  40                  45
Val Ile Arg Tyr Ser Cys Ser Gly Thr Phe Arg Leu Ile Gly Glu
                50                  55                  60
Lys Ser Leu Leu Cys Ile Thr Lys Asp Lys Val Asp Gly Thr Trp
                65                  70                  75
Asp Lys Pro Ala Pro Lys Cys Glu Tyr Phe Asn Lys Tyr Ser Ser
                80                  85                  90
Cys Pro Glu Pro Ile Val Pro Gly Gly Tyr Lys Ile Arg Gly Ser
                95                 100                 105
Thr Pro Tyr Arg His Gly Asp Ser Val Thr Phe Ala Cys Lys Thr
               110                 115                 120
Asn Phe Ser Met Asn Gly Asn Lys Ser Val Trp Cys Gln Ala Asn
               125                 130                 135
Asn Met Trp Gly Pro Thr Arg Leu Pro Thr Cys Val Ser Val Phe
               140                 145                 150
Pro Leu Glu Cys Pro Ala Leu Pro Met Ile His Asn Gly His His
               155                 160                 165
Thr Ser Glu Asn Val Gly Ser Ile Ala Pro Gly Leu Ser Val Thr
               170                 175                 180
Tyr Ser Cys Glu Ser Gly Tyr Leu Leu Val Gly Glu Lys Ile Ile
               185                 190                 195
Asn Cys Leu Ser Ser Gly Lys Trp Ser Ala Val Pro Pro Thr Cys
               200                 205                 210
Glu Glu Ala Arg Cys Lys Ser Leu Gly Arg Phe Pro Asn Gly Lys
               215                 220                 225
Val Lys Glu Pro Pro Ile Leu Arg Val Gly Val Thr Ala Asn Phe
               230                 235                 240
Phe Cys Asp Glu Gly Tyr Arg Leu Gln Gly Pro Pro Ser Ser Arg
               245                 250                 255
Cys Val Ile Ala Gly Gln Gly Val Ala Trp Thr Lys Met Pro Val
               260                 265                 270
Cys Glu Glu Ile Phe Cys Pro Ser Pro Pro Ile Leu Asn Gly
               275                 280                 285
Arg His Ile Gly Asn Ser Leu Ala Asn Val Ser Tyr Gly Ser Ile
               290                 295                 300
Val Thr Tyr Thr Cys Asp Pro Asp Pro Glu Glu Gly Val Asn Phe
               305                 310                 315
Ile Leu Ile Gly Glu Ser Thr Leu Arg Cys Thr Val Asp Ser Gln
               320                 325                 330
Lys Thr Gly Thr Trp Ser Gly Pro Ala Pro Arg Cys Glu Leu Ser
               335                 340                 345
Thr Ser Ala Val Gln Cys Pro His Pro Gln Ile Leu Arg Gly Arg
               350                 355                 360
Met Val Ser Gly Gln Lys Asp Arg Tyr Thr Tyr Asn Asp Thr Val
               365                 370                 375
Ile Phe Ala Cys Met Phe Gly Phe Thr Leu Lys Gly Ser Lys Gln
               380                 385                 390
Ile Arg Cys Asn Ala Gln Gly Thr Trp Glu Pro Ser Ala Pro Val
               395                 400                 405
Cys Glu Lys Glu Cys Gln Ala Pro Pro Asn Ile Leu Asn Gly Gln
               410                 415                 420
```

-continued

```
Lys Glu Asp Arg His Met Val Arg Phe Asp Pro Gly Thr Ser Ile
                425                 430                 435
Lys Tyr Ser Cys Asn Pro Gly Tyr Val Leu Val Gly Glu Glu Ser
                440                 445                 450
Ile Gln Cys Thr Ser Glu Gly Val Trp Thr Pro Pro Val Pro Gln
                455                 460                 465
Cys Lys Val Ala Ala Cys Glu Ala Thr Gly Arg Gln Leu Leu Thr
                470                 475                 480
Lys Pro Gln His Gln Phe Val Arg Pro Asp Val Asn Ser Ser Cys
                485                 490                 495
Gly Glu Gly Tyr Lys Leu Ser Gly Ser Val Tyr Gln Glu Cys Gln
                500                 505                 510
Gly Thr Ile Pro Trp Phe Met Glu Ile Arg Leu Cys Lys Glu Ile
                515                 520                 525
Thr Cys Pro Pro Pro Val Ile Tyr Asn Gly Ala His Thr Gly
                530                 535                 540
Ser Ser Leu Glu Asp Phe Pro Tyr Gly Thr Thr Val Thr Tyr Thr
                545                 550                 555
Cys Asn Pro Gly Pro Glu Arg Gly Val Glu Phe Ser Leu Ile Gly
                560                 565                 570
Glu Ser Thr Ile Arg Cys Thr Ser Asn Asp Gln Glu Arg Gly Thr
                575                 580                 585
Trp Ser Gly Pro Ala Pro Leu Cys Lys Leu Ser Leu Leu Ala Val
                590                 595                 600
Gln Cys Ser His Val His Ile Ala Asn Gly Tyr Lys Ile Ser Gly
                605                 610                 615
Lys Glu Ala Pro Tyr Phe Tyr Asn Asp Thr Val Thr Phe Lys Cys
                620                 625                 630
Tyr Ser Gly Phe Thr Leu Lys Gly Ser Ser Gln Ile Arg Cys Lys
                635                 640                 645
Ala Asp Asn Thr Trp Asp Pro Glu Ile Pro Val Cys Glu Lys Glu
                650                 655                 660
Thr Cys Gln His Val Arg Gln Ser Leu Gln Glu Leu Pro Ala Gly
                665                 670                 675
Ser Arg Val Glu Leu Val Asn Thr Ser Cys Gln Asp Gly Tyr Gln
                680                 685                 690
Leu Thr Gly His Ala Tyr Gln Met Cys Gln Asp Ala Glu Asn Gly
                695                 700                 705
Ile Trp Phe Lys Lys Ile Pro Leu Cys Lys Val Ile His Cys His
                710                 715                 720
Pro Pro Pro Val Ile Val Asn Gly Lys His Thr Gly Met Met Ala
                725                 730                 735
Glu Asn Phe Leu Tyr Gly Asn Glu Val Ser Tyr Glu Cys Asp Gln
                740                 745                 750
Gly Phe Tyr Leu Leu Gly Glu Lys Lys Leu Gln Cys Arg Ser Asp
                755                 760                 765
Ser Lys Gly His Gly Ser Trp Ser Gly Pro Ser Pro Gln Cys Leu
                770                 775                 780
Arg Ser Pro Pro Val Thr Arg Cys Pro Asn Pro Glu Val Lys His
                785                 790                 795
Gly Tyr Lys Leu Asn Lys Thr His Ser Ala Tyr Ser His Asn Asp
                800                 805                 810
Ile Val Tyr Val Asp Cys Asn Pro Gly Phe Ile Met Asn Gly Ser
                815                 820                 825
```

```
Arg Val Ile Arg Cys His Thr Asp Asn Thr Trp Val Pro Gly Val
            830                 835                 840

Pro Thr Cys Ile Lys Lys Ala Phe Ile Gly Cys Pro Pro Pro Pro
            845                 850                 855

Lys Thr Pro Asn Gly Asn His Thr Gly Gly Asn Ile Ala Arg Phe
            860                 865                 870

Ser Pro Gly Met Ser Ile Leu Tyr Ser Cys Asp Gln Gly Tyr Leu
            875                 880                 885

Leu Val Gly Glu Ala Leu Leu Leu Cys Thr His Glu Gly Thr Trp
            890                 895                 900

Ser Gln Pro Ala Pro His Cys Lys Glu Val Asn Cys Ser Ser Pro
            905                 910                 915

Ala Asp Met Asp Gly Ile Gln Lys Gly Leu Glu Pro Arg Lys Met
            920                 925                 930

Tyr Gln Tyr Gly Ala Val Val Thr Leu Glu Cys Glu Asp Gly Tyr
            935                 940                 945

Met Leu Glu Gly Ser Pro Gln Ser Gln Cys Gln Ser Asp His Gln
            950                 955                 960

Trp Asn Pro Pro Leu Ala Val Cys Arg Ser Arg Ser Leu Ala Pro
            965                 970                 975

Val Leu Cys Gly Ile Ala Ala Gly Leu Ile Leu Leu Thr Phe Leu
            980                 985                 990

Ile Val Ile Thr Leu Tyr Val Ile Ser Lys His Arg Glu Arg Asn
            995                 1000                1005

Tyr Tyr Thr Asp Thr Ser Gln Lys Glu Ala Phe His Leu Glu Ala
            1010                1015                1020

Arg Glu Val Tyr Ser Val Asp Pro Tyr Asn Pro Ala Ser
            1025                1030

<210> SEQ ID NO 15
<211> LENGTH: 229
<212> TYPE: PRT
<213> ORGANISM: Homo sapiens

<400> SEQUENCE: 15

Met Ala Arg Leu Ala Leu Ser Pro Val Pro Ser His Trp Met Val
  1               5                  10                  15

Ala Leu Leu Leu Leu Leu Ser Ala Glu Pro Val Pro Ala Ala Arg
                 20                  25                  30

Ser Glu Asp Arg Tyr Arg Asn Pro Lys Gly Ser Ala Cys Ser Arg
                 35                  40                  45

Ile Trp Gln Ser Pro Arg Phe Ile Ala Arg Lys Arg Gly Phe Thr
                 50                  55                  60

Val Lys Met His Cys Tyr Met Asn Ser Ala Ser Gly Asn Val Ser
                 65                  70                  75

Trp Leu Trp Lys Gln Glu Met Asp Glu Asn Pro Gln Gln Leu Lys
                 80                  85                  90

Leu Glu Lys Gly Arg Met Glu Glu Ser Gln Asn Glu Ser Leu Ala
                 95                  100                 105

Thr Leu Thr Ile Gln Gly Ile Arg Phe Glu Asp Asn Gly Ile Tyr
                 110                 115                 120

Phe Cys Gln Gln Lys Cys Asn Asn Thr Ser Glu Val Tyr Gln Gly
                 125                 130                 135

Cys Gly Thr Glu Leu Arg Val Met Gly Phe Ser Thr Leu Ala Gln
                 140                 145                 150
```

```
Leu Lys Gln Arg Asn Thr Leu Lys Asp Gly Ile Ile Met Ile Gln
            155                 160                 165

Thr Leu Leu Ile Ile Leu Phe Ile Ile Val Pro Ile Phe Leu Leu
            170                 175                 180

Leu Asp Lys Asp Asp Ser Lys Ala Gly Met Glu Glu Asp His Thr
            185                 190                 195

Tyr Glu Gly Leu Asp Ile Asp Gln Thr Ala Thr Tyr Glu Asp Ile
            200                 205                 210

Val Thr Leu Arg Thr Gly Glu Val Lys Trp Ser Val Gly Glu His
            215                 220                 225

Pro Gly Gln Glu

<210> SEQ ID NO 16
<211> LENGTH: 508
<212> TYPE: PRT
<213> ORGANISM: Homo sapiens

<400> SEQUENCE: 16

Met Leu Leu Trp Ser Leu Leu Val Ile Phe Asp Ala Val Thr Glu
  1               5                  10                  15

Gln Ala Asp Ser Leu Thr Leu Val Ala Pro Ser Ser Val Phe Glu
             20                  25                  30

Gly Asp Ser Ile Val Leu Lys Cys Gln Gly Glu Gln Asn Trp Lys
             35                  40                  45

Ile Gln Lys Met Ala Tyr His Lys Asp Asn Lys Glu Leu Ser Val
             50                  55                  60

Phe Lys Lys Phe Ser Asp Phe Leu Ile Gln Ser Ala Val Leu Ser
             65                  70                  75

Asp Ser Gly Asn Tyr Phe Cys Ser Thr Lys Gly Gln Leu Phe Leu
             80                  85                  90

Trp Asp Lys Thr Ser Asn Ile Val Lys Ile Lys Val Gln Glu Leu
             95                 100                 105

Phe Gln Arg Pro Val Leu Thr Ala Ser Ser Phe Gln Pro Ile Glu
            110                 115                 120

Gly Gly Pro Val Ser Leu Lys Cys Glu Thr Arg Leu Ser Pro Gln
            125                 130                 135

Arg Leu Asp Val Gln Leu Gln Phe Cys Phe Phe Arg Glu Asn Gln
            140                 145                 150

Val Leu Gly Ser Gly Trp Ser Ser Ser Pro Glu Leu Gln Ile Ser
            155                 160                 165

Ala Val Trp Ser Glu Asp Thr Gly Ser Tyr Trp Cys Lys Ala Glu
            170                 175                 180

Thr Val Thr His Arg Ile Arg Lys Gln Ser Leu Gln Ser Gln Ile
            185                 190                 195

His Val Gln Arg Ile Pro Ile Ser Asn Val Ser Leu Glu Ile Arg
            200                 205                 210

Ala Pro Gly Gly Gln Val Thr Glu Gly Gln Lys Leu Ile Leu Leu
            215                 220                 225

Cys Ser Val Ala Gly Gly Thr Gly Asn Val Thr Phe Ser Trp Tyr
            230                 235                 240

Arg Glu Ala Thr Gly Thr Ser Met Gly Lys Lys Thr Gln Arg Ser
            245                 250                 255

Leu Ser Ala Glu Leu Glu Ile Pro Ala Val Lys Glu Ser Asp Ala
            260                 265                 270
```

```
Gly Lys Tyr Tyr Cys Arg Ala Asp Asn Gly His Val Pro Ile Gln
            275                 280                 285

Ser Lys Val Val Asn Ile Pro Val Arg Ile Pro Val Ser Arg Pro
            290                 295                 300

Val Leu Thr Leu Arg Ser Pro Gly Ala Gln Ala Val Gly Asp
        305                 310                 315

Leu Leu Glu Leu His Cys Glu Ala Leu Arg Gly Ser Pro Pro Ile
            320                 325                 330

Leu Tyr Gln Phe Tyr His Glu Asp Val Thr Leu Gly Asn Ser Ser
            335                 340                 345

Ala Pro Ser Gly Gly Ala Ser Phe Asn Leu Ser Leu Thr Ala
        350                 355                 360

Glu His Ser Gly Asn Tyr Ser Cys Glu Ala Asn Asn Gly Leu Gly
            365                 370                 375

Ala Gln Cys Ser Glu Ala Val Pro Val Ser Ile Ser Gly Pro Asp
            380                 385                 390

Gly Tyr Arg Arg Asp Leu Met Thr Ala Gly Val Leu Trp Gly Leu
            395                 400                 405

Phe Gly Val Leu Gly Phe Thr Gly Val Ala Leu Leu Leu Tyr Ala
            410                 415                 420

Leu Phe His Lys Ile Ser Gly Glu Ser Ser Ala Thr Asn Glu Pro
            425                 430                 435

Arg Gly Ala Ser Arg Pro Asn Pro Gln Glu Phe Thr Tyr Ser Ser
            440                 445                 450

Pro Thr Pro Asp Met Glu Glu Leu Gln Pro Val Tyr Val Asn Val
            455                 460                 465

Gly Ser Val Asp Val Asp Val Val Tyr Ser Gln Val Trp Ser Met
            470                 475                 480

Gln Gln Pro Glu Ser Ser Ala Asn Ile Arg Thr Leu Leu Glu Asn
            485                 490                 495

Lys Asp Ser Gln Val Ile Tyr Ser Ser Val Lys Lys Ser
            500                 505

<210> SEQ ID NO 17
<211> LENGTH: 1255
<212> TYPE: PRT
<213> ORGANISM: Homo sapiens

<400> SEQUENCE: 17

Met Glu Leu Ala Ala Leu Cys Arg Trp Gly Leu Leu Leu Ala Leu
  1               5                  10                  15

Leu Pro Pro Gly Ala Ala Ser Thr Gln Val Cys Thr Gly Thr Asp
            20                  25                  30

Met Lys Leu Arg Leu Pro Ala Ser Pro Glu Thr His Leu Asp Met
            35                  40                  45

Leu Arg His Leu Tyr Gln Gly Cys Gln Val Val Gln Gly Asn Leu
            50                  55                  60

Glu Leu Thr Tyr Leu Pro Thr Asn Ala Ser Leu Ser Phe Leu Gln
            65                  70                  75

Asp Ile Gln Glu Val Gln Gly Tyr Val Leu Ile Ala His Asn Gln
            80                  85                  90

Val Arg Gln Val Pro Leu Gln Arg Leu Arg Ile Val Arg Gly Thr
            95                  100                 105

Gln Leu Phe Glu Asp Asn Tyr Ala Leu Ala Val Leu Asp Asn Gly
            110                 115                 120
```

```
Asp Pro Leu Asn Asn Thr Thr Pro Val Thr Gly Ala Ser Pro Gly
            125                 130                 135

Gly Leu Arg Glu Leu Gln Leu Arg Ser Leu Thr Glu Ile Leu Lys
            140                 145                 150

Gly Gly Val Leu Ile Gln Arg Asn Pro Gln Leu Cys Tyr Gln Asp
            155                 160                 165

Thr Ile Leu Trp Lys Asp Ile Phe His Lys Asn Asn Gln Leu Ala
            170                 175                 180

Leu Thr Leu Ile Asp Thr Asn Arg Ser Arg Ala Cys His Pro Cys
            185                 190                 195

Ser Pro Met Cys Lys Gly Ser Arg Cys Trp Gly Glu Ser Ser Glu
            200                 205                 210

Asp Cys Gln Ser Leu Thr Arg Thr Val Cys Ala Gly Gly Cys Ala
            215                 220                 225

Arg Cys Lys Gly Pro Leu Pro Thr Asp Cys Cys His Glu Gln Cys
            230                 235                 240

Ala Ala Gly Cys Thr Gly Pro Lys His Ser Asp Cys Leu Ala Cys
            245                 250                 255

Leu His Phe Asn His Ser Gly Ile Cys Glu Leu His Cys Pro Ala
            260                 265                 270

Leu Val Thr Tyr Asn Thr Asp Thr Phe Glu Ser Met Pro Asn Pro
            275                 280                 285

Glu Gly Arg Tyr Thr Phe Gly Ala Ser Cys Val Thr Ala Cys Pro
            290                 295                 300

Tyr Asn Tyr Leu Ser Thr Asp Val Gly Ser Cys Thr Leu Val Cys
            305                 310                 315

Pro Leu His Asn Gln Glu Val Thr Ala Glu Asp Gly Thr Gln Arg
            320                 325                 330

Cys Glu Lys Cys Ser Lys Pro Cys Ala Arg Val Cys Tyr Gly Leu
            335                 340                 345

Gly Met Glu His Leu Arg Glu Val Arg Ala Val Thr Ser Ala Asn
            350                 355                 360

Ile Gln Glu Phe Ala Gly Cys Lys Lys Ile Phe Gly Ser Leu Ala
            365                 370                 375

Phe Leu Pro Glu Ser Phe Asp Gly Asp Pro Ala Ser Asn Thr Ala
            380                 385                 390

Pro Leu Gln Pro Glu Gln Leu Gln Val Phe Glu Thr Leu Glu Glu
            395                 400                 405

Ile Thr Gly Tyr Leu Tyr Ile Ser Ala Trp Pro Asp Ser Leu Pro
            410                 415                 420

Asp Leu Ser Val Phe Gln Asn Leu Gln Val Ile Arg Gly Arg Ile
            425                 430                 435

Leu His Asn Gly Ala Tyr Ser Leu Thr Leu Gln Gly Leu Gly Ile
            440                 445                 450

Ser Trp Leu Gly Leu Arg Ser Leu Arg Glu Leu Gly Ser Gly Leu
            455                 460                 465

Ala Leu Ile His His Asn Thr His Leu Cys Phe Val His Thr Val
            470                 475                 480

Pro Trp Asp Gln Leu Phe Arg Asn Pro His Gln Ala Leu Leu His
            485                 490                 495

Thr Ala Asn Arg Pro Glu Asp Glu Cys Val Gly Glu Gly Leu Ala
            500                 505                 510

Cys His Gln Leu Cys Ala Arg Gly His Cys Trp Gly Pro Gly Pro
            515                 520                 525
```

-continued

```
Thr Gln Cys Val Asn Cys Ser Gln Phe Leu Arg Gly Gln Glu Cys
                530                 535                 540
Val Glu Glu Cys Arg Val Leu Gln Gly Leu Pro Arg Glu Tyr Val
                545                 550                 555
Asn Ala Arg His Cys Leu Pro Cys His Pro Glu Cys Gln Pro Gln
                560                 565                 570
Asn Gly Ser Val Thr Cys Phe Gly Pro Glu Ala Asp Gln Cys Val
                575                 580                 585
Ala Cys Ala His Tyr Lys Asp Pro Pro Phe Cys Val Ala Arg Cys
                590                 595                 600
Pro Ser Gly Val Lys Pro Asp Leu Ser Tyr Met Pro Ile Trp Lys
                605                 610                 615
Phe Pro Asp Glu Glu Gly Ala Cys Gln Pro Cys Pro Ile Asn Cys
                620                 625                 630
Thr His Ser Cys Val Asp Leu Asp Asp Lys Gly Cys Pro Ala Glu
                635                 640                 645
Gln Arg Ala Ser Pro Leu Thr Ser Ile Ile Ser Ala Val Val Gly
                650                 655                 660
Ile Leu Leu Val Val Val Leu Gly Val Val Phe Gly Ile Leu Ile
                665                 670                 675
Lys Arg Arg Gln Gln Lys Ile Arg Lys Tyr Thr Met Arg Arg Leu
                680                 685                 690
Leu Gln Glu Thr Glu Leu Val Glu Pro Leu Thr Pro Ser Gly Ala
                695                 700                 705
Met Pro Asn Gln Ala Gln Met Arg Ile Leu Lys Glu Thr Glu Leu
                710                 715                 720
Arg Lys Val Lys Val Leu Gly Ser Gly Ala Phe Gly Thr Val Tyr
                725                 730                 735
Lys Gly Ile Trp Ile Pro Asp Gly Glu Asn Val Lys Ile Pro Val
                740                 745                 750
Ala Ile Lys Val Leu Arg Glu Asn Thr Ser Pro Lys Ala Asn Lys
                755                 760                 765
Glu Ile Leu Asp Glu Ala Tyr Val Met Ala Gly Val Gly Ser Pro
                770                 775                 780
Tyr Val Ser Arg Leu Leu Gly Ile Cys Leu Thr Ser Thr Val Gln
                785                 790                 795
Leu Val Thr Gln Leu Met Pro Tyr Gly Cys Leu Leu Asp His Val
                800                 805                 810
Arg Glu Asn Arg Gly Arg Leu Gly Ser Gln Asp Leu Leu Asn Trp
                815                 820                 825
Cys Met Gln Ile Ala Lys Gly Met Ser Tyr Leu Glu Asp Val Arg
                830                 835                 840
Leu Val His Arg Asp Leu Ala Ala Arg Asn Val Leu Val Lys Ser
                845                 850                 855
Pro Asn His Val Lys Ile Thr Asp Phe Gly Leu Ala Arg Leu Leu
                860                 865                 870
Asp Ile Asp Glu Thr Glu Tyr His Ala Asp Gly Gly Lys Val Pro
                875                 880                 885
Ile Lys Trp Met Ala Leu Glu Ser Ile Leu Arg Arg Arg Phe Thr
                890                 895                 900
His Gln Ser Asp Val Trp Ser Tyr Gly Val Thr Val Trp Glu Leu
                905                 910                 915
Met Thr Phe Gly Ala Lys Pro Tyr Asp Gly Ile Pro Ala Arg Glu
```

```
                920                 925                 930
Ile Pro Asp Leu Leu Glu Lys Gly Glu Arg Leu Pro Gln Pro Pro
                935                 940                 945
Ile Cys Thr Ile Asp Val Tyr Met Ile Met Val Lys Cys Trp Met
                950                 955                 960
Ile Asp Ser Glu Cys Arg Pro Arg Phe Arg Glu Leu Val Ser Glu
                965                 970                 975
Phe Ser Arg Met Ala Arg Asp Pro Gln Arg Phe Val Val Ile Gln
                980                 985                 990
Asn Glu Asp Leu Gly Pro Ala Ser Pro Leu Asp Ser Thr Phe Tyr
                995                1000                1005
Arg Ser Leu Leu Glu Asp Asp Met Gly Asp Leu Val Asp Ala
               1010                1015                1020
Glu Glu Tyr Leu Val Pro Gln Gln Gly Phe Phe Cys Pro Asp Pro
               1025                1030                1035
Ala Pro Gly Ala Gly Gly Met Val His His Arg His Arg Ser Ser
               1040                1045                1050
Ser Thr Arg Ser Gly Gly Gly Asp Leu Thr Leu Gly Leu Glu Pro
               1055                1060                1065
Ser Glu Glu Glu Ala Pro Arg Ser Pro Leu Ala Pro Ser Glu Gly
               1070                1075                1080
Ala Gly Ser Asp Val Phe Asp Gly Asp Leu Gly Met Gly Ala Ala
               1085                1090                1095
Lys Gly Leu Gln Ser Leu Pro Thr His Asp Pro Ser Pro Leu Gln
               1100                1105                1110
Arg Tyr Ser Glu Asp Pro Thr Val Pro Leu Pro Ser Glu Thr Asp
               1115                1120                1125
Gly Tyr Val Ala Pro Leu Thr Cys Ser Pro Gln Pro Glu Tyr Val
               1130                1135                1140
Asn Gln Pro Asp Val Arg Pro Gln Pro Pro Ser Pro Arg Glu Gly
               1145                1150                1155
Pro Leu Pro Ala Ala Arg Pro Ala Gly Ala Thr Leu Glu Arg Pro
               1160                1165                1170
Lys Thr Leu Ser Pro Gly Lys Asn Gly Val Val Lys Asp Val Phe
               1175                1180                1185
Ala Phe Gly Gly Ala Val Glu Asn Pro Glu Tyr Leu Thr Pro Gln
               1190                1195                1200
Gly Gly Ala Ala Pro Gln Pro His Pro Pro Ala Phe Ser Pro
               1205                1210                1215
Ala Phe Asp Asn Leu Tyr Tyr Trp Asp Gln Asp Pro Pro Glu Arg
               1220                1225                1230
Gly Ala Pro Pro Ser Thr Phe Lys Gly Thr Pro Thr Ala Glu Asn
               1235                1240                1245
Pro Glu Tyr Leu Gly Leu Asp Val Pro Val
               1250                1255

<210> SEQ ID NO 18
<211> LENGTH: 344
<212> TYPE: PRT
<213> ORGANISM: Homo sapiens

<400> SEQUENCE: 18

Met Gly Pro Pro Ser Ala Pro Pro Cys Arg Leu His Val Pro Trp
 1               5                  10                  15

Lys Glu Val Leu Leu Thr Ala Ser Leu Leu Thr Phe Trp Asn Pro
```

-continued

```
                20                  25                  30
Pro Thr Thr Ala Lys Leu Thr Ile Glu Ser Thr Pro Phe Asn Val
                35                  40                  45
Ala Glu Gly Lys Glu Val Leu Leu Ala His Asn Leu Pro Gln
                50                  55                  60
Asn Arg Ile Gly Tyr Ser Trp Tyr Lys Gly Glu Arg Val Asp Gly
                65                  70                  75
Asn Ser Leu Ile Val Gly Tyr Val Ile Gly Thr Gln Gln Ala Thr
                80                  85                  90
Pro Gly Pro Ala Tyr Ser Gly Arg Glu Thr Ile Tyr Pro Asn Ala
                95                 100                 105
Ser Leu Leu Ile Gln Asn Val Thr Gln Asn Asp Thr Gly Phe Tyr
               110                 115                 120
Thr Leu Gln Val Ile Lys Ser Asp Leu Val Asn Glu Ala Thr
               125                 130                 135
Gly Gln Phe His Val Tyr Pro Glu Leu Pro Lys Pro Ser Ile Ser
               140                 145                 150
Ser Asn Asn Ser Asn Pro Val Glu Asp Lys Asp Ala Val Ala Phe
               155                 160                 165
Thr Cys Glu Pro Glu Val Gln Asn Thr Thr Tyr Leu Trp Trp Val
               170                 175                 180
Asn Gly Gln Ser Leu Pro Val Ser Pro Arg Leu Gln Leu Ser Asn
               185                 190                 195
Gly Asn Met Thr Leu Thr Leu Leu Ser Val Lys Arg Asn Asp Ala
               200                 205                 210
Gly Ser Tyr Glu Cys Glu Ile Gln Asn Pro Ala Ser Ala Asn Arg
               215                 220                 225
Ser Asp Pro Val Thr Leu Asn Val Leu Tyr Gly Pro Asp Val Pro
               230                 235                 240
Thr Ile Ser Pro Ser Lys Ala Asn Tyr Arg Pro Gly Glu Asn Leu
               245                 250                 255
Asn Leu Ser Cys His Ala Ala Ser Asn Pro Pro Ala Gln Tyr Ser
               260                 265                 270
Trp Phe Ile Asn Gly Thr Phe Gln Gln Ser Thr Gln Glu Leu Phe
               275                 280                 285
Ile Pro Asn Ile Thr Val Asn Asn Ser Gly Ser Tyr Met Cys Gln
               290                 295                 300
Ala His Asn Ser Ala Thr Gly Leu Asn Arg Thr Thr Val Thr Met
               305                 310                 315
Ile Thr Val Ser Gly Ser Ala Pro Val Leu Ser Ala Val Ala Thr
               320                 325                 330
Val Gly Ile Thr Ile Gly Val Leu Ala Arg Val Ala Leu Ile
               335                 340

<210> SEQ ID NO 19
<211> LENGTH: 411
<212> TYPE: PRT
<213> ORGANISM: Homo sapiens

<400> SEQUENCE: 19

Met Trp Ser Gly Trp Trp Leu Trp Pro Leu Val Ala Val Cys Thr
 1               5                  10                  15
Ala Asp Phe Phe Arg Asp Glu Ala Glu Arg Ile Met Arg Asp Ser
                20                  25                  30
Pro Val Ile Asp Gly His Asn Asp Leu Pro Trp Gln Leu Leu Asp
```

-continued

```
                35                  40                  45
Met Phe Asn Asn Arg Leu Gln Asp Glu Arg Ala Asn Leu Thr Thr
         50                  55                  60
Leu Ala Gly Thr His Thr Asn Ile Pro Lys Leu Arg Ala Gly Phe
         65                  70                  75
Val Gly Gly Gln Phe Trp Ser Val Tyr Thr Pro Cys Asp Thr Gln
         80                  85                  90
Asn Lys Asp Ala Val Arg Arg Thr Leu Glu Gln Met Asp Val Val
         95                 100                 105
His Arg Met Cys Arg Met Tyr Pro Glu Thr Phe Leu Tyr Val Thr
        110                 115                 120
Ser Ser Ala Gly Ile Arg Gln Ala Phe Arg Glu Gly Lys Val Ala
        125                 130                 135
Ser Leu Ile Gly Val Glu Gly Gly His Ser Ile Asp Ser Ser Leu
        140                 145                 150
Gly Val Leu Arg Ala Leu Tyr Gln Leu Gly Met Arg Tyr Leu Thr
        155                 160                 165
Leu Thr His Ser Cys Asn Thr Pro Trp Ala Asp Asn Trp Leu Val
        170                 175                 180
Asp Thr Gly Asp Ser Glu Pro Gln Ser Gln Gly Leu Ser Pro Phe
        185                 190                 195
Gly Gln Arg Val Val Lys Glu Leu Asn Arg Leu Gly Val Leu Ile
        200                 205                 210
Asp Leu Ala His Val Ser Val Ala Thr Met Lys Ala Thr Leu Gln
        215                 220                 225
Leu Ser Arg Ala Pro Val Ile Phe Ser His Ser Ser Ala Tyr Ser
        230                 235                 240
Val Cys Ala Ser Arg Arg Asn Val Pro Asp Asp Val Leu Arg Leu
        245                 250                 255
Val Lys Gln Thr Asp Ser Leu Val Met Val Asn Phe Tyr Asn Asn
        260                 265                 270
Tyr Ile Ser Cys Thr Asn Lys Ala Asn Leu Ser Gln Val Ala Asp
        275                 280                 285
His Leu Asp His Ile Lys Glu Val Ala Gly Ala Arg Ala Val Gly
        290                 295                 300
Phe Gly Gly Asp Phe Asp Gly Val Pro Arg Val Pro Glu Gly Leu
        305                 310                 315
Glu Asp Val Ser Lys Tyr Pro Asp Leu Ile Ala Glu Leu Leu Arg
        320                 325                 330
Arg Asn Trp Thr Glu Ala Glu Val Lys Gly Ala Leu Ala Asp Asn
        335                 340                 345
Leu Leu Arg Val Phe Glu Ala Val Glu Gln Ala Ser Asn Leu Thr
        350                 355                 360
Gln Ala Pro Glu Glu Pro Ile Pro Leu Asp Gln Leu Gly Gly
        365                 370                 375
Ser Cys Arg Thr His Tyr Gly Tyr Ser Ser Gly Ala Ser Ser Leu
        380                 385                 390
His Arg His Trp Gly Leu Leu Leu Ala Ser Leu Ala Pro Leu Val
        395                 400                 405
Leu Cys Leu Ser Leu Leu
        410

<210> SEQ ID NO 20
<211> LENGTH: 553
```

```
<212> TYPE: PRT
<213> ORGANISM: Homo sapiens

<400> SEQUENCE: 20

Met Arg Ala Pro Gly Arg Pro Ala Leu Arg Pro Leu Pro Leu Pro
  1               5                  10                  15

Pro Leu Leu Leu Leu Leu Ala Ala Pro Trp Gly Arg Ala Val
             20                  25                  30

Pro Cys Val Ser Gly Gly Leu Pro Lys Pro Ala Asn Ile Thr Phe
             35                  40                  45

Leu Ser Ile Asn Met Lys Asn Val Leu Gln Trp Thr Pro Pro Glu
             50                  55                  60

Gly Leu Gln Gly Val Lys Val Thr Tyr Thr Val Gln Tyr Phe Ile
             65                  70                  75

Tyr Gly Gln Lys Lys Trp Leu Asn Lys Ser Glu Cys Arg Asn Ile
             80                  85                  90

Asn Arg Thr Tyr Cys Asp Leu Ser Ala Glu Thr Ser Asp Tyr Glu
             95                 100                 105

His Gln Tyr Tyr Ala Lys Val Lys Ala Ile Trp Gly Thr Lys Cys
            110                 115                 120

Ser Lys Trp Ala Glu Ser Gly Arg Phe Tyr Pro Phe Leu Glu Thr
            125                 130                 135

Gln Ile Gly Pro Pro Glu Val Ala Leu Thr Thr Asp Glu Lys Ser
            140                 145                 150

Ile Ser Val Val Leu Thr Ala Pro Glu Lys Trp Lys Arg Asn Pro
            155                 160                 165

Glu Asp Leu Pro Val Ser Met Gln Gln Ile Tyr Ser Asn Leu Lys
            170                 175                 180

Tyr Asn Val Ser Val Leu Asn Thr Lys Ser Asn Arg Thr Trp Ser
            185                 190                 195

Gln Cys Val Thr Asn His Thr Leu Val Leu Thr Trp Leu Glu Pro
            200                 205                 210

Asn Thr Leu Tyr Cys Val His Val Glu Ser Phe Val Pro Gly Pro
            215                 220                 225

Pro Arg Arg Ala Gln Pro Ser Glu Lys Gln Cys Ala Arg Thr Leu
            230                 235                 240

Lys Asp Gln Ser Ser Glu Phe Lys Ala Lys Ile Ile Phe Trp Tyr
            245                 250                 255

Val Leu Pro Ile Ser Ile Thr Val Phe Leu Phe Ser Val Met Gly
            260                 265                 270

Tyr Ser Ile Tyr Arg Tyr Ile His Val Gly Lys Glu Lys His Pro
            275                 280                 285

Ala Asn Leu Ile Leu Ile Tyr Gly Asn Glu Phe Asp Lys Arg Phe
            290                 295                 300

Phe Val Pro Ala Glu Lys Ile Val Ile Asn Phe Ile Thr Leu Asn
            305                 310                 315

Ile Ser Asp Asp Ser Lys Ile Ser His Gln Asp Met Ser Leu Leu
            320                 325                 330

Gly Lys Ser Ser Asp Val Ser Ser Leu Asn Asp Pro Gln Pro Ser
            335                 340                 345

Gly Asn Leu Arg Pro Pro Gln Glu Glu Glu Val Lys His Leu
            350                 355                 360

Gly Tyr Ala Ser His Leu Met Glu Ile Phe Cys Asp Ser Glu Glu
            365                 370                 375
```

```
Asn Thr Glu Gly Thr Ser Phe Thr Gln Gln Glu Ser Leu Ser Arg
            380                 385                 390

Thr Ile Pro Pro Asp Lys Thr Val Ile Glu Tyr Glu Tyr Asp Val
            395                 400                 405

Arg Thr Thr Asp Ile Cys Ala Gly Pro Glu Glu Gln Glu Leu Ser
            410                 415                 420

Leu Gln Glu Glu Val Ser Thr Gln Gly Thr Leu Leu Glu Ser Gln
            425                 430                 435

Ala Ala Leu Ala Val Leu Gly Pro Gln Thr Leu Gln Tyr Ser Tyr
            440                 445                 450

Thr Pro Gln Leu Gln Asp Leu Asp Pro Leu Ala Gln Glu His Thr
            455                 460                 465

Asp Ser Glu Glu Gly Pro Glu Glu Pro Ser Thr Thr Leu Val
            470                 475                 480

Asp Trp Asp Pro Gln Thr Gly Arg Leu Cys Ile Pro Ser Leu Ser
            485                 490                 495

Ser Phe Asp Gln Asp Ser Glu Gly Cys Glu Pro Ser Glu Gly Asp
            500                 505                 510

Gly Leu Gly Glu Glu Gly Leu Leu Ser Arg Leu Tyr Glu Glu Pro
            515                 520                 525

Ala Pro Asp Arg Pro Pro Gly Glu Asn Glu Thr Tyr Leu Met Gln
            530                 535                 540

Phe Met Glu Glu Trp Gly Leu Tyr Val Gln Met Glu Asn
            545                 550

<210> SEQ ID NO 21
<211> LENGTH: 911
<212> TYPE: PRT
<213> ORGANISM: Homo sapiens

<400> SEQUENCE: 21

Met Ala Gln Leu Phe Leu Pro Leu Leu Ala Ala Leu Val Leu Ala
 1               5                  10                  15

Gln Ala Pro Ala Ala Leu Ala Asp Val Leu Glu Gly Asp Ser Ser
            20                  25                  30

Glu Asp Arg Ala Phe Arg Val Arg Ile Ala Gly Asp Ala Pro Leu
            35                  40                  45

Gln Gly Val Leu Gly Gly Ala Leu Thr Ile Pro Cys His Val His
            50                  55                  60

Tyr Leu Arg Pro Pro Ser Arg Arg Ala Val Leu Gly Ser Pro
            65                  70                  75

Arg Val Lys Trp Thr Phe Leu Ser Arg Gly Arg Glu Ala Glu Val
            80                  85                  90

Leu Val Ala Arg Gly Val Arg Val Lys Val Asn Glu Ala Tyr Arg
            95                  100                 105

Phe Arg Val Ala Leu Pro Ala Tyr Pro Ala Ser Leu Thr Asp Val
            110                 115                 120

Ser Leu Ala Leu Ser Glu Leu Arg Pro Asn Asp Ser Gly Ile Tyr
            125                 130                 135

Arg Cys Glu Val Gln His Gly Ile Asp Asp Ser Ser Asp Ala Val
            140                 145                 150

Glu Val Lys Val Lys Gly Val Val Phe Leu Tyr Arg Glu Gly Ser
            155                 160                 165

Ala Arg Tyr Ala Phe Ser Phe Ser Gly Ala Gln Glu Ala Cys Ala
            170                 175                 180
```

```
Arg Ile Gly Ala His Ile Ala Thr Pro Glu Gln Leu Tyr Ala Ala
                185                 190                 195

Tyr Leu Gly Gly Tyr Glu Gln Cys Asp Ala Gly Trp Leu Ser Asp
            200                 205                 210

Gln Thr Val Arg Tyr Pro Ile Gln Thr Pro Arg Glu Ala Cys Tyr
            215                 220                 225

Gly Asp Met Asp Gly Phe Pro Gly Val Arg Asn Tyr Gly Val Val
            230                 235                 240

Asp Pro Asp Asp Leu Tyr Asp Val Tyr Cys Tyr Ala Glu Asp Leu
            245                 250                 255

Asn Gly Glu Leu Phe Leu Gly Asp Pro Glu Lys Leu Thr Leu
            260                 265                 270

Glu Glu Ala Arg Ala Tyr Cys Gln Arg Gly Ala Glu Ile Ala
            275                 280                 285

Thr Thr Gly Gln Leu Tyr Ala Ala Trp Asp Gly Gly Leu Asp His
            290                 295                 300

Cys Ser Pro Gly Trp Leu Ala Asp Gly Ser Val Arg Tyr Pro Ile
            305                 310                 315

Val Thr Pro Ser Gln Arg Cys Gly Gly Gly Leu Pro Gly Val Lys
            320                 325                 330

Thr Leu Phe Leu Phe Pro Asn Gln Thr Gly Phe Pro Asn Lys His
            335                 340                 345

Ser Arg Phe Asn Val Tyr Cys Phe Arg Asp Ser Ala Gln Pro Ser
            350                 355                 360

Ala Ile Pro Glu Ala Ser Asn Pro Ala Ser Asn Pro Ala Ser Asp
            365                 370                 375

Gly Leu Glu Ala Ile Val Thr Val Thr Glu Thr Leu Glu Glu Leu
            380                 385                 390

Gln Leu Pro Gln Glu Ala Thr Glu Ser Glu Ser Arg Gly Ala Ile
            395                 400                 405

Tyr Ser Ile Pro Ile Met Glu Asp Gly Gly Gly Ser Ser Thr
            410                 415                 420

Pro Glu Asp Pro Ala Glu Ala Pro Arg Thr Leu Leu Glu Phe Glu
            425                 430                 435

Thr Gln Ser Met Val Pro Pro Thr Gly Phe Ser Glu Glu Gly
            440                 445                 450

Lys Ala Leu Glu Glu Glu Lys Tyr Glu Asp Glu Glu Lys
            455                 460                 465

Glu Glu Glu Glu Glu Glu Glu Val Glu Asp Glu Ala Leu Trp
            470                 475                 480

Ala Trp Pro Ser Glu Leu Ser Ser Pro Gly Pro Glu Ala Ser Leu
            485                 490                 495

Pro Thr Glu Pro Ala Ala Gln Glu Lys Ser Leu Ser Gln Ala Pro
            500                 505                 510

Ala Arg Ala Val Leu Gln Pro Gly Ala Ser Pro Leu Pro Asp Gly
            515                 520                 525

Glu Ser Glu Ala Ser Arg Pro Pro Arg Val His Gly Pro Pro Thr
            530                 535                 540

Glu Thr Leu Pro Thr Pro Arg Glu Arg Asn Leu Ala Ser Pro Ser
            545                 550                 555

Pro Ser Thr Leu Val Glu Ala Arg Glu Val Gly Glu Ala Thr Gly
            560                 565                 570

Gly Pro Glu Leu Ser Gly Val Pro Arg Gly Glu Ser Glu Glu Thr
            575                 580                 585
```

```
Gly Ser Ser Glu Gly Ala Pro Ser Leu Leu Pro Ala Thr Arg Ala
            590                 595                 600

Pro Glu Gly Thr Arg Glu Leu Glu Ala Pro Ser Glu Asp Asn Ser
            605                 610                 615

Gly Arg Thr Ala Pro Ala Gly Thr Ser Val Gln Ala Gln Pro Val
            620                 625                 630

Leu Pro Thr Asp Ser Ala Ser Arg Gly Gly Val Ala Val Val Pro
            635                 640                 645

Ala Ser Gly Asp Cys Val Pro Ser Pro Cys His Asn Gly Gly Thr
            650                 655                 660

Cys Leu Glu Glu Glu Glu Gly Val Arg Cys Leu Cys Leu Pro Gly
            665                 670                 675

Tyr Gly Gly Asp Leu Cys Asp Val Gly Leu Arg Phe Cys Asn Pro
            680                 685                 690

Gly Trp Asp Ala Phe Gln Gly Ala Cys Tyr Lys His Phe Ser Thr
            695                 700                 705

Arg Arg Ser Trp Glu Glu Ala Glu Thr Gln Cys Arg Met Tyr Gly
            710                 715                 720

Ala His Leu Ala Ser Ile Ser Thr Pro Glu Glu Gln Asp Phe Ile
            725                 730                 735

Asn Asn Arg Tyr Arg Glu Tyr Gln Trp Ile Gly Leu Asn Asp Arg
            740                 745                 750

Thr Ile Glu Gly Asp Phe Leu Trp Ser Asp Gly Val Pro Leu Leu
            755                 760                 765

Tyr Glu Asn Trp Asn Pro Gly Gln Pro Asp Ser Tyr Phe Leu Ser
            770                 775                 780

Gly Glu Asn Cys Val Val Met Val Trp His Asp Gln Gly Gln Trp
            785                 790                 795

Ser Asp Val Pro Cys Asn Tyr His Leu Ser Tyr Thr Cys Lys Met
            800                 805                 810

Gly Leu Val Ser Cys Gly Pro Pro Glu Leu Pro Leu Ala Gln
            815                 820                 825

Val Phe Gly Arg Pro Arg Leu Arg Tyr Glu Val Asp Thr Val Leu
            830                 835                 840

Arg Tyr Arg Cys Arg Glu Gly Leu Ala Gln Arg Asn Leu Pro Leu
            845                 850                 855

Ile Arg Cys Gln Glu Asn Gly Arg Trp Glu Ala Pro Gln Ile Ser
            860                 865                 870

Cys Val Pro Arg Arg Pro Ala Arg Ala Leu His Pro Glu Glu Asp
            875                 880                 885

Pro Glu Gly Arg Gln Gly Arg Leu Leu Gly Arg Trp Lys Ala Leu
            890                 895                 900

Leu Ile Pro Pro Ser Ser Pro Met Pro Gly Pro
            905                 910

<210> SEQ ID NO 22
<211> LENGTH: 987
<212> TYPE: PRT
<213> ORGANISM: Homo sapiens

<400> SEQUENCE: 22

Met Ala Leu Arg Arg Leu Gly Ala Ala Leu Leu Leu Leu Pro Leu
 1               5                  10                  15

Leu Ala Ala Val Glu Glu Thr Leu Met Asp Ser Thr Thr Ala Thr
            20                  25                  30
```

Ala Glu Leu Gly Trp Met Val His Pro Pro Ser Gly Trp Glu Glu
                 35                   40                  45

Val Ser Gly Tyr Asp Glu Asn Met Asn Thr Ile Arg Thr Tyr Gln
                 50                   55                  60

Val Cys Asn Val Phe Glu Ser Ser Gln Asn Asn Trp Leu Arg Thr
                 65                   70                  75

Lys Phe Ile Arg Arg Gly Ala His Arg Ile His Val Glu Met
                 80                   85                  90

Lys Phe Ser Val Arg Asp Cys Ser Ser Ile Pro Ser Val Pro Gly
                 95                  100                 105

Ser Cys Lys Glu Thr Phe Asn Leu Tyr Tyr Tyr Glu Ala Asp Phe
                110                  115                 120

Asp Ser Ala Thr Lys Thr Phe Pro Asn Trp Met Glu Asn Pro Trp
                125                  130                 135

Val Lys Val Asp Thr Ile Ala Ala Asp Glu Ser Phe Ser Gln Val
                140                  145                 150

Asp Leu Gly Gly Arg Val Met Lys Ile Asn Thr Glu Val Arg Ser
                155                  160                 165

Phe Gly Pro Val Ser Arg Ser Gly Phe Tyr Leu Ala Phe Gln Asp
                170                  175                 180

Tyr Gly Gly Cys Met Ser Leu Ile Ala Val Arg Val Phe Tyr Arg
                185                  190                 195

Lys Cys Pro Arg Ile Ile Gln Asn Gly Ala Ile Phe Gln Glu Thr
                200                  205                 210

Leu Ser Gly Ala Glu Ser Thr Ser Leu Val Ala Ala Arg Gly Ser
                215                  220                 225

Cys Ile Ala Asn Ala Glu Glu Val Asp Val Pro Ile Lys Leu Tyr
                230                  235                 240

Cys Asn Gly Asp Gly Glu Trp Leu Val Pro Ile Gly Arg Cys Met
                245                  250                 255

Cys Lys Ala Gly Phe Glu Ala Val Glu Asn Gly Thr Val Cys Arg
                260                  265                 270

Gly Cys Pro Ser Gly Thr Phe Lys Ala Asn Gln Gly Asp Glu Ala
                275                  280                 285

Cys Thr His Cys Pro Ile Asn Ser Arg Thr Thr Ser Glu Gly Ala
                290                  295                 300

Thr Asn Cys Val Cys Arg Asn Gly Tyr Tyr Arg Ala Asp Leu Asp
                305                  310                 315

Pro Leu Asp Met Pro Cys Thr Thr Ile Pro Ser Ala Pro Gln Ala
                320                  325                 330

Val Ile Ser Ser Val Asn Glu Thr Ser Leu Met Leu Glu Trp Thr
                335                  340                 345

Pro Pro Arg Asp Ser Gly Gly Arg Glu Asp Leu Val Tyr Asn Ile
                350                  355                 360

Ile Cys Lys Ser Cys Gly Ser Gly Arg Gly Ala Cys Thr Arg Cys
                365                  370                 375

Gly Asp Asn Val Gln Tyr Ala Pro Arg Gln Leu Gly Leu Thr Glu
                380                  385                 390

Pro Arg Ile Tyr Ile Ser Asp Leu Leu Ala His Thr Gln Tyr Thr
                395                  400                 405

Phe Glu Ile Gln Ala Val Asn Gly Val Thr Asp Gln Ser Pro Phe
                410                  415                 420

Ser Pro Gln Phe Ala Ser Val Asn Ile Thr Thr Asn Gln Ala Ala

-continued

```
                425                 430                 435
Pro Ser Ala Val Ser Ile Met His Gln Val Ser Arg Thr Val Asp
                440                 445                 450
Ser Ile Thr Leu Ser Trp Ser Gln Pro Asp Gln Pro Asn Gly Val
                455                 460                 465
Ile Leu Asp Tyr Glu Leu Gln Tyr Tyr Glu Lys Glu Leu Ser Glu
                470                 475                 480
Tyr Asn Ala Thr Ala Ile Lys Ser Pro Thr Asn Thr Val Thr Val
                485                 490                 495
Gln Gly Leu Lys Ala Gly Ala Ile Tyr Val Phe Gln Val Arg Ala
                500                 505                 510
Arg Thr Val Ala Gly Tyr Gly Arg Tyr Ser Gly Lys Met Tyr Phe
                515                 520                 525
Gln Thr Met Thr Glu Ala Glu Tyr Gln Thr Ser Ile Gln Glu Lys
                530                 535                 540
Leu Pro Leu Ile Ile Gly Ser Ser Ala Ala Gly Leu Val Phe Leu
                545                 550                 555
Ile Ala Val Val Val Ile Ala Ile Val Cys Asn Arg Arg Gly
                560                 565                 570
Phe Glu Arg Ala Asp Ser Glu Tyr Thr Asp Lys Leu Gln His Tyr
                575                 580                 585
Thr Ser Gly His Met Thr Pro Gly Met Lys Ile Tyr Ile Asp Pro
                590                 595                 600
Phe Thr Tyr Glu Asp Pro Asn Glu Ala Val Arg Glu Phe Ala Lys
                605                 610                 615
Glu Ile Asp Ile Ser Cys Val Lys Ile Glu Gln Val Ile Gly Ala
                620                 625                 630
Gly Glu Phe Gly Glu Val Cys Ser Gly His Leu Lys Leu Pro Gly
                635                 640                 645
Lys Arg Glu Ile Phe Val Ala Ile Lys Thr Leu Lys Ser Gly Tyr
                650                 655                 660
Thr Glu Lys Gln Arg Arg Asp Phe Leu Ser Glu Ala Ser Ile Met
                665                 670                 675
Gly Gln Phe Asp His Pro Asn Val Ile His Leu Glu Gly Val Val
                680                 685                 690
Thr Lys Ser Thr Pro Val Met Ile Ile Thr Glu Phe Met Glu Asn
                695                 700                 705
Gly Ser Leu Asp Ser Phe Leu Arg Gln Asn Asp Gly Gln Phe Thr
                710                 715                 720
Val Ile Gln Leu Val Gly Met Leu Arg Gly Ile Ala Ala Gly Met
                725                 730                 735
Lys Tyr Leu Ala Asp Met Asn Tyr Val His Arg Asp Leu Ala Ala
                740                 745                 750
Arg Asn Ile Leu Val Asn Ser Asn Leu Val Cys Lys Val Ser Asp
                755                 760                 765
Phe Gly Leu Ser Arg Phe Leu Glu Asp Asp Thr Ser Asp Pro Thr
                770                 775                 780
Tyr Thr Ser Ala Leu Gly Gly Lys Ile Pro Ile Arg Trp Thr Ala
                785                 790                 795
Pro Glu Ala Ile Gln Tyr Arg Lys Phe Thr Ser Ala Ser Asp Val
                800                 805                 810
Trp Ser Tyr Gly Ile Val Met Trp Glu Val Met Ser Tyr Gly Glu
                815                 820                 825
```

-continued

```
Arg Pro Tyr Trp Asp Met Thr Asn Gln Asp Val Ile Asn Ala Ile
                830                 835                 840

Glu Gln Asp Tyr Arg Leu Pro Pro Pro Met Asp Cys Pro Ser Ala
            845                 850                 855

Leu His Gln Leu Met Leu Asp Cys Trp Gln Lys Asp Arg Asn His
        860                 865                 870

Arg Pro Lys Phe Gly Gln Ile Val Asn Thr Leu Asp Lys Met Ile
    875                 880                 885

Arg Asn Pro Asn Ser Leu Lys Ala Met Ala Pro Leu Ser Ser Gly
890                 895                 900

Ile Asn Leu Pro Leu Leu Asp Arg Thr Ile Pro Asp Tyr Thr Ser
            905                 910                 915

Phe Asn Thr Val Asp Glu Trp Leu Glu Ala Ile Lys Met Gly Gln
        920                 925                 930

Tyr Lys Glu Ser Phe Ala Asn Ala Gly Phe Thr Ser Phe Asp Val
    935                 940                 945

Val Ser Gln Met Met Met Glu Asp Ile Leu Arg Val Gly Val Thr
950                 955                 960

Leu Ala Gly His Gln Lys Lys Ile Leu Asn Ser Ile Gln Val Met
            965                 970                 975

Arg Ala Gln Met Asn Gln Ile Gln Ser Val Glu Val
        980                 985

<210> SEQ ID NO 23
<211> LENGTH: 282
<212> TYPE: PRT
<213> ORGANISM: Homo sapiens

<400> SEQUENCE: 23

Met Ala Ser Leu Gly Gln Ile Leu Phe Trp Ser Ile Ile Ser Ile
1               5                   10                  15

Ile Ile Ile Leu Ala Gly Ala Ile Ala Leu Ile Ile Gly Phe Gly
                20                  25                  30

Ile Ser Gly Arg His Ser Ile Thr Val Thr Thr Val Ala Ser Ala
            35                  40                  45

Gly Asn Ile Gly Glu Asp Gly Ile Leu Ser Cys Thr Phe Glu Pro
        50                  55                  60

Asp Ile Lys Leu Ser Asp Ile Val Ile Gln Trp Leu Lys Glu Gly
    65                  70                  75

Val Leu Gly Leu Val His Glu Phe Lys Glu Gly Lys Asp Glu Leu
80                  85                  90

Ser Glu Gln Asp Glu Met Phe Arg Gly Arg Thr Ala Val Phe Ala
            95                  100                 105

Asp Gln Val Ile Val Gly Asn Ala Ser Leu Arg Leu Lys Asn Val
        110                 115                 120

Gln Leu Thr Asp Ala Gly Thr Tyr Lys Cys Tyr Ile Ile Thr Ser
    125                 130                 135

Lys Gly Lys Lys Asn Ala Asn Leu Glu Tyr Lys Thr Gly Ala Phe
140                 145                 150

Ser Met Pro Glu Val Asn Val Asp Tyr Asn Ala Ser Ser Glu Thr
            155                 160                 165

Leu Arg Cys Glu Ala Pro Arg Trp Phe Pro Gln Pro Thr Val Val
        170                 175                 180

Trp Ala Ser Gln Val Asp Gln Gly Ala Asn Phe Ser Glu Val Ser
    185                 190                 195
```

```
Asn Thr Ser Phe Glu Leu Asn Ser Glu Asn Val Thr Met Lys Val
                200                 205                 210

Val Ser Val Leu Tyr Asn Val Thr Ile Asn Asn Thr Tyr Ser Cys
                215                 220                 225

Met Ile Glu Asn Asp Ile Ala Lys Ala Thr Gly Asp Ile Lys Val
                230                 235                 240

Thr Glu Ser Glu Ile Lys Arg Arg Ser His Leu Gln Leu Leu Asn
                245                 250                 255

Ser Lys Ala Ser Leu Cys Val Ser Ser Phe Phe Ala Ile Ser Trp
                260                 265                 270

Ala Leu Leu Pro Leu Ser Pro Tyr Leu Met Leu Lys
                275                 280

<210> SEQ ID NO 24
<211> LENGTH: 123
<212> TYPE: PRT
<213> ORGANISM: Homo sapiens

<400> SEQUENCE: 24

Met Lys Ala Val Leu Leu Ala Leu Leu Met Ala Gly Leu Ala Leu
 1               5                  10                  15

Gln Pro Gly Thr Ala Leu Leu Cys Tyr Ser Cys Lys Ala Gln Val
                20                  25                  30

Ser Asn Glu Asp Cys Leu Gln Val Glu Asn Cys Thr Gln Leu Gly
                35                  40                  45

Glu Gln Cys Trp Thr Ala Arg Ile Arg Ala Val Gly Leu Leu Thr
                50                  55                  60

Val Ile Ser Lys Gly Cys Ser Leu Asn Cys Val Asp Asp Ser Gln
                65                  70                  75

Asp Tyr Tyr Val Gly Lys Lys Asn Ile Thr Cys Cys Asp Thr Asp
                80                  85                  90

Leu Cys Asn Ala Ser Gly Ala His Ala Leu Gln Pro Ala Ala Ala
                95                  100                 105

Ile Leu Ala Leu Leu Pro Ala Leu Gly Leu Leu Leu Trp Gly Pro
                110                 115                 120

Gly Gln Leu

<210> SEQ ID NO 25
<211> LENGTH: 236
<212> TYPE: PRT
<213> ORGANISM: Homo sapiens

<400> SEQUENCE: 25

Met Pro Gly Ala Ala Ala Ala Ala Ala Ala Ala Ala Ala Ala Met
 1               5                  10                  15

Leu Pro Ala Gln Glu Ala Ala Lys Leu Tyr His Thr Asn Tyr Val
                20                  25                  30

Arg Asn Ser Arg Ala Ile Gly Val Leu Trp Ala Ile Phe Thr Ile
                35                  40                  45

Cys Phe Ala Ile Val Asn Val Val Cys Phe Ile Gln Pro Tyr Trp
                50                  55                  60

Ile Gly Asp Gly Val Asp Thr Pro Gln Ala Gly Tyr Phe Gly Leu
                65                  70                  75

Phe His Tyr Cys Ile Gly Asn Gly Phe Ser Arg Glu Leu Thr Cys
                80                  85                  90

Arg Gly Ser Phe Thr Asp Phe Ser Thr Leu Pro Ser Gly Ala Phe
                95                  100                 105
```

```
Lys Ala Ala Ser Phe Phe Ile Gly Leu Ser Met Met Leu Ile Ile
            110                 115                 120

Ala Cys Ile Ile Cys Phe Thr Leu Phe Phe Cys Asn Thr Ala
            125                 130                 135

Thr Val Tyr Lys Ile Cys Ala Trp Met Gln Leu Thr Ser Ala Ala
            140                 145                 150

Cys Leu Val Leu Gly Cys Met Ile Phe Pro Asp Gly Trp Asp Ser
            155                 160                 165

Asp Glu Val Lys Arg Met Cys Gly Glu Lys Thr Asp Lys Tyr Thr
            170                 175                 180

Leu Gly Ala Cys Ser Val Arg Trp Ala Tyr Ile Leu Ala Ile Ile
            185                 190                 195

Gly Ile Leu Asp Ala Leu Ile Leu Ser Phe Leu Ala Phe Val Leu
            200                 205                 210

Gly Asn Arg Gln Asp Ser Leu Met Ala Glu Glu Leu Lys Ala Glu
            215                 220                 225

Asn Lys Val Leu Leu Ser Gln Tyr Ser Leu Glu
            230                 235

<210> SEQ ID NO 26
<211> LENGTH: 184
<212> TYPE: PRT
<213> ORGANISM: Homo sapiens

<400> SEQUENCE: 26

Met Arg Arg Gly Pro Arg Ser Leu Arg Gly Arg Asp Ala Pro Ala
  1               5                  10                 15

Pro Thr Pro Cys Val Pro Ala Glu Cys Phe Asp Leu Leu Val Arg
                 20                 25                  30

His Cys Val Ala Cys Gly Leu Leu Arg Thr Pro Arg Pro Lys Pro
                 35                 40                  45

Ala Gly Ala Ser Ser Pro Ala Pro Arg Thr Ala Leu Gln Pro Gln
                 50                 55                  60

Glu Ser Val Gly Ala Gly Ala Gly Glu Ala Ala Leu Pro Leu Pro
                 65                 70                  75

Gly Leu Leu Phe Gly Ala Pro Ala Leu Leu Gly Leu Ala Leu Val
                 80                 85                  90

Leu Ala Leu Val Leu Val Gly Leu Val Ser Trp Arg Arg Arg Gln
                 95                100                 105

Arg Arg Leu Arg Gly Ala Ser Ser Ala Glu Ala Pro Asp Gly Asp
                110                115                 120

Lys Asp Ala Pro Glu Pro Leu Asp Lys Val Ile Ile Leu Ser Pro
                125                130                 135

Gly Ile Ser Asp Ala Thr Ala Pro Ala Trp Pro Pro Pro Gly Glu
                140                145                 150

Asp Pro Gly Thr Thr Pro Pro Gly His Ser Val Pro Val Pro Ala
                155                160                 165

Thr Glu Leu Gly Ser Thr Glu Leu Val Thr Thr Lys Thr Ala Gly
                170                175                 180

Pro Glu Gln Gln

<210> SEQ ID NO 27
<211> LENGTH: 847
<212> TYPE: PRT
<213> ORGANISM: Homo sapiens
```

```
<400> SEQUENCE: 27

Met His Leu Leu Gly Pro Trp Leu Leu Leu Val Leu Glu Tyr
 1               5                  10                  15

Leu Ala Phe Ser Asp Ser Ser Lys Trp Val Phe Glu His Pro Glu
                20                  25                  30

Thr Leu Tyr Ala Trp Glu Gly Ala Cys Val Trp Ile Pro Cys Thr
                35                  40                  45

Tyr Arg Ala Leu Asp Gly Asp Leu Glu Ser Phe Ile Leu Phe His
                50                  55                  60

Asn Pro Glu Tyr Asn Lys Asn Thr Ser Lys Phe Asp Gly Thr Arg
                65                  70                  75

Leu Tyr Glu Ser Thr Lys Asp Gly Lys Val Pro Ser Glu Gln Lys
                80                  85                  90

Arg Val Gln Phe Leu Gly Asp Lys Asn Lys Asn Cys Thr Leu Ser
                95                 100                 105

Ile His Pro Val His Leu Asn Asp Ser Gly Gln Leu Gly Leu Arg
               110                 115                 120

Met Glu Ser Lys Thr Glu Lys Trp Met Glu Arg Ile His Leu Asn
               125                 130                 135

Val Ser Glu Arg Pro Phe Pro Pro His Ile Gln Leu Pro Pro Glu
               140                 145                 150

Ile Gln Glu Ser Gln Glu Val Thr Leu Thr Cys Leu Leu Asn Phe
               155                 160                 165

Ser Cys Tyr Gly Tyr Pro Ile Gln Leu Gln Trp Leu Leu Glu Gly
               170                 175                 180

Val Pro Met Arg Gln Ala Ala Val Thr Ser Thr Ser Leu Thr Ile
               185                 190                 195

Lys Ser Val Phe Thr Arg Ser Glu Leu Lys Phe Ser Pro Gln Trp
               200                 205                 210

Ser His His Gly Lys Ile Val Thr Cys Gln Leu Gln Asp Ala Asp
               215                 220                 225

Gly Lys Phe Leu Ser Asn Asp Thr Val Gln Leu Asn Val Lys His
               230                 235                 240

Thr Pro Lys Leu Glu Ile Lys Val Thr Pro Ser Asp Ala Ile Val
               245                 250                 255

Arg Glu Gly Asp Ser Val Thr Met Thr Cys Glu Val Ser Ser Ser
               260                 265                 270

Asn Pro Glu Tyr Thr Thr Val Ser Trp Leu Lys Asp Gly Thr Ser
               275                 280                 285

Leu Lys Lys Gln Asn Thr Phe Thr Leu Asn Leu Arg Glu Val Thr
               290                 295                 300

Lys Asp Gln Ser Gly Lys Tyr Cys Cys Gln Val Ser Asn Asp Val
               305                 310                 315

Gly Pro Gly Arg Ser Glu Glu Val Phe Leu Gln Val Gln Tyr Ala
               320                 325                 330

Pro Glu Pro Ser Thr Val Gln Ile Leu His Ser Pro Ala Val Glu
               335                 340                 345

Gly Ser Gln Val Glu Phe Leu Cys Met Ser Leu Ala Asn Pro Leu
               350                 355                 360

Pro Thr Asn Tyr Thr Trp Tyr His Asn Gly Lys Glu Met Gln Gly
               365                 370                 375

Arg Thr Glu Glu Lys Val His Ile Pro Lys Ile Leu Pro Trp His
               380                 385                 390
```

-continued

```
Ala Gly Thr Tyr Ser Cys Val Ala Glu Asn Ile Leu Gly Thr Gly
            395                 400                 405
Gln Arg Gly Pro Gly Ala Glu Leu Asp Val Gln Tyr Pro Pro Lys
            410                 415                 420
Lys Val Thr Thr Val Ile Gln Asn Pro Met Pro Ile Arg Glu Gly
            425                 430                 435
Asp Thr Val Thr Leu Ser Cys Asn Tyr Asn Ser Ser Asn Pro Ser
            440                 445                 450
Val Thr Arg Tyr Glu Trp Lys Pro His Gly Ala Trp Glu Glu Pro
            455                 460                 465
Ser Leu Gly Val Leu Lys Ile Gln Asn Val Gly Trp Asp Asn Thr
            470                 475                 480
Thr Ile Ala Cys Ala Arg Cys Asn Ser Trp Cys Ser Trp Ala Ser
            485                 490                 495
Pro Val Ala Leu Asn Val Gln Tyr Ala Pro Arg Asp Val Arg Val
            500                 505                 510
Arg Lys Ile Lys Pro Leu Ser Glu Ile His Ser Gly Asn Ser Val
            515                 520                 525
Ser Leu Gln Cys Asp Phe Ser Ser Ser His Pro Lys Glu Val Gln
            530                 535                 540
Phe Phe Trp Glu Lys Asn Gly Arg Leu Leu Gly Lys Glu Ser Gln
            545                 550                 555
Leu Asn Phe Asp Ser Ile Ser Pro Glu Asp Ala Gly Ser Tyr Ser
            560                 565                 570
Cys Trp Val Asn Asn Ser Ile Gly Gln Thr Ala Ser Lys Ala Trp
            575                 580                 585
Thr Leu Glu Val Leu Tyr Ala Pro Arg Arg Leu Arg Val Ser Met
            590                 595                 600
Ser Pro Gly Asp Gln Val Met Glu Gly Lys Ser Ala Thr Leu Thr
            605                 610                 615
Cys Glu Ser Asp Ala Asn Pro Pro Val Ser His Tyr Thr Trp Phe
            620                 625                 630
Asp Trp Asn Asn Gln Ser Leu Pro His His Ser Gln Lys Leu Arg
            635                 640                 645
Leu Glu Pro Val Lys Val Gln His Ser Gly Ala Tyr Trp Cys Gln
            650                 655                 660
Gly Thr Asn Ser Val Gly Lys Gly Arg Ser Pro Leu Ser Thr Leu
            665                 670                 675
Thr Val Tyr Tyr Ser Pro Glu Thr Ile Gly Arg Arg Val Ala Val
            680                 685                 690
Gly Leu Gly Ser Cys Leu Ala Ile Leu Ile Leu Ala Ile Cys Gly
            695                 700                 705
Leu Lys Leu Gln Arg Arg Trp Lys Arg Thr Gln Ser Gln Gln Gly
            710                 715                 720
Leu Gln Glu Asn Ser Ser Gly Gln Ser Phe Phe Val Arg Asn Lys
            725                 730                 735
Lys Val Arg Arg Ala Pro Leu Ser Glu Gly Pro His Ser Leu Gly
            740                 745                 750
Cys Tyr Asn Pro Met Met Glu Asp Gly Ile Ser Tyr Thr Thr Leu
            755                 760                 765
Arg Phe Pro Glu Met Asn Ile Pro Arg Thr Gly Asp Ala Glu Ser
            770                 775                 780
Ser Glu Met Gln Arg Pro Pro Arg Thr Cys Asp Asp Thr Val Thr
            785                 790                 795
```

Tyr Ser Ala Leu His Lys Arg Gln Val Gly Asp Tyr Glu Asn Val
            800                 805                 810

Ile Pro Asp Phe Pro Glu Asp Glu Gly Ile His Tyr Ser Glu Leu
            815                 820                 825

Ile Gln Phe Gly Val Gly Glu Arg Pro Gln Ala Gln Glu Asn Val
            830                 835                 840

Asp Tyr Val Ile Leu Lys His
            845

<210> SEQ ID NO 28
<211> LENGTH: 226
<212> TYPE: PRT
<213> ORGANISM: Homo sapiens

<400> SEQUENCE: 28

Met Pro Gly Gly Pro Gly Val Leu Gln Ala Leu Pro Ala Thr Ile
  1               5                  10                  15

Phe Leu Leu Phe Leu Leu Ser Ala Val Tyr Leu Gly Pro Gly Cys
                 20                  25                  30

Gln Ala Leu Trp Met His Lys Val Pro Ala Ser Leu Met Val Ser
                 35                  40                  45

Leu Gly Glu Asp Ala His Phe Gln Cys Pro His Asn Ser Ser Asn
                 50                  55                  60

Asn Ala Asn Val Thr Trp Trp Arg Val Leu His Gly Asn Tyr Thr
                 65                  70                  75

Trp Pro Pro Glu Phe Leu Gly Pro Gly Glu Asp Pro Asn Gly Thr
                 80                  85                  90

Leu Ile Ile Gln Asn Val Asn Lys Ser His Gly Gly Ile Tyr Val
                 95                 100                 105

Cys Arg Val Gln Glu Gly Asn Glu Ser Tyr Gln Gln Ser Cys Gly
                110                 115                 120

Thr Tyr Leu Arg Val Arg Gln Pro Pro Pro Arg Pro Phe Leu Asp
                125                 130                 135

Met Gly Glu Gly Thr Lys Asn Arg Ile Ile Thr Ala Glu Gly Ile
                140                 145                 150

Ile Leu Leu Phe Cys Ala Val Val Pro Gly Thr Leu Leu Leu Phe
                155                 160                 165

Arg Lys Arg Trp Gln Asn Glu Lys Leu Gly Leu Asp Ala Gly Asp
                170                 175                 180

Glu Tyr Glu Asp Glu Asn Leu Tyr Glu Gly Leu Asn Leu Asp Asp
                185                 190                 195

Cys Ser Met Tyr Glu Asp Ile Ser Arg Gly Leu Gln Gly Thr Tyr
                200                 205                 210

Gln Asp Val Gly Ser Leu Asn Ile Gly Asp Val Gln Leu Glu Lys
                215                 220                 225

Pro

<210> SEQ ID NO 29
<211> LENGTH: 372
<212> TYPE: PRT
<213> ORGANISM: Homo sapiens

<400> SEQUENCE: 29

Met Asn Tyr Pro Leu Thr Leu Glu Met Asp Leu Glu Asn Leu Glu
  1               5                  10                  15

Asp Leu Phe Trp Glu Leu Asp Arg Leu Asp Asn Tyr Asn Asp Thr

```
                 20                  25                  30
Ser Leu Val Glu Asn His Leu Cys Pro Ala Thr Glu Gly Pro Leu
             35                  40                  45
Met Ala Ser Phe Lys Ala Val Phe Val Pro Val Ala Tyr Ser Leu
             50                  55                  60
Ile Phe Leu Leu Gly Val Ile Gly Asn Val Leu Val Leu Val Ile
             65                  70                  75
Leu Glu Arg His Arg Gln Thr Arg Ser Ser Thr Glu Thr Phe Leu
             80                  85                  90
Phe His Leu Ala Val Ala Asp Leu Leu Leu Val Phe Ile Leu Pro
             95                 100                 105
Phe Ala Val Ala Glu Gly Ser Val Gly Trp Val Leu Gly Thr Phe
            110                 115                 120
Leu Cys Lys Thr Val Ile Ala Leu His Lys Val Asn Phe Tyr Cys
            125                 130                 135
Ser Ser Leu Leu Leu Ala Cys Ile Ala Val Asp Arg Tyr Leu Ala
            140                 145                 150
Ile Val His Ala Val His Ala Tyr Arg His Arg Arg Leu Leu Ser
            155                 160                 165
Ile His Ile Thr Cys Gly Thr Ile Trp Leu Val Gly Phe Leu Leu
            170                 175                 180
Ala Leu Pro Glu Ile Leu Phe Ala Lys Val Ser Gln Gly His His
            185                 190                 195
Asn Asn Ser Leu Pro Arg Cys Thr Phe Ser Gln Glu Asn Gln Ala
            200                 205                 210
Glu Thr His Ala Trp Phe Thr Ser Arg Phe Leu Tyr His Val Ala
            215                 220                 225
Gly Phe Leu Leu Pro Met Leu Val Met Gly Trp Cys Tyr Val Gly
            230                 235                 240
Val Val His Arg Leu Arg Gln Ala Gln Arg Arg Pro Gln Arg Gln
            245                 250                 255
Lys Ala Val Arg Val Ala Ile Leu Val Thr Ser Ile Phe Phe Leu
            260                 265                 270
Cys Trp Ser Pro Tyr His Ile Val Ile Phe Leu Asp Thr Leu Ala
            275                 280                 285
Arg Leu Lys Ala Val Asp Asn Thr Cys Lys Leu Asn Gly Ser Leu
            290                 295                 300
Pro Val Ala Ile Thr Met Cys Glu Phe Leu Gly Leu Ala His Cys
            305                 310                 315
Cys Leu Asn Pro Met Leu Tyr Thr Phe Ala Gly Val Lys Phe Arg
            320                 325                 330
Ser Asp Leu Ser Arg Leu Leu Thr Lys Leu Gly Cys Thr Gly Pro
            335                 340                 345
Ala Ser Leu Cys Gln Leu Phe Pro Ser Trp Arg Arg Ser Ser Leu
            350                 355                 360
Ser Glu Ser Glu Asn Ala Thr Ser Leu Thr Thr Phe
            365                 370

<210> SEQ ID NO 30
<211> LENGTH: 273
<212> TYPE: PRT
<213> ORGANISM: Homo sapiens

<400> SEQUENCE: 30

Met Gly Ser Gly Trp Val Pro Trp Val Val Ala Leu Leu Val Asn
```

```
                1               5                  10                 15
Leu Thr Arg Leu Asp Ser Ser Met Thr Gln Gly Thr Asp Ser Pro
                20                          25                     30

Glu Asp Phe Val Ile Gln Ala Lys Ala Asp Cys Tyr Phe Thr Asn
                35                          40                     45

Gly Thr Glu Lys Val Gln Phe Val Arg Phe Ile Phe Asn Leu
                50                          55                     60

Glu Glu Tyr Val Arg Phe Asp Ser Asp Val Gly Met Phe Val Ala
                65                          70                     75

Leu Thr Lys Leu Gly Gln Pro Asp Ala Glu Gln Trp Asn Ser Arg
                80                          85                     90

Leu Asp Leu Leu Glu Arg Ser Arg Gln Ala Val Asp Gly Val Cys
                95                         100                    105

Arg His Asn Tyr Arg Leu Gly Ala Pro Phe Thr Val Gly Arg Lys
               110                         115                    120

Val Gln Pro Glu Val Thr Val Tyr Pro Glu Arg Thr Pro Leu Leu
               125                         130                    135

His Gln His Asn Leu Leu His Cys Ser Val Thr Gly Phe Tyr Pro
               140                         145                    150

Gly Asp Ile Lys Ile Lys Trp Phe Leu Asn Gly Gln Glu Glu Arg
               155                         160                    165

Ala Gly Val Met Ser Thr Gly Pro Ile Arg Asn Gly Asp Trp Thr
               170                         175                    180

Phe Gln Thr Val Val Met Leu Glu Met Thr Pro Glu Leu Gly His
               185                         190                    195

Val Tyr Thr Cys Leu Val Asp His Ser Ser Leu Leu Ser Pro Val
               200                         205                    210

Ser Val Glu Trp Arg Ala Gln Ser Glu Tyr Ser Trp Arg Lys Met
               215                         220                    225

Leu Ser Gly Ile Ala Ala Phe Leu Leu Gly Leu Ile Phe Leu Leu
               230                         235                    240

Val Gly Ile Val Ile Gln Leu Arg Ala Gln Lys Gly Tyr Val Arg
               245                         250                    255

Thr Gln Met Ser Gly Asn Glu Val Ser Arg Ala Val Leu Leu Pro
               260                         265                    270

Gln Ser Cys

<210> SEQ ID NO 31
<211> LENGTH: 422
<212> TYPE: PRT
<213> ORGANISM: Homo sapiens

<400> SEQUENCE: 31

Met Gly Gln Ala Gly Cys Lys Gly Leu Cys Leu Ser Leu Phe Asp
  1               5                  10                 15

Tyr Lys Thr Glu Lys Tyr Val Ile Ala Lys Asn Lys Lys Val Gly
                20                          25                     30

Leu Leu Tyr Arg Leu Leu Gln Ala Ser Ile Leu Ala Tyr Leu Val
                35                          40                     45

Val Trp Val Phe Leu Ile Lys Lys Gly Tyr Gln Asp Val Asp Thr
                50                          55                     60

Ser Leu Gln Ser Ala Val Ile Thr Lys Val Lys Gly Val Ala Phe
                65                          70                     75

Thr Asn Thr Ser Asp Leu Gly Gln Arg Ile Trp Asp Val Ala Asp
                80                          85                     90
```

```
Tyr Val Ile Pro Ala Gln Gly Glu Asn Val Phe Val Thr
             95                 100                 105

Asn Leu Ile Val Thr Pro Asn Gln Arg Gln Asn Val Cys Ala Glu
            110                 115                 120

Asn Glu Gly Ile Pro Asp Gly Ala Cys Ser Lys Asp Ser Asp Cys
            125                 130                 135

His Ala Gly Glu Ala Val Thr Ala Gly Asn Gly Val Lys Thr Gly
            140                 145                 150

Arg Cys Leu Arg Arg Glu Asn Leu Ala Arg Gly Thr Cys Glu Ile
            155                 160                 165

Phe Ala Trp Cys Pro Leu Glu Thr Ser Ser Arg Pro Glu Glu Pro
            170                 175                 180

Phe Leu Lys Glu Ala Glu Asp Phe Thr Ile Phe Ile Lys Asn His
            185                 190                 195

Ile Arg Phe Pro Lys Phe Asn Phe Ser Lys Ser Asn Val Met Asp
            200                 205                 210

Val Lys Asp Arg Ser Phe Leu Lys Ser Cys His Phe Gly Pro Lys
            215                 220                 225

Asn His Tyr Cys Pro Ile Phe Arg Leu Gly Ser Val Ile Arg Trp
            230                 235                 240

Ala Gly Ser Asp Phe Gln Asp Ile Ala Leu Glu Gly Gly Val Ile
            245                 250                 255

Gly Ile Asn Ile Glu Trp Asn Cys Asp Leu Asp Lys Ala Ala Ser
            260                 265                 270

Glu Cys His Pro His Tyr Ser Phe Ser Arg Leu Asp Asn Lys Leu
            275                 280                 285

Ser Lys Ser Val Ser Ser Gly Tyr Asn Phe Arg Phe Ala Arg Tyr
            290                 295                 300

Tyr Arg Asp Ala Ala Gly Val Glu Phe Arg Thr Leu Met Lys Ala
            305                 310                 315

Tyr Gly Ile Arg Phe Asp Val Met Val Asn Gly Lys Gly Ala Phe
            320                 325                 330

Phe Cys Asp Leu Val Leu Ile Tyr Leu Ile Lys Lys Arg Glu Phe
            335                 340                 345

Tyr Arg Asp Lys Lys Tyr Glu Val Arg Gly Leu Glu Asp Ser
            350                 355                 360

Ser Gln Glu Ala Glu Asp Glu Ala Ser Gly Leu Gly Leu Ser Glu
            365                 370                 375

Gln Leu Thr Ser Gly Pro Gly Leu Leu Gly Met Pro Glu Gln Gln
            380                 385                 390

Glu Leu Gln Glu Pro Pro Glu Ala Lys Arg Gly Ser Ser Ser Gln
            395                 400                 405

Lys Gly Asn Gly Ser Val Cys Pro Gln Leu Leu Glu Pro His Arg
            410                 415                 420

Ser Thr
```

<210> SEQ ID NO 32
<211> LENGTH: 359
<212> TYPE: PRT
<213> ORGANISM: Homo sapiens

<400> SEQUENCE: 32

```
Met Ala Glu Ala Ile Thr Tyr Ala Asp Leu Arg Phe Val Lys Ala
  1               5                  10                  15
```

```
Pro Leu Lys Lys Ser Ile Ser Ser Arg Leu Gly Gln Asp Pro Gly
            20                  25                  30

Ala Asp Asp Gly Glu Ile Thr Tyr Glu Asn Val Gln Val Pro
        35                  40                  45

Ala Val Leu Gly Val Pro Ser Ser Leu Ala Ser Ser Val Leu Gly
            50                  55                  60

Asp Lys Ala Ala Val Lys Ser Glu Gln Pro Thr Ala Ser Trp Arg
            65                  70                  75

Ala Val Thr Ser Pro Ala Val Gly Arg Ile Leu Pro Cys Arg Thr
            80                  85                  90

Thr Cys Leu Arg Tyr Leu Leu Leu Gly Leu Leu Thr Cys Leu
            95                 100                 105

Leu Leu Gly Val Thr Ala Ile Cys Leu Gly Val Arg Tyr Leu Gln
            110                 115                 120

Val Ser Gln Gln Leu Gln Gln Thr Asn Arg Val Leu Glu Val Thr
            125                 130                 135

Asn Ser Ser Leu Arg Gln Gln Leu Arg Leu Lys Ile Thr Gln Leu
            140                 145                 150

Gly Gln Ser Ala Glu Asp Leu Gln Gly Ser Arg Arg Glu Leu Ala
            155                 160                 165

Gln Ser Gln Glu Ala Leu Gln Val Glu Gln Arg Ala His Gln Ala
            170                 175                 180

Ala Glu Gly Gln Leu Gln Ala Cys Gln Ala Asp Arg Gln Lys Thr
            185                 190                 195

Lys Glu Thr Leu Gln Ser Glu Gln Gln Arg Arg Ala Leu Glu
            200                 205                 210

Gln Lys Leu Ser Asn Met Glu Asn Arg Leu Lys Pro Phe Phe Thr
            215                 220                 225

Cys Gly Ser Ala Asp Thr Cys Cys Pro Ser Gly Trp Ile Met His
            230                 235                 240

Gln Lys Ser Cys Phe Tyr Ile Ser Leu Thr Ser Lys Asn Trp Gln
            245                 250                 255

Glu Ser Gln Lys Gln Cys Glu Thr Leu Ser Ser Lys Leu Ala Thr
            260                 265                 270

Phe Ser Glu Ile Tyr Pro Gln Ser His Ser Tyr Tyr Phe Leu Asn
            275                 280                 285

Ser Leu Leu Pro Asn Gly Gly Ser Gly Asn Ser Tyr Trp Thr Gly
            290                 295                 300

Leu Ser Ser Asn Lys Asp Trp Lys Leu Thr Asp Asp Thr Gln Arg
            305                 310                 315

Thr Arg Thr Tyr Ala Gln Ser Ser Lys Cys Asn Lys Val His Lys
            320                 325                 330

Thr Trp Ser Trp Trp Thr Leu Glu Ser Glu Ser Cys Arg Ser Ser
            335                 340                 345

Leu Pro Tyr Ile Cys Glu Met Thr Ala Phe Arg Phe Pro Asp
            350                 355

<210> SEQ ID NO 33
<211> LENGTH: 661
<212> TYPE: PRT
<213> ORGANISM: Homo sapiens

<400> SEQUENCE: 33

Met Ala Phe Asp Val Ser Cys Phe Phe Trp Val Val Leu Phe Ser
 1               5                  10                  15
```

```
Ala Gly Cys Lys Val Ile Thr Ser Trp Asp Gln Met Cys Ile Glu
                 20                  25                  30

Lys Glu Ala Asn Lys Thr Tyr Asn Cys Glu Asn Leu Gly Leu Ser
                 35                  40                  45

Glu Ile Pro Asp Thr Leu Pro Asn Thr Thr Glu Phe Leu Glu Phe
                 50                  55                  60

Ser Phe Asn Phe Leu Pro Thr Ile His Asn Arg Thr Phe Ser Arg
                 65                  70                  75

Leu Met Asn Leu Thr Phe Leu Asp Leu Thr Arg Cys Gln Ile Asn
                 80                  85                  90

Trp Ile His Glu Asp Thr Phe Gln Ser His Gln Leu Ser Thr
                 95                 100                 105

Leu Val Leu Thr Gly Asn Pro Leu Ile Phe Met Ala Glu Thr Ser
                110                 115                 120

Leu Asn Gly Pro Lys Ser Leu Lys His Leu Phe Leu Ile Gln Thr
                125                 130                 135

Gly Ile Ser Asn Leu Glu Phe Ile Pro Val His Asn Leu Glu Asn
                140                 145                 150

Leu Glu Ser Leu Tyr Leu Gly Ser Asn His Ile Ser Ser Ile Lys
                155                 160                 165

Phe Pro Lys Asp Phe Pro Ala Arg Asn Leu Lys Val Leu Asp Phe
                170                 175                 180

Gln Asn Asn Ala Ile His Tyr Ile Ser Arg Glu Asp Met Arg Ser
                185                 190                 195

Leu Glu Gln Ala Ile Asn Leu Ser Leu Asn Phe Asn Gly Asn Asn
                200                 205                 210

Val Lys Gly Ile Glu Leu Gly Ala Phe Asp Ser Thr Val Phe Gln
                215                 220                 225

Ser Leu Asn Phe Gly Gly Thr Pro Asn Leu Ser Val Ile Phe Asn
                230                 235                 240

Gly Leu Gln Asn Ser Thr Thr Gln Ser Leu Trp Leu Gly Thr Phe
                245                 250                 255

Glu Asp Ile Asp Asp Glu Asp Ile Ser Ser Ala Met Leu Lys Gly
                260                 265                 270

Leu Cys Glu Met Ser Val Glu Ser Leu Asn Leu Gln Glu His Arg
                275                 280                 285

Phe Ser Asp Ile Ser Ser Thr Thr Phe Gln Cys Phe Thr Gln Leu
                290                 295                 300

Gln Glu Leu Asp Leu Thr Ala Thr His Leu Lys Gly Leu Pro Ser
                305                 310                 315

Gly Met Lys Gly Leu Asn Leu Leu Lys Lys Leu Val Leu Ser Val
                320                 325                 330

Asn His Phe Asp Gln Leu Cys Gln Ile Ser Ala Ala Asn Phe Pro
                335                 340                 345

Ser Leu Thr His Leu Tyr Ile Arg Gly Asn Val Lys Lys Leu His
                350                 355                 360

Leu Gly Val Gly Cys Leu Glu Lys Leu Gly Asn Leu Gln Thr Leu
                365                 370                 375

Asp Leu Ser His Asn Asp Ile Glu Ala Ser Asp Cys Cys Ser Leu
                380                 385                 390

Gln Leu Lys Asn Leu Ser His Leu Gln Thr Leu Asn Leu Ser His
                395                 400                 405

Asn Glu Pro Leu Gly Leu Gln Ser Gln Ala Phe Lys Glu Cys Pro
                410                 415                 420
```

```
Gln Leu Glu Leu Leu Asp Leu Ala Phe Thr Arg Leu His Ile Asn
                425                 430                 435

Ala Pro Gln Ser Pro Phe Gln Asn Leu His Phe Leu Gln Val Leu
                440                 445                 450

Asn Leu Thr Tyr Cys Phe Leu Asp Thr Ser Asn Gln His Leu Leu
                455                 460                 465

Ala Gly Leu Pro Val Leu Arg His Leu Asn Leu Lys Gly Asn His
                470                 475                 480

Phe Gln Asp Gly Thr Ile Thr Lys Thr Asn Leu Leu Gln Thr Val
                485                 490                 495

Gly Ser Leu Glu Val Leu Ile Leu Ser Ser Cys Gly Leu Leu Ser
                500                 505                 510

Ile Asp Gln Gln Ala Phe His Ser Leu Gly Lys Met Ser His Val
                515                 520                 525

Asp Leu Ser His Asn Ser Leu Thr Cys Asp Ser Ile Asp Ser Leu
                530                 535                 540

Ser His Leu Lys Gly Ile Tyr Leu Asn Leu Ala Ala Asn Ser Ile
                545                 550                 555

Asn Ile Ile Ser Pro Arg Leu Leu Pro Ile Leu Ser Gln Gln Ser
                560                 565                 570

Thr Ile Asn Leu Ser His Asn Pro Leu Asp Cys Thr Cys Ser Asn
                575                 580                 585

Ile His Phe Leu Thr Trp Tyr Lys Glu Asn Leu His Lys Leu Glu
                590                 595                 600

Gly Ser Glu Glu Thr Thr Cys Ala Asn Pro Pro Ser Leu Arg Gly
                605                 610                 615

Val Lys Leu Ser Asp Val Lys Leu Ser Cys Gly Ile Thr Ala Ile
                620                 625                 630

Gly Ile Phe Phe Leu Ile Val Phe Leu Leu Leu Ala Ile Leu
                635                 640                 645

Leu Phe Phe Ala Val Lys Tyr Leu Leu Arg Trp Lys Tyr Gln His
                650                 655                 660

Ile

<210> SEQ ID NO 34
<211> LENGTH: 429
<212> TYPE: PRT
<213> ORGANISM: Homo sapiens

<400> SEQUENCE: 34

Met Leu Pro Arg Leu Leu Leu Ile Cys Ala Pro Leu Cys Glu
  1               5                  10                  15

Pro Ala Glu Leu Phe Leu Ile Ala Ser Pro Ser His Pro Thr Glu
                 20                  25                  30

Gly Ser Pro Val Thr Leu Thr Cys Lys Met Pro Phe Leu Gln Ser
                 35                  40                  45

Ser Asp Ala Gln Phe Gln Phe Cys Phe Phe Arg Asp Thr Arg Ala
                 50                  55                  60

Leu Gly Pro Gly Trp Ser Ser Ser Pro Lys Leu Gln Ile Ala Ala
                 65                  70                  75

Met Trp Lys Glu Asp Thr Gly Ser Tyr Trp Cys Glu Ala Gln Thr
                 80                  85                  90

Met Ala Ser Lys Val Leu Arg Ser Arg Arg Ser Gln Ile Asn Val
                 95                 100                 105
```

```
His Arg Val Pro Val Ala Asp Val Ser Leu Glu Thr Gln Pro Pro
            110                 115                 120

Gly Gly Gln Val Met Glu Gly Asp Arg Leu Val Leu Ile Cys Ser
            125                 130                 135

Val Ala Met Gly Thr Gly Asp Ile Thr Phe Leu Trp Tyr Lys Gly
            140                 145                 150

Ala Val Gly Leu Asn Leu Gln Ser Lys Thr Gln Arg Ser Leu Thr
            155                 160                 165

Ala Glu Tyr Glu Ile Pro Ser Val Arg Glu Ser Asp Ala Glu Gln
            170                 175                 180

Tyr Tyr Cys Val Ala Glu Asn Gly Tyr Gly Pro Ser Pro Ser Gly
            185                 190                 195

Leu Val Ser Ile Thr Val Arg Ile Pro Val Ser Arg Pro Ile Leu
            200                 205                 210

Met Leu Arg Ala Pro Arg Ala Gln Ala Ala Val Glu Asp Val Leu
            215                 220                 225

Glu Leu His Cys Glu Ala Leu Arg Gly Ser Pro Pro Ile Leu Tyr
            230                 235                 240

Trp Phe Tyr His Glu Asp Ile Thr Leu Gly Ser Arg Ser Ala Pro
            245                 250                 255

Ser Gly Gly Gly Ala Ser Phe Asn Leu Ser Leu Thr Glu Glu His
            260                 265                 270

Ser Gly Asn Tyr Ser Cys Glu Ala Asn Asn Gly Leu Gly Ala Gln
            275                 280                 285

Arg Ser Glu Ala Val Thr Leu Asn Phe Thr Val Pro Thr Gly Ala
            290                 295                 300

Arg Ser Asn His Leu Thr Ser Gly Val Ile Glu Gly Leu Leu Ser
            305                 310                 315

Thr Leu Gly Pro Ala Thr Val Ala Leu Leu Phe Cys Tyr Gly Leu
            320                 325                 330

Lys Arg Lys Ile Gly Arg Arg Ser Ala Arg Asp Pro Leu Arg Ser
            335                 340                 345

Leu Pro Ser Pro Leu Pro Gln Glu Phe Thr Tyr Leu Asn Ser Pro
            350                 355                 360

Thr Pro Gly Gln Leu Gln Pro Ile Tyr Glu Asn Val Asn Val Val
            365                 370                 375

Ser Gly Asp Glu Val Tyr Ser Leu Ala Tyr Tyr Asn Gln Pro Glu
            380                 385                 390

Gln Glu Ser Val Ala Ala Glu Thr Leu Gly Thr His Met Glu Asp
            395                 400                 405

Lys Val Ser Leu Asp Ile Tyr Ser Arg Leu Arg Lys Ala Asn Ile
            410                 415                 420

Thr Asp Val Asp Tyr Glu Asp Ala Met
            425

<210> SEQ ID NO 35
<211> LENGTH: 977
<212> TYPE: PRT
<213> ORGANISM: Homo sapiens

<400> SEQUENCE: 35

Met Leu Leu Trp Val Ile Leu Leu Val Leu Ala Pro Val Ser Gly
  1               5                  10                  15

Gln Phe Ala Arg Thr Pro Arg Pro Ile Ile Phe Leu Gln Pro Pro
             20                  25                  30
```

-continued

```
Trp Thr Thr Val Phe Gln Gly Glu Arg Val Thr Leu Thr Cys Lys
             35                  40                  45
Gly Phe Arg Phe Tyr Ser Pro Gln Lys Thr Lys Trp Tyr His Arg
         50                  55                  60
Tyr Leu Gly Lys Glu Ile Leu Arg Glu Thr Pro Asp Asn Ile Leu
         65                  70                  75
Glu Val Gln Glu Ser Gly Glu Tyr Arg Cys Gln Ala Gln Gly Ser
             80                  85                  90
Pro Leu Ser Ser Pro Val His Leu Asp Phe Ser Ser Ala Ser Leu
             95                 100                 105
Ile Leu Gln Ala Pro Leu Ser Val Phe Glu Gly Asp Ser Val Val
        110                 115                 120
Leu Arg Cys Arg Ala Lys Ala Glu Val Thr Leu Asn Asn Thr Ile
        125                 130                 135
Tyr Lys Asn Asp Asn Val Leu Ala Phe Leu Asn Lys Arg Thr Asp
        140                 145                 150
Phe His Ile Pro His Ala Cys Leu Lys Asp Asn Gly Ala Tyr Arg
        155                 160                 165
Cys Thr Gly Tyr Lys Glu Ser Cys Cys Pro Val Ser Ser Asn Thr
        170                 175                 180
Val Lys Ile Gln Val Gln Glu Pro Phe Thr Arg Pro Val Leu Arg
        185                 190                 195
Ala Ser Ser Phe Gln Pro Ile Ser Gly Asn Pro Val Thr Leu Thr
        200                 205                 210
Cys Glu Thr Gln Leu Ser Leu Glu Arg Ser Asp Val Pro Leu Arg
        215                 220                 225
Phe Arg Phe Phe Arg Asp Asp Gln Thr Leu Gly Leu Gly Trp Ser
        230                 235                 240
Leu Ser Pro Asn Phe Gln Ile Thr Ala Met Trp Ser Lys Asp Ser
        245                 250                 255
Gly Phe Tyr Trp Cys Lys Ala Ala Thr Met Pro His Ser Val Ile
        260                 265                 270
Ser Asp Ser Pro Arg Ser Trp Ile Gln Val Gln Ile Pro Ala Ser
        275                 280                 285
His Pro Val Leu Thr Leu Ser Pro Glu Lys Ala Leu Asn Phe Glu
        290                 295                 300
Gly Thr Lys Val Thr Leu His Cys Glu Thr Gln Glu Asp Ser Leu
        305                 310                 315
Arg Thr Leu Tyr Arg Phe Tyr His Glu Gly Val Pro Leu Arg His
        320                 325                 330
Lys Ser Val Arg Cys Glu Arg Gly Ala Ser Ile Ser Phe Ser Leu
        335                 340                 345
Thr Thr Glu Asn Ser Gly Asn Tyr Tyr Cys Thr Ala Asp Asn Gly
        350                 355                 360
Leu Gly Ala Lys Pro Ser Lys Ala Val Ser Leu Ser Val Thr Val
        365                 370                 375
Pro Val Ser His Pro Val Leu Asn Leu Ser Ser Pro Glu Asp Leu
        380                 385                 390
Ile Phe Glu Gly Ala Lys Val Thr Leu His Cys Glu Ala Gln Arg
        395                 400                 405
Gly Ser Leu Pro Ile Leu Tyr Gln Phe His His Glu Asp Ala Ala
        410                 415                 420
```

```
Leu Glu Arg Arg Ser Ala Asn Ser Ala Gly Gly Val Ala Ile Ser
            425                 430                 435

Phe Ser Leu Thr Ala Glu His Ser Gly Asn Tyr Tyr Cys Thr Ala
            440                 445                 450

Asp Asn Gly Phe Gly Pro Gln Arg Ser Lys Ala Val Ser Leu Ser
            455                 460                 465

Ile Thr Val Pro Val Ser His Pro Val Leu Thr Leu Ser Ser Ala
            470                 475                 480

Glu Ala Leu Thr Phe Glu Gly Ala Thr Val Thr Leu His Cys Glu
            485                 490                 495

Val Gln Arg Gly Ser Pro Gln Ile Leu Tyr Gln Phe Tyr His Glu
            500                 505                 510

Asp Met Pro Leu Trp Ser Ser Ser Thr Pro Ser Val Gly Arg Val
            515                 520                 525

Ser Phe Ser Phe Ser Leu Thr Glu Gly His Ser Gly Asn Tyr Tyr
            530                 535                 540

Cys Thr Ala Asp Asn Gly Phe Gly Pro Gln Arg Ser Glu Val Val
            545                 550                 555

Ser Leu Phe Val Thr Val Pro Val Ser Arg Pro Ile Leu Thr Leu
            560                 565                 570

Arg Val Pro Arg Ala Gln Ala Val Val Gly Asp Leu Leu Glu Leu
            575                 580                 585

His Cys Glu Ala Pro Arg Gly Ser Pro Pro Ile Leu Tyr Trp Phe
            590                 595                 600

Tyr His Glu Asp Val Thr Leu Gly Ser Ser Ala Pro Ser Gly
            605                 610                 615

Gly Glu Ala Ser Phe Asn Leu Ser Leu Thr Ala Glu His Ser Gly
            620                 625                 630

Asn Tyr Ser Cys Glu Ala Asn Asn Gly Leu Val Ala Gln His Ser
            635                 640                 645

Asp Thr Ile Ser Leu Ser Val Ile Val Pro Val Ser Arg Pro Ile
            650                 655                 660

Leu Thr Phe Arg Ala Pro Arg Ala Gln Ala Val Val Gly Asp Leu
            665                 670                 675

Leu Glu Leu His Cys Glu Ala Leu Arg Gly Ser Ser Pro Ile Leu
            680                 685                 690

Tyr Trp Phe Tyr His Glu Asp Val Thr Leu Gly Lys Ile Ser Ala
            695                 700                 705

Pro Ser Gly Gly Gly Ala Ser Phe Asn Leu Ser Leu Thr Thr Glu
            710                 715                 720

His Ser Gly Ile Tyr Ser Cys Glu Ala Asp Asn Gly Pro Glu Ala
            725                 730                 735

Gln Arg Ser Glu Met Val Thr Leu Lys Val Ala Val Pro Val Ser
            740                 745                 750

Arg Pro Val Leu Thr Leu Arg Ala Pro Gly Thr His Ala Ala Val
            755                 760                 765

Gly Asp Leu Leu Glu Leu His Cys Glu Ala Leu Arg Gly Ser Pro
            770                 775                 780

Leu Ile Leu Tyr Arg Phe Phe His Glu Asp Val Thr Leu Gly Asn
            785                 790                 795

Arg Ser Ser Pro Ser Gly Gly Ala Ser Leu Asn Leu Ser Leu Thr
            800                 805                 810
```

```
Ala Glu His Ser Gly Asn Tyr Ser Cys Glu Ala Asp Asn Gly Leu
            815                 820                 825

Gly Ala Gln Arg Ser Glu Thr Val Thr Leu Tyr Ile Thr Gly Leu
            830                 835                 840

Thr Ala Asn Arg Ser Gly Pro Phe Ala Thr Gly Val Ala Gly Gly
            845                 850                 855

Leu Leu Ser Ile Ala Gly Leu Ala Ala Gly Ala Leu Leu Leu Tyr
            860                 865                 870

Cys Trp Leu Ser Arg Lys Ala Gly Arg Lys Pro Ala Ser Asp Pro
            875                 880                 885

Ala Arg Ser Pro Pro Asp Ser Asp Ser Gln Glu Pro Thr Tyr His
            890                 895                 900

Asn Val Pro Ala Trp Glu Glu Leu Gln Pro Val Tyr Thr Asn Ala
            905                 910                 915

Asn Pro Arg Gly Glu Asn Val Val Tyr Ser Glu Val Arg Ile Ile
            920                 925                 930

Gln Glu Lys Lys Lys His Ala Val Ala Ser Asp Pro Arg His Leu
            935                 940                 945

Arg Asn Lys Gly Ser Pro Ile Ile Tyr Ser Glu Val Lys Val Ala
            950                 955                 960

Ser Thr Pro Val Ser Gly Ser Leu Phe Leu Ala Ser Ser Ala Pro
            965                 970                 975

His Arg

<210> SEQ ID NO 36
<211> LENGTH: 374
<212> TYPE: PRT
<213> ORGANISM: Homo sapiens

<400> SEQUENCE: 36

Met Val Leu Trp Glu Ser Pro Arg Gln Cys Ser Ser Trp Thr Leu
 1               5                  10                  15

Cys Glu Gly Phe Cys Trp Leu Leu Leu Leu Pro Val Met Leu Leu
            20                  25                  30

Ile Val Ala Arg Pro Val Lys Leu Ala Ala Phe Pro Thr Ser Leu
            35                  40                  45

Ser Asp Cys Gln Thr Pro Thr Gly Trp Asn Cys Ser Gly Tyr Asp
            50                  55                  60

Asp Arg Glu Asn Asp Leu Phe Leu Cys Asp Thr Asn Thr Cys Lys
            65                  70                  75

Phe Asp Gly Glu Cys Leu Arg Ile Gly Asp Thr Val Thr Cys Val
            80                  85                  90

Cys Gln Phe Lys Cys Asn Asn Asp Tyr Val Pro Val Cys Gly Ser
            95                  100                 105

Asn Gly Glu Ser Tyr Gln Asn Glu Cys Tyr Leu Arg Gln Ala Ala
            110                 115                 120

Cys Lys Gln Gln Ser Glu Ile Leu Val Val Ser Glu Gly Ser Cys
            125                 130                 135

Ala Thr Asp Ala Gly Ser Gly Ser Gly Asp Gly Val His Glu Gly
            140                 145                 150

Ser Gly Glu Thr Ser Gln Lys Glu Thr Ser Thr Cys Asp Ile Cys
            155                 160                 165
```

```
Gln Phe Gly Ala Glu Cys Asp Glu Asp Ala Glu Asp Val Trp Cys
                170                 175                 180
Val Cys Asn Ile Asp Cys Ser Gln Thr Asn Phe Asn Pro Leu Cys
                185                 190                 195
Ala Ser Asp Gly Lys Ser Tyr Asp Asn Ala Cys Gln Ile Lys Glu
                200                 205                 210
Ala Ser Cys Gln Lys Gln Glu Lys Ile Glu Val Met Ser Leu Gly
                215                 220                 225
Arg Cys Gln Asp Asn Thr Thr Thr Thr Lys Ser Glu Asp Gly
                230                 235                 240
His Tyr Ala Arg Thr Asp Tyr Ala Glu Asn Ala Asn Lys Leu Glu
                245                 250                 255
Glu Ser Ala Arg Glu His His Ile Pro Cys Pro Glu His Tyr Asn
                260                 265                 270
Gly Phe Cys Met His Gly Lys Cys Glu His Ser Ile Asn Met Gln
                275                 280                 285
Glu Pro Ser Cys Arg Cys Asp Ala Gly Tyr Thr Gly Gln His Cys
                290                 295                 300
Glu Lys Lys Asp Tyr Ser Val Leu Tyr Val Pro Gly Pro Val
                305                 310                 315
Arg Phe Gln Tyr Val Leu Ile Ala Ala Val Ile Gly Thr Ile Gln
                320                 325                 330
Ile Ala Val Ile Cys Val Val Val Leu Cys Ile Thr Arg Lys Cys
                335                 340                 345
Pro Arg Ser Asn Arg Ile His Arg Gln Lys Gln Asn Thr Gly His
                350                 355                 360
Tyr Ser Ser Asp Asn Thr Thr Arg Ala Ser Thr Arg Leu Ile
                365                 370
```